US011999946B2

(12) United States Patent
Karlson et al.

(10) Patent No.: US 11,999,946 B2
(45) Date of Patent: Jun. 4, 2024

(54) METHODS FOR CONTROLLING MERISTEM SIZE FOR CROP IMPROVEMENT

(71) Applicant: Pairwise Plants Services, Inc., Durham, NC (US)

(72) Inventors: Dale Karlson, Cary, NC (US); Devin O'Connor, Hillsborough, NC (US); Nathaniel Graham, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 49 days.

(21) Appl. No.: 17/212,665

(22) Filed: Mar. 25, 2021

(65) Prior Publication Data

US 2021/0301282 A1 Sep. 30, 2021

Related U.S. Application Data

(60) Provisional application No. 63/000,206, filed on Mar. 26, 2020.

(51) Int. Cl.

| | |
|---|---|
| ***C12N 15/10*** | (2006.01) |
| ***C07K 14/415*** | (2006.01) |
| ***C12N 9/22*** | (2006.01) |
| ***C12N 15/113*** | (2010.01) |
| *A01H 6/46* | (2018.01) |

(52) U.S. Cl.
CPC .......... *C12N 15/102* (2013.01); *C07K 14/415* (2013.01); *C12N 9/22* (2013.01); *C12N 15/113* (2013.01); *A01H 6/4684* (2018.05); *C12N 2310/20* (2017.05)

(58) Field of Classification Search
CPC ...... C12N 15/102; C12N 9/22; C12N 15/113; C12N 2310/20; C07K 14/415; A01H 6/4684
See application file for complete search history.

(56) References Cited

U.S. PATENT DOCUMENTS

| | | | | |
|---|---|---|---|---|
| 10,876,129 | B2 * | 12/2020 | Pennell et al. | A01H 1/06 |
| 2019/0032071 | A1 * | 1/2019 | Pennell et al. | A01H 1/06 |
| 2020/0377900 | A1 * | 12/2020 | Cargill et al. | C12N 15/8223 |

FOREIGN PATENT DOCUMENTS

| | | | |
|---|---|---|---|
| CN | 103088054 | A | 5/2013 |
| CN | 108192912 | A | 6/2018 |
| WO | 0170987 | A2 | 9/2001 |
| WO | 03093450 | A2 | 11/2003 |
| WO | 2008062049 | A1 | 5/2008 |
| WO | 2013138544 | A1 | 9/2013 |

(Continued)

OTHER PUBLICATIONS

Bommert et al. ("Quantitative variation in maize kernel row number is controlled by the Fasciated EAR2 locus" 2013 Nature Genetics 45(3):334-338). (Year: 2013).*

(Continued)

*Primary Examiner* — Matthew R Keogh
*Assistant Examiner* — Rebecca Stephens
(74) *Attorney, Agent, or Firm* — Myers Bigel, P.A.

(57) ABSTRACT

This invention relates to compositions and methods for modifying FACIATED EAR2 (FEA2) genes in plants, optionally to modify meristem size. The invention further relates to plants having increased kernel row number produced using the methods and compositions of the invention.

4 Claims, 5 Drawing Sheets

Specification includes a Sequence Listing.

(56) References Cited

FOREIGN PATENT DOCUMENTS

| | | | |
|---|---|---|---|
| WO | 2017139309 | A1 | 8/2017 |
| WO | 2020023258 | A1 | 1/2020 |
| WO | 2021195458 | A1 | 9/2021 |

OTHER PUBLICATIONS

UniProtKB Accession No. Q940E8 (B4G061) "FEA2_MAIZE" version 102 dated Feb. 13, 2019 (Year: 2019).*
Li et al. "Genetic and Molecular Mechanisms of Quantitative Trait Loci Controlling Maize Inflorescence Architecture" 2018 Plant Cell Physiology 59(3): 448-457 (Year: 2018).*
International Search Report and Written Opinion corresponding to PCT/US2021/024283; dated Jul. 16, 2021 (13 pgaes).
Bommert, Peter, et al., "Quantitative variation in maize kernel row number is controlled by the FASCIATED EAR2 locus", Nature Genetics 45(3), 2013, 334-337.
Fletcher, Jennifer C., "The CLV-WUS Stem Cell Signaling Pathway: A Roadmap to Crop Yield Optimization", Plants 7(4), 2018, 1-11.
Je, Byoung Il , et al., "Signaling from maize organ primordia via FASCIATED EAR3 regulates stem cell proliferation and yield traits", Nature Genetics 48, 2016, 785-791.
Laux, Thomas , et al., "the WUSCHEL gene is required for shoot and floral meristem integrity in *Arabidopsis*", Development (Cambridge, England) 122, 1996, 87-96.
Schoof, Heiko , et al., "The Stem Cell Population of *Arabidopsis* Shoot Meristems Is Maintained by a Regulatory Loop between the CLAVATA and WUSCHEL Genes", Cell 100(6), 2000, 635-644.
Taguchi-Shiobara, Fumio , et al., "The fasciated ear2 gene encodes a leucine-rich repeat receptor-like protein that regulates shoot meristem proliferation in maize", Gene Dev 15, 2001, 2755-2766.
Wu, Qingyu , et al., "All together now, a magical mystery tour of the maize shoot meristem", Current Opinion in Plant Biology 45(part A), 2018, 26-35.
Zsogon, Agustin , et al., "Genome editing as a tool to achieve the crop ideotype and de novo domestication of wild relatives: Case study in tomato", Plant Science 256, 2017, 120-130.
International Search Report and Written Opinion corresponding to International Application No. PCT/US2021/027609 dated Sep. 28, 2021, 22 pages.
International Search Report and Written Opinion corresponding to International Application No. PCT/US2021/035114, mailed Sep. 21, 2021, 14 pages.
International Search Report and Written Opinion corresponding to International Application No. PCT/US2021/037740, mailed Dec. 2, 2021, 22 pages.
International Search Report and Written Opinion corresponding to International Application No. PCT/US2023/069210, mailed Oct. 16, 2023, 21 pages.
International Search Report and Written Opinion corresponding to International Application No. PCT/US2023/069211, mailed Oct. 16, 2023, 21 pages.
Leucine-rich repeat receptor-like protein fasciatef ear2, Uniprot Database Accession No. Q940E8 (Dec. 1, 2001).
Receptor-like protein kinase 5 [*Zea mays*], EMBL/GenBank Accession No. ONM34918.1 (2017).
Database: UniProt [online]: A0A5J9V4K0_9POAL. Protein Recommended Name: Protein kinase domain-containing protein, Dec. 11, 2019. Retrieved from: https://www.uniprot.org/uniprot/A0A5J9V4K0, 2 pages.
Fon2-like cle protein1 [*Zea mays*], Retrieved from https://www.ncbi.nlm.nih.gov/protein/ONM16738.1?report=genbank&log$=protalign&blast_rank=1&RID=BF2FPXGG013 on Jul. 19, 2023, 2023.
Hypothetical protein ZEAMMB73_Zm00001d007576 [*Zea mays*], Retrieved from https://www.ncbi.nlm.nih.gov/protein/ONM27114.1?report=genbank&log$=protalign&blast_rank=1&RID=BHMXAB2Y016 on Jul. 20, 2023, 2023.
*Zea mays* clone 462207 mRNA sequence, Retrieved from https://www.ncbi.nlm.nih.gov/nucleotide/EU974983.1?report=genbank&log$=nuclalign&blast_rank=2&RID=BF1RUX1A013 on Jul. 19, 2023, 2023.
Bettembourg, Mathilde , et al., "Root cone angle is enlarged in docs1 LRR-RLK mutants in rice", Rice, 10(1), 2017, 1-8.
Bleckmann , et al., "Stem Cell Signaling in *Arabidopsis* Requires CRN to Localize CLV2 to the Plasma Membrane", Plant Physiology, 152:166-176 2010.
Bommert, Peter , et al., "thick tassel dwarf1 encodes a putative maize ortholog of the *Arabidopsis* CLAVATA1 leucine-rich repeat receptor-like kinase", Development, 132(6), 2005, 1235-1245.
Carballo, Jose , et al., "A high-quality genome of *Eragrostis curvula* grass provides insights into Poaceae evolution and supports new strategies to enhance forage quality", Scientific Reports, 9(Article: 10250), 2019, 1-15.
Crook, Ashley D., et al., "The systemic nodule No. regulation kinase SUNN in Medicago truncatula interacts with MtCLV2 and MtCRN", The Plant Journal 88, 2016, 108-119.
Czyzewicz, Nathan , et al., "Antagonistic peptide technology for functional dissection of CLE peptides revisited", Journal of Experimental Botany 66, 2015, 5367-5374.
Deyoung, Brody J., et al., "The CLAVATA1-related BAM1, BAM2 and BAM3 receptor kinase-like proteins are required for meristem function in *Arabidopsis*", The Plant Journal, 45(1), 2006, 1-16.
Dievart, Anne , et al., "CLAVATA1 Dominant-Negative Alleles Reveal Functional Overlap between Multiple Receptor Kinases That Regulate Meristem and Organ Development", The Plant Cell, 15(5), 2003, 1198-1211.
Ellison, Erika L., et al., "Mutator transposon insertions within maize genes often provide a novel outward reading promoter", bioRxiv. https://doi.org/10.1101/2023.06.05.543741, 2023, 1-33.
Fan, C. , et al., "A Novel Single-Nucleotide Mutation in a CLAVATA3 Gene Homolog Controls a Multilocular Silique Trait in *Brassica rapa* L", Mol Plant 7, 2014, 1788-1792.
Goad, David M., et al., "Comprehensive identification and clustering of CLV3/ESR-related (CLE) genes in plants finds groups with potentially shared function", New Phytologist 216, 2017, 605-616.
Guo, Y. , et al., "CLAVATA2 forms a distinct CLE-binding receptor complex regulating *Arabidopsis* stem cell specification", Plant J 63: 889-900, 2010.
Hu, Chong , et al., "A group of receptor kinases are essential for CLAVATA signalling to maintain stem cell homeostasis", Nature Plants, 4, 2018, 205-211.
Je, B. , et al., "The CLAVATA receptor FASCIATED EAR2 responds to distinct CLE peptides by signaling through two downstream effectors", eLife 7: e35673.
Kinoshita, Atsuko , et al., "RPK2 is an essential receptor-like kinase that transmits the CLV3 signal in *Arabidopsis*", Development, 137(22), 2010, 3911-3920.
Liu, Lei , et al., "Enhancing grain-yield-related traits by CRISPR-Cas9 promoter editing of maize CLE genes", Nature plants, 7(3), 2021, 287-294.
Liu, Chang , et al., "Natural variation in the Thick Tassel DWARF1 (TD1) gene in the regulation of maize (*Zea mays* L.) ear-related traits", Breeding Science, 69(2), 2019, 323-331.
Miwa, H. , "The Receptor-Like Kinase SOL2 Mediates CLE Signaling in *Arabidopsis*", Plant Cell Physiol 49: 1752-1757, 2008.
Muller, R., et al., "The Receptor Kinase CORYNE of *Arabidopsis* Transmits the Stem Cell-Limiting Signal CLAVATA3 Independently of CLAVATA1", The Plant Cell Online 20: 934-946, 2008.
Nimchuk, Z.L. , et al., "An Evolutionarily Conserved Pseudokinase Mediates Stem Cell Production in Plants", Plant Cell 23: 851-854, 2011.
Nimchuk, Zachary L., et al., "Plant stem cell maintenance by transcriptional cross-regulation of related receptor kinases", Development, 142(6), 2015, 1043-1049.
Nowak, Stephen , et al., "The Medicago truncatula CLAVATA3-Like CLE12/13 signaling peptides regulate nodule number depending on the CORYNE but not the Compact Root Architecture2 receptor", Plant Signaling & Behavior. vol. 14, No. 6, 2019, e1598730.

(56) References Cited

OTHER PUBLICATIONS

Rodriguez-Leal, Daniel , et al., "Evolution of buffering in a genetic circuit controlling plant stem cell proliferation", Nature Genetics. 51, 2019, 786-792.
Rodriguez-Villalon, Antia , et al., "Molecular genetic framework for protophloem formation", Proceedings of the National Academy of Sciences 111, 2014, 11551-11556.
Shpak, Elena D., et al., "Dominant-Negative Receptor Uncovers Redundancy in the Arabidopsis ERECTA Leucine-Rich Repeat Receptor-Like Kinase Signaling Pathway That Regulates Organ Shape", The Plant Cell, 15(5), 2003, 1095-1110.
Somssich, Marc , "On Receptor Kinase Interactions and Complex Formations", Inaugural dissertation zur Erlangung des Doktorgrades der Mathematisch-Naturwissenschaftlichen Fakultat der Heinrich-Heine-Universitat D0sseldorf vorgelegt van Nov. 18, 14 Dissertation.
Somssich, Marc , et al., "Shared and distinct functions of the pseudokinase CORYNE (CRN) in shoot and root stem cell maintenance of *Arabidopsis*", Journal of Experimental Botany, vol. 67, No. 16, 20116, 4901-4915.
Song, Xiu-Fen , et al., "Antagonistic Peptide Technology for Functional Dissection of CLV3/ESR Genes in *Arabidopsis*", Plant Physiol 161, 2013, 1076-1085.
Song, Xiu-Fen , et al., "Contributions of Individual Amino Acid Residues to the Endogenous CLV3 Function in Shoot Apical Meristem Maintenance in *Arabidopsis*", Mol Plant 5, 2012, 515-523.
Tran, Quan Hong , et al., "Mapping-by-Sequencing via MutMap Identifies a Mutation in ZmCLE7 Underlying Fasciation in a Newly Developed EMS Mutant Population in an Elite Tropical Maize Inbred", Genes vol. 11, No. 3, 2020.
Trung, Khuat Huu , et al., "A Weak Allele of FASCIATED Ear 2 (FEA2) Increases Maize Kernel Row Number (KRN) and Yield in Elite Maize Hybrids", Agronomy 10, 2020, 1774.
Xu, Cao , et al., "A cascade of arabinosyltransferases controls shoot meristem size in tomato", Nature Genetics, 47(7), 2015, 784-792.
Yamaguchi, Yasuka L., et al., "A Collection of Mutants for CLE-Peptide-Encoding Genes in *Arabidopsis* Generated by CRISPR/Cas9-Mediated Gene Targeting", Plant and Cell Phsiology vol. 58, No. 11, 2017, 1848-1856.
Yang, Yang , et al., "Precise editing of CLAVATA genes in *Brassica napus* L. regulates multilocular silique development", Plant Biotechnol J 16, 2018, 1322-1335.
Zhu, Y., et al., "Analysis of interactions among the CLAVATA3 receptors reveals a directCLAVATA2 and CORYNE in *Arabidopsis*", Plant J 61: 223-233, 2009.

* cited by examiner

METHODS FOR CONTROLLING MERISTEM SIZE FOR CROP IMPROVEMENT

STATEMENT REGARDING ELECTRONIC FILING OF A SEQUENCE LISTING

A Sequence Listing in ASCII text format, submitted under 37 C.F.R. § 1.821, entitled 1499.26.WO_ST25.txt, 536,102 bytes in size, generated on Jan. 25, 2023, is provided in lieu of a paper copy. This Sequence Listing is hereby incorporated herein by reference into the specification for its disclosures.

STATEMENT OF PRIORITY

This application claims the benefit, under 35 U.S.C. § 119 (e), of U.S. Provisional Application No. 63/000,206 filed on Mar. 26, 2020, the entire contents of which is incorporated by reference herein.

PARTIES TO A JOINT RESEARCH AGREEMENT

The claimed invention was made by, or on behalf of, the below listed parties to a joint research agreement. The parties to the joint research agreement are Pairwise Plants Services, Inc. and Monsanto Company.

FIELD OF THE INVENTION

This invention relates to compositions and methods for modifying FACIATED EAR2 (FEA2) genes in plants, optionally to modify meristem size. The invention further relates to plants having increased kernel row number produced using the methods and compositions of the invention.

BACKGROUND OF THE INVENTION

New plant organs are initiated at the growing tip of the plant called the meristem. In the meristem a population of undifferentiated stem cells is maintained. During growth, the meristem allocates stem-cells to newly formed organs, including seeds, while at the same time reserving some stem-cells to continually maintain the meristem. Several conserved molecular mechanisms have been described that control the size of the stem cell population to ensure organized growth and proper meristem size.

As a result of the modular nature of maize ear development, larger meristems tend to initiate more flowers, and thus, meristem size has a direct effect on kernel row number and yield. The number of flowers initiated during the development of the maize ear directly limits grain yield. An increased number of flowers initiated around the circumference of the ear (kernel row number or KRN) was a major trait selected during maize domestication. Significant advancements through breeding have resulted in dramatic increases in kernel row number, from 2 in teosinte, the ancestor of maize, to ~8-20 rows in modern elite maize varieties. In diverse maize lines kernel row number can get as high as 36.

In the canonical regulatory pathway described in the model plant Arabidopsis, CLAVATA3 (CLV3) peptide is secreted from cells in the meristem apex and moves through the apoplast into the central stem-cell domain where it interacts with several Leucine Rich Receptors (LRRs) including CLAVATA1 (CLV1) and CLAVATA2 (CLV2).

This receptor-ligand interaction stimulates signaling that ultimately acts to reduce WUS expression and restrict the expansion of the stem cell population. One of the targets of WUS is the CLV3 gene itself, and in this way WUS acts to limit its own expression and maintain stem cell homeostasis (Fletcher, J. C., *Plants* 7: 87 (2018)).

Loss of function mutations in CLVJ, CLV2, or CLV3 result in an expansion of the WUS domain and increased meristem size (Schoof et al., *Cell* 100: 635-644 (2000)). Often this increase in meristem size results in aberrant plant growth because the meristem expands uncontrollably and becomes disorganized, a phenomenon called fasciation (Je et al., *Nat Genet* 48: ng.3567 (2016a)). Importantly, a larger meristem does not just make larger organs, but rather an increased number of organs around a larger area. Because of this relationship between meristem size and organ number, mutations in maize CLV-WUS signaling genes can lead to increased flower number and yield. However, while strong loss-of-function mutations in the maize CLV2 ortholog FACIATED EAR2 (FEA2) result in enlarged meristems and an increase in KRN, the ear is disordered and as a result there is no yield increase (Taguchi-Shiobara et al., *Gene Dev* 15:2755-2766 (2001)).

Novel strategies for modulating meristem size are needed to improve crop performance.

SUMMARY OF THE INVENTION

One aspect of the invention provides a plant or plant part thereof comprising at least one non-natural mutation in an endogenous FACIATED EAR2 (FEA2) gene that encodes a FEA2 protein.

A second aspect of the invention provides a plant cell, comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding an FEA2 protein.

A third aspect of the invention provides a corn plant cell comprising at least one non-naturally occurring mutation within a FEA2 gene, wherein the mutation is a substitution, insertion or a deletion that is introduced using an editing system that comprises a nucleic acid binding domain that binds to a target site in the FEA2 gene.

A fourth aspect of the invention provides a method of producing/breeding a transgene-free edited corn plant, comprising: crossing the corn plant of the invention with a transgene free corn plant, thereby introducing the at least one non-natural mutation into the corn plant that is transgene-free; and selecting a progeny corn plant that comprises the at least one non-natural mutation and is transgene-free, thereby producing a transgene free edited corn plant.

A fifth aspect of the invention provides a method of providing a plurality of corn plants having increased kernel row number, the method comprising planting two or more plants of the invention in a growing area, thereby providing a plurality of corn plants having increased kernel row number as compared to a plurality of control corn plants not comprising the mutation.

A sixth aspect of the invention provides a method of generating variation in a region of a corn FEA2 protein, comprising: introducing an editing system into a corn plant cell, wherein the editing system is targeted to a region of a corn FEA2 gene that encodes the region of the corn FEA2 protein, wherein the region comprises the amino acid sequence of SEQ ID NO:69 or SEQ ID NO:70 or the region is encoded by the nucleotide sequence of SEQ ID NO:71 or SEQ ID NO:72; and contacting the region of the corn FEA2 gene with the editing system, thereby introducing into the corn plant cell a mutation into the region of the corn FEA2 protein; and generating variation in the region of the FEA2 protein.

A seventh aspect of the invention provides a method for editing a specific site in the genome of a corn plant cell, the method comprising: cleaving, in a site specific manner, a target site within an endogenous FEA2 gene in the corn plant cell, the endogenous FEA2 gene comprising a sequence having at least 90% sequence identity to the nucleotide sequence of SEQ ID NO:66 or SEQ ID NO:67, or encoding a sequence having at least 95% sequence identity to the amino acid sequence of SEQ ID NO:68 thereby generating an edit in the endogenous FEA2 gene of the corn plant cell and producing a corn plant cell comprising the edit in the endogenous FEA2 gene.

An eighth aspect provides a method for making a corn plant, comprising: (a) contacting a population of corn plant cells comprising a wild-type endogenous FEA2 gene with a nuclease linked to a nucleic acid binding domain (e.g., a DNA binding domain; e.g., an editing system) that binds to a sequence having at least 90% sequence identity to the nucleotide sequence of SEQ ID NO:71 or SEQ ID NO:72; or to a sequence encoding an amino acid sequence having at least 90% sequence identity to SEQ ID NO:69 or SEQ ID NO:70; (b) selecting a corn plant cell from the population in which at least one wild-type endogenous FEA2 gene has been mutated; and (c) growing the selected plant cell into a corn plant.

A ninth aspect provides a method for increasing kernel row number in a corn plant, comprising (a) contacting a corn plant cell comprising a wild type endogenous FEA2 gene with a nuclease targeting the wild type endogenous FEA2 gene, wherein the nuclease is linked to a nucleic acid binding domain (e.g., a DNA binding domain; an RNA binding domain; e.g., an editing system) that binds to a target site in the wild type endogenous FEA2 gene, wherein the wild type endogenous FEA2 gene: (i) encodes a sequence having at least 95% sequence identity to the amino acid sequence of SEQ ID NO:68; (ii) comprises a sequence having at least 90% sequence identity to the nucleotide sequence of SEQ ID NO:66 or SEQ ID NO:67; (iii) comprises a sequence having at least 90% sequence identity to the nucleotide sequence of SEQ ID NO:71 or SEQ ID NO:72; (iv) or encodes a sequence having at least 90% sequence identity to the amino acid sequence of SEQ ID NO:69 or SEQ ID NO:70 to produce a corn plant cell comprising a mutation in the wild type endogenous FEA2 gene, thereby producing the corn plant comprising at least one cell having a mutation in the endogenous FEA2 gene; and (b) growing the corn plant cell into a corn plant comprising the mutation in the wild type endogenous FEA2 gene, thereby producing a corn plant have a mutated endogenous FEA2 gene and producing one or more ears having an increased kernel row number, optionally wherein the length of the one or more ears having an increased kernel row number is not substantially decreased.

A tenth aspect provides method for producing a corn plant or part thereof comprising at least one cell having a mutated endogenous FEA2 gene, the method comprising contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene (a) encodes a sequence having at least 95% sequence identity to the amino acid sequence of SEQ ID NO:68; (b) comprises a sequence having at least 90% sequence identity to the nucleotide sequence of SEQ ID NO:66 or SEQ ID NO:67; (c) comprises a sequence having at least 90% sequence identity to the nucleotide sequence of SEQ ID NO:71 or SEQ ID NO:72; and/or (d) encodes a sequence having at least 90% sequence identity to the amino acid sequence of SEQ ID NO:69 or SEQ ID NO:70 to produce a plant cell comprising a mutation in the wild type endogenous FEA2 gene, thereby producing the corn plant or part thereof comprising at least one cell having a mutation in the endogenous FEA2 gene.

An eleventh aspect of the invention provides a method for producing a corn plant or part thereof comprising a mutated endogenous FEA2 gene and exhibiting increased kernel row number (e.g., producing ears having increased kernel row number, optionally without substantially decreasing the length of the ears), the method comprising contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene: (a) encodes a sequence having at least 95% sequence identity to the amino acid sequence of SEQ ID NO:68; (b) comprises a sequence having at least 90% sequence identity to the nucleotide sequence of SEQ ID NO:66 or SEQ ID NO:67; (c) comprises a sequence having at least 90% sequence identity to the nucleotide sequence of SEQ ID NO:71 or SEQ ID NO:72; and/or (d) encodes a sequence having at least 90% sequence identity to the amino acid sequence of SEQ ID NO:69 or SEQ ID NO:70, thereby producing the corn plant or part thereof comprising an endogenous FEA2 gene having a mutation and exhibiting increased kernel row number.

A twelfth aspect provides a guide nucleic acid that binds to a target site in a FEA2 gene, the target site comprising the nucleotide sequence of SEQ ID NO:71 or SEQ ID NO:72 or a nucleotide sequence encoding an amino acid sequence of SEQ ID NO:69 or SEQ ID NO:70.

In a thirteenth aspect, a system is provided comprising a guide nucleic acid of the invention and a CRISPR-Cas effector protein that associates with the guide nucleic acid A fourteenth aspect provides a gene editing system comprising a CRISPR-Cas effector protein in association with a guide nucleic acid, wherein the guide nucleic acid comprises a spacer sequence that binds to an endogenous FEA2 gene.

In a fifteenth aspect, a complex is provided, the complex comprising a guide nucleic acid and a CRISPR-Cas effector protein comprising a cleavage domain, wherein the guide nucleic acid binds to a target site in an endogenous FEA2 gene, wherein the endogenous FEA2 gene, wherein the endogenous FEA2 gene: (a) encodes a sequence having at least 95% sequence identity to the amino acid sequence of SEQ ID NO:68; (b) comprises a sequence having at least 90% sequence identity to the nucleotide sequence of SEQ ID NO:66 or SEQ ID NO:67; (c) comprises a sequence having at least 90% sequence identity to the nucleotide sequence of SEQ ID NO:71 or SEQ ID NO:72; and/or (d) encodes a sequence having at least 90% sequence identity to the amino acid sequence of SEQ ID NO:69 or SEQ ID NO:70, wherein the cleavage domain cleaves a target strand in the FEA2 gene.

In sixteenth aspect, an expression cassette is provided, the expression cassette comprising (a) a polynucleotide encoding CRISPR-Cas effector protein comprising a cleavage domain and (b) a guide nucleic acid that binds to a target site in an endogenous FEA2 gene, wherein the guide nucleic acid comprises a spacer sequence that is complementary to and binds to (i) a portion of a nucleic acid encoding an amino acid sequence having at least 95% sequence identity the amino acid sequence of SEQ ID NO:68; (ii) a portion of a sequence having at least 90% sequence identity to the nucleotide sequence of SEQ ID NO:66 or SEQ ID NO:67; (iii) a portion of a sequence having at least 90% sequence identity to any one of the nucleotide sequences of SEQ ID NO:71 or SEQ ID NO:72; and/or (iv) a sequence having at least 90% sequence identity to a sequence encoding the amino acid sequence of SEQ ID NO:69 or SEQ ID NO:70.

In an additional aspect, a method of creating a mutation in an endogenous FEA2 gene in a plant provided, comprising: (a) targeting a gene editing system to a portion of the FEA2 gene that encodes amino acid residues located at positions 475, 476, 477, 478 or 479 with reference to amino acid position numbering of SEQ ID NO:68, and (b) selecting a plant that comprises an alternative amino acid at one of positions 475-479 with reference to amino acid position numbering of SEQ ID NO:68, optionally an alternative amino acid in amino acid residue at position 477.

A further aspect of the invention provides a nucleic acid encoding a dominant negative mutation, a semi-dominant mutation or a weak loss-of-function mutation of a corn FEA2 protein. In some embodiments, the nucleic acid comprises a nucleotide sequence of any one of SEQ ID NOs:83-113 and/or encodes an amino acid sequence of any one of SEQ ID NOs:159-186. In some embodiments, a portion of a nucleic acid of the invention comprises a sequence of any one of SEQ ID NOs:114-128 and/or encodes an amino acid sequence of any one of SEQ ID NOs:134-148.

Also provided herein is a FEA2 polypeptide modified as described herein, the modified FEA2 polypeptide comprising a mutation in one or more amino acid residue(s) located at positions 475, 476, 477, 478 or 479 with reference to amino acid position numbering of SEQ ID NO:74 and/or comprising the amino acid sequence of any one of SEQ ID NOs:134-148.

In an additional aspect, a corn plant or part thereof is provided comprising a nucleic acid of the invention and/or a modified FEA2 polypeptide as described herein.

In a further aspect, a corn plant or part thereof is provided comprising at least one non-natural mutation in an endogenous FEA2 gene that exhibits increased kernel row number (e.g., producing ears having increased kernel row number, optionally without substantially decreasing the length of the ears). In some aspects, a corn plant is provided that also exhibits increased yield, and improved disease resistance as well as exhibits larger meristems and root meristems that are maintained.

Further provided are plants comprising in their genome one or more mutated FACIATED EAR2 (FEA2) genes produced by the methods of the invention as well as polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provides an example of a protospacer adjacent motif position for a Type V CRISPR-Cas12a nuclease.

SEQ ID NOs:45-47 provide example peptide tags and affinity polypeptides useful with this invention.

SEQ ID NOs:48-58 provide example RNA recruiting motifs and corresponding affinity polypeptides useful with this invention.

SEQ ID NOs:59-60 are exemplary Cas9 polypeptide sequences useful with this invention.

SEQ ID NOs:61-71 are exemplary Cas9 polynucleotide sequences useful with this invention.

SEQ ID NO:72 is an example FEA2 genomic sequence.

SEQ ID NO:73 is an example FEA2 coding (cds) sequence.

SEQ ID NO:74 is an example FEA2 polypeptide sequence.

SEQ ID NO:75 and SEQ ID NO:76 are example target regions of an FEA2 polypeptide.

SEQ ID NO:77 and SEQ ID NO:78 are example target regions of an FEA2 genomic sequence.

SEQ ID NOs:79-82 are example spacer sequences for nucleic acid guides useful with this invention.

SEQ ID NOs:83-113 are example edited FEA2 nucleic acid sequences.

SEQ ID NOs:114-128 are portions of edited FEA2 nucleic acid sequences shown in FIG. 3.

SEQ ID NO:129 is a portion an FEA2 nucleic acid sequence showing an example target region for editing as shown in FIG. 4.

SEQ ID NO:130 shows the consensus FEA2 nucleotide sequence in FIG. 3.

SEQ ID NO:131 shows the consensus wild type (WT) FEA2 coding sequence in FIG. 3.

SEQ ID NOs:132-148 are portions of edited FEA2 amino acid sequences shown in FIG. 3.

SEQ ID NO:149 is a portion of a wild type FEA2 nucleotide sequence shown in FIG. 4.

SEQ ID NOs:150-153 are portions of edited FEA2 nucleotide sequences shown in FIG. 4.

SEQ ID NO:154 is a portion of a wild type FEA2 polypeptide sequence shown in FIG. 4.

SEQ ID NOs:155-158 are portions of edited FEA2 amino acid sequences shown in FIG. 4.

SEQ ID NOs:159-186 are the polypeptides encoded by the edited FEA2 nucleic acid sequences SEQ ID NOs:83-113, respectively.

DETAILED DESCRIPTION

Figure 1:
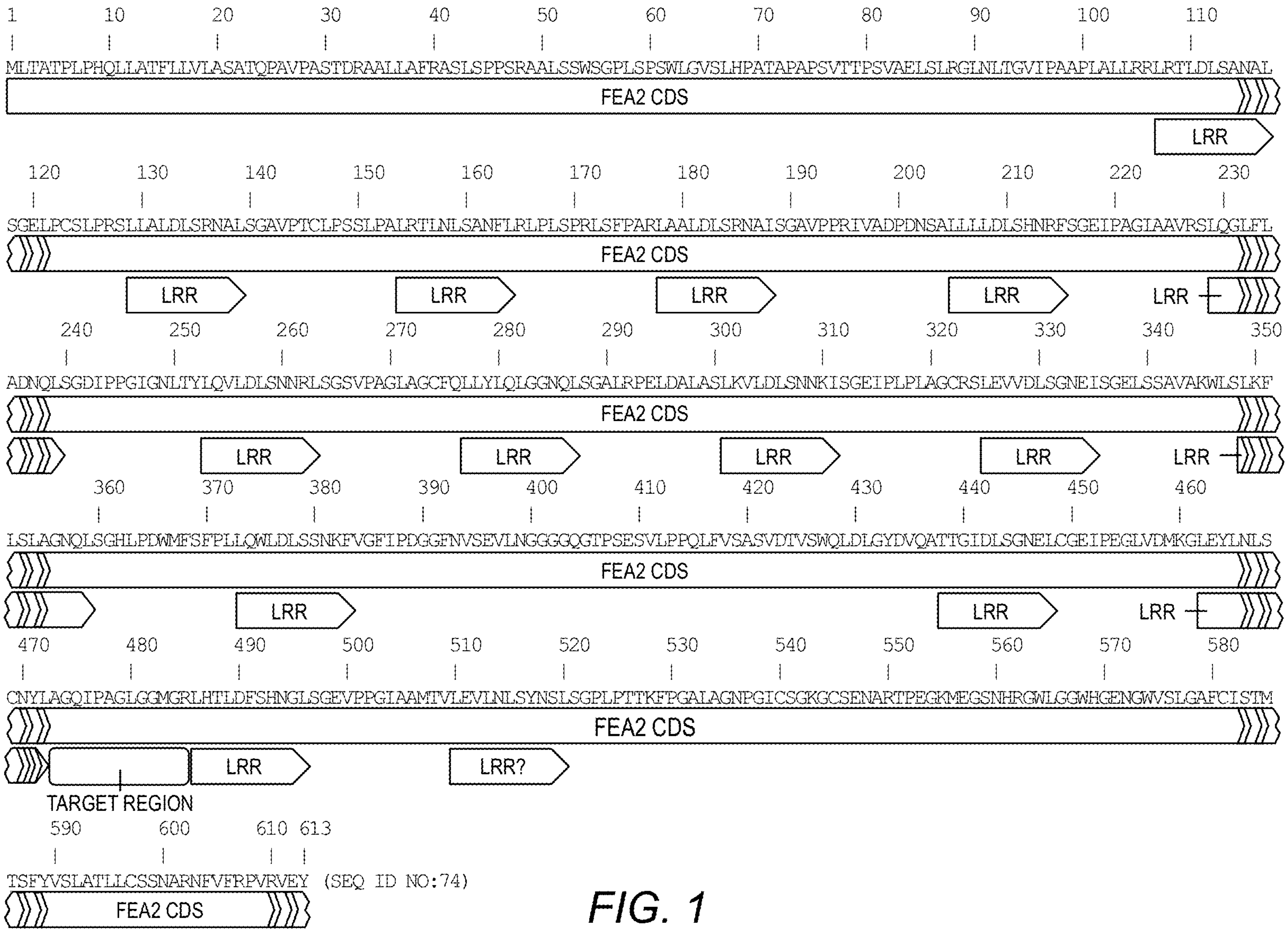
FIG. 1 provides a map of an FEA2 polypeptide showing the locations of leucine-rich repeat (LRR) domains and an example target region.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms “a,” “an” and “the” are intended to include the plural forms as well, unless the context clearly indicates otherwise.

Also as used herein, “and/or” refers to and encompasses any and all possible combinations of one or more of the associated listed items, as well as the lack of combinations when interpreted in the alternative (“or”).

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term “comprise,” “comprises” and “comprising” as used herein, specify the presence of the stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

As used herein, the terms “increase,” “increasing,” “increased,” “enhance,” “enhanced,” “enhancing,” and “enhancement” (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in an FEA2 gene as described herein can exhibit increased kernel row number (e.g., producing ears having increased kernel row number) that is at least about 5% or greater than that of a control plant not comprising the same mutation, optionally wherein the length of the ears comprising increased kernel row number is not substantially decreased (e.g., a decrease in length of less than 30% as compared to an ear of a plant not comprising the same FEA2 mutation). A control plant is typically the same plant as the edited plant but the control plant has not been similarly edited and therefore does not comprise the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type endogenous FACIATED EAR2 (FEA2) gene "is an FEA2 gene that is naturally occurring in or endogenous to the reference organism, e.g., a corn plant.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation." A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild Type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 800, 810, 820, 850, 860, 870, 880, 890, 900, 1000, 1050, 1100, 1150, 1200, 1250, 1300, 1350, 1400, 1450 1500, 1550, 1600, 1650, 1700, 1750, 1800, 1810, 1820, 1830 1840, 1841, 1842, 1843, 1844, 1845, 1850, 1900, 2000, 2100, 2200, 2300 or 2319 consecutive nucleotides or any range or value therein of a nucleic acid encoding a FEA2 polypeptide, optionally a fragment of a FEA2 gene may be about 850 to about 1000 consecutive nucleotides in length, about 750 to about 950 consecutive nucleotides in length, about 700 to about 800 consecutive nucleotides in length, about 500 to about 800 consecutive nucleotides in length, about 400 to about 600 consecutive nucleotides in length, about 300 to about 400 consecutive nucleotides in length, about 200 to about 300 consecutive nucleotides in length, about 100 to about 200 consecutive nucleotides in length, about 100 to about 150 consecutive nucleotides in length, about 50 to about 100 consecutive nucleotides in length, about 10 to about 50 consecutive nucleotides in length, or any range or value therein.

In some embodiments, a "sequence-specific nucleic acid binding domain" (e.g., sequence-specific DNA binding domain) may bind to one or more fragments or portions of nucleotide sequences encoding FEA2 polypeptides as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, 290, or more consecutive amino acids of a reference polypeptide. In some embodiments, a polypeptide fragment may comprise, consist essentially of or consist of about 10, 11, 12, 13, 14, 15, 16, 17, 18, 19, 20, 25, 30, 35, 40, 45, 50, 60, 70, 80, 90, 100, 125, 150, 175, 200, 225, 250, 275, 300, 350, 400, 450, 500, 550, or 600 consecutive amino acid residues, or any range or value therein, of a FEA2 polypeptide (e.g., a fragment or a portion of SEQ ID NO:74 (e.g., SEQ ID NO:75 or SEQ ID NO:76)). In some embodiments, a deletion may result in an in-frame deletion allele. In some embodiments, such a deletion may be dominant negative mutation, a semi-dominant mutation or a weak loss-of-function mutation, which when comprised in a plant can result in the plant exhibiting increased kernel row number (e.g., producing one or more ears exhibiting increased kernel row number) as compared to a plant not comprising said deletion, optionally wherein length of the one or more ears exhibiting increased kernel row number is not substantially decreased. In some embodiments, such a plant may also exhibit increased yield and increased disease resistance as well as larger meristems and maintenance of root meristems. In some embodiments, a deletion may be a deletion of about 3 consecutive base pairs to about 42 consecutive base pairs in length, optionally about 9 consecutive base pairs to about 33 consecutive base pairs in length (e.g., about 3 to about 11 amino acids in length). An FEA2 gene may be edited in more than one location, thereby providing an FEA2 gene comprising more than one mutation.

Figure 2:
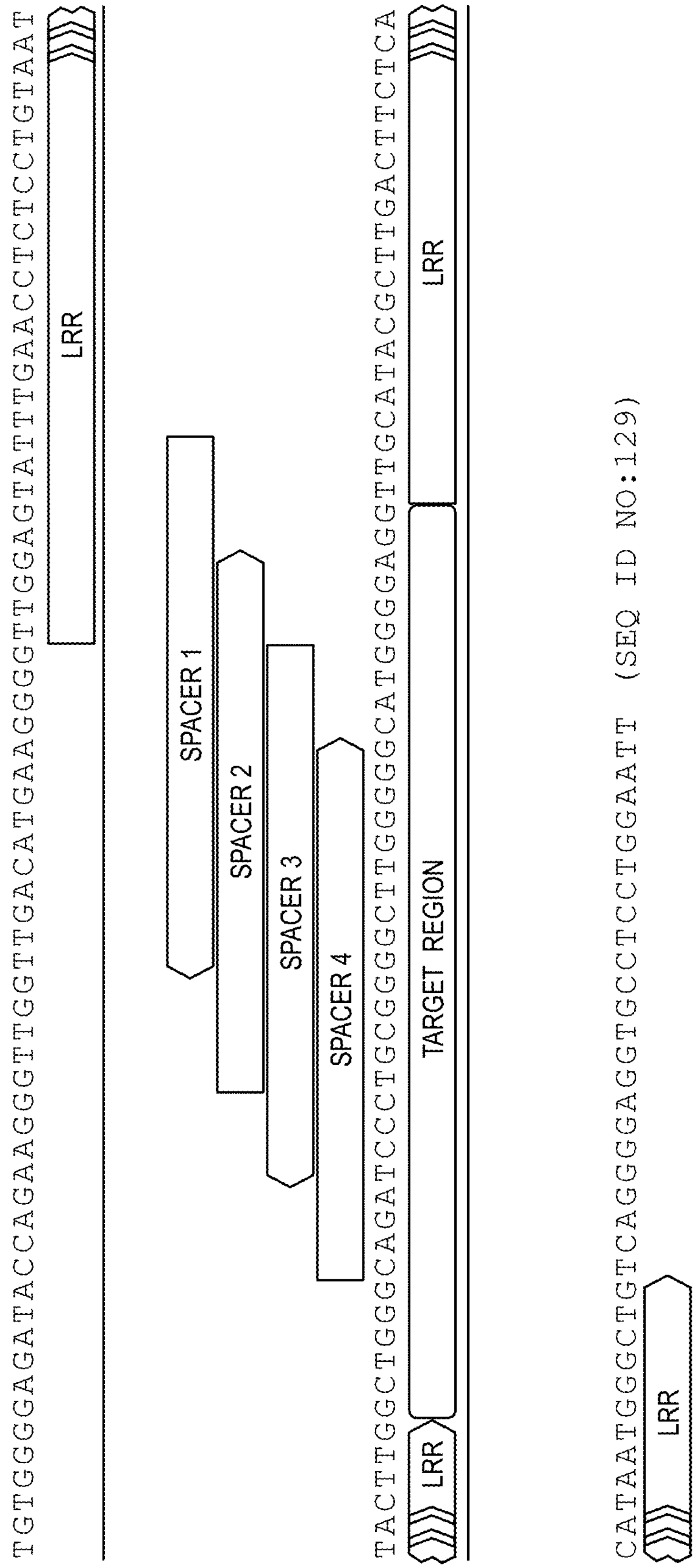
FIG. 2 provides a schematic of a region or portion of the FEA2 coding sequence (cds) (SEQ ID NO:129) showing the LRR domains and an example target regions and example spacers for editing the target region. Spacer 1 (SEQ ID NO:74), spacer 2 (SEQ ID NO:75), spacer 3 (SEQ ID NO:76), and spacer 4 (SEQ ID NO:73).
Figure 3:
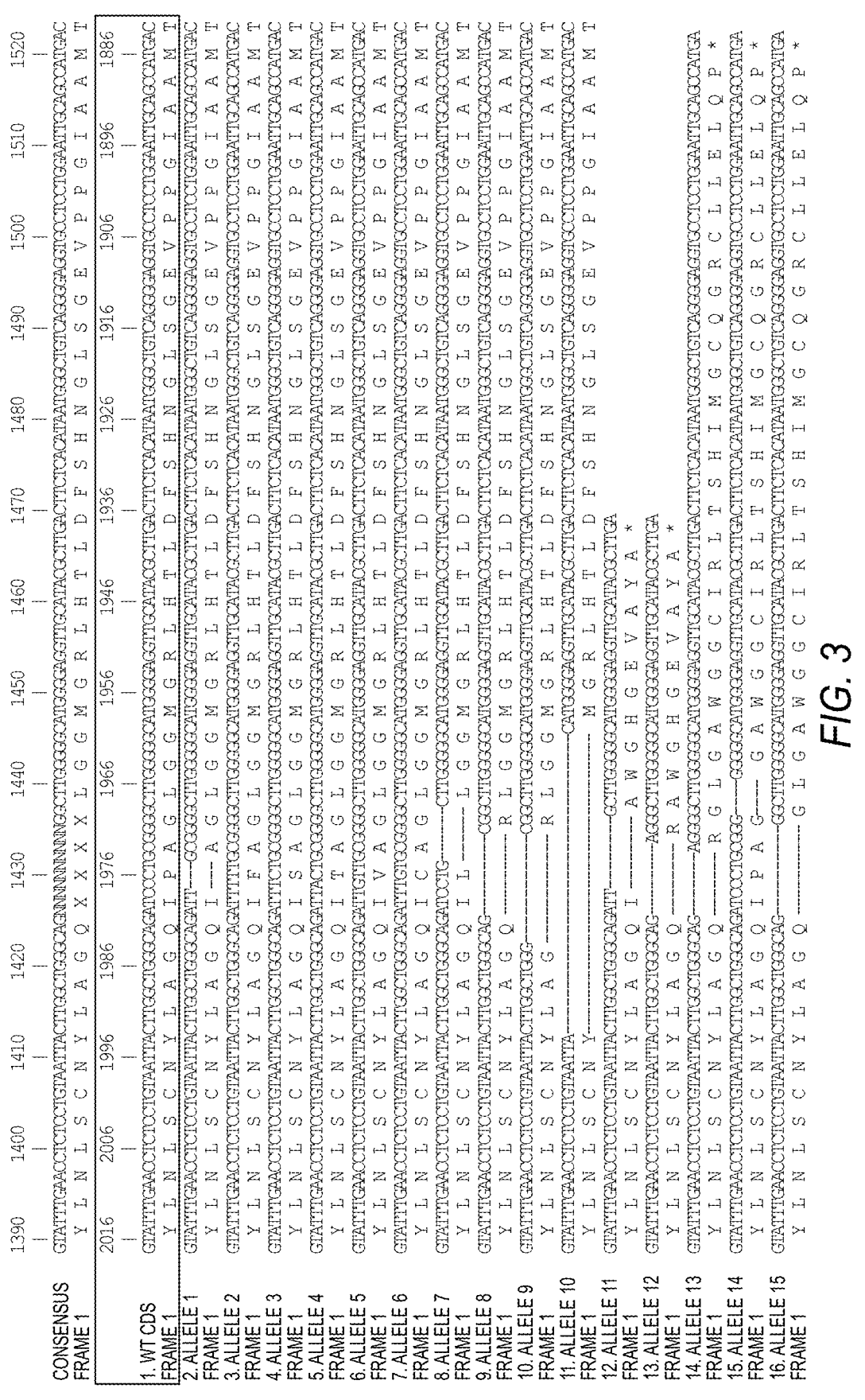
FIG. 3 provides an alignment of edited FEA2 nucleic acid and amino acid sequences (from top to bottom, FEA2 consensus sequences (SEQ ID NO:130, SEQ ID NO:131, corresponding amino acid sequences SEQ ID NO:132 and SEQ ID NO:133, respectively), SEQ ID NO:114 (corresponding amino acid sequence SEQ ID NO:134), SEQ ID NO:115 (corresponding amino acid sequence SEQ ID NO:135), SEQ ID NO:116 (corresponding amino acid sequence SEQ ID NO:136), SEQ ID NO:117 (corresponding amino acid sequence SEQ ID NO:137), SEQ ID NO:118 (corresponding amino acid sequence SEQ ID NO:138), SEQ ID NO:119 (corresponding amino acid sequence SEQ ID NO:139), SEQ ID NO:120 (corresponding amino acid sequence SEQ ID NO:140), SEQ ID NO:121 (corresponding amino acid sequence SEQ ID NO:141), SEQ ID NO:122 (corresponding amino acid sequence SEQ ID NO:142), SEQ ID NO:123 (corresponding amino acid sequence SEQ ID NO:143), SEQ ID NO:124 (corresponding amino acid sequence SEQ ID NO:144), SEQ ID NO:125 (corresponding amino acid sequence SEQ ID NO:145), SEQ ID NO:126 (corresponding amino acid sequence SEQ ID NO:146), SEQ ID NO:127 (corresponding amino acid sequence SEQ ID NO:147), and SEQ ID NO:128 (corresponding amino acid sequence SEQ ID NO:148).
Figure 4:
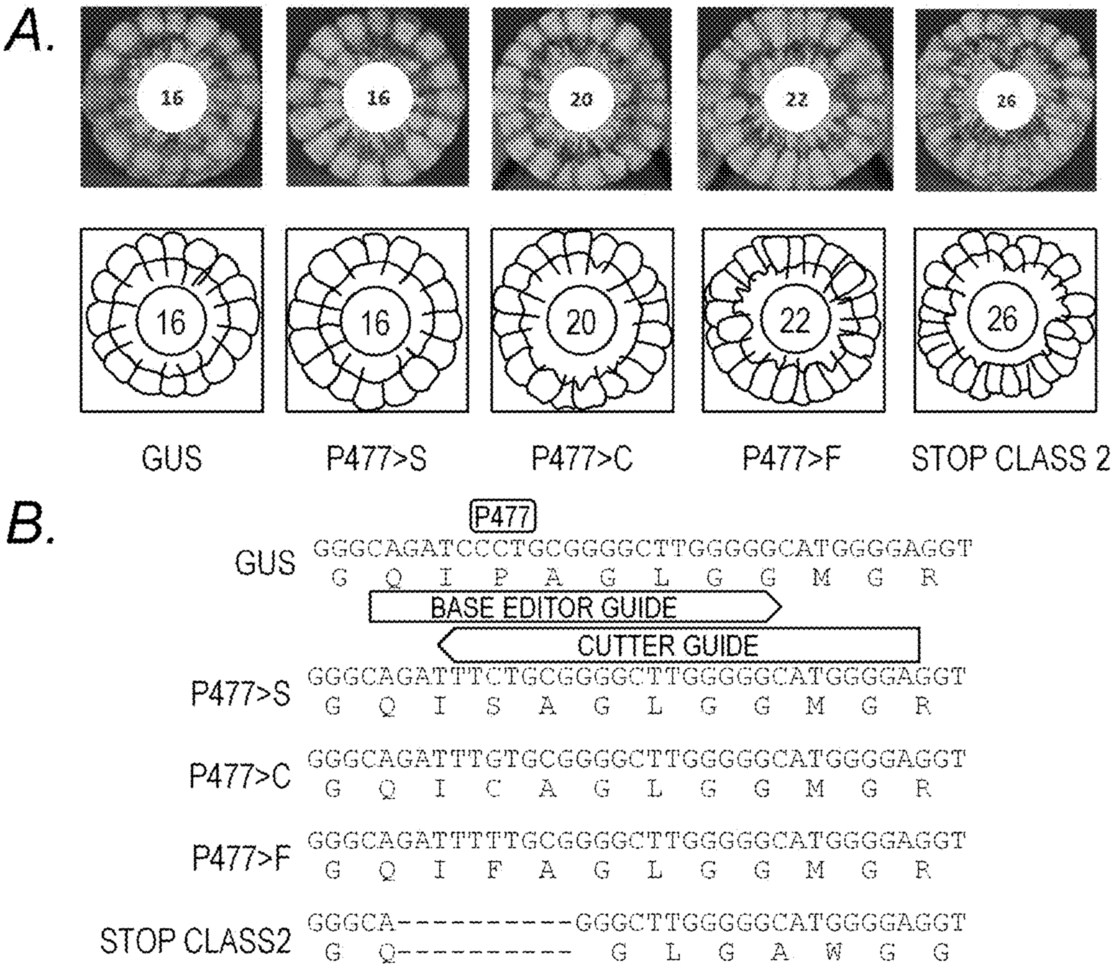
FIG. 4 shows the results of modifying a target region of an endogenous FEA2 to generate multiple alleles. Panel A shows the impact on kernel row number (KRN) with a photograph of cross sections of corn cobs from plants comprising the edited alleles and a graphical depiction of the same below. Panel B shows the region of the endogenous FEA2 gene that is edited and the specific edits generated (from top to bottom portion of endogenous WT FEA2 gene (GUS control) (SEQ ID NO:149, and corresponding amino acid sequence SEQ ID NO:154), P477>S, (SEQ ID NO:150, and corresponding amino acid sequence SEQ ID NO:155), P477>C (SEQ ID NO:151, and corresponding amino acid sequence SEQ ID NO:156), P477>F (SEQ ID NO:152, and corresponding amino acid sequence SEQ ID NO:157), Stop Class2 (SEQ ID NO:153, and corresponding amino acid sequence SEQ ID NO:158)). Panel C provides a bar graph for average kernel row number (KRN) and for average ear length (cm) for each of the edited alleles.
Figure 4:
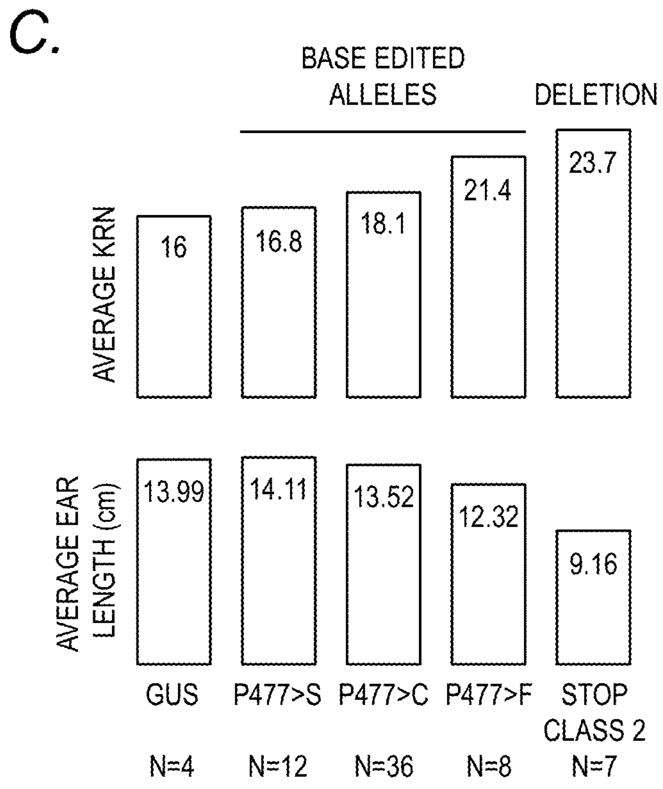

In some embodiments, a "portion" or "region" in reference to a nucleic acid means at least 2,4, 5,6,7, 8,9, 10, 11, 12, 13, 14, 15, 16, 17, 18, 19,20,21,22,23,24,25,26,27,28, 29,30,31,32,33,34,35,36,37,38,39,40,41,42,43,44,45,46,47, 48,49,50,51,52,53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more consecutive nucleotides from a gene (e.g., a FEA2 gene). In some embodiments, a portion of a FEA2 gene may be about 35, 36, 37, 38, 39, 40, 41, 42, 43, 45, 46, 47, 48, 49, 50, 51, 52, 53, 54, 55, 56, 57, 58, 59, 60, 61, 62, 63 or more consecutive nucleotides (e.g., nucleotide 1500-1538 from SEQ ID NO:72 or nucleotide 1417-1455 from SEQ ID NO:73; e.g., SEQ ID NO:77; or nucleotide 1488-1550 from SEQ ID NO:72 or nucleotide 1405-1467 from SEQ ID NO:73, e.g., SEQ ID NO:78). In some embodiments, a "portion" or "region" in reference to a polypeptide means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more consecutive amino acid residues from a polypeptide (e.g., a FEA2 polypeptide). In some embodiments, a portion of a FEA2 polypeptide may be about 8, 9, 10, 11, 12, 13, 14, 15, 16, 17, 18, 19, 20, 21, 22, 23, 24, or 25 or more consecutive amino acid residues (e.g., amino acid residues 473-485 from SEQ ID NO:74; e.g., SEQ ID NO:75; or amino acid residues 468-489 from SEQ ID NO:74; e.g., SEQ ID NO:76). (see, e.g., FIGS. 2-4) In some embodiments, a "sequence-specific nucleic acid binding domain" may bind to one or more fragments or portions of nucleotide sequences encoding FEA2 polypeptides as described herein.

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene. Frameshift mutations in a gene can result in the production of a polypeptide that is longer, shorter or the same length as the wild type polypeptide depending on when the first stop codon occurs following the mutated region of the gene.

The terms "complementary" or "complementarity," as used herein, refer to the natural binding of polynucleotides under permissive salt and temperature conditions by base-pairing.

For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I*(Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175,200,225,250, 300, 350 or more amino acids in length or more consecutive amino acid residues). In some embodiments, two or more FEA2 polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic AcidProbes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in

*Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from Zea mays may be useful with constructs of this invention. In some embodiments, the U6c promoter and/or 7SL promoter from Zea mays may be useful for driving expression of a guide nucleic acid. In some embodiments, a U6c promoter, U6i promoter and/or 7SL promoter from Glycine max may be useful with constructs of this invention. In some embodiments, the U6c promoter, U6i promoter and/or 7SL promoter from Glycine max may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zml3 (U.S. Pat. No. 10,421,972), $PLA_2$-δ promoter from arabidopsis (U.S. Pat. No. 7,141,424), and/or the ZrC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958~2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-menthioine symihetase (SAMS) (Vander Mijnsbrugge et al. (1996) *Plant and Cell Physiology,* 37(8):1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from Arabidopsis (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid (e.g., DNA) binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, “selectable marker” means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term “vector” refers to a composition for transferring, delivering or introducing a nucleic acid (or nucleic acids) into a cell. A vector comprises a nucleic acid construct (e.g. expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, “contact,” “contacting,” “contacted,” and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, “modifying” or “modification” in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

“Introducing,” “introduce,” “introduced” (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms “transformation” or transfection” may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

“Transient transformation” in the context of a polynucleotide means that a polynucleotide is introduced into the cell and does not integrate into the genome of the cell.

By “stably introducing” or “stably introduced” in the context of a polynucleotide introduced into a cell is intended that the introduced polynucleotide is stably incorporated into the genome of the cell, and thus the cell is stably transformed with the polynucleotide.

“Stable transformation” or “stably transformed” as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention provides methods and compositions for reducing the influence of genes that normally act to restrict meristem size to generate plants with larger meristems, to maintain the root meristem, to increase kernel row number (optionally without substantially decreasing ear length (e.g., without decreasing ear length more than 30% as compared to an ear of a plant not comprising the same FEA2 mutation)) and yield, as well as to improve disease resistance.

The CLV1, CLV2, and CLV3 genes are part of several overlapping signaling pathways that utilize a similar mechanism to regulate meristem size. Plants express many CLV3-like (CLE) peptides which are sensed by many leucine-rich repeat (LRR) domains, and the downstream signaling regulates a myriad of growth processes in the plant (Fletcher, J. C., *Plants* 7: 87 (2018)). The CLV2 ortholog in maize is FACIATED EAR2 (FEA2)

Accordingly, as described herein, editing technology is used to target FEA2 genes in plants to generate plants with larger meristems, having increased kernel row number, increased yield, and improved disease resistance as well as to generate plants that maintain their root meristem. Mutations that may be useful for production of plants exhibiting increased kernel row number include, for example, substitutions, deletions and insertions. In some aspects, a mutation generated by the editing technology can be a point mutation, a dominant negative mutation, a semi-dominant mutation, or a weak loss-of-function mutation.

In some embodiments, the invention provides a plant or plant part thereof, the plant or plant part comprising at least one non-natural mutation (e.g., 1, 2, 3, 4, 5, or more mutations) in an endogenous FACIATED EAR2 (FEA2) gene that encodes a FEA2 protein. In some embodiments, the at least one non-natural mutation results in a dominant negative mutation, a semi-dominant mutation, and/or a weak loss-of-function mutation.

In some embodiments, a plant cell is provided, the plant cell comprising an editing system comprising: (a) a CRISPR-Cas effector protein; and (b) a guide nucleic acid (gRNA, gDNA, crRNA, crDNA, sgRNA, sgDNA) comprising a spacer sequence with complementarity to an endogenous target gene encoding a FEA2 protein. The editing system may be used to generate a mutation in the endogenous target gene encoding an FEA2protein. In some embodiments, the mutation is a non-natural mutation. In some embodiments, a guide nucleic acid of an editing system may comprise the nucleotide sequence (a spacer sequence) of any one of SEQ ID NOs:79-82 (e.g., SEQ ID NO:79, 80, 81, 82).

The mutation in a FEA2 gene of the plant, plant part thereof or the plant cell may be any type of mutation, including a base substitution, a deletion and/or an insertion. In some embodiments, a non-natural mutation may comprise a base substitution to an A, a T, a G, or a C. In some embodiments, the at least one non-natural mutation may be a base substitution to from a C to a T (C>T). In some embodiments, a non-natural mutation may be a deletion of at least one base pair (e.g., 1 base pair to about 50 base pairs) or an insertion of at least one base pair (e.g., 1 base pair to about 50 base pairs). In some embodiments, a deletion may comprise 1 base pair to about 10 consecutive base pairs (e.g., 1, 2 bp to about 3, 4, 5, 6, 7, 8, 9, or 10 bp; e.g., 1, 2, 3, 4, 5, 6, 7, 8, 9, 10 consecutive base pairs), 1 base pair to about 20 consecutive base pairs (e.g., 1, 2, 3, 4, 56, 7, 8, 9, 101, 12, 13, 14, 15, 16, 17, 18, 19, or 20 consecutive base pairs; e.g., 1, 2 3, 4, 5, 6 bp to about 7, 8, 9, 10, 11, 12, 13, 14, 15, 16, 17, 18, 19, or 20 consecutive base pairs), 1 base pair to about 30 consecutive base pairs, 1 base pair to about 40 consecutive base pairs, 1 base pair to about 50 consecutive base pairs (e.g., 1, 2, 4, 5, 6, 7, 8,9, 10, 11, 12, 13, 14, 15, 16, 17, 18, 19,20,21,22,23,24,25 consecutive base pairs to about 26, 27, 28, 29, 30, 31, 32, 33, 34, 35, 36, 37, 38, 39, 40, 41, 42, 43, 44, 45, 46, 47, 48, 49, 50 consecutive base pairs, or more, or any value or range therein of an FEA2 gene. In some embodiments, a deletion is an in-frame deletion.

An endogenous FEA2 gene useful with this invention may (a) encode a sequence having at least 95% sequence identity to the amino acid sequence of SEQ ID NO:74; (b) comprise a sequence having at least 90% sequence identity to the nucleotide sequence of SEQ ID NO:72 or SEQ ID NO:73; (c) comprise a sequence having at least 90% sequence identity to the nucleotide sequence of SEQ ID NO:77 or SEQ ID NO:78; and/or (d) encode a sequence having at least 90% sequence identity to the amino acid sequence of SEQ ID NO:75 or SEQ ID NO:76. An exemplary non-natural mutation in an FEA2 gene may result in a mutated FEA2 gene. An exemplary non-natural mutation in an endogenous FEA2 gene may encode an FEA2 protein. In some embodiments, a mutated FEA2 gene comprises at least about 90% sequence identity to any one of the nucleic acid sequences of SEQ ID NOs:83-113 or encodes a polypeptide having at least 90% sequence identity to any one of the amino acid sequences of SEQ ID NOs:159-186. In some embodiments, a mutated FEA2 gene comprises a portion or region having at least about 90% sequence identity to any one of the nucleic acid sequences of SEQ ID NOs:114-128 or a portion or region encoding a sequence having at least about 90% sequence identity to any one of SEQ ID NOs: 134-148.

In some embodiments, a plant comprising at least one mutation (e.g., non-natural mutation) in an endogenous FEA2 gene exhibits increased maintenance of meristems and/or increased kernel row number as compared to a plant without the at least one mutation (e.g., non-natural mutation), optionally without substantially decreasing ear length (e.g., a decrease of less than 30%). In some embodiments, the plant comprising at least one mutation in an endogenous FEA2 gene is a corn plant which exhibits increased kernel row number. In some embodiments, the plant comprising at least one mutation in an endogenous FEA2 gene is a corn plant which exhibits increased yield as well as increased disease resistance. In some embodiments, a plant (e.g., a corn plant) may be regenerated from a plant part and/or plant cell of the invention, wherein the regenerated plant (e.g., regenerated corn plant) comprises the mutation in the endogenous FEA2 gene and a phenotype of increased kernel row number as compared to a plant (e.g., a corn plant) not comprising the mutation, optionally wherein the length of the ear(s) having an increased kernel row number is not substantially decreased (e.g., exhibits a decrease in ear length of no more than 30% as compared to an ear of a plant not comprising the same FEA2 mutation).

In some embodiments, a corn plant cell is provided, the corn plant cell comprising at least one non-natural mutation within a FEA2 gene, wherein the mutation is a substitution, an insertion or a deletion that is introduced using an editing system that comprises a nucleic acid binding domain that binds to a target site in the FEA2 gene. In some embodiments, the substitution, insertion or a deletion within a FEA2 gene results in a dominant negative allele, a semi-dominant allele or a weak loss-of-function allele. In some embodiments, a deletion results in an in-frame deletion allele. In some embodiments, the target site is within a region of the FEA2 gene, the region comprising a sequence having at least 90% sequence identity (e.g., about 90, 91, 92, 93, 94, 95, 96, 97, 98, 99, 99.5, 99.6, 99.7, 99.8, 99.9, or 100% sequence identity) to the nucleotide sequence of SEQ ID NO:77 or SEQ ID NO:78 and/or encoding a sequence having at least 95% sequence identity (e.g., about 95, 96, 97, 98, 99, 99.5, 99.5, 99.6, 99.7, 99.8, 99.9, or 100% sequence identity) to the amino acid sequence of SEQ ID NO:75 or SEQ ID NO:76. In some embodiments, the FEA2 gene comprises a sequence having at least 90% sequence identity to the nucleotide sequence of SEQ ID NO:72 or SEQ ID NO:73 or encodes a sequence having at least 95% sequence identity to the amino acid sequence of SEQ ID NO:74.

In some embodiments, a method of producing/breeding a transgene-free edited corn plant is provided, the method comprising: crossing a corn plant of the present invention (e.g., a corn plant comprising a mutation in a FEA2 gene and having increased kernel row number, optionally without substantially decreasing ear length (e.g., a decrease of less than 30%)) with a transgene free corn plant, thereby introducing the at least one non-natural mutation into the corn plant that is transgene-free; and selecting a progeny corn plant that comprises the at least one non-natural mutation and is transgene-free, thereby producing a transgene free edited corn plant.

Also provided herein is a method of providing a plurality of corn plants having increased kernel row number, the method comprising planting two or more corn plants of the invention (e.g., 2, 3, 4, 5, 6, 7, 8, 9, 10 or more corn plants comprising a mutation in a FEA2 polypeptide and having increased kernel row number, optionally without having substantially decreased ear length (e.g., a decrease of less than 30%)) in a growing area (e.g., a field (e.g., a cultivated field, an agricultural field), a growth chamber, a greenhouse, a recreational area, a lawn, and/or a roadside and the like), thereby providing a plurality of corn plants having increased kernel row number as compared to a plurality of control corn plants not comprising the mutation. In some embodiments, the plurality of plants may also exhibit larger meristems, increased yield, increased disease resistance as well as maintenance of their root meristems.

The invention further provides a method of generating variation in a region of a corn FEA2 protein, comprising: introducing an editing system into a corn plant cell, wherein the editing system is targeted to a region of a corn FEA2 gene that encodes the region of the corn FEA2 protein, wherein the region comprises the amino acid sequence of SEQ ID NO:75 or SEQ ID NO:76 or the region is encoded by the nucleotide sequence of SEQ ID NO:77 or SEQ ID NO:78; and contacting the region of the corn FEA2 gene with the editing system, thereby introducing into the corn plant cell a mutation into the region of the corn FEA2 protein; and generating variation in the region of the FEA2 protein.

In some embodiments, a method for editing a specific site in the genome of a corn plant cell, the method comprising: cleaving, in a site specific manner, a target site within an endogenous FEA2 gene in the corn plant cell, the endogenous FEA2 gene comprising a sequence having at least 90% sequence identity to the nucleotide sequence of SEQ ID NO:72 or SEQ ID NO:73, or encoding a sequence having at least 95% sequence identity to the amino acid sequence of SEQ ID NO:74, thereby generating an edit in the endogenous FEA2 gene of the corn plant cell and producing a corn plant cell comprising the edit in the endogenous FEA2 gene. The endogenous FEA2 gene encodes a FEA2 protein and the edit results in variation of amino acids in the coding region of the FEA2 protein. In some embodiments, the edit results in a non-naturally occurring mutation, including but not limited to a deletion, substitution, or insertion, wherein the edit may result in a dominant negative mutation, a semi-dominant mutation or a weak loss-of-function mutation. In some embodiments, the non-naturally occurring mutation is a deletion, optionally wherein the deletion comprises at least 1 bp to about 50 bp of the FEA2 gene. In some embodiments, the deletion may result in an edited FEA2 nucleic acid having at least 90% sequence identity to any one of SEQ ID NOs:83-91, SEQ ID NOs:92-98 or SEQ ID NOs: 99-113. In some embodiments, a deletion results in an in-frame deletion allele, optionally wherein the in-frame deletion comprises a sequence having at least 90% identity to any one of the sequences of SEQ ID NOs:91-98 or 105-108. In some embodiments, a deletion results in the generation of a premature stop codon, optionally wherein the stop codon deletion comprises a sequence having at least 90% identity to any one of the sequences of SEQ ID NOs:83-91, 99, or 109-113. In some embodiments, the non-naturally occurring mutation is a substitution, optionally wherein the substitution comprises at least 1 bp to about 5, 6, 7, 8, 9, or 10 bp of the FEA2 gene. In some embodiments, one or more substitutions results in a sequence having at least 90% identity to any one of the sequences of SEQ ID NOs:100-104. In some embodiments, the deletion and/or substitution produces variability in a region of the FEA2 polypeptide (e.g., amino acid residues 461-613 or 473-485, e.g., amino acid residue 461, 462, 463, 464, 465, 466, 467, 468, 469, 470, 471, 472, 473, 474, 475, 476, 477, 478, 479, 480, 481, 482, 483, 484, 485, 486, 487, 488, 489, or 490 or more amino acid residues) of SEQ ID NO:74. In some embodiments, the endogenous FEA2 gene encodes an FEA2 protein and the edit results in variation in the amino acid residues located at positions 475, 476, 477, 478 or 479 with reference to amino acid position numbering of SEQ ID NO:74.

In some embodiments, a method of editing may further comprise regenerating a corn plant from the corn plant cell comprising the edit in the endogenous FEA2 gene, thereby producing a corn plant comprising the edit in its endogenous FEA2 gene and having a phenotype of increased kernel row number (e.g., producing one or more ears having an increased kernel row number) when compared to a control corn plant that does not comprise the edit, optionally wherein the length of the one or more ears having an increased kernel row number is not substantially decreased.

In some embodiments, a method for making a corn plant, comprising: (a) contacting a population of corn plant cells comprising a wild-type endogenous FEA2 gene with a nuclease linked to a nucleic acid binding domain (e.g., DNA binding domain, e.g., editing system) that binds to a sequence having at least 90% sequence identity to the nucleotide sequence of SEQ ID NO:77 or SEQ ID NO:78 or to a sequence encoding an amino acid sequence having at least 90% sequence identity to SEQ ID NO:75 or SEQ ID NO:76; (b) selecting a corn plant cell from the population in which at least one wild-type endogenous FEA2 gene has been mutated; and (c) growing the selected plant cell into a corn plant.

In some embodiments, a method increasing kernel row number, optionally without decreasing ear length, in a corn plant, comprising (a) contacting a corn plant cell comprising a wild type endogenous FEA2 gene with a nuclease targeting the wild type endogenous FEA2 gene, wherein the nuclease is linked to a nucleic acid binding domain (e.g., editing system) that binds to a target site in the wild type endogenous FEA2 gene, wherein the wild type endogenous FEA2 gene: (i) encodes a sequence having at least 95% sequence identity to the amino acid sequence of SEQ ID NO:74; (ii) comprises a sequence having at least 90% sequence identity to the nucleotide sequence of SEQ ID NO:72 or SEQ ID NO:73; (iii) comprises a sequence having at least 90% sequence identity to the nucleotide sequence of SEQ ID NO:77 or SEQ ID NO:78; and/or (iv) encodes a sequence having at least 90% sequence identity to the amino acid sequence of SEQ ID NO:75 or SEQ ID NO:76 to produce a corn plant cell comprising a mutation in the wild type endogenous FEA2 gene, thereby producing the corn plant comprising at least one cell having a mutation in the endogenous FEA2 gene; and (b) growing the corn plant cell into a corn plant comprising the mutation in the wild type endogenous FEA2 gene, thereby producing a corn plant have a mutated endogenous FEA2 gene and an increased kernel row number, optionally wherein ear length is not substantially decreased (e.g., a decrease of less than 30%).

In some embodiments, a method for producing a corn plant or part thereof comprising at least one cell having a mutated endogenous FEA2 gene, the method comprising contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene (a) encodes a sequence having at least 95% sequence identity to the amino acid sequence of SEQ ID NO:74; (b) comprises a sequence having at least 90% sequence identity to the nucleotide sequence of SEQ ID NO:72 or SEQ ID NO:73; (c) comprises a sequence having at least 90% sequence identity to the nucleotide sequence of SEQ ID NO:77 or SEQ ID NO:78; and/or (d) encodes a sequence having at least 90% sequence identity to the amino acid sequence of SEQ ID NO:75 or SEQ ID NO:76 to produce a plant cell comprising a mutation in the wild type endogenous FEA2 gene, thereby producing the corn plant or part thereof comprising at least one cell having a mutation in the endogenous FEA2 gene.

Also provided herein is a method for producing a corn plant or part thereof comprising a mutated endogenous FEA2 gene and exhibiting increased kernel row number increased yield, and improved disease resistance as well as larger meristems and root meristems that are maintained, the method comprising contacting a target site in an endogenous FEA2 gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene: (a) encodes a sequence having at least 95% sequence identity to the amino acid sequence of SEQ ID NO:74; (b) comprises a sequence having at least 90% sequence identity to the nucleotide sequence of SEQ ID NO:72 or SEQ ID NO:73; (c) comprises a sequence having at least 90% sequence identity to the nucleotide sequence of SEQ ID NO:77 or SEQ ID NO:78; and/or (d) encodes a sequence having at least 90% sequence identity to the amino acid sequence of SEQ ID NO:75 or SEQ ID NO:76, thereby producing the corn plant or part thereof comprising an endogenous FEA2 gene having a mutation and exhibiting increased kernel row number (e.g., producing one or more ears having an increased kernel row number), optionally wherein the length of the one or more ears having an increased kernel row number is not substantially decreased (e.g., a decrease of less than 30%).

In some embodiments, a corn plant or part thereof comprising at least one cell having a mutation in the endogenous FEA2 gene as described herein, comprises a sequence having at least 90% identity to any one of the sequences of SEQ ID NOs:83-98.

In some embodiments, a nuclease may cleave an endogenous FEA2 gene, thereby introducing a mutation into the endogenous FEA2 gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain (e.g., DNA binding domain, RNA binding domain) useful with the invention may be any nucleic acid binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a method of editing an endogenous FEA2 gene in a corn plant or plant part is provided, the method comprising contacting a target site in an FEA2 gene in the corn plant or plant part with a cytosine base editing system comprising a cytosine deaminase and a nucleic acid binding domain that binds to a target site in the FEA2 gene, the FEA2 gene (a) encoding a sequence having at least 95% sequence identity to the amino acid sequence of SEQ ID NO:74; (b) comprising a sequence having at least 90% sequence identity to the nucleotide sequence of SEQ ID NO:72 or SEQ ID NO:73; (c) comprising a sequence having at least 90% sequence identity to the nucleotide sequence of SEQ ID NO:77 or SEQ ID NO:78; and/or (d) encoding a sequence having at least 90% sequence identity to the amino acid sequence of SEQ ID NO:75 or SEQ ID NO:76, thereby editing the endogenous FEA2 gene in the corn plant or part thereof and producing a corn plant or part thereof comprising at least one cell having a mutation in the endogenous FEA2 gene.

In some embodiments, a method of editing an endogenous FEA2 gene in a corn plant or plant part is provided, the method comprising contacting a target site in an FEA2 gene in the corn plant or plant part with an adenosine base editing system comprising an adenosine deaminase and a nucleic acid binding domain that binds to a target site in the FEA2 gene, the FEA2 gene (a) encoding a sequence having at least 95% sequence identity to the amino acid sequence of SEQ ID NO:74; (b) comprising a sequence having at least 90% sequence identity to the nucleotide sequence of SEQ ID NO:72 or SEQ ID NO:73; (c) comprising a sequence having at least 90% sequence identity to the nucleotide sequence of SEQ ID NO:77 or SEQ ID NO:78; and/or (d) encoding a sequence having at least 90% sequence identity to the amino acid sequence of SEQ ID NO:75 or SEQ ID NO:76, thereby editing the endogenous FEA2 gene in the corn plant or part thereof and producing a plant or part thereof comprising at least one cell having a mutation in the endogenous FEA2 gene.

In some embodiments, a mutation in an edited endogenous FEA2 gene as described herein produces a sequence having at least 90% identity to any one of the sequences of SEQ ID NOs:83-98.

In some embodiments, a method of detecting a mutant FEA2 gene (a mutation in an endogenous FEA2 gene) is provide, the method comprising detecting in the genome of a plant a deletion in a nucleic acid encoding the amino acid sequence of SEQ ID NO:74, wherein the amino acid sequence of SEQ ID NO:74 comprises a mutation in one or more amino acid residue(s) located at positions 475, 476, 477, 478 or 479 with reference to amino acid position numbering of SEQ ID NO:74, optionally wherein the at least one mutation is in the amino acid residue at position 477 with reference to amino acid position numbering of SEQ ID NO:74. In some embodiments, the mutation is the result of a nucleotide substitution of C>T.

In some embodiments, the present invention provides a method of detecting a mutation in an endogenous FEA2 gene, comprising detecting in the genome of a plant a mutated FEA2 gene. In some embodiments, the mutated FEA2 gene comprises a sequence having at least 90% sequence identity to the nucleotide sequence of any one of SEQ ID NOs:83-113 or encodes a polypeptide having at least 90% sequence identity to any one of the amino acid sequences of SEQ ID NOs:159-186. In some embodiments, a mutated FEA2 gene comprises a portion or region having at least about 90% sequence identity to any one of the nucleic acid sequences of SEQ ID NOs:114-128 or a portion or region encodes a sequence having at least about 90% sequence identity to any one of SEQ ID NOs:134-148.

In some embodiments, the present invention provides a method of producing a plant comprising a mutation in an endogenous FEA2 gene and at least one polynucleotide of interest, the method comprising crossing a plant of the invention comprising at least one mutation in an endogenous FEA2 gene (a first plant) with a second plant that comprises the at least one polynucleotide of interest to produce progeny plants; and selecting progeny plants comprising at least one mutation in the FEA2 gene and the at least one polynucleotide of interest, thereby producing the plant comprising a mutation in an endogenous FEA2 gene and at least one polynucleotide of interest.

The present invention further provides a method of producing a plant comprising a mutation in an endogenous FEA2 gene and at least one polynucleotide of interest, the method comprising introducing at least one polynucleotide of interest into a plant of the present invention comprising at least one mutation in a FEA2 gene, thereby producing a plant comprising at least one mutation in a FEA2 gene and at least one polynucleotide of interest. In some embodiments, the plant is a corn plant.

In some embodiments, the present invention provides a method of producing a plant comprising a mutation in an endogenous FEA2 gene and at least one polynucleotide of interest, the method comprising introducing at least one polynucleotide of interest into a plant of the invention comprising at least one mutation in an endogenous FEA2 gene, thereby producing a plant comprising at least one mutation in a FEA2 gene and at least one polynucleotide of interest. In some embodiments, the plant is a corn plant.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

An FEA2 useful with this invention includes any FEA2 in which a mutation as described herein can confer increased kernel row number in a plant or part thereof comprising the mutation. In some embodiments, an FEA2 polypeptide comprises an amino acid sequence having at least 95% identity (e.g., about 95, 96, 97, 98, 99, 99.5, 100% sequence identity) to SEQ ID NO:74 or comprising the amino acid sequence of SEQ ID NO:75 or SEQ ID NO:77 (e.g., the FEA2 polypeptide comprises a domain comprising the sequence of AGQIPAGLGGMGR (SEQ ID NO:75) within the FEA2 polypeptide or comprising the sequence of CNYLAGQIPAGLGGMGRLHTL (SEQ ID NO:76) within the FEA2 polypeptide). In some embodiments, a FEA2 gene may comprise a sequence having at least about 90% sequence identity (e.g., about 90, 91, 92, 93, 94, 95, 96, 97, 98, 99, 99.5, 100% sequence identity) to the nucleotide sequence of SEQ ID NO:72 or SEQ ID NO:73, or the FEA2 gene comprises within it a sequence having at least 90% identity (e.g., about 90, 91, 92, 93, 94, 95, 96, 97, 98, 99, 99.5, 100% sequence identity) to any one of the nucleotide sequences of SEQ ID NO:77 or SEQ ID NO:78.

In some embodiments, the at least one non-natural mutation in an endogenous FEA2 gene in a corn plant may be a substitution, a deletion and/or an insertion. In some embodiments, the at least one non-natural mutation in an endogenous FEA2 gene in a corn plant may be a substitution, a deletion and/or an insertion that results in a dominant negative mutation, a semi-dominant mutation or a weak loss-of-function mutation and a plant having the phenotype of increased kernel row number (e.g., a phenotype of producing ears having increased kernel row number) as compared to a control corn plant not comprising the edit/mutation, optionally wherein the ears having increased kernel row number do not have a substantially decreased length (e.g., a decrease of less than 30% as compared to a plant not comprising the same FEA2 mutation). For example, the mutation may be a substitution, a deletion and/or an insertion of one or more amino acid residues (e.g., 1, 2, 3, 4, 5, 6, 7, 8, 9, 10 or more amino acids of the FEA2 polypeptide) or the mutation may be a substitution, a deletion and/or an insertion of at least 1 nucleotide to about 50 consecutive nucleotides (e.g., about 1,2,3,4, 5,6,7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleotides, or any range or value therein) (e.g., a base substitution, deletion and/or insertion) from the gene encoding the FEA2 polypeptide. In some embodiments, a deletion results in an in-frame deletion allele. In some embodiments, the at least one non-natural mutation may be a base substitution to an A, a T, a G, or a C. In some embodiments, the at least one non-natural mutation may be a base substitution to from a C to a T (C>T), a C to an A (C>A) or a C to a G (C>G).

In some embodiments, a mutation in an endogenous FEA2 gene may be made following cleavage by an editing system that comprises a nuclease and a nucleic acid binding domain that binds to a target site within a target nucleic acid (e.g., a FEA2 gene) comprising the nucleotide sequence of SEQ ID NO:72 or SEQ ID NO:73 or a nucleotide sequence having at least 90% identity to any one of the nucleotide sequences of SEQ ID NOs:77-78, or a target nucleic acid (e.g., a FEA2 gene) encoding a polypeptide comprising a sequence having at least 95% sequence identity to the amino acid sequence of SEQ ID NO:74 or any one of the amino acid sequences of SEQ ID NOs:75-76. In some embodiments, the nuclease cleaves the endogenous FEA2 gene and a mutation is introduced into the endogenous FEA2 gene. In some embodiments, the cleavage results in a mutation in an endogenous FEA2 gene comprising a sequence having at least 90% identity to any one of the sequences of SEQ ID NOs:83-98.

Further provided herein are guide nucleic acids (e.g., gRNA, gDNA, crRNA, crDNA) that bind to a target site in FEA2 gene, wherein the endogenous FEA2 gene: (a) encodes a sequence having at least 95% sequence identity to the amino acid sequence of SEQ ID NO:74; (b) comprises a sequence having at least 90% sequence identity to the nucleotide sequence of SEQ ID NO:72 or SEQ ID NO:73; and/or (c) comprises a sequence having at least 90% identity to any one of the nucleotide sequences of SEQ ID NO:77-78. In some embodiments, a guide nucleic acid comprises a spacer having the nucleotide sequence of any one of SEQ ID NOs:75-76.

In some embodiments, a guide nucleic acid is provided that binds to a target nucleic acid in a FACIATED EAR2 (FEA2) gene in a corn plant, wherein the target nucleic acid is located in a chromosome interval defined by and including base pair (bp) position 136,766,300 to base pair position 136,766,251 on chromosome 4. With regard to corn (Zea mays), markers of the present invention are described herein with respect to the positions of marker loci in the B73 corn genome, version 4, “B73 RefGen_v4” (assembly aka B73 RefGen_v4, AGPv4) at the MaizeGDB internet resource (maizegdb.org/assembly). In some embodiments, the invention provides a guide nucleic acid that binds to a target nucleic acid in a FACIATED EAR2 (FEA2) gene having the gene identification number (gene ID) of Zm00001d051012 (reference B73 corn genome).

In some embodiments, a system is provided comprising a guide nucleic acid comprising a spacer having the nucleotide sequence of any one of SEQ ID NOs:79-82 and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

The invention further provides a gene editing system comprising a CRISPR-Cas effector protein in association with a guide nucleic acid and the guide nucleic acid comprises a spacer sequence that binds to a FEA2 gene, the FEA2 gene (a) encoding a sequence having at least 95% sequence identity to the amino acid sequence of SEQ ID NO:74; (b) comprising a sequence having at least 90% sequence identity to the nucleotide sequence of SEQ ID NO:72 or SEQ ID NO:73; (c) comprising a sequence having at least 90% sequence identity to the nucleotide sequence of SEQ ID NO:77 or SEQ ID NO:78; and/or (d) encoding a sequence having at least 90% sequence identity to the amino acid sequence of SEQ ID NO:75 or SEQ ID NO:76. In some embodiments, a spacer sequence of the guide nucleic acid may comprise the nucleotide sequence of any one of SEQ ID NOs:79-82. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked. As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The present invention further provides a complex comprising a guide nucleic acid and a CRISPR-Cas effector protein comprising a cleavage domain, wherein the guide nucleic acid binds to a target site in an endogenous FEA2 gene, wherein the endogenous FEA2 gene, wherein the endogenous FEA2 gene: (a) encodes a sequence having at least 95% sequence identity to the amino acid sequence of SEQ ID NO:74; (b) comprises a sequence having at least 90% sequence identity to the nucleotide sequence of SEQ ID NO:72 or SEQ ID NO:73; (c) comprises a sequence having at least 90% sequence identity to the nucleotide sequence of SEQ ID NO:77 or SEQ ID NO:78; and/or (d) encodes a sequence having at least 90% sequence identity to the amino acid sequence of SEQ ID NO:75 or SEQ ID NO:76, wherein the cleavage domain cleaves a target strand in the FEA2 gene. In some embodiments, the cleavage domain cleaves a target strand in the FEA2 gene such that it results in a mutation in an endogenous FEA2 gene comprising a sequence having at least 90% identity to any one of the sequences of SEQ ID NOs:83-98.

In some embodiments, expression cassettes are provided that comprise (a) a polynucleotide encoding CRISPR-Cas effector protein comprising a cleavage domain and (b) a guide nucleic acid that binds to a target site in an endogenous FEA2 gene, wherein the guide nucleic acid comprises a spacer sequence that is complementary to and binds to (i) a portion of a nucleic acid encoding an amino acid sequence having at least 95% sequence identity the amino acid sequence of SEQ ID NO:74; (ii) a portion of a sequence having at least 90% sequence identity to the nucleotide sequence of SEQ ID NO:72 or SEQ ID NO:73; (iii) a portion of a sequence having at least 90% sequence identity to any one of the nucleotide sequences of SEQ ID NO:77 or SEQ ID NO:78; and/or (iv) a sequence having at least 90% sequence identity to a sequence encoding the amino acid sequence of SEQ ID NO:75 or SEQ ID NO:76.

Also provided herein are nucleic acids encoding a mutated FEA2 gene that when present in a corn plant or plant part results in the corn plant comprising a phenotype of increased kernel row number (e.g., a phenotype of producing ears having increased kernel row number) as compared to a control corn plant not comprising the FEA2 mutation, optionally wherein the ears having increased kernel row number do not have a substantially decreased length (e.g., a decrease in length of less than 30% as compared to an ear of a plant not comprising the same FEA2 mutation). In some embodiments, a mutated FEA2 gene may comprise a sequence having at least 90% sequence identity to the nucleotide sequence of any one of SEQ ID NOs:83-113 or encodes a polypeptide having at least 90% sequence identity to any one of the amino acid sequences of SEQ ID NOs: 159-186. In some embodiments, a mutated FEA2 gene comprises a portion or region having at least about 90% sequence identity to any one of the nucleic acid sequences of SEQ ID NOs:114-128 or a portion or region encodes a sequence having at least about 90% sequence identity to any one of SEQ ID NOs:134-148.

Nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous FEA2 genes) and/or their expression. Any corn plant comprising an endogenous FEA2 gene that is capable of conferring increased kernel row number when modified as described herein may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to increase kernel row number in the corn plant. A plant exhibiting increased kernel row number (e.g., a corn plant) may have an increase in kernel row number by about 5% to about 500% (e.g., about 5, 6, 7, 8, 9, 10, 11, 12, 13, 14, 15, 16, 17, 18, 19, 20, 21, 22, 23,24,25,26,27,28,29,30,31,32, 33,34,35,36,37,38,39,40,41,42,43,44,45,46,47, 48, 49, or 50% or any range or value therein; e.g., about 5% to about 10%, about 5% to about 15%, about 5% to about 20%, about 10% to about 50%, about 20% to about 50%, about 30% to about 50%, and any range or value therein) (e.g., about 1, 2, 3, 4, 5, 6, 7, 8, 9, 10, 11, 12, 13, 14, or 15 more rows) as compared to a plant or part thereof that does not comprise the mutated endogenous FEA2 gene. In some embodiments, plants exhibiting increased kernel row number as described herein (e.g., a plant that produces ears having increased kernel row number) produce ears that are also not substantially decreased in length. As used herein, an ear of a plant comprising a mutation as described herein that is "not substantially decreased in length" has a length that is reduced by less than 30% (e.g., reduced by 0% or reduced by about 1,2,3,4, 5,6,7, 8,9, 10, 11, 12, 13, 14, 15, 16, 17, 18, 19, 20, 21, 22, 23, 24, 25, 26, 27, 28, 29, 30%) as compared to a plant that does not comprise the same FEA2 mutation.

In some embodiments, a corn plant or plant part thereof is provided comprising at least one non-natural mutation in at least one endogenous FACIATED EAR2 (FEA2) gene that is located in a chromosome interval defined by and including base pair (bp) position 136,766,300 to base pair position 136,766,251 on chromosome 4. With regard to corn (Zea mays), markers of the present invention are described herein with respect to the positions of marker loci in the B73 corn genome, version 4, "B73 RefGen_v4" (assembly aka B73 RefGen_v4, AGPv4) at the MaizeGDB internet resource (maizegdb.org/assembly). In some embodiments, a corn plant or plant part thereof is provided, the corn plant or plant part thereof comprising at least one non-natural mutation in at least one endogenous FACIATED EAR2 (FEA2) gene having the gene identification number (gene ID) of Zm00001d051012 (reference B73 corn genome).

The term "plant part," as used herein, includes but is not limited to reproductive tissues (e.g., petals, sepals, stamens, pistils, receptacles, anthers, pollen, flowers, fruits, flower bud, ovules, seeds, and embryos); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term “plant part” also includes plant cells, including plant cells that are intact in plants and/or parts of plants, plant protoplasts, plant tissues, plant organs, plant cell tissue cultures, plant calli, plant clumps, and the like. As used herein, “shoot” refers to the above ground parts including the leaves and stems. As used herein, the term “tissue culture” encompasses cultures of tissue, cells, protoplasts and callus.

As used herein, “plant cell” refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. A “protoplast” is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

“Plant cell culture” means cultures of plant units such as, for example, protoplasts, cell culture cells, cells in plant tissues, pollen, pollen tubes, ovules, embryo sacs, zygotes and embryos at various stages of development.

As used herein, a “plant organ” is a distinct and visibly structured and differentiated part of a plant such as a root, stem, leaf, flower bud, or embryo.

“Plant tissue” as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing an FEA2 gene may comprise contacting a target nucleic acid (e.g., a nucleic acid encoding an FEA2) with a base-editing fusion protein (e.g., a sequence specific nucleic acid binding protein, a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing an FEA2 gene may comprise contacting a target nucleic acid (e.g., a nucleic acid encoding an FEA2) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fuse to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous FEA2 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain (e.g., a sequence-specific DNA binding domain) may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifzdobacterium* spp., *Kandleria* spp., *Leuconostoc* spp., Oenococcus spp., *Pediococcus* spp., Weissella spp., and/or *Olsenella* spp. Example Cas9 sequences include, but are not limited to, the amino acid sequences of SEQ ID NO:59 and SEQ ID NO:60 or the nucleotide sequences of SEQ ID NOs:61-71.

In some embodiments, the CRISPR-Cas effector protein may be a Cas9 polypeptide derived from Streptococcuspyogenes and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus* thermophiles and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., SEQ ID NOs:1-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term “Cas12a”, “Cas12a polypeptide” or “Cas12a domain” refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%7, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%0, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs:31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof, a repeat of a Type V C2c1 CRISPR Cas system, or a fragment thereof, a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer) (e.g., consecutive nucleotides of a sequence that (a) encodes a sequence having at least 95% sequence identity to the amino acid sequence of SEQ ID NO:74; (b) comprises a sequence having at least 90% sequence identity to the nucleotide sequence of SEQ ID NO:72 or SEQ ID NO:73; (c) comprises a sequence having at least 90% sequence identity to the nucleotide sequence of SEQ ID NO:77 or SEQ ID NO:78; and/or (d) encodes a sequence having at least 90% sequence identity to the amino acid sequence of SEQ ID NO:75 or SEQ ID NO:76). In some embodiments, a spacer sequence may include, but is not limited to, the nucleotide sequences of any one of SEQ ID NOs:79-82. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

5'-NNNNNNNNNNNNNNNNNN-3' RNA Spacer (SEQ ID NO:42)
3'AAANNNNNNNNNNN-5' Target strand (SEQ ID NO:43)
5'TTTNNNNNNNNNNNNNNNNNNNN-3' Non-target strand (SEQ ID NO:44)

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types, and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g, one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Corn stem-loop and the corresponding affinity polypeptide Corn RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Design of the Editing Constructs for Fea2 Editing

The genomic sequence of the Fea2 gene was identified in a proprietary maize line. From this reference sequence, spacer sequences (SEQ ID NOs: 73-76) were designed for use in editing constructs. The editing constructs contained a CRISPR-Cas effector and a spacer sequence designed to target amino acid position 477 of the FEA2 protein encoded by the Fea2 gene. Spacers were deployed with either a Cas-effector cutting enzyme or a Cas-effector base editing complex.

Example 2. Transformation and Selection of Edited E0 Plants

A vector encoding the spacer (Table 1) as well as the chosen CRISPR-Cas effector were introduced into dried excised maize embryos using *Agrobacterium*. Transformed tissue was maintained in vitro with antibiotic selection to regenerate positive transformants. Healthy non-chimeric plants (E0) were selected and plugged in growth trays. Tissue was collected from regenerating plants (E0 generation) for DNA extraction and subsequent molecular screening was employed to identify edits in the Fea2. Plants identified to be (1) healthy, non-chimeric and fertile, with (2) low transgene copy and (3) an edit near position 477 were advanced to the next generation. E0 plants that satisfied all the above criteria were selfed to produce the E1 generation. Selected E1s were selfed to generate the E2 generation. We identified several families with deletions and substitutions in and around amino acid position 477.

TABLE 1

| Spacers present in each pWISE vector | | |
|---|---|---|
| Vector | Spacers | Spacer SEQ ID NO. |
| pWISE682 | PWg090079 | 79 |
| pWISE683 | PWg120223 | 81 |
| | PWg120224 | 82 |
| pWISE684 | PWg120224 | 82 |
| pWISE685 | PWg120222 | 80 |
| pWISE723 | PWg090079 | 79 |

Example 3. Phenotypic Assessment of Trait Activity

Seeds for E1 and E2 material were sown in flats and later transferred to pots after seedlings were established. All materials were cultivated under standard greenhouse conditions and grown to reproductive maturity. Following standard practices, emerging ears were covered with small paper bags prior to the emergence of silk and tassels were covered during anthesis for the capture of pollen on a plant-by-plant basis. In some cases, anthesis and silking were not synchronized, and ears were not pollinated. We designated these as 'unpollinated' ears and evaluated them separately for kernel row number determination (as described below) once all ears were removed from the plants after dry-down.

After ear harvest and dry-down, kernel row number was manually counted for all ears. Data represent the average of three row counts per ear taken from the mid-section of the ear where row lineages were most defined. In order to prevent double counting of rows, a marker (e.g., paper clip) was inserted in between the rows where the counts initiated and to designate where row counting should cease.

All ears were photo-documented with a Canon digital camera and EOS application. Images were subsequently imported into ImageJ and all ears were measured using the line trace function. Ear length was determined in centimeters by a setting scale in the image analysis program to output distance in centimeters after ears were traced with lines along the length of ear from its tip to the base of ear. Un-edited germplasm (Line 01DKD2), and lines transformed with a Gus plasmid were used as wild-type controls for phenotyping. Tables 2 and 3 show kernel row number (KRN) and ear length measurements for E1 families derived from selfed E0 ears, and Tables 4 and 5 show kernel row number and ear length measurements for E2 families derived from selfed E1 ears.

TABLE 2

| E1 Homozygous Alleles | | | | | | |
|---|---|---|---|---|---|---|
| Allele ID # | pWISE | Allele Description | Average KRN | Ear Length (cm) | Sample Size (# of plants) | Comments |
| 7 | PWISE684 | Homozygous 2aa in-frame deletion | 21.8 | 10.07 | 5 | pollinated |
| 7 | PWISE684 | Homozygous 2aa in-frame deletion | 18 | 5.49 | 3 | unpollinated ears |
| 8 | PWISE684 | Homozygous 3aa in-frame deletion | 27 | 11.11 | 1 | pollinated |
| 9 | PWISE684 | Homozygous 4aa in-frame deletion | 25.5 | 9.46 | 2 | pollinated |
| 9 | PWISE684 | Homozygous 4aa in-frame deletion | 25 | 6.4 | 4 | unpollinated ears |
| 10 | PWISE685 | Homozygous 11aa in-frame deletion | 27.67 | 5.9 | 3 | pollinated |
| 11 | PWISE684 | Homozygous premature stop | 22.6 | 7 | 5 | pollinated |
| 11 | PWISE684 | Homozygous premature stop | 26.8 | 5.04 | 5 | unpollinated ears |
| 12 | PWISE683 | Homozygous premature stop | 24.33 | 6.99 | 3 | pollinated |
| 12 | PWISE683 | Homozygous premature stop | 30 | 9.47 | 1 | unpollinated ears |
| 13 | PWISE684 | Homozygous premature stop | 26 | 6.8 | 2 | pollinated |
| 13 | PWISE684 | Homozygous premature stop | 36 | 7.06 | 1 | unpollinated ears |
| 14 | PWISE685 | Homozygous premature stop | 27.67 | 8.92 | 3 | pollinated |
| 14 | PWISE685 | Homozygous premature stop | 32 | 6.47 | 1 | unpollinated ears |
| 15 | PWISE684 | Homozygous premature stop | 26.67 | 9 | 3 | pollinated |
| 15 | PWISE684 | Homozygous premature stop | 30 | 5.23 | 4 | unpollinated ears |
| | WT | WT | 16.35 | 12.19 | 17 | pollinated |
| | PWISE1 | GUS Control | 16 | 10.06 | 7 | pollinated |

TABLE 3

| E1 Homozygous Alleles | | | | | | |
|---|---|---|---|---|---|---|
| Allele ID# | pWISE | Allele Description | AVE KRN | Ear length (cm) | Sample Size (# of plants) | Comments |
| 1 | pWISE682 | homo P477 deletion | 19.8 | 12.32 | 25 | pollinated |
| 2 | pWISE682 | homo P477 > F | 20.8 | 12.08 | 22 | pollinated |
| 3 | pWISE682 | homo P477 > S | 17.1 | 12.98 | 15 | pollinated |
| 4 | pWISE682 | homo P477 > T | 18.0 | 11.57 | 2 | pollinated |
| 5 | pWISE682 | Homo P477 > V | 21.33 | 11.09 | 4 | pollinated |
| | pWISE1 | GUS Control | 16.5 | 14.44 | 4 | pollinated |
| | pWISE1 | GUS Control | 16.86 | 13.45 | 6 | pollinated |
| | WT | WT | 16.58 | 14.31 | 25 | pollinated |

TABLE 4

| E2 Homozygous alleles | | | | | | |
|---|---|---|---|---|---|---|
| Allele ID # | pWISE | Allele Description | AVE KRN | Ear length (cm) | Sample Size (number of plants) | Comments |
| 1 | pWISE682 | P477 deletion homo | 19.4 | 12.67 | 7 | pollinated |
| 6 | pWISE723 | P477 > C homo | 18.1 | 13.52 | 36 | pollinated |

TABLE 4-continued

| E2 Homozygous alleles | | | | | | |
|---|---|---|---|---|---|---|
| Allele ID # | pWISE | Allele Description | AVE KRN | Ear length (cm) | Sample Size (number of plants) | Comments |
| 2 | pWISE682 | P477 > F homo | 21.4 | 12.32 | 8 | pollinated |
| 3 | pWISE682 | P477 > S homo | 16.8 | 14.11 | 12 | pollinated |
| 15 | pWISE684 | stop class 2 homo | 23.7 | 9.16 | 7 | pollinated |
| | WT | WT Control | 16.0 | 14.13 | 12 | pollinated |
| | pWISE1 | GUS Control | 16.0 | 13.99 | 4 | pollinated |

TABLE 5

| E2 Homozygous alleles | | | | | | |
|---|---|---|---|---|---|---|
| Allele ID # | pWISE | Allele Description | AVE KRN | Ear length (cm) | Sample Size (# of plants) | |
| 3 | pWISE682 | homo P477 > S | 17.3 | 14.6 | 25 | pollinated |
| 2 | pWISE682 | homo P477 > F | 18.8 | 12.1 | 20 | pollinated |
| 1 | pWISE682 | homo P477 deletion | 18.8 | 12.8 | 16 | pollinated |
| | WT | WT Control | 15.4 | 14.6 | 24 | pollinated |

The foregoing is illustrative of the present invention and is not to be construed as limiting thereof. The invention is defined by the following claims, with equivalents of the claims to be included therein.

That which is claimed is:

1. A corn plant comprising at least one mutation in an endogenous FACIATED EAR2 (FEA2) gene, wherein the at least one mutation is a deletion, the endogenous FEA2 gene comprises a nucleotide sequence having at least 90% sequence identity to the nucleotide sequence SEQ ID NO:72 or SEQ ID NO:73 and/or encodes an amino acid sequence having at least 90% sequence identity to the amino acid sequence SEQ ID NO:74 and the at least one mutation is within a region of the endogenous FEA2 gene, the region comprising a sequence having at least 90% sequence identity to the nucleotide sequence SEQ ID NO:77 or SEQ ID NO:78 and/or encoding a sequence having at least 95% sequence identity to the amino acid sequence SEQ ID NO:75 or SEQ ID NO:76, and an ear of the corn plant comprising the deletion comprises an increased kernel row number and a length that is decreased by less than 30% as compared to an ear of a control corn plant not comprising the deletion and grown under the same environmental conditions, wherein the at least one mutation results in a mutated gene comprising the nucleotide sequence SEQ ID NOs: 88, 91, 92, 96, 97, 99, 105-107, 112-114, 120-122, 127, 128, or 153 and/or encoding the amino acid sequence SEQ ID NOs:134, 140-142, 147, 148, 158, 163, 165, 166, 169, 170, 172,178-180, 185, or 186.

2. A method for producing a corn plant or part thereof comprising at least one cell having a mutated endogenous FEA2 gene, the method comprising contacting a target site in an endogenous FEA2gene in the corn plant or plant part with a nuclease comprising a cleavage domain and a nucleic acid binding domain, wherein the nucleic acid binding domain binds to a target site in the endogenous FEA2 gene, wherein the endogenous FEA2 gene (a) encodes a sequence having at least 95% sequence identity to the amino acid sequence SEQ ID NO:74;

(b) comprises a sequence having at least 90% sequence identity to the nucleotide sequence SEQ ID NO:72 or SEQ ID NO:73;

(c) comprises a sequence having at least 90% sequence identity to the nucleotide sequence SEQ ID NO:77 or SEQ ID NO:78; and/or (d) encodes a sequence having at least 90% sequence identity to the amino acid sequence SEQ ID NO:75 or SEQ ID NO:76, thereby producing the corn plant or part thereof comprising at least one cell having a mutation in the endogenous FEA2 gene, wherein the target site is within a region of the endogenous FEA2 gene, the region comprising a sequence having at least 90% sequence identity to the nucleotide sequence SEQ ID NO:77 or SEQ ID NO:78 and/or encoding a sequence having at least 95% sequence identity to the amino acid sequence SEQ ID NO:75 or SEQ ID NO:76, and following cleavage by the nuclease, an edit is made that results in a deletion within the region of the endogenous FEA2 gene of the at least one cell of the corn plant or part thereof, and the corn plant comprising the at least one cell having the deletion produces an ear that comprises an increased kernel row number and a length that is decreased by less than 30% as compared to an ear of a control corn plant not comprising the deletion and grown under the same environmental conditions, and wherein the mutation results in a mutated FEA2 gene comprising the nucleotide sequence SEQ ID NOs:88, 91, 92, 96, 97, 99, 105-107, 112-114, 120-122, 127, 128, or 153 and/or encoding the amino acid sequence SEQ ID NOs:134, 140-142, 147,148,158,163,165, 166, 169, 170, 172, 178-180, 185, or 186.

3. A nucleic acid encoding a mutated corn FEA2 protein, wherein the nucleic acid comprises the sequence SEQ ID NOs: 88, 91, 92, 96, 97, 99, 105-107, 112-114, 120-122, 127, 128, or 153 and/or encodes the amino acid sequence SEQ ID NOs:134, 140-142, 147, 148, 158, 163, 165, 166, 169, 170, 172, 178-180, 185 or 186.

4. A modified corn FEA2 protein comprising the amino acid sequence SEQ ID NOs: 134, 140-142, 147, 148, 158, 163, 165, 166, 169, 170, 172, 178-180, 185 or 186.

* * * * *

UNITED STATES PATENT AND TRADEMARK OFFICE
CERTIFICATE OF CORRECTION

| | |
|---|---|
| PATENT NO. | : 11,999,946 B2 |
| APPLICATION NO. | : 17/212665 |
| DATED | : June 4, 2024 |
| INVENTOR(S) | : Karlson et al. |

It is certified that error appears in the above-identified patent and that said Letters Patent is hereby corrected as shown below:

In the Specification

Column 2, Line 7: Please correct "CLVJ" to read --CLV1--

Column 10, Line 8: Please insert a paragraph break between "mutation."" and "A "semi-dominant"

Column 14, Line 53: Please insert a paragraph break between "2-4)" and "In"

Column 15, Lines 32-33: Please remove the paragraph break between "pairing." and "For"

Column 51, Lines 49-55: Please delete SEQ ID NOs: 42, 43 and 44 and replace with the following:
```
    5'-NNNNNNNNNNNNNNNNNNNN-3' RNA Spacer (SEQ ID NO:42)
       | | | | | | | | | | | | | | | | | |
3'AAANNNNNNNNNNNNNNNNNNNN-5' Target strand (SEQ ID NO:43)
      | | | |
5'TTTNNNNNNNNNNNNNNNNNNNN-3' Non-target strand (SEQ ID NO:44)
```

Column 53, Line 63: Please correct "Corn" to read --Com--

Column 53, Line 64: Please correct "Corn" to read --Com--

Signed and Sealed this
Third Day of September, 2024

Katherine Kelly Vidal
*Director of the United States Patent and Trademark Office*

SEQUENCE LISTING

```
<160> NUMBER OF SEQ ID NOS: 186

<210> SEQ ID NO 1
<211> LENGTH: 1228
<212> TYPE: PRT
<213> ORGANISM: Lachnospiraceae sp.

<400> SEQUENCE: 1

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140
```

-continued

```
Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560
```

-continued

```
Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
```

-continued

```
        980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                 1015                1020

Ser Lys  Lys Phe Ile Ser Ser  Phe Asp Arg Ile Met  Tyr Val Pro
    1025                 1030                1035

Glu Glu  Asp Leu Phe Glu Phe  Ala Leu Asp Tyr Lys  Asn Phe Ser
    1040                 1045                1050

Arg Thr  Asp Ala Asp Tyr Ile  Lys Lys Trp Lys Leu  Tyr Ser Tyr
    1055                 1060                1065

Gly Asn  Arg Ile Arg Ile Phe  Arg Asn Pro Lys Lys  Asn Asn Val
    1070                 1075                1080

Phe Asp  Trp Glu Glu Val Cys  Leu Thr Ser Ala Tyr  Lys Glu Leu
    1085                 1090                1095

Phe Asn  Lys Tyr Gly Ile Asn  Tyr Gln Gln Gly Asp  Ile Arg Ala
    1100                 1105                1110

Leu Leu  Cys Glu Gln Ser Asp  Lys Ala Phe Tyr Ser  Ser Phe Met
    1115                 1120                1125

Ala Leu  Met Ser Leu Met Leu  Gln Met Arg Asn Ser  Ile Thr Gly
    1130                 1135                1140

Arg Thr  Asp Val Asp Phe Leu  Ile Ser Pro Val Lys  Asn Ser Asp
    1145                 1150                1155

Gly Ile  Phe Tyr Asp Ser Arg  Asn Tyr Glu Ala Gln  Glu Asn Ala
    1160                 1165                1170

Ile Leu  Pro Lys Asn Ala Asp  Ala Asn Gly Ala Tyr  Asn Ile Ala
    1175                 1180                1185

Arg Lys  Val Leu Trp Ala Ile  Gly Gln Phe Lys Lys  Ala Glu Asp
    1190                 1195                1200

Glu Lys  Leu Asp Lys Val Lys  Ile Ala Ile Ser Asn  Lys Glu Trp
    1205                 1210                1215

Leu Glu  Tyr Ala Gln Thr Ser  Val Lys His
    1220                 1225


<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110
```

-continued

```
Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
```

```
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960
```

-continued

Val Gly Thr Ile Lys Asp Leu Lys Gln Gly Tyr Leu Ser Gln Val Ile
965 970 975

His Glu Ile Val Asp Leu Met Ile His Tyr Gln Ala Val Val Val Leu
980 985 990

Glu Asn Leu Asn Phe Gly Phe Lys Ser Lys Arg Thr Gly Ile Ala Glu
995 1000 1005

Lys Ala Val Tyr Gln Gln Phe Glu Lys Met Leu Ile Asp Lys Leu
1010 1015 1020

Asn Cys Leu Val Leu Lys Asp Tyr Pro Ala Glu Lys Val Gly Gly
1025 1030 1035

Val Leu Asn Pro Tyr Gln Leu Thr Asp Gln Phe Thr Ser Phe Ala
1040 1045 1050

Lys Met Gly Thr Gln Ser Gly Phe Leu Phe Tyr Val Pro Ala Pro
1055 1060 1065

Tyr Thr Ser Lys Ile Asp Pro Leu Thr Gly Phe Val Asp Pro Phe
1070 1075 1080

Val Trp Lys Thr Ile Lys Asn His Glu Ser Arg Lys His Phe Leu
1085 1090 1095

Glu Gly Phe Asp Phe Leu His Tyr Asp Val Lys Thr Gly Asp Phe
1100 1105 1110

Ile Leu His Phe Lys Met Asn Arg Asn Leu Ser Phe Gln Arg Gly
1115 1120 1125

Leu Pro Gly Phe Met Pro Ala Trp Asp Ile Val Phe Glu Lys Asn
1130 1135 1140

Glu Thr Gln Phe Asp Ala Lys Gly Thr Pro Phe Ile Ala Gly Lys
1145 1150 1155

Arg Ile Val Pro Val Ile Glu Asn His Arg Phe Thr Gly Arg Tyr
1160 1165 1170

Arg Asp Leu Tyr Pro Ala Asn Glu Leu Ile Ala Leu Leu Glu Glu
1175 1180 1185

Lys Gly Ile Val Phe Arg Asp Gly Ser Asn Ile Leu Pro Lys Leu
1190 1195 1200

Leu Glu Asn Asp Asp Ser His Ala Ile Asp Thr Met Val Ala Leu
1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn
1295 1300 1305

<210> SEQ ID NO 3
<211> LENGTH: 1241
<212> TYPE: PRT
<213> ORGANISM: Butyrivibrio proteoclasticus

<400> SEQUENCE: 3

Met Leu Leu Tyr Glu Asn Tyr Thr Lys Arg Asn Gln Ile Thr Lys Ser

-continued 1 5 10 15

Leu Arg Leu Glu Leu Arg Pro Gln Gly Lys Thr Leu Arg Asn Ile Lys
20 25 30

Glu Leu Asn Leu Leu Glu Gln Asp Lys Ala Ile Tyr Ala Leu Leu Glu
35 40 45

Arg Leu Lys Pro Val Ile Asp Glu Gly Ile Lys Asp Ile Ala Arg Asp
50 55 60

Thr Leu Lys Asn Cys Glu Leu Ser Phe Glu Lys Leu Tyr Glu His Phe
65 70 75 80

Leu Ser Gly Asp Lys Lys Ala Tyr Ala Lys Glu Ser Glu Arg Leu Lys
85 90 95

Lys Glu Ile Val Lys Thr Leu Ile Lys Asn Leu Pro Glu Gly Ile Gly
100 105 110

Lys Ile Ser Glu Ile Asn Ser Ala Lys Tyr Leu Asn Gly Val Leu Tyr
115 120 125

Asp Phe Ile Asp Lys Thr His Lys Asp Ser Glu Glu Lys Gln Asn Ile
130 135 140

Leu Ser Asp Ile Leu Glu Thr Lys Gly Tyr Leu Ala Leu Phe Ser Lys
145 150 155 160

Phe Leu Thr Ser Arg Ile Thr Thr Leu Glu Gln Ser Met Pro Lys Arg
165 170 175

Val Ile Glu Asn Phe Glu Ile Tyr Ala Ala Asn Ile Pro Lys Met Gln
180 185 190

Asp Ala Leu Glu Arg Gly Ala Val Ser Phe Ala Ile Glu Tyr Glu Ser
195 200 205

Ile Cys Ser Val Asp Tyr Tyr Asn Gln Ile Leu Ser Gln Glu Asp Ile
210 215 220

Asp Ser Tyr Asn Arg Leu Ile Ser Gly Ile Met Asp Glu Asp Gly Ala
225 230 235 240

Lys Glu Lys Gly Ile Asn Gln Thr Ile Ser Glu Lys Asn Ile Lys Ile
245 250 255

Lys Ser Glu His Leu Glu Glu Lys Pro Phe Arg Ile Leu Lys Gln Leu
260 265 270

His Lys Gln Ile Leu Glu Glu Arg Glu Lys Ala Phe Thr Ile Asp His
275 280 285

Ile Asp Ser Asp Glu Glu Val Val Gln Val Thr Lys Glu Ala Phe Glu
290 295 300

Gln Thr Lys Glu Gln Trp Glu Asn Ile Lys Lys Ile Asn Gly Phe Tyr
305 310 315 320

Ala Lys Asp Pro Gly Asp Ile Thr Leu Phe Ile Val Val Gly Pro Asn
325 330 335

Gln Thr His Val Leu Ser Gln Leu Ile Tyr Gly Glu His Asp Arg Ile
340 345 350

Arg Leu Leu Leu Glu Glu Tyr Glu Lys Asn Thr Leu Glu Val Leu Pro
355 360 365

Arg Arg Thr Lys Ser Glu Asp Ala Arg Tyr Asp Lys Phe Val Asn Ala
370 375 380

Val Pro Lys Lys Val Ala Lys Glu Ser His Thr Phe Asp Gly Leu Gln
385 390 395 400

Lys Met Thr Gly Asp Asp Arg Leu Phe Ile Leu Tyr Arg Asp Glu Leu
405 410 415

Ala Arg Asn Tyr Met Arg Ile Lys Glu Ala Tyr Gly Thr Phe Glu Arg
420 425 430

-continued

```
Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
    450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met
    530                 535                 540

Ile Arg Arg Gly Asp Glu Tyr Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
            580                 585                 590

Phe Lys Cys Ile Leu Glu Pro Tyr Phe Glu Ser Pro Glu His Lys Asn
        595                 600                 605

Asp Lys Asn Cys Val Ile Glu Glu Tyr Val Ser Lys Pro Leu Thr Ile
    610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
            660                 665                 670

Tyr Ser Cys Phe Asn Met Ser Gly Leu Lys Arg Ala Asp Glu Tyr Asn
        675                 680                 685

Asp Ile Gly Glu Phe Phe Ser Asp Val Asp Thr Arg Leu Cys Thr Met
    690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
            740                 745                 750

Asn Met Glu His Thr Ser Met Leu Leu Asn Ser Arg Ala Met Ile Gln
        755                 760                 765

Tyr Arg Ala Ala Ser Leu Pro Arg Arg Val Thr His Lys Lys Gly Ser
    770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
            820                 825                 830

Ile Lys Lys Ala Asn Glu Asp Ile Ile Arg Asn Arg Arg Tyr Thr Glu
        835                 840                 845
```

```
Asp Lys Phe Phe Leu Ser Leu Ser Tyr Thr Lys Asn Ala Asp Ile Ser
    850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
    930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Val Glu Ser
                965                 970                 975

Met Ser Ser Thr Phe Lys Asp Lys Phe Ser Phe Leu Asp Glu Gln Ile
            980                 985                 990

Phe Lys Ala Phe Glu Ala Arg Leu  Cys Ala Arg Met Ser  Asp Leu Ser
        995                 1000                1005

Phe Asn  Thr Ile Lys Glu Gly  Glu Ala Gly Ser Ile  Ser Asn Pro
    1010                 1015                 1020

Ile Gln  Val Ser Asn Asn Asn  Gly Asn Ser Tyr Gln  Asp Gly Val
    1025                 1030                 1035

Ile Tyr  Phe Leu Asn Asn Ala  Tyr Thr Arg Thr Leu  Cys Pro Asp
    1040                 1045                 1050

Thr Gly  Phe Val Asp Val Phe  Asp Lys Thr Arg Leu  Ile Thr Met
    1055                 1060                 1065

Gln Ser  Lys Arg Gln Phe Phe  Ala Lys Met Lys Asp  Ile Arg Ile
    1070                 1075                 1080

Asp Asp  Gly Glu Met Leu Phe  Thr Phe Asn Leu Glu  Glu Tyr Pro
    1085                 1090                 1095

Thr Lys  Arg Leu Leu Asp Arg  Lys Glu Trp Thr Val  Lys Ile Ala
    1100                 1105                 1110

Gly Asp  Gly Ser Tyr Phe Asp  Lys Asp Lys Gly Glu  Tyr Val Tyr
    1115                 1120                 1125

Val Asn  Asp Ile Val Arg Glu  Gln Ile Ile Pro Ala  Leu Leu Glu
    1130                 1135                 1140

Asp Lys  Ala Val Phe Asp Gly  Asn Met Ala Glu Lys  Phe Leu Asp
    1145                 1150                 1155

Lys Thr  Ala Ile Ser Gly Lys  Ser Val Glu Leu Ile  Tyr Lys Trp
    1160                 1165                 1170

Phe Ala  Asn Ala Leu Tyr Gly  Ile Ile Thr Lys Lys  Asp Gly Glu
    1175                 1180                 1185

Lys Ile  Tyr Arg Ser Pro Ile  Thr Gly Thr Glu Ile  Asp Val Ser
    1190                 1195                 1200

Lys Asn  Thr Thr Tyr Asn Phe  Gly Lys Lys Phe Met  Phe Lys Gln
    1205                 1210                 1215

Glu Tyr  Arg Gly Asp Gly Asp  Phe Leu Asp Ala Phe  Leu Asn Tyr
    1220                 1225                 1230

Met Gln  Ala Gln Asp Ile Ala  Val
    1235                 1240
```

```
<210> SEQ ID NO 4
<211> LENGTH: 1238
<212> TYPE: PRT
<213> ORGANISM: Candidatus Methanoplasma termitum

<400> SEQUENCE: 4

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Ile Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380
```

-continued

```
Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
    610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
    690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
    770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
```

-continued

```
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
    850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
    930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu  Ser Phe Ala Lys Leu  Gly Lys Gln
        995                 1000                1005

Thr Gly  Ile Leu Phe Tyr Val  Pro Ala Ala Tyr Thr  Ser Lys Ile
    1010                1015                1020

Asp Pro  Thr Thr Gly Phe Val  Asn Leu Phe Asn Thr  Ser Ser Lys
    1025                1030                1035

Thr Asn  Ala Gln Glu Arg Lys  Glu Phe Leu Gln Lys  Phe Glu Ser
    1040                1045                1050

Ile Ser  Tyr Ser Ala Lys Asp  Gly Gly Ile Phe Ala  Phe Ala Phe
    1055                1060                1065

Asp Tyr  Arg Lys Phe Gly Thr  Ser Lys Thr Asp His  Lys Asn Val
    1070                1075                1080

Trp Thr  Ala Tyr Thr Asn Gly  Glu Arg Met Arg Tyr  Ile Lys Glu
    1085                1090                1095

Lys Lys  Arg Asn Glu Leu Phe  Asp Pro Ser Lys Glu  Ile Lys Glu
    1100                1105                1110

Ala Leu  Thr Ser Ser Gly Ile  Lys Tyr Asp Gly Gly  Gln Asn Ile
    1115                1120                1125

Leu Pro  Asp Ile Leu Arg Ser  Asn Asn Asn Gly Leu  Ile Tyr Thr
    1130                1135                1140

Met Tyr  Ser Ser Phe Ile Ala  Ala Ile Gln Met Arg  Val Tyr Asp
    1145                1150                1155

Gly Lys  Glu Asp Tyr Ile Ile  Ser Pro Ile Lys Asn  Ser Lys Gly
    1160                1165                1170

Glu Phe  Phe Arg Thr Asp Pro  Lys Arg Arg Glu Leu  Pro Ile Asp
    1175                1180                1185

Ala Asp  Ala Asn Gly Ala Tyr  Asn Ile Ala Leu Arg  Gly Glu Leu
    1190                1195                1200

Thr Met  Arg Ala Ile Ala Glu  Lys Phe Asp Pro Asp  Ser Glu Lys
    1205                1210                1215
```

```
Met Ala  Lys Leu Glu Leu Lys  His Lys Asp Trp Phe  Glu Phe Met
    1220                1225                1230

Gln Thr  Arg Gly Asp
    1235


<210> SEQ ID NO 5
<211> LENGTH: 1281
<212> TYPE: PRT
<213> ORGANISM: Eubacterium eligens

<400> SEQUENCE: 5

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285

Leu Ala Tyr Thr Ser Thr Ser Phe Glu Val Pro Lys Met Phe Glu Asp
    290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
```

-continued

```
            340                 345                 350

Leu Ser Cys Phe Met Ser Gly Asn Trp Asn Leu Ile Thr Gly Cys Val
        355                 360                 365

Glu Asn Phe Tyr Asp Glu Asn Ile His Ala Lys Gly Lys Ser Lys Glu
    370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
        435                 440                 445

Ser Leu Ile Glu Ser Glu Glu Lys Ala Asp Glu Met Lys Lys Arg Leu
    450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
        755                 760                 765
```

```
Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
    850                 855                 860

Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
            900                 905                 910

Lys Lys Leu Val Glu Lys Glu Lys Thr Arg Glu Tyr Ala Arg Lys Asn
        915                 920                 925

Trp Lys Ser Ile Gly Asn Ile Lys Glu Leu Lys Glu Gly Tyr Ile Ser
    930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
            980                 985                 990

Leu Asn Tyr Phe Ala Ser Lys Glu  Lys Ser Val Asp Glu  Pro Gly Gly
        995                 1000                 1005

Leu Leu  Lys Gly Tyr Gln Leu  Thr Tyr Val Pro Asp  Asn Ile Lys
    1010                 1015                 1020

Asn Leu  Gly Lys Gln Cys Gly  Val Ile Phe Tyr Val  Pro Ala Ala
    1025                 1030                 1035

Phe Thr  Ser Lys Ile Asp Pro  Ser Thr Gly Phe Ile  Ser Ala Phe
    1040                 1045                 1050

Asn Phe  Lys Ser Ile Ser Thr  Asn Ala Ser Arg Lys  Gln Phe Phe
    1055                 1060                 1065

Met Gln  Phe Asp Glu Ile Arg  Tyr Cys Ala Glu Lys  Asp Met Phe
    1070                 1075                 1080

Ser Phe  Gly Phe Asp Tyr Asn  Asn Phe Asp Thr Tyr  Asn Ile Thr
    1085                 1090                 1095

Met Gly  Lys Thr Gln Trp Thr  Val Tyr Thr Asn Gly  Glu Arg Leu
    1100                 1105                 1110

Gln Ser  Glu Phe Asn Asn Ala  Arg Arg Thr Gly Lys  Thr Lys Ser
    1115                 1120                 1125

Ile Asn  Leu Thr Glu Thr Ile  Lys Leu Leu Leu Glu  Asp Asn Glu
    1130                 1135                 1140

Ile Asn  Tyr Ala Asp Gly His  Asp Ile Arg Ile Asp  Met Glu Lys
    1145                 1150                 1155

Met Asp  Glu Asp Lys Lys Ser  Glu Phe Phe Ala Gln  Leu Leu Ser
    1160                 1165                 1170
```

Leu Tyr Lys Leu Thr Val Gln Met Arg Asn Ser Tyr Thr Glu Ala
1175 1180 1185

Glu Glu Gln Glu Asn Gly Ile Ser Tyr Asp Lys Ile Ile Ser Pro
1190 1195 1200

Val Ile Asn Asp Glu Gly Glu Phe Phe Asp Ser Asp Asn Tyr Lys
1205 1210 1215

Glu Ser Asp Asp Lys Glu Cys Lys Met Pro Lys Asp Ala Asp Ala
1220 1225 1230

Asn Gly Ala Tyr Cys Ile Ala Leu Lys Gly Leu Tyr Glu Val Leu
1235 1240 1245

Lys Ile Lys Ser Glu Trp Thr Glu Asp Gly Phe Asp Arg Asn Cys
1250 1255 1260

Leu Lys Leu Pro His Ala Glu Trp Leu Asp Phe Ile Gln Asn Lys
1265 1270 1275

Arg Tyr Glu
1280

<210> SEQ ID NO 6
<211> LENGTH: 1300
<212> TYPE: PRT
<213> ORGANISM: Francisella novicida

<400> SEQUENCE: 6

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Val Asn Tyr Ser Ser
180 185 190

Asn Asp Ile Pro Thr Ser Ile Ile Tyr Arg Ile Val Asp Asp Asn Leu
195 200 205

Pro Lys Phe Leu Glu Asn Lys Ala Lys Tyr Glu Ser Leu Lys Asp Lys
210 215 220

Ala Pro Glu Ala Ile Asn Tyr Glu Gln Ile Lys Lys Asp Leu Ala Glu
225 230 235 240

Glu Leu Thr Phe Asp Ile Asp Tyr Lys Thr Ser Glu Val Asn Gln Arg
245 250 255

```
Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670
```

-continued

```
Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
```

```
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300


<210> SEQ ID NO 7
<211> LENGTH: 1206
<212> TYPE: PRT
<213> ORGANISM: Lachnospiraceae sp.

<400> SEQUENCE: 7

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140
```

-continued

```
Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
    370                 375                 380

Glu Asp Ser Cys Asn Leu Ile Glu Asn Tyr Ile His Gln Ile Ser Asp
385                 390                 395                 400

Asp Ile Glu Asn Ile Ile Ile Asn Asn Glu Thr Phe Leu Arg Ile Val
                405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
    450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
    530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
```

-continued

```
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
        675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
    770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
        835                 840                 845

Ile Glu Thr Asp Tyr His Ala Leu Leu Asp Glu Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990
```

Thr Gly Phe Ala Asn Leu Phe Tyr Met Lys Cys Glu Asn Val Glu Lys
995 1000 1005

Ser Lys Arg Phe Phe Asp Gly Phe Asp Phe Ile Arg Phe Asn Ala
1010 1015 1020

Leu Glu Asn Val Phe Glu Phe Gly Phe Asp Tyr Arg Ser Phe Thr
1025 1030 1035

Gln Arg Ala Cys Gly Ile Asn Ser Lys Trp Thr Val Cys Thr Asn
1040 1045 1050

Gly Glu Arg Ile Ile Lys Tyr Arg Asn Pro Asp Lys Asn Asn Met
1055 1060 1065

Phe Asp Glu Lys Val Val Val Val Thr Asp Glu Met Lys Asn Leu
1070 1075 1080

Phe Glu Gln Tyr Lys Ile Pro Tyr Glu Asp Gly Arg Asn Val Lys
1085 1090 1095

Asp Met Ile Ile Ser Asn Glu Glu Ala Glu Phe Tyr Arg Arg Leu
1100 1105 1110

Tyr Arg Leu Leu Gln Gln Thr Leu Gln Met Arg Asn Ser Thr Ser
1115 1120 1125

Asp Gly Thr Arg Asp Tyr Ile Ile Ser Pro Val Lys Asn Lys Arg
1130 1135 1140

Glu Ala Tyr Phe Asn Ser Glu Leu Ser Asp Gly Ser Val Pro Lys
1145 1150 1155

Asp Ala Asp Ala Asn Gly Ala Tyr Asn Ile Ala Arg Lys Gly Leu
1160 1165 1170

Trp Val Leu Glu Gln Ile Arg Gln Lys Ser Glu Gly Glu Lys Ile
1175 1180 1185

Asn Leu Ala Met Thr Asn Ala Glu Trp Leu Glu Tyr Ala Gln Thr
1190 1195 1200

His Leu Leu
1205

<210> SEQ ID NO 8
<211> LENGTH: 1233
<212> TYPE: PRT
<213> ORGANISM: Lachnospiraceae sp.

<400> SEQUENCE: 8

Met Asp Tyr Gly Asn Gly Gln Phe Glu Arg Arg Ala Pro Leu Thr Lys
1 5 10 15

Thr Ile Thr Leu Arg Leu Lys Pro Ile Gly Glu Thr Arg Glu Thr Ile
20 25 30

Arg Glu Gln Lys Leu Leu Glu Gln Asp Ala Ala Phe Arg Lys Leu Val
35 40 45

Glu Thr Val Thr Pro Ile Val Asp Asp Cys Ile Arg Lys Ile Ala Asp
50 55 60

Asn Ala Leu Cys His Phe Gly Thr Glu Tyr Asp Phe Ser Cys Leu Gly
65 70 75 80

Asn Ala Ile Ser Lys Asn Asp Ser Lys Ala Ile Lys Lys Glu Thr Glu
85 90 95

Lys Val Glu Lys Leu Leu Ala Lys Val Leu Thr Glu Asn Leu Pro Asp
100 105 110

Gly Leu Arg Lys Val Asn Asp Ile Asn Ser Ala Ala Phe Ile Gln Asp
115 120 125

Thr Leu Thr Ser Phe Val Gln Asp Asp Ala Asp Lys Arg Val Leu Ile

```
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
        355                 360                 365

Arg Lys Glu Ser Lys Lys Arg Leu Glu Gly Leu Glu Glu His Ile Arg
    370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
    450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
        515                 520                 525

Lys Phe Asn Val Lys Phe His Thr Ile Val Arg Arg Asp Gly Arg Leu
    530                 535                 540

Tyr Tyr Phe Ile Leu Pro Lys Gly Ala Lys Pro Val Glu Leu Glu Asp
545                 550                 555                 560
```

-continued

```
Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

Ala Pro Val Thr Ile Thr Arg Glu Thr Tyr Glu Ala Tyr Arg Tyr Lys
    610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
        675                 680                 685

Asn Thr Phe Met Cys Trp Ala Lys Val Ser Ser Ser Gln Leu Asp Asp
    690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765

Ser Ser Lys Pro Met Val Val His Arg Asp Gly Ser Arg Val Val Asp
    770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
    850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
    930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975
```

-continued

```
Ala Phe Lys Asp Lys Tyr Ser Phe Leu Asp Asp Val Thr Phe Lys Gly
            980                 985                 990

Phe Glu Thr Lys Lys Leu Ala Lys  Leu Ser Asp Leu His  Phe Arg Gly
        995                 1000                1005

Ile Lys  Asp Gly Glu Pro Cys  Ser Phe Thr Asn Pro  Leu Gln Leu
    1010                 1015                 1020

Cys Gln  Asn Asp Ser Asn Lys  Ile Leu Gln Asp Gly  Val Ile Phe
    1025                 1030                 1035

Met Val  Pro Asn Ser Met Thr  Arg Ser Leu Asp Pro  Asp Thr Gly
    1040                 1045                 1050

Phe Ile  Phe Ala Ile Asn Asp  His Asn Ile Arg Thr  Lys Lys Ala
    1055                 1060                 1065

Lys Leu  Asn Phe Leu Ser Lys  Phe Asp Gln Leu Lys  Val Ser Ser
    1070                 1075                 1080

Glu Gly  Cys Leu Ile Met Lys  Tyr Ser Gly Asp Ser  Leu Pro Thr
    1085                 1090                 1095

His Asn  Thr Asp Asn Arg Val  Trp Asn Cys Cys Cys  Asn His Pro
    1100                 1105                 1110

Ile Thr  Asn Tyr Asp Arg Glu  Thr Lys Lys Val Glu  Phe Ile Glu
    1115                 1120                 1125

Glu Pro  Val Glu Glu Leu Ser  Arg Val Leu Glu Glu  Asn Gly Ile
    1130                 1135                 1140

Glu Thr  Asp Thr Glu Leu Asn  Lys Leu Asn Glu Arg  Glu Asn Val
    1145                 1150                 1155

Pro Gly  Lys Val Val Asp Ala  Ile Tyr Ser Leu Val  Leu Asn Tyr
    1160                 1165                 1170

Leu Arg  Gly Thr Val Ser Gly  Val Ala Gly Gln Arg  Ala Val Tyr
    1175                 1180                 1185

Tyr Ser  Pro Val Thr Gly Lys  Lys Tyr Asp Ile Ser  Phe Ile Gln
    1190                 1195                 1200

Ala Met  Asn Leu Asn Arg Lys  Cys Asp Tyr Tyr Arg  Ile Gly Ser
    1205                 1210                 1215

Lys Glu  Arg Gly Glu Trp Thr  Asp Phe Val Ala Gln  Leu Ile Asn
    1220                 1225                 1230


<210> SEQ ID NO 9
<211> LENGTH: 1227
<212> TYPE: PRT
<213> ORGANISM: Lachnospiraceae sp.

<400> SEQUENCE: 9

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110
```

Glu Gly Tyr Lys Ser Leu Phe Lys Lys Asp Ile Ile Glu Thr Ile Leu
115 120 125

Pro Glu Phe Leu Asp Asp Lys Asp Glu Ile Ala Leu Val Asn Ser Phe
130 135 140

Asn Gly Phe Thr Thr Ala Phe Thr Gly Phe Phe Asp Asn Arg Glu Asn
145 150 155 160

Met Phe Ser Glu Glu Ala Lys Ser Thr Ser Ile Ala Phe Arg Cys Ile
165 170 175

Asn Glu Asn Leu Thr Arg Tyr Ile Ser Asn Met Asp Ile Phe Glu Lys
180 185 190

Val Asp Ala Ile Phe Asp Lys His Glu Val Gln Glu Ile Lys Glu Lys
195 200 205

Ile Leu Asn Ser Asp Tyr Asp Val Glu Asp Phe Phe Glu Gly Glu Phe
210 215 220

Phe Asn Phe Val Leu Thr Gln Glu Gly Ile Asp Val Tyr Asn Ala Ile
225 230 235 240

Ile Gly Gly Phe Val Thr Glu Ser Gly Glu Lys Ile Lys Gly Leu Asn
245 250 255

Glu Tyr Ile Asn Leu Tyr Asn Gln Lys Thr Lys Gln Lys Leu Pro Lys
260 265 270

Phe Lys Pro Leu Tyr Lys Gln Val Leu Ser Asp Arg Glu Ser Leu Ser
275 280 285

Phe Tyr Gly Glu Gly Tyr Thr Ser Asp Glu Glu Val Leu Glu Val Phe
290 295 300

Arg Asn Thr Leu Asn Lys Asn Ser Glu Ile Phe Ser Ser Ile Lys Lys
305 310 315 320

Leu Glu Lys Leu Phe Lys Asn Phe Asp Glu Tyr Ser Ser Ala Gly Ile
325 330 335

Phe Val Lys Asn Gly Pro Ala Ile Ser Thr Ile Ser Lys Asp Ile Phe
340 345 350

Gly Glu Trp Asn Val Ile Arg Asp Lys Trp Asn Ala Glu Tyr Asp Asp
355 360 365

Ile His Leu Lys Lys Lys Ala Val Val Thr Glu Lys Tyr Glu Asp Asp
370 375 380

Arg Arg Lys Ser Phe Lys Lys Ile Gly Ser Phe Ser Leu Glu Gln Leu
385 390 395 400

Gln Glu Tyr Ala Asp Ala Asp Leu Ser Val Val Glu Lys Leu Lys Glu
405 410 415

Ile Ile Ile Gln Lys Val Asp Glu Ile Tyr Lys Val Tyr Gly Ser Ser
420 425 430

Glu Lys Leu Phe Asp Ala Asp Phe Val Leu Glu Lys Ser Leu Lys Lys
435 440 445

Asn Asp Ala Val Val Ala Ile Met Lys Asp Leu Leu Asp Ser Val Lys
450 455 460

Ser Phe Glu Asn Tyr Ile Lys Ala Phe Phe Gly Glu Gly Lys Glu Thr
465 470 475 480

Asn Arg Asp Glu Ser Phe Tyr Gly Asp Phe Val Leu Ala Tyr Asp Ile
485 490 495

Leu Leu Lys Val Asp His Ile Tyr Asp Ala Ile Arg Asn Tyr Val Thr
500 505 510

Gln Lys Pro Tyr Ser Lys Asp Lys Phe Lys Leu Tyr Phe Gln Asn Pro
515 520 525

-continued

```
Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
```

-continued 945 950 955 960

Lys Lys Ser Asn Pro Cys Ala Thr Gly Gly Ala Leu Lys Gly Tyr Gln
965 970 975

Ile Thr Asn Lys Phe Glu Ser Phe Lys Ser Met Ser Thr Gln Asn Gly
980 985 990

Phe Ile Phe Tyr Ile Pro Ala Trp Leu Thr Ser Lys Ile Asp Pro Ser
995 1000 1005

Thr Gly Phe Val Asn Leu Leu Lys Thr Lys Tyr Thr Ser Ile Ala
1010 1015 1020

Asp Lys Lys Phe Ile Ser Ser Phe Asp Arg Ile Met Tyr Val Pro
1025 1030 1035

Glu Glu Asp Leu Phe Glu Phe Ala Leu Asp Tyr Lys Asn Phe Ser
1040 1045 1050

Arg Thr Asp Ala Asp Tyr Ile Lys Lys Trp Lys Leu Tyr Ser Tyr
1055 1060 1065

Gly Asn Arg Ile Arg Ile Phe Arg Asn Pro Lys Lys Asn Asn Val
1070 1075 1080

Phe Asp Trp Glu Glu Val Cys Leu Thr Ser Ala Tyr Lys Glu Leu
1085 1090 1095

Phe Asn Lys Tyr Gly Ile Asn Tyr Gln Gln Gly Asp Ile Arg Ala
1100 1105 1110

Leu Leu Cys Glu Gln Ser Asp Lys Ala Phe Tyr Ser Ser Phe Met
1115 1120 1125

Ala Leu Met Ser Leu Met Leu Gln Met Arg Asn Ser Ile Thr Gly
1130 1135 1140

Arg Thr Asp Val Asp Phe Leu Ile Ser Pro Val Lys Asn Ser Asp
1145 1150 1155

Gly Ile Phe Tyr Asp Ser Arg Asn Tyr Glu Ala Gln Glu Asn Ala
1160 1165 1170

Ile Leu Pro Lys Asn Ala Asp Ala Asn Gly Ala Tyr Asn Ile Ala
1175 1180 1185

Arg Lys Val Leu Trp Ala Ile Gly Gln Phe Lys Lys Ala Glu Asp
1190 1195 1200

Glu Lys Leu Asp Lys Val Lys Ile Ala Ser Asn Lys Glu Trp Leu
1205 1210 1215

Glu Tyr Ala Gln Thr Ser Val Lys His
1220 1225

<210> SEQ ID NO 10
<211> LENGTH: 1264
<212> TYPE: PRT
<213> ORGANISM: Leptospira inadai

<400> SEQUENCE: 10

Met Glu Asp Tyr Ser Gly Phe Val Asn Ile Tyr Ser Ile Gln Lys Thr
1 5 10 15

Leu Arg Phe Glu Leu Lys Pro Val Gly Lys Thr Leu Glu His Ile Glu
20 25 30

Lys Lys Gly Phe Leu Lys Lys Asp Lys Ile Arg Ala Glu Asp Tyr Lys
35 40 45

Ala Val Lys Lys Ile Ile Asp Lys Tyr His Arg Ala Tyr Ile Glu Glu
50 55 60

Val Phe Asp Ser Val Leu His Gln Lys Lys Lys Lys Asp Lys Thr Arg
65 70 75 80

-continued

```
Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Asn Lys Asn Leu Phe Ser Lys Glu
    130                 135                 140

Leu Ile Arg Asn Glu Ile Glu Lys Phe Cys Glu Thr Asp Glu Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Glu Lys Lys Ser Thr Ala
            180                 185                 190

Ile Gly Tyr Arg Ile Ile His Gln Asn Leu Pro Lys Phe Leu Asp Asn
        195                 200                 205

Leu Lys Ile Ile Glu Ser Ile Gln Arg Arg Phe Lys Asp Phe Pro Trp
    210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
        275                 280                 285

Lys Asn Asn Ile Asp Arg Lys Asn Pro Leu Asn Val Lys Ile Leu Phe
    290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
        355                 360                 365

Ala Asn Asp Asn Ser Leu Ala Ser Ile Ser Thr Phe Leu Phe Asp Asp
    370                 375                 380

Trp Ser Phe Ile Lys Lys Ser Val Ser Phe Lys Tyr Asp Glu Ser Val
385                 390                 395                 400

Gly Asp Pro Lys Lys Lys Ile Lys Ser Pro Leu Lys Tyr Glu Lys Glu
                405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
        435                 440                 445

Ile Arg Leu Glu Ala Tyr Phe Ala Glu Phe Lys Ser Lys Asp Asp Ala
    450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
```

500 505 510

Lys Ser Leu Gln Phe Phe Leu Lys Pro Leu Leu Ser Ala Glu Ile Phe
515 520 525

Asp Glu Lys Asp Leu Gly Phe Tyr Asn Gln Leu Glu Gly Tyr Tyr Glu
530 535 540

Glu Ile Asp Ile Ser Gly His Leu Tyr Asn Lys Val Arg Asn Tyr Leu
545 550 555 560

Thr Gly Lys Ile Tyr Ser Lys Glu Lys Phe Lys Leu Asn Phe Glu Asn
565 570 575

Ser Thr Leu Leu Lys Gly Trp Asp Glu Asn Arg Glu Val Ala Asn Leu
580 585 590

Cys Val Ile Phe Arg Glu Asp Gln Lys Tyr Tyr Leu Gly Val Met Asp
595 600 605

Lys Glu Asn Asn Thr Ile Leu Ser Asp Ile Pro Lys Val Lys Pro Asn
610 615 620

Glu Leu Phe Tyr Glu Lys Met Val Tyr Lys Leu Ile Pro Thr Pro His
625 630 635 640

Met Gln Leu Pro Arg Ile Ile Phe Ser Ser Asp Asn Leu Ser Ile Tyr
645 650 655

Asn Pro Ser Lys Ser Ile Leu Lys Ile Arg Glu Ala Lys Ser Phe Lys
660 665 670

Glu Gly Lys Asn Phe Lys Leu Lys Asp Cys His Lys Phe Ile Asp Phe
675 680 685

Tyr Lys Glu Ser Ile Ser Lys Asn Glu Asp Trp Ser Arg Phe Asp Phe
690 695 700

Lys Phe Ser Lys Thr Ser Ser Tyr Glu Asn Ile Ser Glu Phe Tyr Arg
705 710 715 720

Glu Val Glu Arg Gln Gly Tyr Asn Leu Asp Phe Lys Lys Val Ser Lys
725 730 735

Phe Tyr Ile Asp Ser Leu Val Glu Asp Gly Lys Leu Tyr Leu Phe Gln
740 745 750

Ile Tyr Asn Lys Asp Phe Ser Ile Phe Ser Lys Gly Lys Pro Asn Leu
755 760 765

His Thr Ile Tyr Phe Arg Ser Leu Phe Ser Lys Glu Asn Leu Lys Asp
770 775 780

Val Cys Leu Lys Leu Asn Gly Glu Ala Glu Met Phe Phe Arg Lys Lys
785 790 795 800

Ser Ile Asn Tyr Asp Glu Lys Lys Lys Arg Glu Gly His His Pro Glu
805 810 815

Leu Phe Glu Lys Leu Lys Tyr Pro Ile Leu Lys Asp Lys Arg Tyr Ser
820 825 830

Glu Asp Lys Phe Gln Phe His Leu Pro Ile Ser Leu Asn Phe Lys Ser
835 840 845

Lys Glu Arg Leu Asn Phe Asn Leu Lys Val Asn Glu Phe Leu Lys Arg
850 855 860

Asn Lys Asp Ile Asn Ile Ile Gly Ile Asp Arg Gly Glu Arg Asn Leu
865 870 875 880

Leu Tyr Leu Val Met Ile Asn Gln Lys Gly Glu Ile Leu Lys Gln Thr
885 890 895

Leu Leu Asp Ser Met Gln Ser Gly Lys Gly Arg Pro Glu Ile Asn Tyr
900 905 910

Lys Glu Lys Leu Gln Glu Lys Glu Ile Glu Arg Asp Lys Ala Arg Lys
915 920 925

Ser Trp Gly Thr Val Glu Asn Ile Lys Glu Leu Lys Glu Gly Tyr Leu
930 935 940

Ser Ile Val Ile His Gln Ile Ser Lys Leu Met Val Glu Asn Asn Ala
945 950 955 960

Ile Val Val Leu Glu Asp Leu Asn Ile Gly Phe Lys Arg Gly Arg Gln
965 970 975

Lys Val Glu Arg Gln Val Tyr Gln Lys Phe Glu Lys Met Leu Ile Asp
980 985 990

Lys Leu Asn Phe Leu Val Phe Lys Glu Asn Lys Pro Thr Glu Pro Gly
995 1000 1005

Gly Val Leu Lys Ala Tyr Gln Leu Thr Asp Glu Phe Gln Ser Phe
1010 1015 1020

Glu Lys Leu Ser Lys Gln Thr Gly Phe Leu Phe Tyr Val Pro Ser
1025 1030 1035

Trp Asn Thr Ser Lys Ile Asp Pro Arg Thr Gly Phe Ile Asp Phe
1040 1045 1050

Leu His Pro Ala Tyr Glu Asn Ile Glu Lys Ala Lys Gln Trp Ile
1055 1060 1065

Asn Lys Phe Asp Ser Ile Arg Phe Asn Ser Lys Met Asp Trp Phe
1070 1075 1080

Glu Phe Thr Ala Asp Thr Arg Lys Phe Ser Glu Asn Leu Met Leu
1085 1090 1095

Gly Lys Asn Arg Val Trp Val Ile Cys Thr Thr Asn Val Glu Arg
1100 1105 1110

Tyr Phe Thr Ser Lys Thr Ala Asn Ser Ser Ile Gln Tyr Asn Ser
1115 1120 1125

Ile Gln Ile Thr Glu Lys Leu Lys Glu Leu Phe Val Asp Ile Pro
1130 1135 1140

Phe Ser Asn Gly Gln Asp Leu Lys Pro Glu Ile Leu Arg Lys Asn
1145 1150 1155

Asp Ala Val Phe Phe Lys Ser Leu Leu Phe Tyr Ile Lys Thr Thr
1160 1165 1170

Leu Ser Leu Arg Gln Asn Asn Gly Lys Lys Gly Glu Glu Glu Lys
1175 1180 1185

Asp Phe Ile Leu Ser Pro Val Val Asp Ser Lys Gly Arg Phe Phe
1190 1195 1200

Asn Ser Leu Glu Ala Ser Asp Asp Glu Pro Lys Asp Ala Asp Ala
1205 1210 1215

Asn Gly Ala Tyr His Ile Ala Leu Lys Gly Leu Met Asn Leu Leu
1220 1225 1230

Val Leu Asn Glu Thr Lys Glu Glu Asn Leu Ser Arg Pro Lys Trp
1235 1240 1245

Lys Ile Lys Asn Lys Asp Trp Leu Glu Phe Val Trp Glu Arg Asn
1250 1255 1260

Arg

<210> SEQ ID NO 11
<211> LENGTH: 1373
<212> TYPE: PRT
<213> ORGANISM: Moraxella bovoculi

<400> SEQUENCE: 11

Met Leu Phe Gln Asp Phe Thr His Leu Tyr Pro Leu Ser Lys Thr Val
1 5 10 15

-continued

```
Arg Phe Glu Leu Phe Ile Asp Arg Thr Leu Glu His Ile His Ala Lys
            20                  25                  30

Asn Phe Leu Ser Gln Asp Glu Thr Met Ala Asp Met His Gln Lys Val
        35                  40                  45

Lys Val Ile Leu Asp Asp Tyr His Arg Asp Phe Ile Ala Asp Met Met
    50                  55                  60

Gly Glu Val Lys Leu Thr Lys Leu Ala Glu Phe Tyr Asp Val Tyr Leu
65                  70                  75                  80

Lys Phe Arg Lys Asn Pro Lys Asp Asp Glu Leu Gln Lys Ala Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430
```

-continued

```
His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
```

```
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Lys
    930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                1005

Ser Leu  Asn Asp Ile Thr Thr  Ala Ser Ala Asn Gly  Thr Gln Met
    1010                1015                1020

Thr Thr  Pro Tyr His Lys Ile  Leu Asp Lys Arg Glu  Ile Glu Arg
    1025                1030                1035

Leu Asn  Ala Arg Val Gly Trp  Gly Glu Ile Glu Thr  Ile Lys Glu
    1040                1045                1050

Leu Lys  Ser Gly Tyr Leu Ser  His Val Val His Gln  Ile Ser Gln
    1055                1060                1065

Leu Met  Leu Lys Tyr Asn Ala  Ile Val Val Leu Glu  Asp Leu Asn
    1070                1075                1080

Phe Gly  Phe Lys Arg Gly Arg  Phe Lys Val Glu Lys  Gln Ile Tyr
    1085                1090                1095

Gln Asn  Phe Glu Asn Ala Leu  Ile Lys Lys Leu Asn  His Leu Val
    1100                1105                1110

Leu Lys  Asp Lys Ala Asp Asp  Glu Ile Gly Ser Tyr  Lys Asn Ala
    1115                1120                1125

Leu Gln  Leu Thr Asn Asn Phe  Thr Asp Leu Lys Ser  Ile Gly Lys
    1130                1135                1140

Gln Thr  Gly Phe Leu Phe Tyr  Val Pro Ala Trp Asn  Thr Ser Lys
    1145                1150                1155

Ile Asp  Pro Glu Thr Gly Phe  Val Asp Leu Leu Lys  Pro Arg Tyr
    1160                1165                1170

Glu Asn  Ile Gln Ala Ser Gln  Ala Phe Phe Gly Lys  Phe Asp Lys
    1175                1180                1185

Ile Cys  Tyr Asn Ala Asp Lys  Asp Tyr Phe Glu Phe  His Ile Asp
    1190                1195                1200

Tyr Ala  Lys Phe Thr Asp Lys  Ala Lys Asn Ser Arg  Gln Ile Trp
    1205                1210                1215

Thr Ile  Cys Ser His Gly Asp  Lys Arg Tyr Val Tyr  Asp Lys Thr
    1220                1225                1230

Ala Asn  Gln Asn Lys Gly Ala  Ala Lys Gly Ile Asn  Val Asn Asp
    1235                1240                1245

Ile Leu  Lys Ser Leu Phe Ala  Arg His His Ile Asn  Glu Lys Gln
    1250                1255                1260
```

```
Pro Asn  Leu Val Met Asp Ile  Cys Gln Asn Asn Asp  Lys Glu Phe
    1265                 1270                 1275

His Lys  Ser Leu Met Tyr Leu  Leu Lys Thr Leu Leu  Ala Leu Arg
    1280                 1285                 1290

Tyr Ser  Asn Ala Ser Ser Asp  Glu Asp Phe Ile Leu  Ser Pro Val
    1295                 1300                 1305

Ala Asn  Asp Glu Gly Val Phe  Phe Asn Ser Ala Leu  Ala Asp Asp
    1310                 1315                 1320

Thr Gln  Pro Gln Asn Ala Asp  Ala Asn Gly Ala Tyr  His Ile Ala
    1325                 1330                 1335

Leu Lys  Gly Leu Trp Leu Leu  Asn Glu Leu Lys Asn  Ser Asp Asp
    1340                 1345                 1350

Leu Asn  Lys Val Lys Leu Ala  Ile Asp Asn Gln Thr  Trp Leu Asn
    1355                 1360                 1365

Phe Ala  Gln Asn Arg
    1370


<210> SEQ ID NO 12
<211> LENGTH: 1352
<212> TYPE: PRT
<213> ORGANISM: Parcubacteria bacterium

<400> SEQUENCE: 12

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
```

-continued

```
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670
```

```
Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
        755                 760                 765

Gln Lys Tyr Gly Tyr Lys Ile Ser Phe Arg Asp Ile Asp Asp Glu Tyr
    770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
        835                 840                 845

Asn Glu Arg Glu Lys Ile Thr Thr Gln Lys Asn Gln Cys Ile Leu Asp
    850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
    930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys  Tyr Ser Ala Ile Val  Val Leu Glu
        995                 1000                1005

Asp Leu  Asn Met Arg Phe Lys  Gln Ile Arg Gly Gly  Ile Glu Arg
    1010                1015                1020

Ser Val  Tyr Gln Gln Phe Glu  Lys Ala Leu Ile Asp  Lys Leu Gly
    1025                1030                1035

Tyr Leu  Val Phe Lys Asp Asn  Arg Asp Leu Arg Ala  Pro Gly Gly
    1040                1045                1050

Val Leu  Asn Gly Tyr Gln Leu  Ser Ala Pro Phe Val  Ser Phe Glu
    1055                1060                1065

Lys Met  Arg Lys Gln Thr Gly  Ile Leu Phe Tyr Thr  Gln Ala Glu
    1070                1075                1080
```

-continued

Tyr Thr Ser Lys Thr Asp Pro Ile Thr Gly Phe Arg Lys Asn Val
1085 1090 1095

Tyr Ile Ser Asn Ser Ala Ser Leu Asp Lys Ile Lys Glu Ala Val
1100 1105 1110

Lys Lys Phe Asp Ala Ile Gly Trp Asp Gly Lys Glu Gln Ser Tyr
1115 1120 1125

Phe Phe Lys Tyr Asn Pro Tyr Asn Leu Ala Asp Glu Lys Tyr Lys
1130 1135 1140

Asn Ser Thr Val Ser Lys Glu Trp Ala Ile Phe Ala Ser Ala Pro
1145 1150 1155

Arg Ile Arg Arg Gln Lys Gly Glu Asp Gly Tyr Trp Lys Tyr Asp
1160 1165 1170

Arg Val Lys Val Asn Glu Glu Phe Glu Lys Leu Leu Lys Val Trp
1175 1180 1185

Asn Phe Val Asn Pro Lys Ala Thr Asp Ile Lys Gln Glu Ile Ile
1190 1195 1200

Lys Lys Ile Lys Ala Gly Asp Leu Gln Gly Glu Lys Glu Leu Asp
1205 1210 1215

Gly Arg Leu Arg Asn Phe Trp His Ser Phe Ile Tyr Leu Phe Asn
1220 1225 1230

Leu Val Leu Glu Leu Arg Asn Ser Phe Ser Leu Gln Ile Lys Ile
1235 1240 1245

Lys Ala Gly Glu Val Ile Ala Val Asp Glu Gly Val Asp Phe Ile
1250 1255 1260

Ala Ser Pro Val Lys Pro Phe Phe Thr Thr Pro Asn Pro Tyr Ile
1265 1270 1275

Pro Ser Asn Leu Cys Trp Leu Ala Val Glu Asn Ala Asp Ala Asn
1280 1285 1290

Gly Ala Tyr Asn Ile Ala Arg Lys Gly Val Met Ile Leu Lys Lys
1295 1300 1305

Ile Arg Glu His Ala Lys Lys Asp Pro Glu Phe Lys Lys Leu Pro
1310 1315 1320

Asn Leu Phe Ile Ser Asn Ala Glu Trp Asp Glu Ala Ala Arg Asp
1325 1330 1335

Trp Gly Lys Tyr Ala Gly Thr Thr Ala Leu Asn Leu Asp His
1340 1345 1350

<210> SEQ ID NO 13
<211> LENGTH: 1260
<212> TYPE: PRT
<213> ORGANISM: Porphyromonas crevioricanis

<400> SEQUENCE: 13

Met Asp Ser Leu Lys Asp Phe Thr Asn Leu Tyr Pro Val Ser Lys Thr
1 5 10 15

Leu Arg Phe Glu Leu Lys Pro Val Gly Lys Thr Leu Glu Asn Ile Glu
20 25 30

Lys Ala Gly Ile Leu Lys Glu Asp Glu His Arg Ala Glu Ser Tyr Arg
35 40 45

Arg Val Lys Lys Ile Ile Asp Thr Tyr His Lys Val Phe Ile Asp Ser
50 55 60

Ser Leu Glu Asn Met Ala Lys Met Gly Ile Glu Asn Glu Ile Lys Ala
65 70 75 80

Met Leu Gln Ser Phe Cys Glu Leu Tyr Lys Lys Asp His Arg Thr Glu
85 90 95

-continued

```
Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510
```

-continued

```
Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
```

-continued 930 935 940

Ala Val His Arg Ile Ala Glu Leu Met Val Ala Tyr Lys Ala Val Val
945 950 955 960

Ala Leu Glu Asp Leu Asn Met Gly Phe Lys Arg Gly Arg Gln Lys Val
965 970 975

Glu Ser Ser Val Tyr Gln Gln Phe Glu Lys Gln Leu Ile Asp Lys Leu
980 985 990

Asn Tyr Leu Val Asp Lys Lys Lys Arg Pro Glu Asp Ile Gly Gly Leu
995 1000 1005

Leu Arg Ala Tyr Gln Phe Thr Ala Pro Phe Lys Ser Phe Lys Glu
1010 1015 1020

Met Gly Lys Gln Asn Gly Phe Leu Phe Tyr Ile Pro Ala Trp Asn
1025 1030 1035

Thr Ser Asn Ile Asp Pro Thr Thr Gly Phe Val Asn Leu Phe His
1040 1045 1050

Val Gln Tyr Glu Asn Val Asp Lys Ala Lys Ser Phe Phe Gln Lys
1055 1060 1065

Phe Asp Ser Ile Ser Tyr Asn Pro Lys Lys Asp Trp Phe Glu Phe
1070 1075 1080

Ala Phe Asp Tyr Lys Asn Phe Thr Lys Lys Ala Glu Gly Ser Arg
1085 1090 1095

Ser Met Trp Ile Leu Cys Thr His Gly Ser Arg Ile Lys Asn Phe
1100 1105 1110

Arg Asn Ser Gln Lys Asn Gly Gln Trp Asp Ser Glu Glu Phe Ala
1115 1120 1125

Leu Thr Glu Ala Phe Lys Ser Leu Phe Val Arg Tyr Glu Ile Asp
1130 1135 1140

Tyr Thr Ala Asp Leu Lys Thr Ala Ile Val Asp Glu Lys Gln Lys
1145 1150 1155

Asp Phe Phe Val Asp Leu Leu Lys Leu Phe Lys Leu Thr Val Gln
1160 1165 1170

Met Arg Asn Ser Trp Lys Glu Lys Asp Leu Asp Tyr Leu Ile Ser
1175 1180 1185

Pro Val Ala Gly Ala Asp Gly Arg Phe Phe Asp Thr Arg Glu Gly
1190 1195 1200

Asn Lys Ser Leu Pro Lys Asp Ala Asp Ala Asn Gly Ala Tyr Asn
1205 1210 1215

Ile Ala Leu Lys Gly Leu Trp Ala Leu Arg Gln Ile Arg Gln Thr
1220 1225 1230

Ser Glu Gly Gly Lys Leu Lys Leu Ala Ile Ser Asn Lys Glu Trp
1235 1240 1245

Leu Gln Phe Val Gln Glu Arg Ser Tyr Glu Lys Asp
1250 1255 1260

<210> SEQ ID NO 14
<211> LENGTH: 1324
<212> TYPE: PRT
<213> ORGANISM: Prevotella disiens

<400> SEQUENCE: 14

Met Glu Asn Tyr Gln Glu Phe Thr Asn Leu Phe Gln Leu Asn Lys Thr
1 5 10 15

Leu Arg Phe Glu Leu Lys Pro Ile Gly Lys Thr Cys Glu Leu Leu Glu
20 25 30

```
Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
        435                 440                 445

Asn Ser Gly Asn Met Pro Arg Lys Val Glu Asp Tyr Phe Ser Leu Met
```

450 455 460

Arg Lys Gly Asp Phe Gly Ser Asn Asp Leu Ile Glu Asn Ile Lys Thr
465 470 475 480

Lys Leu Ser Ala Ala Glu Lys Leu Leu Gly Thr Lys Tyr Gln Glu Thr
485 490 495

Ala Lys Asp Ile Phe Lys Lys Asp Glu Asn Ser Lys Leu Ile Lys Glu
500 505 510

Leu Leu Asp Ala Thr Lys Gln Phe Gln His Phe Ile Lys Pro Leu Leu
515 520 525

Gly Thr Gly Glu Glu Ala Asp Arg Asp Leu Val Phe Tyr Gly Asp Phe
530 535 540

Leu Pro Leu Tyr Glu Lys Phe Glu Glu Leu Thr Leu Leu Tyr Asn Lys
545 550 555 560

Val Arg Asn Arg Leu Thr Gln Lys Pro Tyr Ser Lys Asp Lys Ile Arg
565 570 575

Leu Cys Phe Asn Lys Pro Lys Leu Met Thr Gly Trp Val Asp Ser Lys
580 585 590

Thr Glu Lys Ser Asp Asn Gly Thr Gln Tyr Gly Gly Tyr Leu Phe Arg
595 600 605

Lys Lys Asn Glu Ile Gly Glu Tyr Asp Tyr Phe Leu Gly Ile Ser Ser
610 615 620

Lys Ala Gln Leu Phe Arg Lys Asn Glu Ala Val Ile Gly Asp Tyr Glu
625 630 635 640

Arg Leu Asp Tyr Tyr Gln Pro Lys Ala Asn Thr Ile Tyr Gly Ser Ala
645 650 655

Tyr Glu Gly Glu Asn Ser Tyr Lys Glu Asp Lys Lys Arg Leu Asn Lys
660 665 670

Val Ile Ile Ala Tyr Ile Glu Gln Ile Lys Gln Thr Asn Ile Lys Lys
675 680 685

Ser Ile Ile Glu Ser Ile Ser Lys Tyr Pro Asn Ile Ser Asp Asp Asp
690 695 700

Lys Val Thr Pro Ser Ser Leu Leu Glu Lys Ile Lys Lys Val Ser Ile
705 710 715 720

Asp Ser Tyr Asn Gly Ile Leu Ser Phe Lys Ser Phe Gln Ser Val Asn
725 730 735

Lys Glu Val Ile Asp Asn Leu Leu Lys Thr Ile Ser Pro Leu Lys Asn
740 745 750

Lys Ala Glu Phe Leu Asp Leu Ile Asn Lys Asp Tyr Gln Ile Phe Thr
755 760 765

Glu Val Gln Ala Val Ile Asp Glu Ile Cys Lys Gln Lys Thr Phe Ile
770 775 780

Tyr Phe Pro Ile Ser Asn Val Glu Leu Glu Lys Glu Met Gly Asp Lys
785 790 795 800

Asp Lys Pro Leu Cys Leu Phe Gln Ile Ser Asn Lys Asp Leu Ser Phe
805 810 815

Ala Lys Thr Phe Ser Ala Asn Leu Arg Lys Lys Arg Gly Ala Glu Asn
820 825 830

Leu His Thr Met Leu Phe Lys Ala Leu Met Glu Gly Asn Gln Asp Asn
835 840 845

Leu Asp Leu Gly Ser Gly Ala Ile Phe Tyr Arg Ala Lys Ser Leu Asp
850 855 860

Gly Asn Lys Pro Thr His Pro Ala Asn Glu Ala Ile Lys Cys Arg Asn
865 870 875 880

```
Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
        915                 920                 925

Thr Glu Tyr Ile Arg Lys Ala Asp Asp Leu His Ile Ile Gly Ile Asp
    930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
            980                 985                 990

Ala Asn Arg Gln Asn Trp Glu Ala  Val Glu Gly Ile Lys  Asp Leu Lys
        995                 1000                 1005

Lys Gly  Tyr Leu Ser Gln Ala  Val His Gln Ile Ala  Gln Leu Met
    1010                 1015                 1020

Leu Lys  Tyr Asn Ala Ile Ile  Ala Leu Glu Asp Leu  Gly Gln Met
    1025                 1030                 1035

Phe Val  Thr Arg Gly Gln Lys  Ile Glu Lys Ala Val  Tyr Gln Gln
    1040                 1045                 1050

Phe Glu  Lys Ser Leu Val Asp  Lys Leu Ser Tyr Leu  Val Asp Lys
    1055                 1060                 1065

Lys Arg  Pro Tyr Asn Glu Leu  Gly Gly Ile Leu Lys  Ala Tyr Gln
    1070                 1075                 1080

Leu Ala  Ser Ser Ile Thr Lys  Asn Asn Ser Asp Lys  Gln Asn Gly
    1085                 1090                 1095

Phe Leu  Phe Tyr Val Pro Ala  Trp Asn Thr Ser Lys  Ile Asp Pro
    1100                 1105                 1110

Val Thr  Gly Phe Thr Asp Leu  Leu Arg Pro Lys Ala  Met Thr Ile
    1115                 1120                 1125

Lys Glu  Ala Gln Asp Phe Phe  Gly Ala Phe Asp Asn  Ile Ser Tyr
    1130                 1135                 1140

Asn Asp  Lys Gly Tyr Phe Glu  Phe Glu Thr Asn Tyr  Asp Lys Phe
    1145                 1150                 1155

Lys Ile  Arg Met Lys Ser Ala  Gln Thr Arg Trp Thr  Ile Cys Thr
    1160                 1165                 1170

Phe Gly  Asn Arg Ile Lys Arg  Lys Lys Asp Lys Asn  Tyr Trp Asn
    1175                 1180                 1185

Tyr Glu  Glu Val Glu Leu Thr  Glu Glu Phe Lys Lys  Leu Phe Lys
    1190                 1195                 1200

Asp Ser  Asn Ile Asp Tyr Glu  Asn Cys Asn Leu Lys  Glu Glu Ile
    1205                 1210                 1215

Gln Asn  Lys Asp Asn Arg Lys  Phe Phe Asp Asp Leu  Ile Lys Leu
    1220                 1225                 1230

Leu Gln  Leu Thr Leu Gln Met  Arg Asn Ser Asp Asp  Lys Gly Asn
    1235                 1240                 1245

Asp Tyr  Ile Ile Ser Pro Val  Ala Asn Ala Glu Gly  Gln Phe Phe
    1250                 1255                 1260

Asp Ser  Arg Asn Gly Asp Lys  Lys Leu Pro Leu Asp  Ala Asp Ala
    1265                 1270                 1275
```

Asn Gly Ala Tyr Asn Ile Ala Arg Lys Gly Leu Trp Asn Ile Arg
    1280                1285                1290

Gln Ile Lys Gln Thr Lys Asn Lys Asp Asp Leu Asn Leu Ser Ile
    1295                1300                1305

Ser Ser Thr Glu Trp Leu Asp Phe Val Arg Glu Lys Pro Tyr Leu
    1310                1315                1320

Lys

<210> SEQ ID NO 15
<211> LENGTH: 1484
<212> TYPE: PRT
<213> ORGANISM: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 15

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

-continued

```
Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
    370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445

Glu Asp Asp Ile Lys Ile Pro Glu Ala Ile Glu Leu Ser Gly Leu Phe
    450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
            500                 505                 510

Met Glu Ser Phe Leu Lys Glu Thr Asn Asp Ile Ile Thr Leu Lys Lys
        515                 520                 525

Tyr Lys Gly Asn Lys Glu Gly Thr Glu Lys Ile Lys Gln Trp Phe Asp
    530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
            580                 585                 590

Ala Leu Arg Asn Tyr Leu Thr Gln Lys Pro Gln Asp Glu Ala Lys Glu
        595                 600                 605

Asn Lys Leu Lys Leu Asn Phe Asp Asn Pro Ser Leu Ala Gly Gly Trp
    610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
        675                 680                 685

Glu Tyr Asp Phe Trp Ala Asp Val Ser Lys Met Ile Pro Lys Cys Ser
    690                 695                 700

Thr Gln Leu Lys Ala Val Val Asn His Phe Lys Gln Ser Asp Asn Glu
705                 710                 715                 720
```

-continued

```
Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
        755                 760                 765

Ser Thr Gln Glu Lys Gln Tyr Ile Lys Ala Phe Gln Lys Glu Tyr Trp
    770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
            820                 825                 830

Asn Phe Cys Lys Tyr Phe Leu Ser Lys Tyr Pro Lys Thr Thr Leu Phe
        835                 840                 845

Asn Tyr Ser Phe Lys Glu Ser Glu Asn Tyr Asn Ser Leu Asp Glu Phe
    850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
                885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
        915                 920                 925

Phe Asp Asn Arg Pro Lys Leu Asn Gly Glu Ala Glu Ile Phe Tyr Arg
    930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr  Lys Phe Tyr Asn Phe  Ser Asn Leu
        995                 1000                 1005

His Phe  Leu Gly Ile Asp Arg  Gly Glu Lys His Leu  Ala Tyr Tyr
    1010                 1015                 1020

Ser Leu  Val Asn Lys Asn Gly  Glu Ile Val Asp Gln  Gly Thr Leu
    1025                 1030                 1035

Asn Leu  Pro Phe Thr Asp Lys  Asp Gly Asn Gln Arg  Ser Ile Lys
    1040                 1045                 1050

Lys Glu  Lys Tyr Phe Tyr Asn  Lys Gln Glu Asp Lys  Trp Glu Ala
    1055                 1060                 1065

Lys Glu  Val Asp Xaa Trp Asn  Tyr Asn Asp Leu Leu  Asp Ala Met
    1070                 1075                 1080

Ala Ser  Asn Arg Asp Met Ala  Arg Lys Asn Trp Gln  Arg Ile Gly
    1085                 1090                 1095

Thr Ile  Lys Glu Ala Lys Asn  Gly Tyr Val Ser Leu  Val Ile Arg
    1100                 1105                 1110

Lys Ile  Ala Asp Leu Ala Val  Asn Asn Glu Arg Pro  Ala Phe Ile
    1115                 1120                 1125

Val Leu  Glu Asp Leu Asn Thr  Gly Phe Lys Arg Ser  Arg Gln Lys
```

-continued

```
    1130                1135                1140

Ile Asp  Lys Ser Val Tyr Gln  Lys Phe Glu Leu Ala  Leu Ala Lys
    1145                1150                1155

Lys Leu  Asn Phe Leu Val Asp  Lys Asn Ala Lys Arg  Asp Glu Ile
    1160                1165                1170

Gly Ser  Pro Thr Lys Ala Leu  Gln Leu Thr Pro Pro  Val Asn Asn
    1175                1180                1185

Tyr Gly  Asp Ile Glu Asn Lys  Lys Gln Ala Gly Ile  Met Leu Tyr
    1190                1195                1200

Thr Arg  Ala Asn Tyr Thr Ser  Gln Thr Asp Pro Ala  Thr Gly Trp
    1205                1210                1215

Arg Lys  Thr Ile Tyr Leu Lys  Ala Gly Pro Glu Glu  Thr Thr Tyr
    1220                1225                1230

Lys Lys  Asp Gly Lys Ile Lys  Asn Lys Ser Val Lys  Asp Gln Ile
    1235                1240                1245

Ile Glu  Thr Phe Thr Asp Ile  Gly Phe Asp Gly Lys  Asp Tyr Tyr
    1250                1255                1260

Phe Glu  Tyr Asp Lys Gly Glu  Phe Val Asp Glu Lys  Thr Gly Glu
    1265                1270                1275

Ile Lys  Pro Lys Lys Trp Arg  Leu Tyr Ser Gly Glu  Asn Gly Lys
    1280                1285                1290

Ser Leu  Asp Arg Phe Arg Gly  Glu Arg Glu Lys Asp  Lys Tyr Glu
    1295                1300                1305

Trp Lys  Ile Asp Lys Ile Asp  Ile Val Lys Ile Leu  Asp Asp Leu
    1310                1315                1320

Phe Val  Asn Phe Asp Lys Asn  Ile Ser Leu Leu Lys  Gln Leu Lys
    1325                1330                1335

Glu Gly  Val Glu Leu Thr Arg  Asn Asn Glu His Gly  Thr Gly Glu
    1340                1345                1350

Ser Leu  Arg Phe Ala Ile Asn  Leu Ile Gln Gln Ile  Arg Asn Thr
    1355                1360                1365

Gly Asn  Asn Glu Arg Asp Asn  Asp Phe Ile Leu Ser  Pro Val Arg
    1370                1375                1380

Asp Glu  Asn Gly Lys His Phe  Asp Ser Arg Glu Tyr  Trp Asp Lys
    1385                1390                1395

Glu Thr  Lys Gly Glu Lys Ile  Ser Met Pro Ser Ser  Gly Asp Ala
    1400                1405                1410

Asn Gly  Ala Phe Asn Ile Ala  Arg Lys Gly Ile Ile  Met Asn Ala
    1415                1420                1425

His Ile  Leu Ala Asn Ser Asp  Ser Lys Asp Leu Ser  Leu Phe Val
    1430                1435                1440

Ser Asp  Glu Glu Trp Asp Leu  His Leu Asn Asn Lys  Thr Glu Trp
    1445                1450                1455

Lys Lys  Gln Leu Asn Ile Phe  Ser Ser Arg Lys Ala  Met Ala Lys
    1460                1465                1470

Arg Lys  Lys Lys Arg Pro Ala  Ala Thr Lys Lys
    1475                1480
```

<210> SEQ ID NO 16
<211> LENGTH: 1245
<212> TYPE: PRT
<213> ORGANISM: Porphyromonas macacae

<400> SEQUENCE: 16

-continued

```
Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
    130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
```

-continued

```
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845
```

```
Ala Gln Asn Asp Asp Leu Gln His Gly Ile Asp Arg Gly Glu Arg Asn
    850                 855                 860

Leu Leu Tyr Ile Ser Arg Ile Asp Thr Arg Gly Asn Leu Leu Glu Gln
865                 870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
            900                 905                 910

Gln Glu Trp Lys Ser Ile Glu Ser Ile Lys Asp Leu Lys Asp Gly Tyr
        915                 920                 925

Met Ser Gln Val Val His Lys Ile Cys Asn Met Val Val Glu His Lys
    930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
            980                 985                 990

Pro Gly Gly Leu Tyr Ala Ala Tyr  Gln Leu Thr Asn Pro  Leu Phe Ser
        995                 1000                1005

Phe Glu  Glu Leu His Arg Tyr  Pro Gln Ser Gly Ile  Leu Phe Phe
    1010                 1015                 1020

Val Asp  Pro Trp Asn Thr Ser  Leu Thr Asp Pro Ser  Thr Gly Phe
    1025                 1030                 1035

Val Asn  Leu Leu Gly Arg Ile  Asn Tyr Thr Asn Val  Gly Asp Ala
    1040                 1045                 1050

Arg Lys  Phe Phe Asp Arg Phe  Asn Ala Ile Arg Tyr  Asp Gly Lys
    1055                 1060                 1065

Gly Asn  Ile Leu Phe Asp Leu  Asp Leu Ser Arg Phe  Asp Val Arg
    1070                 1075                 1080

Val Glu  Thr Gln Arg Lys Leu  Trp Thr Leu Thr Thr  Phe Gly Ser
    1085                 1090                 1095

Arg Ile  Ala Lys Ser Lys Lys  Ser Gly Lys Trp Met  Val Glu Arg
    1100                 1105                 1110

Ile Glu  Asn Leu Ser Leu Cys  Phe Leu Glu Leu Phe  Glu Gln Phe
    1115                 1120                 1125

Asn Ile  Gly Tyr Arg Val Glu  Lys Asp Leu Lys Lys  Ala Ile Leu
    1130                 1135                 1140

Ser Gln  Asp Arg Lys Glu Phe  Tyr Val Arg Leu Ile  Tyr Leu Phe
    1145                 1150                 1155

Asn Leu  Met Met Gln Ile Arg  Asn Ser Asp Gly Glu  Glu Asp Tyr
    1160                 1165                 1170

Ile Leu  Ser Pro Ala Leu Asn  Glu Lys Asn Leu Gln  Phe Asp Ser
    1175                 1180                 1185

Arg Leu  Ile Glu Ala Lys Asp  Leu Pro Val Asp Ala  Asp Ala Asn
    1190                 1195                 1200

Gly Ala  Tyr Asn Val Ala Arg  Lys Gly Leu Met Val  Val Gln Arg
    1205                 1210                 1215

Ile Lys  Arg Gly Asp His Glu  Ser Ile His Arg Ile  Gly Arg Ala
    1220                 1225                 1230

Gln Trp  Leu Arg Tyr Val Gln  Glu Gly Ile Val Glu
    1235                 1240                 1245
```

<210> SEQ ID NO 17
<211> LENGTH: 1250
<212> TYPE: PRT
<213> ORGANISM: Smithella sp.

<400> SEQUENCE: 17

```
Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285

Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
        355                 360                 365

Gly Glu Trp Ser Ile Ile Asn Arg Ala Leu Asp Asn Tyr Tyr Ala Thr
    370                 375                 380
```

```
Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
        435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510

Glu Thr Phe Tyr Ser Leu Phe Thr Pro Leu Tyr Asp His Leu Thr Gln
        515                 520                 525

Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590

Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
    610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
    690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
    770                 775                 780

Lys Asn Thr Thr Ile His Lys Ala Asn Glu Ser Ile Ile Asn Lys Asn
785                 790                 795                 800
```

```
Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
        835                 840                 845

Gln Phe Leu Lys Ala Asn Pro Asp Ile Asn Ile Ile Gly Ile Asp Arg
    850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
    930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala  Phe Gln Leu Ala Asn  Lys Phe Glu
        995                 1000                1005

Ser Phe  Gln Lys Met Gly Lys  Gln Asn Gly Phe Ile  Phe Tyr Val
    1010                1015                1020

Pro Ala  Trp Asn Thr Ser Lys  Thr Asp Pro Ala Thr  Gly Phe Ile
    1025                1030                1035

Asp Phe  Leu Lys Pro Arg Tyr  Glu Asn Leu Asn Gln  Ala Lys Asp
    1040                1045                1050

Phe Phe  Glu Lys Phe Asp Ser  Ile Arg Leu Asn Ser  Lys Ala Asp
    1055                1060                1065

Tyr Phe  Glu Phe Ala Phe Asp  Phe Lys Asn Phe Thr  Glu Lys Ala
    1070                1075                1080

Asp Gly  Gly Arg Thr Lys Trp  Thr Val Cys Thr Thr  Asn Glu Asp
    1085                1090                1095

Arg Tyr  Gln Trp Asn Arg Ala  Leu Asn Asn Asn Arg  Gly Ser Gln
    1100                1105                1110

Glu Lys  Tyr Asp Ile Thr Ala  Glu Leu Lys Ser Leu  Phe Asp Gly
    1115                1120                1125

Lys Val  Asp Tyr Lys Ser Gly  Lys Asp Leu Lys Gln  Gln Ile Ala
    1130                1135                1140

Ser Gln  Glu Ser Ala Asp Phe  Phe Lys Ala Leu Met  Lys Asn Leu
    1145                1150                1155

Ser Ile  Thr Leu Ser Leu Arg  His Asn Asn Gly Glu  Lys Gly Asp
    1160                1165                1170

Asn Glu  Gln Asp Tyr Ile Leu  Ser Pro Val Ala Asp  Ser Lys Gly
    1175                1180                1185

Arg Phe  Phe Asp Ser Arg Lys  Ala Asp Asp Asp Met  Pro Lys Asn
    1190                1195                1200

Ala Asp  Ala Asn Gly Ala Tyr  His Ile Ala Leu Lys  Gly Leu Trp
```

-continued 1205 1210 1215

Cys Leu Glu Gln Ile Ser Lys Thr Asp Asp Leu Lys Lys Val Lys
1220 1225 1230

Leu Ala Ile Ser Asn Lys Glu Trp Leu Glu Phe Val Gln Thr Leu
1235 1240 1245

Lys Gly
1250

<210> SEQ ID NO 18
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 18
atggccggga gcaagaagcg ccggataaag caggacacgc agttcgaggg cttcaccaac 60
ctgtaccaag tctccaagac gctccggttc gagcttatcc cgcaagggaa gaccctgaaa 120
cacatccagg aacaaggttt catcgaggag gacaaggccc gcaacgacca ctacaaggag 180
ctcaagccca taatcgatcg gatctacaag acgtacgccg accagtgcct ccaactggtg 240
cagctcgact gggagaacct gagcgccgcc attgacagct accgcaagga aaagacggag 300
gagacgcgca acgcccttat tgaggagcaa gccacctacc gcaacgccat ccacgactac 360
ttcatcgggc gcaccgacaa cctgacggac gcgatcaaca agcgccacgc ggaaatctac 420
aagggccttt tcaaggccga gctcttcaac gggaaggtcc taaaacagct cgggactgtc 480
acgacaaccg agcatgagaa cgccctcctt cgcagcttcg acaagttcac cacatacttc 540
tcgggcttct accggaaccg caagaacgtt ttcagcgccg aggacatctc caccgccatc 600
ccgcacagga tcgtccagga caacttcccc aagttcaagg agaactgcca catcttcacg 660
cgcctgatta cagccgtacc ttcacttcgt gagcacttcg agaacgtcaa aaaggccatc 720
gggatcttcg tctccacgtc catcgaggag gtattctctt tcccgttcta taaccagctc 780
ctgacccaga cgcagatcga cctctacaac cagctactgg gcggcatcag ccgggaggcc 840
gggaccgaga aaataaaggg cctcaacgaa gttctcaacc tggccatcca gaagaacgac 900
gagaccgcgc atatcatcgc atccctgccg catcgcttca ttcctttgtt caagcagata 960
ttgagcgacc ggaacaccct ctcgttcatc ctcgaagaat tcaagagcga cgaggaggtc 1020
attcagtctt tctgcaagta caagacgctc ctacggaatg agaatgtgct ggagaccgcg 1080
gaggcactct tcaatgagct gaactccatt gacctgaccc acatcttcat tagccacaag 1140
aaactggaga cgatctccag cgccctgtgc gaccactggg acactctccg caacgccctc 1200
tacgaacgcc ggatctccga acttaccggc aagataacta agtcggctaa ggagaaggtg 1260
caacggagcc tcaagcacga ggacatcaac cttcaggaaa tcatctcagc cgcgggcaag 1320
gagctgagcg aggcgtttaa gcagaaaaca tcggagatac tgagccacgc gcacgcggcc 1380
ctggatcaac cgctgccgac gactctcaag aagcaagagg agaaggaaat ccttaagtcc 1440
cagctcgact cgctgctcgg cctctatcac ttgctcgact ggttcgcggt tgatgagtcc 1500
aacgaggtgg acccggagtt ctccgcgcgc ctcacgggta ttaagctgga gatggagcca 1560
agcttaagct tctacaacaa ggcccgcaac tacgcgacca aaaaaccgta ctcagtcgag 1620
aaattcaagc tgaatttcca gatgcctaca ttggcgaggg ggtgggacgt gaaccgcgag 1680
aagaacaatg gagccatcct gttcgtcaaa aatgggttgt actacctggg catcatgccc 1740

-continued

```
aagcagaagg gccgttacaa ggccctgtca ttcgagccta ccgagaagac ctcggagggc   1800
ttcgacaaga tgtactacga ctatttcccg gacgccgcca agatgatccc gaagtgctcc   1860
acgcagctca aagccgtcac ggcccacttc cagacgcata ccacgccgat acttctgagc   1920
aacaacttca ttgagccgct agagatcacg aaggagatat acgacctaaa caaccccgaa   1980
aaggagccca agaagttcca gacagcctac gctaagaaga caggtgatca gaagggatat   2040
agggaggcac tctgcaagtg gatcgacttc acgcgcgact tcctgtcgaa atatacaaag   2100
acgaccagca ttgacctaag ttctctccgc ccatcctccc agtacaagga tctgggcgag   2160
tattatgcgg agctgaaccc attgctgtac cacatcagct tccagaggat cgccgagaag   2220
gagattatgg acgcggtgga gacggggaaa ctatacctgt tccaaatata taacaaggac   2280
ttcgctaaag ggcaccacgg gaagcccaac ctgcacacac tctactggac gggcttgttt   2340
tcgccagaaa atttggccaa gacttcgatc aagctcaacg gccaggcgga gttgttttac   2400
cgtcccaagt ctcgcatgaa gcgcatggcg catcgcctcg gagagaaaat gcttaacaag   2460
aagctcaagg atcagaagac gcccatacct gatacgttgt accaggaatt gtacgactac   2520
gtgaaccacc gcctatcgca cgacctctca gacgaggccc gcgccctcct cccaaacgtg   2580
attactaagg aggtttccca tgaaataatc aaggaccgac ggttcaccag cgacaaattt   2640
tttttccacg tgcctatcac gctcaattac caggcggcca actccccatc gaagttcaac   2700
cagcgcgtga acgcctacct taaggagcac ccggagaccc caatcatcgg gatcgaccgt   2760
ggcgagcgga acctgatcta tattacggtg atcgatagca ccgggaagat cctggagcag   2820
cgctccctga acacaatcca gcagtttgac taccagaaga aactcgacaa ccgggagaag   2880
gagcgcgtcg cagcccggca agcatggagt gtggtcggca ccataaagga cctgaaacag   2940
ggttacctaa gtcaagttat ccacgagatc gttgacctga tgatacacta tcaagccgta   3000
gtcgtgctgg agaacctcaa cttcgggttt aagtccaagc gcaccggcat cgcggagaag   3060
gcggtgtacc agcagttcga gaagatgctg atcgacaagc tgaactgcct ggtgctcaag   3120
gactaccctg cggagaaggt cggcggggtc ttgaacccgt accagctaac cgaccagttc   3180
acgagcttcg ccaaaatggg cacgcagtcc ggattcttgt tttatgtccc ggctccatat   3240
acaagtaaga tcgacccgct gacagggttt gttgacccat tcgtgtggaa gaccatcaag   3300
aaccacgaga gcaggaaaca cttcttagag ggcttcgact tcctgcatta cgacgttaag   3360
acaggcgact tcatcctgca cttcaagatg aaccgcaacc tgtcgttcca gaggggcctg   3420
cccggcttca tgcccgcctg ggatatcgtc tttgagaaga atgagacgca gttcgacgcg   3480
aaggggacgc cgttcatcgc tggaaagcgg atcgtgccgg tcatcgagaa ccaccgcttc   3540
acgggtcgct accgagattt ataccccgcc aacgaactaa ttgcgctgct ggaggagaag   3600
gggatcgtgt tccgagatgg cagcaacatt ctcccgaagc tgctggagaa cgacgactcg   3660
cacgctattg acacgatggt cgccctcata cggagcgtgc ttcagatgcg gaacagtaac   3720
gctgccacgg gcgaggacta cattaactcc cccgtccgcg acctcaacgg ggtctgcttc   3780
gatagccgct tccagaaccc ggagtggcct atggatgcgg acgcgaacgg ggcctaccac   3840
atcgccctca agggccaact cctgctcaac cacttgaagg aaagcaaaga cctcaaattg   3900
cagaatggca tcagtaacca ggactggctc gcgtacatcc aggaactgag aaacgggtcc   3960
aagaagcggc gtatcaagca agattga                                       3987
```

<210> SEQ ID NO 19
<211> LENGTH: 3987

<212> TYPE: DNA
<213> ORGANISM: Artificial sequence
<220> FEATURE:
<223> OTHER INFORMATION: Synthetic polynucleotide

<400> SEQUENCE: 19
atggcgggaa gcaaaaagcg ccggattaag caagacacgc agttcgaggg cttcacgaac 60
ctctaccaag tcagcaagac cctccggttc gagctgatac cacagggaaa gacgctcaag 120
cacatccagg aacagggctt catcgaggag gacaaggcgc gcaacgacca ctacaaggag 180
ttgaaaccga tcatcgaccg catctacaag acgtacgccg accagtgcct ccagctcgtg 240
cagctcgact gggagaacct ctccgccgcc attgactcgt accggaagga gaagactgag 300
gagacccgca acgccctgat cgaggagcaa gcaacctacc ggaacgccat ccacgactac 360
ttcatcggcc gcaccgacaa cctcaccgac gcgatcaaca agcggcacgc ggagatatac 420
aaagggctgt tcaaggcgga gctgttcaac ggcaaggtgc tcaagcagct agggacggtg 480
accacgaccg agcacgagaa cgcgctcctc cgcagcttcg acaagttcac cacctacttc 540
agcggcttct accggaaccg caagaatgtg ttcagcgcgg aggacatcag cacggccatc 600
ccgcaccgca tcgtccagga caacttcccg aagttcaagg agaactgcca catcttcacc 660
cgcctgataa ccgccgtccc ctccctgcgg gagcacttcg agaacgtcaa aaaggcaatt 720
gggatcttcg tctcgaccag cattgaggag gtgttcagct tccccttcta caaccagctc 780
ctcacccaga cgcagatcga cctgtacaat cagttgctcg gcgggataag ccgcgaggcg 840
ggaaccgaaa aaatcaaggg gctgaacgaa gtgttgaacc tcgccatcca gaagaacgac 900
gagaccgcgc acatcatcgc ctccctgccc caccggttca tcccgctgtt caagcagatc 960
ctctctgacc ggaacaccct gtccttcatt cttgaggagt tcaagtcgga cgaggaggtc 1020
atccagagct tctgcaagta caagacgctg ctacggaacg agaacgtgct ggagacggcg 1080
gaggcactgt tcaacgagct aaacagcatc gacctcacgc acatcttcat cagtcacaag 1140
aaactggaga ccatctcctc cgcgctgtgc gaccactggg acacgctcag gaacgcgctc 1200
tacgagcgcc gaatcagtga gctgacgggc aagatcacga agtccgcgaa ggagaaggtg 1260
cagcggtccc tcaagcacga ggacatcaac ctccaggaga tcatctcagc ggctgggaaa 1320
gagctgtccg aggcgttcaa gcagaaaacg agcgaaatcc tgtcccacgc gcacgcggcc 1380
ctggatcagc ctctgccgac gaccctcaag aaacaagaag aaaaggaaat cctcaagtcg 1440
cagctcgact cgctgctggg cctgtaccat ctcctcgact ggttcgccgt ggacgagagc 1500
aacgaggtgg accccgagtt ctccgcgcgg cttacgggga tcaagctgga gatggagccc 1560
agcctgtcct tctacaacaa ggcgcgcaac tacgccacca agaagcccta cagcgtggag 1620
aagttcaagc tcaacttcca gatgcccact ctcgcacgtg ggtgggacgt caaccgcgaa 1680
aaaaataatg gggcgatcct gttcgtcaag aacggcctgt actacttggg catcatgccg 1740
aaacagaagg gccgctacaa ggccctgagc ttcgaaccga ccgagaaaac gagcgagggg 1800
ttcgacaaga tgtactacga ctacttcccc gacgccgcga agatgattcc aaagtgctcc 1860
acgcagctta aggccgtgac ggcccacttc cagacgcaca cgaccccgat cctcctcagc 1920
aacaacttca tcgagcccct ggagatcacg aaggagatat acgacctgaa caaccccggag 1980 aaggagccca agaaattcca gaccgcctac gccaagaaga caggcgacca aaagggttac 2040
agggaggccc tctgcaagtg gatcgacttc actagggact tcctgtccaa gtacaccaag 2100
actacctcta tcgacctgtc cagcctccgc ccgtcgtccc agtacaaaga tttgggcgag 2160
tattacgcgg agctgaaccc actgctctac cacatcagct tccagcgcat cgcggagaag 2220
gagatcatgg acgcagtgga gacgggcaag ctatacctat ttcagatata caacaaagac 2280
ttcgctaagg gacaccacgg caagcctaac ctgcacaccc tctactggac ggggctcttc 2340
agcccggaga acctcgccaa gacctcgatc aagctcaacg gccaggccga gctgttctac 2400
cggcccaagt cccgcatgaa gcggatggcc caccggctcg gggagaaaat gctcaacaag 2460
aaattgaagg accaaaaaac gccgataccc gacaccctat accaggagct gtacgactat 2520
gtgaaccacc gcctgagcca cgacctcagc gacgaggcgc gggccctcct gccgaacgtc 2580
atcacaaagg aggtcagcca cgagatcatc aaggaccggc gcttcacctc cgacaagttt 2640
ttctttcacg tgcccatcac gctcaactac caggccgcca actcgccgtc caagttcaac 2700
cagcgcgtga acgcctacct caaggagcac cccgagaccc cgatcatcgg gattgaccga 2760
ggggagcgga acctcatcta catcaccgtc atcgacagca ccgggaagat ccttgaacag 2820
cggtcgctca acaccatcca gcagttcgac taccagaaga aactcgacaa ccgggagaag 2880
gagagagtgg cggcccgcca ggcttggtcc gtcgtcggga cgattaagga cttgaaacaa 2940
ggttacctgt cgcaagtgat ccacgagatc gttgacctga tgatccacta ccaagccgtc 3000
gtggtcctgg agaacctcaa cttcggcttc aagagcaaac gaaccggcat cgcggagaag 3060
gccgtgtacc agcagttcga aaaaatgctg atcgacaagc tgaactgcct cgtgctcaag 3120
gactaccccg ctgagaaggt cggcggggtg ctgaacccgt accagctcac tgaccagttc 3180
accagcttcg caaagatggg cacccagtcc ggcttcctgt tctacgtgcc tgcgccatac 3240
acctcgaaga tcgacccgct caccgggttc gtggacccct tcgtctggaa gaccatcaag 3300
aaccacgaga gccgcaagca cttcctggag ggcttcgact tcctccacta cgacgtcaag 3360
accggggact tcatcctgca cttcaagatg aaccgcaacc tcagtttcca gcgcggcctg 3420
ccggggttca tgcccgcttg ggatatagtc ttcgagaaga atgagacgca gttcgacgcg 3480
aagggcaccc cgttcatcgc cgggaagcgc atcgtgccgg tcatcgagaa ccaccggttc 3540
accgggcgct accgcgacct atacccggcg aacgagttga tcgccctcct ggaggagaag 3600
ggcatcgtgt tccgcgacgg ctccaacatc ctcccgaagc tgctcgaaaa cgacgactcc 3660
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactcccggt tccagaaccc cgagtggccg atggacgcgg acgcgaacgg cgcataccac 3840
atcgccctaa aagggcaatt gctgctcaac cacctcaagg aatccaaaga cctaaagctc 3900
cagaacggca tctccaacca ggactggctg gcgtacatcc aggaactgcg gaacgggagc 3960
aaaaaacgtc ggatcaagca agattga 3987

<210> SEQ ID NO 20
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 20
atggcgggct ccaagaaacg ccggattaag caagataccc agttcgaggg gttcacgaac 60
ctctaccaag tgagcaagac cctccgattc gaactgattc ctcaggggaa gaccctcaag 120
cacatccagg agcaagggtt catcgaggag gacaaggcgc ggaacgacca ctacaaggaa 180
ctcaaaccca tcatcgaccg catctacaag acctacgccg atcagtgcct ccagctcgtg 240

-continued

```
cagttggact gggagaacct cagcgcggcc attgactcct accggaagga gaaaacggag    300
gagacgcgca acgcgctcat cgaggaacag gcaacctatc gcaacgccat ccacgactac    360
ttcatcggga ggactgacaa cctcactgac gcgattaaca agcgccacgc ggagatatac    420
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccgggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct tccctttcta caaccagctc    780
cttacgcaga cccagataga cctgtacaat cagctcctcg gtgggatcag ccgggaggcg    840
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacacctt gagctttatc ctagaggagt tcaagagcga cgaggaggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acaccctccg caacgcgctc   1200
tacgagcgcc gcatctcgga gctgaccggg aagatcacca aatccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa aagcaggaag aaaaagagat cctcaagagc   1440
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggcccgcaac tacgcgacca aaaaaccccta cagcgtggag  1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggccctttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca cgacgccgat cctgctgagc   1920
aacaacttca tcgagcccct tgagatcact aaggagatat acgacctgaa caaccccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg ggcaccacgg gaagcccaac cttcatacgc tctactggac gggcctattc   2340
agccccgaaa atctggccaa gacctccatc aagctgaacg gccaagcgga gctgttctac   2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgacctttcc gacgaggccc gtgccctact cccgaacgtc   2580
```

-continued attaccaaag aggtttcgca cgagatcatc aaggaccggc ggttcacgag cgacaagttt 2640
ttctttcacg tccccatcac ccttaactac caggcggcca actccccatc caagttcaac 2700
cagcgtgtga atgcctacct caaggagcac ccagagaccc cgatcattgg gatcgaccgg 2760
ggcgagcgga acctgatcta catcaccgtc atcgactcga cgggcaagat tcttgagcag 2820
agatcgttga ataccataca gcagttcgac taccagaaga aactcgacaa ccgcgagaag 2880
gagcgcgtgg cggcccgcca ggcgtggtcc gtcgttggga cgattaagga cttgaaacaa 2940
ggttatctgt cccaagtcat ccacgagatc gttgatctga tgatccacta tcaggcagtg 3000
gtggtgctgg agaatctcaa cttcggcttc aagagtaagc ggacgggaat cgccgagaag 3060
gccgtgtacc agcagttcga gaagatgctg atcgacaagc tcaactgcct tgtgctgaaa 3120
gactacccgg ccgagaaggt cggcggcgtc ctcaacccgt accaacttac cgaccagttc 3180
acctccttcg ccaagatggg cactcagtcc gggttcttgt tctacgtccc cgcaccttac 3240
acctctaaga tcgaccctct gactggcttc gtagatccat tcgtgtggaa gaccattaag 3300
aaccacgaga gccgcaagca cttcctggag ggcttcgact tcctgcacta cgacgtgaag 3360
accggggact tcatccttca cttcaagatg aaccggaacc tcagcttcca gcggggcctg 3420
ccggggttca tgcccgcctg ggacatcgtg ttcgagaaga acgagaccca gttcgacgcg 3480
aagggcacgc ccttcatcgc cgggaagcgt atcgtgccgg tgatcgagaa ccatcgtttc 3540
acgggtcgct accgtgacct ctacccggcg aacgagctta tcgcactcct ggaggagaag 3600
ggcatcgtct tccgggacgg ctccaacatc ctcccgaaac tgctggaaaa cgacgactct 3660
cacgccatcg acacgatggt ggccctcatc cggtccgtgc tccaaatgcg gaacagcaac 3720
gccgccaccg gtgaggacta catcaacagc ccggtccggg atctgaacgg ggtgtgcttc 3780
gattcgcggt tccagaatcc tgagtggccg atggacgcgg atgcaaacgg ggcgtaccac 3840
atcgcgctca agggccagtt acttctgaac caccttaagg agtctaaaga tttgaaactc 3900
cagaacggga tctcgaacca ggactggctg gcctacatcc aagagttgcg gaacggcagc 3960
aagaagcggc ggattaagca agattag 3987

<210> SEQ ID NO 21
<211> LENGTH: 1592
<212> TYPE: DNA
<213> ORGANISM: Medicago truncatula

<400> SEQUENCE: 21
actgttaata atttttaaac gtcagcgcac taaaaaaacg aaaagacgga cacgtgaaaa 60
taaaaaacac acactagttt atgacgcaat actattttac ttatgatttg ggtacattag 120
acaaaaccgt gaaagagatg tatcagctat gaaacctgta tacttcaata cagagactta 180
ctcatatcgg atacgtacgc acgaagtatc atattaatta ttttaatttt taataaatat 240
tttatcggat acttatgtga tactctacat atacacaagg atatttctaa gatactttat 300
agatacgtat cctagaaaaa catgaagagt aaaaaagtga gacaatgttg taaaaattca 360
ttataaatgt atatgattca attttagata tgcatcagta taattgattc tcgatgaaac 420
acttaaaatt atatttcttg tggaagaacg tagcgagaga ggtgattcag ttagacaaca 480
ttaaataaaa ttaatgttaa gttcttttaa tgatgtttct ctcaatatca catcatatga 540
aaatgtaata tgatttataa gaaaattttt aaaaaattta ttttaataat cacatgtact 600 atttttaaa aattgtatct tttataataa tacaataata aagagtaatc agtgttaatt 660
tttcttcaaa tataagtttt attataaatc attgttaacg tatcataagt cattaccgta 720

-continued tcgtatctta attttttttt aaaaaccgct aattcacgta cccgtattgt attgtacccg 780
cacctgtatc acaatcgatc ttagttagaa gaattgtctc gaggcggtgc aagacagcat 840
ataatagacg tggactctct tataccaaac gttgtcgtat cacaaagggt taggtaacaa 900
gtcacagttt gtccacgtgt cacgttttaa ttggaagagg tgccgttggc gtaatataac 960
agccaatcga tttttgctat aaaagcaaat caggtaaact aaacttcttc attcttttct 1020
tccccatcgc tacaaaaccg gttcctttgg aaaagagatt cattcaaacc tagcacccaa 1080
ttccgtttca aggtataatc tactttctat tcttcgatta ttttattatt attagctact 1140
atcgtttaat cgatcttttc ttttgatccg tcaaatttaa attcaattag ggttttgttc 1200
ttttctttca tctgattgaa atccttctga attgaaccgt ttacttgatt ttactgttta 1260
ttgtatgatt taatcctttg tttttcaaag acagtcttta gattgtgatt aggggttcat 1320
ataaattttt agatttggat ttttgtattg tatgattcaa aaaatacgtc ctttaattag 1380
attagtacat ggatattttt tacccgattt attgattgtc agggagaatt tgatgagcaa 1440 gttttttga tgtctgttgt aaattgaatt gattataatt gctgatctgc tgcttccagt 1500
tttcataacc catattcttt taaccttgtt gtacacacaa tgaaaaattg gtgattgatt 1560
catttgtttt tctttgtttt ggattataca gg 1592

<210> SEQ ID NO 22
<211> LENGTH: 2000
<212> TYPE: DNA
<213> ORGANISM: Zea mays

<400> SEQUENCE: 22
gtcgtgcccc tctctagaga taaagagcat tgcatgtcta aagtataaaa aattaccaca 60
tatttttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccettta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccccct ccacaccctc tttccccaac ctcgtgttcg ttcggagcgc 900
acacacacgc aaccagatct cccccaaatc cagccgtcgg cacctccgct tcaaggtacg 960
ccgctcatcc tccccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200

```
gttacgagtt taagatgatg gatggaaata tcgatctagg ataggtatac atgttgatgc   1260

gggttttact gatgcatata cagagatgct ttttttctcg cttggttgtg atgatatggt   1320

ctggttgggc ggtcgttcta gatcggagta gaatactgtt tcaaactacc tggtggattt   1380

attaaaggat aaagggtcgt tctagatcgg agtagaatac tgtttcaaac tacctggtgg   1440

atttattaaa ggatctgtat gtatgtgcct acatcttcat agttacgagt ttaagatgat   1500

ggatggaaat atcgatctag gataggtata catgttgatg cgggttttac tgatgcatat   1560

acagagatgc tttttttcgc ttggttgtga tgatgtggtc tggttgggcg gtcgttctag   1620

atcggagtag aatactgttt caaactacct ggtggattta ttaattttgt atctttatgt   1680

gtgtgccata catcttcata gttacgagtt taagatgatg gatggaaata ttgatctagg   1740

ataggtatac atgttgatgt gggttttact gatgcatata catgatggca tatgcggcat   1800

ctattcatat gctctaacct tgagtaccta tctattataa taaacaagta tgttttataa   1860

ttattttgat cttgatatac ttggatgatg gcatatgcag cagctatatg tggatttttt   1920

agccctgcct tcatacgcta tttatttgct tggtactgtt tcttttgtcc gatgctcacc   1980

ctgttgtttg gtgatacttc                                                2000


<210> SEQ ID NO 23
<211> LENGTH: 228
<212> TYPE: PRT
<213> ORGANISM: Rattus norvegicus

<400> SEQUENCE: 23

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
```

225

<210> SEQ ID NO 24
<211> LENGTH: 199
<212> TYPE: PRT
<213> ORGANISM: Homo sapiens

<400> SEQUENCE: 24

Met Glu Ala Ser Pro Ala Ser Gly Pro Arg His Leu Met Asp Pro His
1 5 10 15

Ile Phe Thr Ser Asn Phe Asn Asn Gly Ile Gly Arg His Lys Thr Tyr
20 25 30

Leu Cys Tyr Glu Val Glu Arg Leu Asp Asn Gly Thr Ser Val Lys Met
35 40 45

Asp Gln His Arg Gly Phe Leu His Asn Gln Ala Lys Asn Leu Leu Cys
50 55 60

Gly Phe Tyr Gly Arg His Ala Glu Leu Arg Phe Leu Asp Leu Val Pro
65 70 75 80

Ser Leu Gln Leu Asp Pro Ala Gln Ile Tyr Arg Val Thr Trp Phe Ile
85 90 95

Ser Trp Ser Pro Cys Phe Ser Trp Gly Cys Ala Gly Glu Val Arg Ala
100 105 110

Phe Leu Gln Glu Asn Thr His Val Arg Leu Arg Ile Phe Ala Ala Arg
115 120 125

Ile Tyr Asp Tyr Asp Pro Leu Tyr Lys Glu Ala Leu Gln Met Leu Arg
130 135 140

Asp Ala Gly Ala Gln Val Ser Ile Met Thr Tyr Asp Glu Phe Lys His
145 150 155 160

Cys Trp Asp Thr Phe Val Asp His Gln Gly Cys Pro Phe Gln Pro Trp
165 170 175

Asp Gly Leu Asp Glu His Ser Gln Ala Leu Ser Gly Arg Leu Arg Ala
180 185 190

Ile Leu Gln Asn Gln Gly Asn
195

<210> SEQ ID NO 25
<211> LENGTH: 621
<212> TYPE: DNA
<213> ORGANISM: Petromyzon marinus

<400> SEQUENCE: 25
acagatgcag agtatgtgag aattcacgaa aagctggaca tctatacctt caagaagcag 60
ttctttaaca ataagaagtc tgtgagccat aggtgctacg tgctgttcga gctgaagaga 120
aggggtgaaa gaagggcatg tttttggggg tatgctgtga acaagcccca gtctggaact 180
gagagaggca ttcacgccga aattttcagc atcagaaagg tggaggaata cctgagggat 240
aaccctggac agtttacaat taattggtat tctagctggt ctccatgcgc tgactgtgcc 300
gagaagatcc tggaatggta caaccaggag ctgagaggaa atggccatac cctgaagatt 360
tgggcctgca agctgtacta tgaaaagaac gcaagaaatc agatcggact gtggaacctg 420
agggataatg gtgtggggct gaacgtgatg gtgtccgagc actatcagtg ctgtagaaag 480
attttcattc agtcctcaca taatcagctg aacgagaata gatggctgga aaagactctg 540
aagagggctg agaagagaag gtccgaactg tcaattatga tccaggtgaa gatcctgcac 600
accactaagt cacctgccgt g 621

<210> SEQ ID NO 26
<211> LENGTH: 160
<212> TYPE: PRT
<213> ORGANISM: Artificial sequence
<220> FEATURE:
<223> OTHER INFORMATION: Synthetic polypeptide

<400> SEQUENCE: 26

```
Phe Glu Arg Asn Tyr Asp Pro Arg Glu Leu Arg Lys Glu Thr Tyr Leu
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
        35                  40                  45

Ile Phe Asn Ala Arg Arg Phe Asn Pro Ser Thr His Cys Ser Ile Thr
    50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Glu Ile Tyr Val Ala Arg
                85                  90                  95

Leu Tyr Tyr His Glu Asp Glu Arg Asn Arg Gln Gly Leu Arg Asp Leu
            100                 105                 110

Val Asn Ser Gly Val Thr Ile Arg Ile Met Asp Leu Pro Asp Tyr Asn
        115                 120                 125

Tyr Cys Trp Lys Thr Phe Val Ser Asp Gln Gly Gly Asp Glu Asp Tyr
    130                 135                 140

Trp Pro Gly His Phe Ala Pro Trp Ile Lys Gln Tyr Ser Leu Lys Leu
145                 150                 155                 160
```

<210> SEQ ID NO 27
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 27

```
Thr Asp Ala Glu Tyr Val Arg Ile His Glu Lys Leu Asp Ile Tyr Thr
1               5                   10                  15

Phe Lys Lys Gln Phe Ser Asn Asn Lys Lys Ser Val Ser His Arg Cys
            20                  25                  30

Tyr Val Leu Phe Glu Leu Lys Arg Arg Gly Glu Arg Arg Ala Cys Phe
        35                  40                  45

Trp Gly Tyr Ala Val Asn Lys Pro Gln Ser Gly Thr Glu Arg Gly Ile
    50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Ser Trp Ser Pro Cys
                85                  90                  95

Ala Asp Cys Ala Glu Lys Ile Leu Glu Trp Tyr Asn Gln Glu Leu Arg
            100                 105                 110

Gly Asn Gly His Thr Leu Lys Ile Trp Val Cys Lys Leu Tyr Tyr Glu
        115                 120                 125

Lys Asn Ala Arg Asn Gln Ile Gly Leu Trp Asn Leu Arg Asp Asn Gly
    130                 135                 140

Val Gly Leu Asn Val Met Val Ser Glu His Tyr Gln Cys Cys Arg Lys
145                 150                 155                 160
```

```
Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
            180                 185                 190

Met Phe Gln Val Lys Ile Leu His Thr Thr Lys Ser Pro Ala Val
        195                 200                 205


<210> SEQ ID NO 28
<211> LENGTH: 228
<212> TYPE: PRT
<213> ORGANISM: Artificial sequence
<220> FEATURE:
<223> OTHER INFORMATION: Synthetic polypeptide

<400> SEQUENCE: 28

Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro Asn Val Thr Leu Phe
            100                 105                 110

Ile Tyr Ile Ala Arg Leu Tyr His Leu Ala Asn Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Ser Gln Leu Thr Ser Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225


<210> SEQ ID NO 29
<211> LENGTH: 162
<212> TYPE: PRT
<213> ORGANISM: Artificial sequence
<220> FEATURE:
<223> OTHER INFORMATION: Synthetic polypeptide

<400> SEQUENCE: 29

Ser Phe Glu Arg Asn Tyr Asp Pro Arg Glu Leu Arg Lys Glu Thr Tyr
1               5                   10                  15

Leu Leu Tyr Glu Ile Lys Trp Gly Lys Ser Gly Lys Leu Trp Arg His
```

20 25 30

Trp Cys Gln Asn Asn Arg Thr Gln His Ala Glu Val Tyr Phe Leu Glu
35 40 45

Asn Ile Phe Asn Ala Arg Arg Phe Asn Pro Ser Thr His Cys Ser Ile
50 55 60

Thr Trp Tyr Leu Ser Trp Ser Pro Cys Ala Glu Cys Ser Gln Lys Ile
65 70 75 80

Val Asp Phe Leu Lys Glu His Pro Asn Val Asn Leu Glu Ile Tyr Val
85 90 95

Ala Arg Leu Tyr Tyr Pro Glu Asn Glu Arg Asn Arg Gln Gly Leu Arg
100 105 110

Asp Leu Val Asn Ser Gly Val Thr Ile Arg Ile Met Asp Leu Pro Asp
115 120 125

Tyr Asn Tyr Cys Trp Lys Thr Phe Val Ser Asp Gln Gly Gly Asp Glu
130 135 140

Asp Tyr Trp Pro Gly His Phe Ala Pro Trp Ile Lys Gln Tyr Ser Leu
145 150 155 160

Lys Leu

<210> SEQ ID NO 30
<211> LENGTH: 166
<212> TYPE: PRT
<213> ORGANISM: Escherichia coli

<400> SEQUENCE: 30

Ser Glu Val Glu Phe Ser His Glu Tyr Trp Met Arg His Ala Leu Thr
1 5 10 15

Leu Ala Lys Arg Ala Trp Asp Glu Arg Glu Val Pro Val Gly Ala Val
20 25 30

Leu Val His Asn Asn Arg Val Ile Gly Glu Gly Trp Asn Arg Pro Ile
35 40 45

Gly Arg His Asp Pro Thr Ala His Ala Glu Ile Met Ala Leu Arg Gln
50 55 60

Gly Gly Leu Val Met Gln Asn Tyr Arg Leu Ile Asp Ala Thr Leu Tyr
65 70 75 80

Val Thr Leu Glu Pro Cys Val Met Cys Ala Gly Ala Met Ile His Ser
85 90 95

Arg Ile Gly Arg Val Val Phe Gly Ala Arg Asp Ala Lys Thr Gly Ala
100 105 110

Ala Gly Ser Leu Met Asp Val Leu His His Pro Gly Met Asn His Arg
115 120 125

Val Glu Ile Thr Glu Gly Ile Leu Ala Asp Glu Cys Ala Ala Leu Leu
130 135 140

Ser Asp Phe Phe Arg Met Arg Arg Gln Glu Ile Lys Ala Gln Lys Lys
145 150 155 160

Ala Gln Ser Ser Thr Asp
165

<210> SEQ ID NO 31
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 31

```
Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165


<210> SEQ ID NO 32
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 32

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val Leu Asn Asn Arg Val Ile Gly Glu Gly Trp Asn Arg Ser Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165


<210> SEQ ID NO 33
<211> LENGTH: 166
```

<212> TYPE: PRT
<213> ORGANISM: Artificial sequence
<220> FEATURE:
<223> OTHER INFORMATION: Synthetic polypeptide

<400> SEQUENCE: 33

```
Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165
```

<210> SEQ ID NO 34
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 34

```
Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Pro Arg Gln Val Phe Asn Ala Gln Lys Lys
145                 150                 155                 160
```

```
Ala Gln Ser Ser Thr Asp
                165


<210> SEQ ID NO 35
<211> LENGTH: 1763
<212> TYPE: PRT
<213> ORGANISM: Artificial sequence
<220> FEATURE:
<223> OTHER INFORMATION: Synthetic polypeptide

<400> SEQUENCE: 35

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350
```

-continued

```
Phe Asn Ala Gln Lys Lys Ala Gln Ser Ser Thr Asp Ser Gly Gly Ser
        355                 360                 365

Ser Gly Gly Ser Ser Gly Ser Glu Thr Pro Gly Thr Ser Glu Ser Ala
    370                 375                 380

Thr Pro Glu Ser Ser Gly Gly Ser Ser Gly Gly Ser Asp Lys Lys Tyr
385                 390                 395                 400

Ser Ile Gly Leu Ala Ile Gly Thr Asn Ser Val Gly Trp Ala Val Ile
                405                 410                 415

Thr Asp Glu Tyr Lys Val Pro Ser Lys Lys Phe Lys Val Leu Gly Asn
            420                 425                 430

Thr Asp Arg His Ser Ile Lys Lys Asn Leu Ile Gly Ala Leu Leu Phe
        435                 440                 445

Asp Ser Gly Glu Thr Ala Glu Ala Thr Arg Leu Lys Arg Thr Ala Arg
    450                 455                 460

Arg Arg Tyr Thr Arg Arg Lys Asn Arg Ile Cys Tyr Leu Gln Glu Ile
465                 470                 475                 480

Phe Ser Asn Glu Met Ala Lys Val Asp Asp Ser Phe Phe His Arg Leu
                485                 490                 495

Glu Glu Ser Phe Leu Val Glu Glu Asp Lys Lys His Glu Arg His Pro
            500                 505                 510

Ile Phe Gly Asn Ile Val Asp Glu Val Ala Tyr His Glu Lys Tyr Pro
        515                 520                 525

Thr Ile Tyr His Leu Arg Lys Lys Leu Val Asp Ser Thr Asp Lys Ala
    530                 535                 540

Asp Leu Arg Leu Ile Tyr Leu Ala Leu Ala His Met Ile Lys Phe Arg
545                 550                 555                 560

Gly His Phe Leu Ile Glu Gly Asp Leu Asn Pro Asp Asn Ser Asp Val
                565                 570                 575

Asp Lys Leu Phe Ile Gln Leu Val Gln Thr Tyr Asn Gln Leu Phe Glu
            580                 585                 590

Glu Asn Pro Ile Asn Ala Ser Gly Val Asp Ala Lys Ala Ile Leu Ser
        595                 600                 605

Ala Arg Leu Ser Lys Ser Arg Arg Leu Glu Asn Leu Ile Ala Gln Leu
    610                 615                 620

Pro Gly Glu Lys Lys Asn Gly Leu Phe Gly Asn Leu Ile Ala Leu Ser
625                 630                 635                 640

Leu Gly Leu Thr Pro Asn Phe Lys Ser Asn Phe Asp Leu Ala Glu Asp
                645                 650                 655

Ala Lys Leu Gln Leu Ser Lys Asp Thr Tyr Asp Asp Asp Leu Asp Asn
            660                 665                 670

Leu Leu Ala Gln Ile Gly Asp Gln Tyr Ala Asp Leu Phe Leu Ala Ala
        675                 680                 685

Lys Asn Leu Ser Asp Ala Ile Leu Leu Ser Asp Ile Leu Arg Val Asn
    690                 695                 700

Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                725                 730                 735

Gln Leu Pro Glu Lys Tyr Lys Glu Ile Phe Phe Asp Gln Ser Lys Asn
            740                 745                 750

Gly Tyr Ala Gly Tyr Ile Asp Gly Gly Ala Ser Gln Glu Glu Phe Tyr
        755                 760                 765
```

-continued

```
Lys Phe Ile Lys Pro Ile Leu Glu Lys Met Asp Gly Thr Glu Glu Leu
    770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                805                 810                 815

Ile Leu Arg Arg Gln Glu Asp Phe Tyr Pro Phe Leu Lys Asp Asn Arg
            820                 825                 830

Glu Lys Ile Glu Lys Ile Leu Thr Phe Arg Ile Pro Tyr Tyr Val Gly
        835                 840                 845

Pro Leu Ala Arg Gly Asn Ser Arg Phe Ala Trp Met Thr Arg Lys Ser
    850                 855                 860

Glu Glu Thr Ile Thr Pro Trp Asn Phe Glu Glu Val Val Asp Lys Gly
865                 870                 875                 880

Ala Ser Ala Gln Ser Phe Ile Glu Arg Met Thr Asn Phe Asp Lys Asn
                885                 890                 895

Leu Pro Asn Glu Lys Val Leu Pro Lys His Ser Leu Leu Tyr Glu Tyr
            900                 905                 910

Phe Thr Val Tyr Asn Glu Leu Thr Lys Val Lys Tyr Val Thr Glu Gly
        915                 920                 925

Met Arg Lys Pro Ala Phe Leu Ser Gly Glu Gln Lys Lys Ala Ile Val
    930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
                965                 970                 975

Gly Val Glu Asp Arg Phe Asn Ala Ser Leu Gly Thr Tyr His Asp Leu
            980                 985                 990

Leu Lys Ile Ile Lys Asp Lys Asp  Phe Leu Asp Asn Glu  Glu Asn Glu
        995                 1000                1005

Asp Ile  Leu Glu Asp Ile Val  Leu Thr Leu Thr Leu  Phe Glu Asp
    1010                1015                1020

Arg Glu  Met Ile Glu Glu Arg  Leu Lys Thr Tyr Ala  His Leu Phe
    1025                1030                1035

Asp Asp  Lys Val Met Lys Gln  Leu Lys Arg Arg Arg  Tyr Thr Gly
    1040                1045                1050

Trp Gly  Arg Leu Ser Arg Lys  Leu Ile Asn Gly Ile  Arg Asp Lys
    1055                1060                1065

Gln Ser  Gly Lys Thr Ile Leu  Asp Phe Leu Lys Ser  Asp Gly Phe
    1070                1075                1080

Ala Asn  Arg Asn Phe Met Gln  Leu Ile His Asp Asp  Ser Leu Thr
    1085                1090                1095

Phe Lys  Glu Asp Ile Gln Lys  Ala Gln Val Ser Gly  Gln Gly Asp
    1100                1105                1110

Ser Leu  His Glu His Ile Ala  Asn Leu Ala Gly Ser  Pro Ala Ile
    1115                1120                1125

Lys Lys  Gly Ile Leu Gln Thr  Val Lys Val Val Asp  Glu Leu Val
    1130                1135                1140

Lys Val  Met Gly Arg His Lys  Pro Glu Asn Ile Val  Ile Glu Met
    1145                1150                1155

Ala Arg  Glu Asn Gln Thr Thr  Gln Lys Gly Gln Lys  Asn Ser Arg
    1160                1165                1170

Glu Arg  Met Lys Arg Ile Glu  Glu Gly Ile Lys Glu  Leu Gly Ser
```

```
    1175                1180                1185

Gln Ile  Leu Lys Glu His Pro  Val Glu Asn Thr Gln  Leu Gln Asn
    1190                1195                1200

Glu Lys  Leu Tyr Leu Tyr Tyr  Leu Gln Asn Gly Arg  Asp Met Tyr
    1205                1210                1215

Val Asp  Gln Glu Leu Asp Ile  Asn Arg Leu Ser Asp  Tyr Asp Val
    1220                1225                1230

Asp His  Ile Val Pro Gln Ser  Phe Leu Lys Asp Asp  Ser Ile Asp
    1235                1240                1245

Asn Lys  Val Leu Thr Arg Ser  Asp Lys Asn Arg Gly  Lys Ser Asp
    1250                1255                1260

Asn Val  Pro Ser Glu Glu Val  Val Lys Lys Met Lys  Asn Tyr Trp
    1265                1270                1275

Arg Gln  Leu Leu Asn Ala Lys  Leu Ile Thr Gln Arg  Lys Phe Asp
    1280                1285                1290

Asn Leu  Thr Lys Ala Glu Arg  Gly Gly Leu Ser Glu  Leu Asp Lys
    1295                1300                1305

Ala Gly  Phe Ile Lys Arg Gln  Leu Val Glu Thr Arg  Gln Ile Thr
    1310                1315                1320

Lys His  Val Ala Gln Ile Leu  Asp Ser Arg Met Asn  Thr Lys Tyr
    1325                1330                1335

Asp Glu  Asn Asp Lys Leu Ile  Arg Glu Val Lys Val  Ile Thr Leu
    1340                1345                1350

Lys Ser  Lys Leu Val Ser Asp  Phe Arg Lys Asp Phe  Gln Phe Tyr
    1355                1360                1365

Lys Val  Arg Glu Ile Asn Asn  Tyr His His Ala His  Asp Ala Tyr
    1370                1375                1380

Leu Asn  Ala Val Val Gly Thr  Ala Leu Ile Lys Lys  Tyr Pro Lys
    1385                1390                1395

Leu Glu  Ser Glu Phe Val Tyr  Gly Asp Tyr Lys Val  Tyr Asp Val
    1400                1405                1410

Arg Lys  Met Ile Ala Lys Ser  Glu Gln Glu Ile Gly  Lys Ala Thr
    1415                1420                1425

Ala Lys  Tyr Phe Phe Tyr Ser  Asn Ile Met Asn Phe  Phe Lys Thr
    1430                1435                1440

Glu Ile  Thr Leu Ala Asn Gly  Glu Ile Arg Lys Arg  Pro Leu Ile
    1445                1450                1455

Glu Thr  Asn Gly Glu Thr Gly  Glu Ile Val Trp Asp  Lys Gly Arg
    1460                1465                1470

Asp Phe  Ala Thr Val Arg Lys  Val Leu Ser Met Pro  Gln Val Asn
    1475                1480                1485

Ile Val  Lys Lys Thr Glu Val  Gln Thr Gly Gly Phe  Ser Lys Glu
    1490                1495                1500

Ser Ile  Leu Pro Lys Arg Asn  Ser Asp Lys Leu Ile  Ala Arg Lys
    1505                1510                1515

Lys Asp  Trp Asp Pro Lys Lys  Tyr Gly Gly Phe Asp  Ser Pro Thr
    1520                1525                1530

Val Ala  Tyr Ser Val Leu Val  Val Ala Lys Val Glu  Lys Gly Lys
    1535                1540                1545

Ser Lys  Lys Leu Lys Ser Val  Lys Glu Leu Leu Gly  Ile Thr Ile
    1550                1555                1560

Met Glu  Arg Ser Ser Phe Glu  Lys Asn Pro Ile Asp  Phe Leu Glu
    1565                1570                1575
```

```
Ala Lys Gly Tyr Lys Glu Val Lys Lys Asp Leu Ile Ile Lys Leu
    1580                1585                1590

Pro Lys Tyr Ser Leu Phe Glu Leu Glu Asn Gly Arg Lys Arg Met
    1595                1600                1605

Leu Ala Ser Ala Gly Glu Leu Gln Lys Gly Asn Glu Leu Ala Leu
    1610                1615                1620

Pro Ser Lys Tyr Val Asn Phe Leu Tyr Leu Ala Ser His Tyr Glu
    1625                1630                1635

Lys Leu Lys Gly Ser Pro Glu Asp Asn Glu Gln Lys Gln Leu Phe
    1640                1645                1650

Val Glu Gln His Lys His Tyr Leu Asp Glu Ile Ile Glu Gln Ile
    1655                1660                1665

Ser Glu Phe Ser Lys Arg Val Ile Leu Ala Asp Ala Asn Leu Asp
    1670                1675                1680

Lys Val Leu Ser Ala Tyr Asn Lys His Arg Asp Lys Pro Ile Arg
    1685                1690                1695

Glu Gln Ala Glu Asn Ile Ile His Leu Phe Thr Leu Thr Asn Leu
    1700                1705                1710

Gly Ala Pro Ala Ala Phe Lys Tyr Phe Asp Thr Thr Ile Asp Arg
    1715                1720                1725

Lys Arg Tyr Thr Ser Thr Lys Glu Val Leu Asp Ala Thr Leu Ile
    1730                1735                1740

His Gln Ser Ile Thr Gly Leu Tyr Glu Thr Arg Ile Asp Leu Ser
    1745                1750                1755

Gln Leu Gly Gly Asp
    1760


<210> SEQ ID NO 36
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 36

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ser Lys Arg Gly Ala
            100                 105                 110

Ala Gly Ser Leu Met Asn Val Leu Asn Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Asp Phe Tyr Arg Met Pro Arg Gln Val Phe Asn Ala Gln Lys Lys
145                 150                 155                 160
```

-continued

```
Ala Gln Ser Ser Ile Asn Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
    290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575
```

```
Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn  Thr Gln Leu Gln Asn  Glu Lys Leu
```

-continued 995 1000 1005

Tyr Leu Tyr Tyr Leu Gln Asn Gly Arg Asp Met Tyr Val Asp Gln
1010 1015 1020

Glu Leu Asp Ile Asn Arg Leu Ser Asp Tyr Asp Val Asp His Ile
1025 1030 1035

Val Pro Gln Ser Phe Leu Lys Asp Asp Ser Ile Asp Asn Lys Val
1040 1045 1050

Leu Thr Arg Ser Asp Lys Asn Arg Gly Lys Ser Asp Asn Val Pro
1055 1060 1065

Ser Glu Glu Val Val Lys Lys Met Lys Asn Tyr Trp Arg Gln Leu
1070 1075 1080

Leu Asn Ala Lys Leu Ile Thr Gln Arg Lys Phe Asp Asn Leu Thr
1085 1090 1095

Lys Ala Glu Arg Gly Gly Leu Ser Glu Leu Asp Lys Ala Gly Phe
1100 1105 1110

Ile Lys Arg Gln Leu Val Glu Thr Arg Gln Ile Thr Lys His Val
1115 1120 1125

Ala Gln Ile Leu Asp Ser Arg Met Asn Thr Lys Tyr Asp Glu Asn
1130 1135 1140

Asp Lys Leu Ile Arg Glu Val Lys Val Ile Thr Leu Lys Ser Lys
1145 1150 1155

Leu Val Ser Asp Phe Arg Lys Asp Phe Gln Phe Tyr Lys Val Arg
1160 1165 1170

Glu Ile Asn Asn Tyr His His Ala His Asp Ala Tyr Leu Asn Ala
1175 1180 1185

Val Val Gly Thr Ala Leu Ile Lys Lys Tyr Pro Lys Leu Glu Ser
1190 1195 1200

Glu Phe Val Tyr Gly Asp Tyr Lys Val Tyr Asp Val Arg Lys Met
1205 1210 1215

Ile Ala Lys Ser Glu Gln Glu Ile Gly Lys Ala Thr Ala Lys Tyr
1220 1225 1230

Phe Phe Tyr Ser Asn Ile Met Asn Phe Phe Lys Thr Glu Ile Thr
1235 1240 1245

Leu Ala Asn Gly Glu Ile Arg Lys Arg Pro Leu Ile Glu Thr Asn
1250 1255 1260

Gly Glu Thr Gly Glu Ile Val Trp Asp Lys Gly Arg Asp Phe Ala
1265 1270 1275

Thr Val Arg Lys Val Leu Ser Met Pro Gln Val Asn Ile Val Lys
1280 1285 1290

Lys Thr Glu Val Gln Thr Gly Gly Phe Ser Lys Glu Ser Ile Leu
1295 1300 1305

Pro Lys Arg Asn Ser Asp Lys Leu Ile Ala Arg Lys Lys Asp Trp
1310 1315 1320

Asp Pro Lys Lys Tyr Gly Gly Phe Asp Ser Pro Thr Val Ala Tyr
1325 1330 1335

Ser Val Leu Val Val Ala Lys Val Glu Lys Gly Lys Ser Lys Lys
1340 1345 1350

Leu Lys Ser Val Lys Glu Leu Leu Gly Ile Thr Ile Met Glu Arg
1355 1360 1365

Ser Ser Phe Glu Lys Asn Pro Ile Asp Phe Leu Glu Ala Lys Gly
1370 1375 1380

Tyr Lys Glu Val Lys Lys Asp Leu Ile Ile Lys Leu Pro Lys Tyr
1385 1390 1395

Ser Leu Phe Glu Leu Glu Asn Gly Arg Lys Arg Met Leu Ala Ser
    1400                1405                1410

Ala Gly Glu Leu Gln Lys Gly Asn Glu Leu Ala Leu Pro Ser Lys
    1415                1420                1425

Tyr Val Asn Phe Leu Tyr Leu Ala Ser His Tyr Glu Lys Leu Lys
    1430                1435                1440

Gly Ser Pro Glu Asp Asn Glu Gln Lys Gln Leu Phe Val Glu Gln
    1445                1450                1455

His Lys His Tyr Leu Asp Glu Ile Ile Glu Gln Ile Ser Glu Phe
    1460                1465                1470

Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala
    1490                1495                1500

Glu Asn Ile Ile His Leu Phe Thr Leu Thr Asn Leu Gly Ala Pro
    1505                1510                1515

Ala Ala Phe Lys Tyr Phe Asp Thr Thr Ile Asp Arg Lys Arg Tyr
    1520                1525                1530

Thr Ser Thr Lys Glu Val Leu Asp Ala Thr Leu Ile His Gln Ser
    1535                1540                1545

Ile Thr Gly Leu Tyr Glu Thr Arg Ile Asp Leu Ser Gln Leu Gly
    1550                1555                1560

Gly Asp
    1565

<210> SEQ ID NO 37
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 37

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Tyr Asp Ala Thr Leu Tyr
65                  70                  75                  80

Ser Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Cys Arg Phe Phe Arg Met Pro Arg Arg Val Phe Asn Ala Gln Lys Lys
145                 150                 155                 160

Ala Gln Ser Ser Thr Asp Ser Gly Gly Ser Ser Gly Gly Ser Ser Gly
                165                 170                 175

```
Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
    290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590
```

-continued

```
Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn  Thr Gln Leu Gln Asn  Glu Lys Leu
        995                 1000                 1005

Tyr Leu  Tyr Tyr Leu Gln Asn  Gly Arg Asp Met Tyr  Val Asp Gln
```

-continued

```
    1010                1015                1020

Glu Leu  Asp Ile Asn Arg Leu  Ser Asp Tyr Asp Val  Asp His Ile
    1025                1030                1035

Val Pro  Gln Ser Phe Leu Lys  Asp Asp Ser Ile Asp  Asn Lys Val
    1040                1045                1050

Leu Thr  Arg Ser Asp Lys Asn  Arg Gly Lys Ser Asp  Asn Val Pro
    1055                1060                1065

Ser Glu  Glu Val Val Lys Lys  Met Lys Asn Tyr Trp  Arg Gln Leu
    1070                1075                1080

Leu Asn  Ala Lys Leu Ile Thr  Gln Arg Lys Phe Asp  Asn Leu Thr
    1085                1090                1095

Lys Ala  Glu Arg Gly Gly Leu  Ser Glu Leu Asp Lys  Ala Gly Phe
    1100                1105                1110

Ile Lys  Arg Gln Leu Val Glu  Thr Arg Gln Ile Thr  Lys His Val
    1115                1120                1125

Ala Gln  Ile Leu Asp Ser Arg  Met Asn Thr Lys Tyr  Asp Glu Asn
    1130                1135                1140

Asp Lys  Leu Ile Arg Glu Val  Lys Val Ile Thr Leu  Lys Ser Lys
    1145                1150                1155

Leu Val  Ser Asp Phe Arg Lys  Asp Phe Gln Phe Tyr  Lys Val Arg
    1160                1165                1170

Glu Ile  Asn Asn Tyr His His  Ala His Asp Ala Tyr  Leu Asn Ala
    1175                1180                1185

Val Val  Gly Thr Ala Leu Ile  Lys Lys Tyr Pro Lys  Leu Glu Ser
    1190                1195                1200

Glu Phe  Val Tyr Gly Asp Tyr  Lys Val Tyr Asp Val  Arg Lys Met
    1205                1210                1215

Ile Ala  Lys Ser Glu Gln Glu  Ile Gly Lys Ala Thr  Ala Lys Tyr
    1220                1225                1230

Phe Phe  Tyr Ser Asn Ile Met  Asn Phe Phe Lys Thr  Glu Ile Thr
    1235                1240                1245

Leu Ala  Asn Gly Glu Ile Arg  Lys Arg Pro Leu Ile  Glu Thr Asn
    1250                1255                1260

Gly Glu  Thr Gly Glu Ile Val  Trp Asp Lys Gly Arg  Asp Phe Ala
    1265                1270                1275

Thr Val  Arg Lys Val Leu Ser  Met Pro Gln Val Asn  Ile Val Lys
    1280                1285                1290

Lys Thr  Glu Val Gln Thr Gly  Gly Phe Ser Lys Glu  Ser Ile Leu
    1295                1300                1305

Pro Lys  Arg Asn Ser Asp Lys  Leu Ile Ala Arg Lys  Lys Asp Trp
    1310                1315                1320

Asp Pro  Lys Lys Tyr Gly Gly  Phe Asp Ser Pro Thr  Val Ala Tyr
    1325                1330                1335

Ser Val  Leu Val Val Ala Lys  Val Glu Lys Gly Lys  Ser Lys Lys
    1340                1345                1350

Leu Lys  Ser Val Lys Glu Leu  Leu Gly Ile Thr Ile  Met Glu Arg
    1355                1360                1365

Ser Ser  Phe Glu Lys Asn Pro  Ile Asp Phe Leu Glu  Ala Lys Gly
    1370                1375                1380

Tyr Lys  Glu Val Lys Lys Asp  Leu Ile Ile Lys Leu  Pro Lys Tyr
    1385                1390                1395

Ser Leu  Phe Glu Leu Glu Asn  Gly Arg Lys Arg Met  Leu Ala Ser
    1400                1405                1410
```

```
Ala Gly  Glu Leu Gln Lys Gly  Asn Glu Leu Ala Leu  Pro Ser Lys
    1415                 1420                 1425

Tyr Val  Asn Phe Leu Tyr Leu  Ala Ser His Tyr Glu  Lys Leu Lys
    1430                 1435                 1440

Gly Ser  Pro Glu Asp Asn Glu  Gln Lys Gln Leu Phe  Val Glu Gln
    1445                 1450                 1455

His Lys  His Tyr Leu Asp Glu  Ile Ile Glu Gln Ile  Ser Glu Phe
    1460                 1465                 1470

Ser Lys  Arg Val Ile Leu Ala  Asp Ala Asn Leu Asp  Lys Val Leu
    1475                 1480                 1485

Ser Ala  Tyr Asn Lys His Arg  Asp Lys Pro Ile Arg  Glu Gln Ala
    1490                 1495                 1500

Glu Asn  Ile Ile His Leu Phe  Thr Leu Thr Asn Leu  Gly Ala Pro
    1505                 1510                 1515

Ala Ala  Phe Lys Tyr Phe Asp  Thr Thr Ile Asp Arg  Lys Arg Tyr
    1520                 1525                 1530

Thr Ser  Thr Lys Glu Val Leu  Asp Ala Thr Leu Ile  His Gln Ser
    1535                 1540                 1545

Ile Thr  Gly Leu Tyr Glu Thr  Arg Ile Asp Leu Ser  Gln Leu Gly
    1550                 1555                 1560

Gly Asp
    1565


<210> SEQ ID NO 38
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 38

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190
```

```
Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp
        355                 360
```

<210> SEQ ID NO 39
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 39

```
Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
    50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Cys Arg Phe Phe Arg Met Pro Arg Arg Val Phe Asn Ala Gln Lys
145                 150                 155                 160

Lys Ala Gln Ser Ser Thr Asp
                165
```

<210> SEQ ID NO 40

<211> LENGTH: 167
<212> TYPE: PRT
<213> ORGANISM: Artificial sequence
<220> FEATURE:
<223> OTHER INFORMATION: Synthetic polypeptide

<400> SEQUENCE: 40

Met Ser Glu Val Glu Phe Ser His Glu Tyr Trp Met Arg His Ala Leu
1 5 10 15

Thr Leu Ala Lys Arg Ala Arg Asp Glu Arg Glu Val Pro Val Gly Ala
20 25 30

Val Leu Val Leu Asn Asn Arg Val Ile Gly Glu Gly Trp Asn Arg Ala
35 40 45

Ile Gly Leu His Asp Pro Thr Ala His Ala Glu Ile Met Ala Leu Arg
50 55 60

Gln Gly Gly Leu Val Met Gln Asn Tyr Arg Leu Ile Asp Ala Thr Leu
65 70 75 80

Tyr Val Thr Phe Glu Pro Cys Val Met Cys Ala Gly Ala Met Ile His
85 90 95

Ser Arg Ile Gly Arg Val Val Phe Gly Val Arg Asn Ser Lys Arg Gly
100 105 110

Ala Ala Gly Ser Leu Met Asn Val Leu Asn Tyr Pro Gly Met Asn His
115 120 125

Arg Val Glu Ile Thr Glu Gly Ile Leu Ala Asp Glu Cys Ala Ala Leu
130 135 140

Leu Cys Asp Phe Tyr Arg Met Pro Arg Gln Val Phe Asn Ala Gln Lys
145 150 155 160

Lys Ala Gln Ser Ser Ile Asn
165

<210> SEQ ID NO 41
<211> LENGTH: 83
<212> TYPE: PRT
<213> ORGANISM: Bacillus phage AR9

<400> SEQUENCE: 41

Thr Asn Leu Ser Asp Ile Ile Glu Lys Glu Thr Gly Lys Gln Leu Val
1 5 10 15

Ile Gln Glu Ser Ile Leu Met Leu Pro Glu Glu Val Glu Glu Val Ile
20 25 30

Gly Asn Lys Pro Glu Ser Asp Ile Leu Val His Thr Ala Tyr Asp Glu
35 40 45

Ser Thr Asp Glu Asn Val Met Leu Leu Thr Ser Asp Ala Pro Glu Tyr
50 55 60

Lys Pro Trp Ala Leu Val Ile Gln Asp Ser Asn Gly Glu Asn Lys Ile
65 70 75 80

Lys Met Leu

<210> SEQ ID NO 42
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: n is a, c, g, or u

<400> SEQUENCE: 42
nnnnnnnnnn nnnnnnnnn 19

<210> SEQ ID NO 43
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(22)
<223> OTHER INFORMATION: n is a, c, g, or t

<400> SEQUENCE: 43
aaannnnnnn nnnnnnnnnn nn 22

<210> SEQ ID NO 44
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(22)
<223> OTHER INFORMATION: n is a, c, g, or t

<400> SEQUENCE: 44
tttnnnnnnn nnnnnnnnnn nn 22

<210> SEQ ID NO 45
<211> LENGTH: 24
<212> TYPE: PRT
<213> ORGANISM: Artificial sequence
<220> FEATURE:
<223> OTHER INFORMATION: Synthetic peptide

<400> SEQUENCE: 45

Glu Glu Leu Leu Ser Lys Asn Tyr His Leu Glu Asn Glu Val Ala Arg
1 5 10 15

Leu Lys Lys Gly Ser Gly Ser Gly
20

<210> SEQ ID NO 46
<211> LENGTH: 241
<212> TYPE: PRT
<213> ORGANISM: Artificial sequence
<220> FEATURE:
<223> OTHER INFORMATION: Synthetic polypeptide

<400> SEQUENCE: 46

Glu Glu Glu Leu Leu Ser Lys Asn Tyr His Leu Glu Asn Glu Val Ala
1 5 10 15

Arg Leu Lys Lys Gly Ser Gly Ser Gly Glu Glu Leu Leu Ser Lys Asn
20 25 30

Tyr His Leu Glu Asn Glu Val Ala Arg Leu Lys Lys Gly Ser Gly Ser
35 40 45

Gly Glu Glu Leu Leu Ser Lys Asn Tyr His Leu Glu Asn Glu Val Ala
50 55 60

Arg Leu Lys Lys Gly Ser Gly Ser Gly Glu Glu Leu Leu Ser Lys Asn
65 70 75 80

Tyr His Leu Glu Asn Glu Val Ala Arg Leu Lys Lys Gly Ser Gly Ser
85 90 95

Gly Glu Glu Leu Leu Ser Lys Asn Tyr His Leu Glu Asn Glu Val Ala
100 105 110

Arg Leu Lys Lys Gly Ser Gly Ser Gly Glu Glu Leu Leu Ser Lys Asn
115 120 125

Tyr His Leu Glu Asn Glu Val Ala Arg Leu Lys Lys Gly Ser Gly Ser
130 135 140

Gly Glu Glu Leu Leu Ser Lys Asn Tyr His Leu Glu Asn Glu Val Ala
145 150 155 160

Arg Leu Lys Lys Gly Ser Gly Ser Gly Glu Glu Leu Leu Ser Lys Asn
165 170 175

Tyr His Leu Glu Asn Glu Val Ala Arg Leu Lys Lys Gly Ser Gly Ser
180 185 190

Gly Glu Glu Leu Leu Ser Lys Asn Tyr His Leu Glu Asn Glu Val Ala
195 200 205

Arg Leu Lys Lys Gly Ser Gly Ser Gly Glu Glu Leu Leu Ser Lys Asn
210 215 220

Tyr His Leu Glu Asn Glu Val Ala Arg Leu Lys Lys Gly Ser Gly Ser
225 230 235 240

Gly

<210> SEQ ID NO 47
<211> LENGTH: 277
<212> TYPE: PRT
<213> ORGANISM: Artificial sequence
<220> FEATURE:
<223> OTHER INFORMATION: Synthetic polypeptide

<400> SEQUENCE: 47

Met Gly Pro Asp Ile Val Met Thr Gln Ser Pro Ser Ser Leu Ser Ala
1 5 10 15

Ser Val Gly Asp Arg Val Thr Ile Thr Cys Arg Ser Ser Thr Gly Ala
20 25 30

Val Thr Thr Ser Asn Tyr Ala Ser Trp Val Gln Glu Lys Pro Gly Lys
35 40 45

Leu Phe Lys Gly Leu Ile Gly Gly Thr Asn Asn Arg Ala Pro Gly Val
50 55 60

Pro Ser Arg Phe Ser Gly Ser Leu Ile Gly Asp Lys Ala Thr Leu Thr
65 70 75 80

Ile Ser Ser Leu Gln Pro Glu Asp Phe Ala Thr Tyr Phe Cys Ala Leu
85 90 95

Trp Tyr Ser Asn His Trp Val Phe Gly Gln Gly Thr Lys Val Glu Leu
100 105 110

Lys Arg Gly Gly Gly Gly Ser Gly Gly Gly Gly Ser Gly Gly Gly Gly
115 120 125

Ser Ser Gly Gly Gly Ser Glu Val Lys Leu Leu Glu Ser Gly Gly Gly
130 135 140

Leu Val Gln Pro Gly Gly Ser Leu Lys Leu Ser Cys Ala Val Ser Gly
145 150 155 160

Phe Ser Leu Thr Asp Tyr Gly Val Asn Trp Val Arg Gln Ala Pro Gly
165 170 175

Arg Gly Leu Glu Trp Ile Gly Val Ile Trp Gly Asp Gly Ile Thr Asp
180 185 190

Tyr Asn Ser Ala Leu Lys Asp Arg Phe Ile Ile Ser Lys Asp Asn Gly
195 200 205

Lys Asn Thr Val Tyr Leu Gln Met Ser Lys Val Arg Ser Asp Asp Thr

```
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Gly Ser Gly Gly Gly Gly Ser Gly Gly Gly Gly Ser
            260                 265                 270

Gly Gly Gly Gly Ser
        275


<210> SEQ ID NO 48
<211> LENGTH: 66
<212> TYPE: DNA
<213> ORGANISM: Saccharomyces bayanus

<400> SEQUENCE: 48

ttcttgtcgt acttatagat cgctacgtta tttcaatttt gaaaatctga gtcctgggag      60

tgcgga                                                                  66


<210> SEQ ID NO 49
<211> LENGTH: 605
<212> TYPE: PRT
<213> ORGANISM: Homo sapiens

<400> SEQUENCE: 49

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Trp Phe Tyr Gly Thr Glu Lys Asp Lys Asn Ser Val
                85                  90                  95

Asn Phe Lys Ile Tyr Val Leu Gln Glu Leu Asp Asn Pro Gly Ala Lys
            100                 105                 110

Arg Ile Leu Glu Leu Asp Gln Phe Lys Gly Gln Gln Gly Gln Lys Arg
        115                 120                 125

Phe Gln Asp Met Met Gly His Gly Ser Asp Tyr Ser Leu Ser Glu Val
    130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asn Pro His Gly Asn
                165                 170                 175

Asp Ser Ala Lys Ala Ser Arg Ala Arg Thr Lys Ala Gly Asp Leu Arg
            180                 185                 190

Asp Thr Gly Ile Phe Leu Asp Leu His Leu Lys Lys Pro Gly Gly Phe
        195                 200                 205

Asp Ile Ser Leu Phe Tyr Arg Asp Ile Ile Ser Ile Ala Glu Asp Glu
    210                 215                 220

Asp Leu Arg Val His Phe Glu Glu Ser Ser Lys Leu Glu Asp Leu Leu
225                 230                 235                 240
```

-continued

```
Arg Lys Val Arg Ala Lys Glu Thr Arg Lys Arg Ala Leu Ser Arg Leu
                245                 250                 255

Lys Leu Lys Leu Asn Lys Asp Ile Val Ile Ser Val Gly Ile Tyr Asn
            260                 265                 270

Leu Val Gln Lys Ala Leu Lys Pro Pro Pro Ile Lys Leu Tyr Arg Glu
        275                 280                 285

Thr Asn Glu Pro Val Lys Thr Lys Thr Arg Thr Phe Asn Thr Ser Thr
    290                 295                 300

Gly Gly Leu Leu Leu Pro Ser Asp Thr Lys Arg Ser Gln Ile Tyr Gly
305                 310                 315                 320

Ser Arg Gln Ile Ile Leu Glu Lys Glu Glu Thr Glu Glu Leu Lys Arg
                325                 330                 335

Phe Asp Asp Pro Gly Leu Met Leu Met Gly Phe Lys Pro Leu Val Leu
            340                 345                 350

Leu Lys Lys His His Tyr Leu Arg Pro Ser Leu Phe Val Tyr Pro Glu
        355                 360                 365

Glu Ser Leu Val Ile Gly Ser Ser Thr Leu Phe Ser Ala Leu Leu Ile
    370                 375                 380

Lys Cys Leu Glu Lys Glu Val Ala Ala Leu Cys Arg Tyr Thr Pro Arg
385                 390                 395                 400

Arg Asn Ile Pro Pro Tyr Phe Val Ala Leu Val Pro Gln Glu Glu Glu
                405                 410                 415

Leu Asp Asp Gln Lys Ile Gln Val Thr Pro Pro Gly Phe Gln Leu Val
            420                 425                 430

Phe Leu Pro Phe Ala Asp Asp Lys Arg Lys Met Pro Phe Thr Glu Lys
        435                 440                 445

Ile Met Ala Thr Pro Glu Gln Val Gly Lys Met Lys Ala Ile Val Glu
    450                 455                 460

Lys Leu Arg Phe Thr Tyr Arg Ser Asp Ser Phe Glu Asn Pro Val Leu
465                 470                 475                 480

Gln Gln His Phe Arg Asn Leu Glu Ala Leu Ala Leu Asp Leu Met Glu
                485                 490                 495

Pro Glu Gln Ala Val Asp Leu Thr Leu Pro Lys Val Glu Ala Met Asn
            500                 505                 510

Lys Arg Leu Gly Ser Leu Val Asp Glu Phe Lys Glu Leu Val Tyr Pro
        515                 520                 525

Pro Asp Tyr Asn Pro Glu Gly Lys Val Thr Lys Arg Lys His Asp Asn
    530                 535                 540

Glu Gly Ser Gly Ser Lys Arg Pro Lys Val Glu Tyr Ser Glu Glu Glu
545                 550                 555                 560

Leu Lys Thr His Ile Ser Lys Gly Thr Leu Gly Lys Phe Thr Val Pro
                565                 570                 575

Leu Lys Glu Ala Cys Arg Ala Tyr Gly Leu Lys Ser Gly Leu Lys Lys
            580                 585                 590

Gln Glu Leu Leu Glu Ala Leu Thr Lys His Phe Gln Asp
        595                 600                 605
```

<210> SEQ ID NO 50
<211> LENGTH: 482
<212> TYPE: PRT
<213> ORGANISM: Artificial sequence
<220> FEATURE:
<223> OTHER INFORMATION: Synthetic polypeptide

<400> SEQUENCE: 50

```
Met Val Arg Ser Gly Asn Lys Ala Ala Trp Leu Cys Met Asp Val Gly
1               5                   10                  15

Phe Thr Met Ser Asn Ser Ile Pro Gly Ile Glu Ser Pro Phe Glu Gln
            20                  25                  30

Ala Lys Lys Val Ile Thr Met Phe Val Gln Arg Gln Val Phe Ala Glu
        35                  40                  45

Asn Lys Asp Glu Ile Ala Leu Val Leu Phe Gly Thr Asp Gly Thr Asp
    50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                85                  90                  95

Ile Gln Pro Gly Ser Gln Gln Ala Asp Phe Leu Asp Ala Leu Ile Val
            100                 105                 110

Ser Met Asp Val Ile Gln His Glu Thr Ile Gly Lys Lys Phe Glu Lys
        115                 120                 125

Arg His Ile Glu Ile Phe Thr Asp Leu Ser Ser Arg Phe Ser Lys Ser
    130                 135                 140

Gln Leu Asp Ile Ile Ile His Ser Leu Lys Lys Cys Asp Ile Ser Glu
145                 150                 155                 160

Arg His Ser Ile His Trp Pro Cys Arg Leu Thr Ile Gly Ser Asn Leu
                165                 170                 175

Ser Ile Arg Ile Ala Ala Tyr Lys Ser Ile Leu Gln Glu Arg Val Lys
            180                 185                 190

Lys Thr Thr Trp Asp Ala Lys Thr Leu Lys Lys Glu Asp Ile Gln Lys
        195                 200                 205

Glu Thr Val Tyr Cys Leu Asn Asp Asp Asp Glu Thr Glu Val Leu Lys
    210                 215                 220

Glu Asp Ile Ile Gln Gly Phe Arg Tyr Gly Ser Asp Ile Val Pro Phe
225                 230                 235                 240

Ser Lys Val Asp Glu Glu Gln Met Lys Tyr Lys Ser Glu Gly Lys Cys
                245                 250                 255

Phe Ser Val Leu Gly Phe Cys Lys Ser Ser Gln Val Gln Arg Arg Phe
            260                 265                 270

Phe Met Gly Asn Gln Val Leu Lys Val Phe Ala Ala Arg Asp Asp Glu
        275                 280                 285

Ala Ala Ala Val Ala Leu Ser Ser Leu Ile His Ala Leu Asp Asp Leu
    290                 295                 300

Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
    370                 375                 380

Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
```

```
            420                 425                 430

Leu Asn Pro Pro Ala Glu Val Thr Thr Lys Ser Gln Ile Pro Leu Ser
        435                 440                 445

Lys Ile Lys Thr Leu Phe Pro Leu Ile Glu Ala Lys Lys Lys Asp Gln
    450                 455                 460

Val Thr Ala Gln Glu Ile Phe Gln Asp Asn His Glu Asp Gly Pro Thr
465                 470                 475                 480

Ala Lys


<210> SEQ ID NO 51
<211> LENGTH: 10
<212> TYPE: DNA
<213> ORGANISM: Methanobacterium thermoautotrophicum

<400> SEQUENCE: 51

aatttttgga                                                              10


<210> SEQ ID NO 52
<211> LENGTH: 83
<212> TYPE: PRT
<213> ORGANISM: Methanobacterium thermoautotrophicum

<400> SEQUENCE: 52

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro


<210> SEQ ID NO 53
<211> LENGTH: 25
<212> TYPE: DNA
<213> ORGANISM: Bacteriophage MS2

<400> SEQUENCE: 53

gcgcacatga ggatcaccca tgtgc                                             25


<210> SEQ ID NO 54
<211> LENGTH: 116
<212> TYPE: PRT
<213> ORGANISM: Bacteriophage MS2

<400> SEQUENCE: 54

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Gly Ala Trp Arg Ser Tyr Leu Asn Met Glu Leu Thr Ile Pro
```

```
65                  70                  75                  80

Ile Phe Ala Thr Asn Ser Asp Cys Glu Leu Ile Val Lys Ala Met Gln
                85                  90                  95

Gly Leu Leu Lys Asp Gly Asn Pro Ile Pro Ser Ala Ile Ala Ala Asn
            100                 105                 110

Ser Gly Ile Tyr
        115


<210> SEQ ID NO 55
<211> LENGTH: 26
<212> TYPE: DNA
<213> ORGANISM: Bacteriophage PP7

<400> SEQUENCE: 55

ataaggagtt tatatggaaa ccctta                                          26


<210> SEQ ID NO 56
<211> LENGTH: 127
<212> TYPE: PRT
<213> ORGANISM: Bacteriophage PP7

<400> SEQUENCE: 56

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
            100                 105                 110

Ser Gln Val Glu Asp Leu Val Val Asn Leu Val Pro Leu Gly Arg
        115                 120                 125


<210> SEQ ID NO 57
<211> LENGTH: 19
<212> TYPE: DNA
<213> ORGANISM: Shigella phage

<400> SEQUENCE: 57

ctgaatgcct gcgagcatc                                                  19


<210> SEQ ID NO 58
<211> LENGTH: 62
<212> TYPE: PRT
<213> ORGANISM: Shigella phage

<400> SEQUENCE: 58

Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45
```

```
Lys Arg Glu Lys Ile Thr His Ser Asp Glu Thr Val Arg Tyr
    50                  55                  60


<210> SEQ ID NO 59
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 59

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350
```

```
Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765
```

```
Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
```

```
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 60
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 60

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
```

-continued

```
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590
```

```
Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Ala Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Ala Leu Glu Ser  Glu Phe Val
        995                 1000                1005
```

Tyr Gly Asp Tyr Lys Val Tyr Asp Val Arg Lys Met Ile Ala Lys
1010 1015 1020

Ser Glu Gln Glu Ile Gly Lys Ala Thr Ala Lys Tyr Phe Phe Tyr
1025 1030 1035

Ser Asn Ile Met Asn Phe Phe Lys Thr Glu Ile Thr Leu Ala Asn
1040 1045 1050

Gly Glu Ile Arg Lys Ala Pro Leu Ile Glu Thr Asn Gly Glu Thr
1055 1060 1065

Gly Glu Ile Val Trp Asp Lys Gly Arg Asp Phe Ala Thr Val Arg
1070 1075 1080

Lys Val Leu Ser Met Pro Gln Val Asn Ile Val Lys Lys Thr Glu
1085 1090 1095

Val Gln Thr Gly Gly Phe Ser Lys Glu Ser Ile Leu Pro Lys Arg
1100 1105 1110

Asn Ser Asp Lys Leu Ile Ala Arg Lys Lys Asp Trp Asp Pro Lys
1115 1120 1125

Lys Tyr Gly Gly Phe Asp Ser Pro Thr Val Ala Tyr Ser Val Leu
1130 1135 1140

Val Val Ala Lys Val Glu Lys Gly Lys Ser Lys Lys Leu Lys Ser
1145 1150 1155

Val Lys Glu Leu Leu Gly Ile Thr Ile Met Glu Arg Ser Ser Phe
1160 1165 1170

Glu Lys Asn Pro Ile Asp Phe Leu Glu Ala Lys Gly Tyr Lys Glu
1175 1180 1185

Val Lys Lys Asp Leu Ile Ile Lys Leu Pro Lys Tyr Ser Leu Phe
1190 1195 1200

Glu Leu Glu Asn Gly Arg Lys Arg Met Leu Ala Ser Ala Gly Glu
1205 1210 1215

Leu Gln Lys Gly Asn Glu Leu Ala Leu Pro Ser Lys Tyr Val Asn
1220 1225 1230

Phe Leu Tyr Leu Ala Ser His Tyr Glu Lys Leu Lys Gly Ser Pro
1235 1240 1245

Glu Asp Asn Glu Gln Lys Gln Leu Phe Val Glu Gln His Lys His
1250 1255 1260

Tyr Leu Asp Glu Ile Ile Glu Gln Ile Ser Glu Phe Ser Lys Arg
1265 1270 1275

Val Ile Leu Ala Asp Ala Asn Leu Asp Lys Val Leu Ser Ala Tyr
1280 1285 1290

Asn Lys His Arg Asp Lys Pro Ile Arg Glu Gln Ala Glu Asn Ile
1295 1300 1305

Ile His Leu Phe Thr Leu Thr Asn Leu Gly Ala Pro Ala Ala Phe
1310 1315 1320

Lys Tyr Phe Asp Thr Thr Ile Asp Arg Lys Arg Tyr Thr Ser Thr
1325 1330 1335

Lys Glu Val Leu Asp Ala Thr Leu Ile His Gln Ser Ile Thr Gly
1340 1345 1350

Leu Tyr Glu Thr Arg Ile Asp Leu Ser Gln Leu Gly Gly Asp
1355 1360 1365

<210> SEQ ID NO 61
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 61
gacaagaagt acagcatcgg gctggcgatc gggaccaact ccgtcggctg ggctgtgatt 60
accgacgagt acaaggtgcc atccaagaag ttcaaggtcc tcggcaacac tgaccggcac 120
agcattaaga agaacctgat tggggcgctg ctgttcgatt cgggggagac tgcggaggcg 180
accaggctga agcggactgc gcgccggagg tacaccagga ggaagaatcg gatctgctac 240
ctccaggaga ttttctcgaa tgagatggcc aaggtggacg attccttctt ccatcgcctg 300
gaggagtcgt tcctcgttga ggaggacaag aagcatgaga ggcatcccat tttcgggaat 360
atcgttgacg aggtggctta ccatgagaag tacccgacca tctaccatct gcggaagaag 420
ctcgtcgatt cgaccgataa ggccgacctg cggctgatct acctggccct cgcgcacatg 480
attaagttcc ggggccattt cctcatcgag ggcgacctca acccggacaa ctcggacgtg 540
gataagctct tcattcagct cgtgcagaca tacaaccagc tcttcgagga gaatcccatt 600
aacgcctcgg gggtcgacgc taaggctatt ctctcggctc ggctgtcgaa gtcgcgccgg 660
ctggagaatc tcattgccca gctcccaggc gagaagaaga acggcctctt cggcaacctg 720
attgccctgt cgctggggct cacaccgaat ttcaagtcga acttcgacct cgccgaggac 780
gctaagctcc agctcagcaa ggatacttac gatgatgacc tcgataacct gctcgcccag 840
attggggatc agtacgcgga tctgttcctc gcggccaaga atctcagcga tgctattctc 900
ctgtcggaca ttctccgcgt caacacagag attactaagg ccccactgtc ggcgagcatg 960
attaagaggt acgatgagca tcatcaggac ctgacactgc tcaaggcgct ggtccggcag 1020
cagctccccg agaagtacaa ggagattttc ttcgatcagt caaagaatgg gtacgcgggc 1080
tacattgatg gcggcgcgtc ccaggaggag ttctacaagt tcattaagcc catcctggag 1140
aagatggacg ggaccgagga gctgctggtg aagctcaatc gggaggacct gctccggaag 1200
cagcgcacat tcgacaatgg ctcgattcct caccagattc acctgggcga gctgcacgcc 1260
attctccgca ggcaggagga cttctacccg ttcctcaagg acaaccgcga gaagatcgag 1320
aagatcctga ccttccggat tccatactac gtggggccgc tcgcgcgggg gaactcccgg 1380
ttcgcgtgga tgactcgcaa gtccgaagaa acgattacac cgtggaattt cgaggaggtc 1440
gtcgacaagg gcgctagtgc gcagtcattc attgagagga tgaccaattt cgataagaac 1500
ctgcctaacg agaaggtgct gccgaagcat tcgctgctct acgagtactt caccgtttac 1560
aatgagctga ccaaggtgaa gtatgtgact gagggcatga ggaagccagc gttcctgagc 1620
ggcgagcaga agaaggctat cgtggacctg ctcttcaaga ctaaccggaa ggtgactgtg 1680
aagcagctca aggaggacta cttcaagaag attgagtgct tcgattccgt tgagattagc 1740
ggggtggagg atcggttcaa tgcttcgctc gggacatacc acgatctcct gaagatcatt 1800
aaggataagg acttcctcga caacgaggag aacgaggaca ttctcgaaga tattgtcctg 1860
accctcaccc tcttcgagga tcgggagatg atcgaggaga ggctcaagac atacgctcat 1920
ctgttcgatg ataaggtcat gaagcagctg aagcgcaggc ggtacacagg gtgggggcgg 1980
ctgagccgga agctgatcaa cgggattcgg gataagcagt ccgggaagac aattctcgac 2040
ttcctcaagt ccgacgggtt cgctaaccgg aacttcatgc agctcattca tgatgactcg 2100
ctgacattca aggaggatat tcagaaggcg caggtttcgg ggcagggcga ctcgctccac 2160
gagcatattg cgaatctggc gggctccccc gcgattaaga agggcattct gcaaaccgtc 2220
aaggtggttg atgagctggt caaggtcatg ggcggcata agccagagaa tattgtcatc 2280

```
gagatggcgc gggagaatca gaccacacag aaggggcaga agaactcacg ggagcggatg   2340

aagcgcatcg aggagggcat caaggagctg ggtcgcaga tcctgaagga gcatcccgtg   2400

gagaacactc agctgcaaaa tgagaagctg tacctctact acctccagaa cgggagggac   2460

atgtatgtgg atcaggagct ggatattaat aggctgagcg attacgatgt cgaccacatt   2520

gtcccacagt cgttcctgaa ggacgacagc attgacaaca aggtgctgac ccgctcggat   2580

aagaacaggg gcaagagcga taatgttcca agcgaggagg ttgtgaagaa gatgaagaac   2640

tactggcggc agctcctgaa cgcgaagctc atcacacagc ggaagttcga caacctcacc   2700

aaggctgagc gcgggggcct gagcgagctg gacaaggcgg ggttcattaa gaggcagctg   2760

gtcgagacac ggcagattac aaagcatgtt gcgcagattc tcgattcccg gatgaacacc   2820

aagtacgatg agaacgataa gctgattcgg gaggtcaagg taattaccct gaagtccaag   2880

ctggtgtccg acttcaggaa ggacttccag ttctacaagg ttcgggagat caacaactac   2940

caccacgcgc atgatgccta cctcaacgcg gtcgtgggga ccgctctcat caagaagtac   3000

ccaaagctgg agtcagagtt cgtctacggg gattacaagg tttacgacgt gcggaagatg   3060

atcgctaaga gcgagcagga gattggcaag gctaccgcta agtacttctt ctactccaac   3120

atcatgaact tcttcaagac agagattacc ctcgcgaatg gcgagatccg gaagaggccc   3180

ctcatcgaga caaatgggga gacaggggag attgtctggg ataaggggcg ggatttcgcg   3240

accgtccgga aggtcctgtc gatgccccag gttaatattg tcaagaagac tgaggtccag   3300

actggcggct tctcaaagga gtcgattctc ccaaagagga actccgataa gctcattgct   3360

cggaagaagg attgggaccc caagaagtac gggggattcg actcccccac tgttgcttac   3420

tctgttctgg ttgttgctaa ggtggagaag gggaagtcga agaagctgaa gagcgtgaag   3480

gagctgctcg ggattacaat tatggagagg tcatccttcg agaagaatcc catcgacttc   3540

ctggaggcca agggctacaa ggaggtgaag aaggacctga ttattaagct gcccaagtac   3600

tcgctcttcg agctggagaa tgggcggaag cggatgctgg cgtccgcggg ggagctgcaa   3660

aaggggaacg agctggcgct cccctccaag tatgtgaact tcctctacct ggcgtcgcac   3720

tacgagaagc tgaaggggtc cccagaggat aatgagcaga agcagctctt cgtcgagcag   3780

cataagcact acctggacga gattatcgag cagattagcg agttctcgaa gcgggtcatc   3840

ctcgcggatg cgaacctgga taaggtgctc agcgcctaca ataagcaccg ggacaagccg   3900

attcgggagc aggcggagaa tattattcac ctcttcacac tcaccaacct cggggcacca   3960

gctgcgttca agtacttcga cactactatc gaccggaagc ggtacacctc gacgaaggag   4020

gtgctcgacg ccaccctcat tcaccagtcg atcacaggcc tgtacgagac acggattgac   4080

ctgtcccagc tcgggggcga c                                            4101
```

<210> SEQ ID NO 62
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 62

```
gacaagaagt actccattgg cctggcgatt gggacaaact cggtggggtg ggccgtgatt     60

acggatgagt acaaggttcc aagcaagaag ttcaaggtcc tcgggaacac agatcggcat    120

tcgattaaga agaatctcat tggggcgctc ctcttcgact cgggggagac agcggaggct    180

accaggctca agcggacagc caggcggcgg tacacaaggc ggaagaatcg catctgctac    240
```

```
ctccaggaga ttttctcgaa tgagatggcg aaggtggacg acagcttctt ccatcggctg    300
gaggagtcct tcctggtgga ggaggataag aagcacgaga ggcatccaat tttcgggaac    360
atcgtggacg aggttgcgta ccatgagaag taccctacaa tctaccatct gcggaagaag    420
ctggttgact ccacagacaa ggcggacctg aggctgatct acctcgctct ggcccacatg    480
attaagttcc gcgggcattt cctgatcgag ggggacctga atcccgacaa ttcggatgtg    540
gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga atgggctctt cgggaatctg    720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt tcgacaacgg gtcgattccc catcagatcc acctggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga agaactcgcg ggagcgcatg   2340
aagaggatcg aggaggggat taaggagctg ggcagccaga ttctcaagga gcaccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
```

aagaatcgcg gcaagagcga caacgtgccg agcgaggagg tcgtgaagaa gatgaagaac 2640
tactggcggc agctgctgaa cgcgaagctc attacacagc ggaagttcga taacctgacg 2700
aaggcggaga ggggcggcct ctccgagctg gacaaggcgg gcttcattaa gaggcagctc 2760
gtggagactc gccagatcac caagcacgtg gctcagatcc tcgatagccg gatgaatacg 2820
aagtacgatg agaatgacaa gctcatccgg gaggtgaagg taatcaccct gaagtcaaag 2880
ctcgttagcg atttccggaa ggacttccag ttctacaagg tgcgggagat taacaactac 2940
catcatgcgc acgatgcgta cctcaatgcg gtggtgggca cagccctgat taagaagtac 3000
cccaagctgg agagcgagtt cgtctacggg gactacaagg tgtacgatgt tcggaagatg 3060
atcgccaaga gcgagcagga gattgggaag gccaccgcta agtacttctt ctactcgaat 3120
attatgaatt tcttcaagac cgagatcaca ctcgctaatg ggagagattcg gaagcggccc 3180 ctcatcgaga ctaacgggga gactggcgag attgtgtggg acaaggggcg cgacttcgct 3240
accgtgcgca aggtcctctc gatgccccag gttaatattg ttaagaagac agaggtgcag 3300
acgggcgggt tctccaagga gtctatcctg ccgaagcgga actcggacaa gctgatcgcc 3360
cgcaagaagg attgggaccc caagaagtac gggggattcg atagcccaac cgtggcttac 3420
agcgtcctgg tggtcgccaa ggttgagaag gggaagtcga agaagctcaa gagcgttaag 3480
gagctgctgg gcatcaccat catggagcgg tccagcttcg agaagaatcc tatcgacttc 3540
ctggaggcta aggggtacaa ggaggtcaag aaggacctga tcattaagct gcccaagtac 3600
tctctgttcg agctggagaa cgggaggaag cggatgctgg cgtctgctgg cgagctacag 3660
aagggcaatg agctggcgct cccctcgaag tatgtcaact tcctctacct ggcttcccat 3720
tacgagaagc tgaagggctc gcccgaggat aatgagcaga agcagctctt cgtggagcag 3780
cacaagcact acctcgacga gatcattgag cagatttcgg agttctcgaa gcgggtcatt 3840
ctcgcggacg cgaacctcga caaggtcctc tcggcgtaca acaagcaccg ggacaagccc 3900
atccgggagc aggccgagaa cattatccac ctcttcacac tgaccaacct cggcgctccc 3960
gccgcgttca agtacttcga caccaccatt gaccgcaaga gatacacatc caccaaggag 4020
gtgctggacg cgaccctcat ccaccagagc atcacaggcc tctacgagac acggatcgac 4080
ctctcgcagc tcgggggcga t 4101

<210> SEQ ID NO 63
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 63
gacaagaagt actcgatcgg cctggcgatt ggcacaaaca gcgtggggtg ggctgtgatc 60
actgatgagt acaaggtgcc atcgaagaag ttcaaggtgc tggggaatac agaccggcat 120
tcgatcaaga agaatctcat tggcgctctc ctcttcgatt ccggcgagac tgctgaggcg 180
acccgcctga agcgcaccgc ccggcggcgc tacactcggc ggaagaatag gatttgctac 240
ctccaggaga ttttctcgaa tgagatggcc aaggtggatg acagcttctt ccaccgcctg 300
gaggagtcgt tcctggtcga ggaggacaag aagcatgagc ggcaccctat cttcgggaat 360
atcgttgatg aggtcgccta ccacgagaag taccccacta tctaccatct ccgcaagaag 420
ctcgtggaca gcacagataa ggccgacctc cgcctgatct acctcgccct cgcgcacatg 480
attaagttcc gggggcactt cctcattgag ggggatctga atcccgataa ctccgacgtg 540

```
gacaagctgt tcatccagct ggtgcagaca tacaaccagc tgttcgagga gaatcccatc    600
aacgcgagcg gcgtggacgc taaggccatt ctgtcggcta ggctctcgaa gtcgaggcgg    660
ctggagaacc tgattgcgca gctccccggc gagaagaaga acgggctgtt cgggaatctc    720
atcgccctct ccctcggcct cacaccaaac ttcaagagca atttcgacct ggctgaggac    780
gctaagctgc aactctcaaa ggatacatac gatgacgacc tggacaatct cctggctcag    840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagattttc ttcgatcaga gcaagaatgg ctacgccggc   1080
tacatcgacg gggcgcgag ccaggaggag ttctacaagt tcatcaagcc catcctggag   1140
aagatggacg gcaccgagga gctactcgtg aagctcaatc gggaggatct cctccggaag   1200
cagcggacat tcgataacgg gtctatccca caccagatcc acctcggcga gctgcatgcg   1260
attctgcggc ggcaggagga tttctaccct ttcctgaagg acaaccggga gaagatcgag   1320
aagatcctca cattccggat tccatactac gtcggccccc tggcgagggg caatagccgg   1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga agaaggccat tgtggacctc ctgttcaaga caaaccgcaa ggtgacagtg   1680
aagcagctga aggaggatta cttcaagaag attgagtgct tcgactcagt ggagatttca   1740
ggcgtggagg atcggttcaa cgcgagcctg gggacttacc acgacctgct gaagattatt   1800
aaggacaagg acttcctgga taacgaggag aatgaggaca tcctggagga tattgtgctc   1860
accctcaccc tgttcgagga cagggagatg attgaggaga ggctcaagac ctacgcgcac   1920
ctgttcgatg acaaggtcat gaagcagctg aagaggcggc gctacactgg gtggggccgc   1980
ctgtcgcgga agctgatcaa cggcattcgg gataagcagt ccgggaagac cattctggat   2040
ttcctgaagt cggacggctt cgccaacagg aatttcatgc agctgatcca cgacgactcc   2100
ctcaccttca aggaggacat tcagaaggcc caggttagcg gccagggga ctcactccac   2160
gagcatattg ccaatctggc cggctctcca gctatcaaga agggcatcct gcaaacagtt   2220
aaggttgttg acgagctggt taaggtcatg ggcggcata agcccgagaa cattgtcatc   2280
gagatggctc gggagaacca gacaactcag aagggccaga agaactccag ggagcgcatg   2340
aagcggattg aggagggcat taaggagctg ggtcccaga tcctcaagga gcaccctgtc   2400
gagaacactc agctgcaaaa cgagaagctc tacctgtact acctccagaa cgggcgggat   2460
atgtatgtgg atcaggagct ggacatcaac aggctctccg actacgacgt ggatcacatt   2520
gtcccacagt ctttcctcaa ggatgattcc atcgacaaca aggtgctgac gcgcagcgac   2580
aagaataggg ggaagtcgga caacgttccg agcgaggagg tcgtgaagaa gatgaagaat   2640
tactggaggc agctcctgaa tgcgaagctg atcactcaga ggaagttcga caatctgaca   2700
aaggcggaga ggggcgggct ctcggagctg gataaggcgg gcttcatcaa gcggcagctc   2760
gttgaaaccc ggcagatcac caagcatgtc gcccagatcc tcgatagccg catgaacacc   2820
aagtacgatg agaacgacaa gctcattcgg gaggttaagg tcattacgct gaagtccaag   2880
```

ctcgtcagcg acttcaggaa ggatttccag ttctacaagg ttcgggagat taacaactac 2940
caccacgcgc atgatgcgta cctgaacgct gttgtcggca ctgctctcat caagaagtac 3000
ccaaagctgg agtccgagtt cgtctacggg gactacaagg tctacgatgt ccggaagatg 3060
atcgccaagt cggagcagga gatcgggaag gctactgcga agtacttctt ctacagcaac 3120
attatgaatt tcttcaagac ggagattacg ctggcgaacg gggagattag gaagaggccc 3180
ctcattgaga ctaatgggga gacaggcgag attgtttggg acaagggccg cgacttcgcg 3240
actgtgcgga aggtcctgtc catgccacag gtgaatattg ttaagaagac agaggtgcag 3300
actgggggct tctcgaagga gagcattctc ccaaagcgga acagcgataa gctcatcgcg 3360
cgcaagaagg attgggaccc taagaagtac ggcggcttcg attctcccac tgtggcctac 3420
tccgttctcg tggttgccaa ggttgagaag gggaagtcga agaagctgaa gtcggtcaag 3480
gagctgctcg ggattacaat catggagcgg agcagcttcg agaagaaccc tattgatttc 3540
ctggaggcca agggctacaa ggaggttaag aaggatctca ttatcaagct ccctaagtac 3600
tctctgttcg agctggagaa tggccggaag aggatgctgg cctcggctgg cgagctacag 3660
aaggggaatg agctggccct cccgtcgaag tatgtgaatt tcctgtacct cgcgtcgcac 3720
tacgagaagc tcaagggcag cccggaggat aatgagcaga agcagctctt cgtggagcag 3780
cataagcact acctggacga gatcattgag cagatcagcg agttctcgaa gcgggttatt 3840
ctggctgatg ctaacctgga caaggttctg agcgcctaca ataagcatcg cgacaagccg 3900
attcgcgagc aggcggagaa tattatccac ctgttcaccc tcactaacct cggggctccc 3960
gcggccttca agtacttcga taccacaata gataggaagc ggtacacctc gacgaaggag 4020
gtcctcgacg ccacactcat ccatcagtcg attacaggcc tgtacgagac acggattgac 4080
ctctcgcagc tg 4092

<210> SEQ ID NO 64
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 64
gacaagaagt attccatagg cctggctatc ggcaccaaca gcgtgggctg ggccgtcatc 60
accgacgagt acaaagtgcc gagtaaaaag ttcaaagtgc tcggcaacac cgaccgccac 120
tccataaaga aaaacctgat cggggcgctc ctgttcgaca gcggcgagac ggcggaggcc 180
acccgcttga aacgcacggc ccgacggcgc tacacgcggc gcaagaaccg gatctgttac 240
ctacaggaga ttttctctaa cgagatggcg aaggtggacg actcgttctt tcaccgcctc 300
gaagagtcct tcctcgtgga ggaggacaag aaacacgagc gccacccgat cttcggcaac 360
atcgtggacg aggtggccta ccacgagaag tacccgacca tctaccacct ccggaagaaa 420
ctcgtggaca gcacggacaa ggccgacctg aggctcatct acctcgccct ggcgcacatg 480
attaagttcc ggggccactt cctgatcgag ggcgacctga acccggacaa cagcgacgtg 540
gacaagctgt tcatccagct agtccagacc tacaaccagc ttttcgagga aaaccccatc 600
aacgccagcg gggtggacgc gaaggcgatc ctgtccgccc ggctgagcaa gtcccggcgg 660
ctggagaacc tcatcgcgca gttgcccggc gagaagaaga acgggctgtt cgggaacctg 720
atcgccctct ccctggggct caccccgaac ttcaagtcca acttcgacct cgccgaggac 780
gccaaactac agctgagcaa ggacacctac gacgacgacc tcgacaacct gctggcccag 840
atcggggacc agtacgcaga cctgttcctc gccgccaaga acctctccga cgccatcctg 900
ctgtcggaca tcctgcgggt gaacacggag atcacgaagg ccccgctctc ggcctcgatg 960
attaaacgct acgacgagca ccaccaggac ttgaccctcc tcaaggcgct ggtccgccag 1020
cagcttcccg agaagtacaa ggaaatcttt ttcgatcaga gcaagaacgg gtacgccggg 1080
tacatcgacg gcggggcgtc ccaggaggag ttctacaagt tcatcaagcc catcctggag 1140
aaaatggacg ggaccgagga gctgctcgtg aagctcaacc gcgaagattt gctccgcaag 1200
cagcgcacgt tcgacaacgg gtcgatcccg caccagatcc acctgggcga gctgcacgcg 1260
atcctcaggc gtcaggaaga cttctacccc ttcctcaagg acaaccgcga gaagatagag 1320
aagattctga ccttcagaat tccttattac gtgggcccgc tggctcgggg caactcgcgc 1380
ttcgcctgga tgacgcgcaa gtccgaggag accatcaccc cgtggaactt cgaggaggtg 1440
gtggataagg gtgcctcggc ccagtccttc atcgagcgga tgaccaactt cgacaagaac 1500
ctgccgaacg agaaggtgct ccccaagcac agcctgctct acgaatattt cacggtgtac 1560
aacgagctga cgaaggtcaa gtacgtgacc gagggaatga ggaaacctgc attcctctcc 1620
ggggagcaga agaaagccat agtcgacctc ctgttcaaga ccaaccggaa ggtcaccgtc 1680
aagcagctca aggaggacta cttcaagaag atcgagtgct tcgattcagt ggagatcagc 1740
ggcgtcgagg accggttcaa cgccagcctg ggcacctacc acgacctgct caagatcatc 1800
aaggacaagg acttcctcga caacgaggag aacgaggaca tcctggagga catcgtgctg 1860
accctgacgc tcttcgagga ccgcgagatg atcgaggagc gcctcaagac ctacgcccac 1920
ctgttcgacg acaaggtgat gaagcagctc aagcggcgga gatatactgg gtggggccgc 1980
ctctcccgga agctcattaa cggtatcagg gataagcagt ccgggaagac gatcctcgac 2040
ttcctcaagt cggacgggtt cgccaaccgc aacttcatgc agctcatcca cgacgactcc 2100
ctgacgttca aggaggacat ccagaaggcc caagtgtctg gtcaaggtga ctcgctccac 2160
gagcacatcg ccaacctcgc gggcagcccg gccatcaaga agggaatact ccagaccgtc 2220
aaggtggtgg acgagctggt gaaggtcatg ggccgccaca agccggagaa catcgtcatc 2280
gagatggcgc gggagaacca gaccacgcag aaggggcaga aaaatagccg tgagcgcatg 2340
aagcgcatcg aggaggggat taaggagttg ggcagccaga tcctcaagga gcaccctgtg 2400
gagaacacgc agttgcaaaa cgagaagctc tacctgtact acctccagaa cgggagggat 2460
atgtacgtgg accaagaact ggacatcaac cgcctgtccg actacgacgt ggaccacatc 2520
gtgccgcaga gcttcctcaa ggacgacagc atcgacaaca aggtgctcac ccggtccgac 2580
aagaatcggg gcaagtccga caacgtgccc agcgaggagg tcgtcaaaaa gatgaaaaac 2640
tactggcgac aactactgaa cgccaagctc atcacccagc gcaagttcga caacctcaca 2700
aaagccgagc gcggcgggtt gagcgagctg gacaaggccg ggttcatcaa gcgccagctc 2760
gtcgagacgc gccagatcac gaagcacgtc gcgcagatac tcgacagccg gatgaacacc 2820
aagtacgacg agaacgacaa gctcatccgg gaggtgaagg tcatcaccct caagtcgaag 2880
ctcgtgagcg acttccgcaa ggacttccag ttctacaagg tccgggagat caacaactac 2940
caccacgccc acgatgctta tcttaacgcc gtggtgggga cggccctcat taagaaatac 3000
ccgaagctgg agtcggagtt cgtgtacggc gactacaagg tgtacgacgt caggaagatg 3060
atcgccaagt ccgaacagga gatcgggaag gccacggcga aatacttctt ctacagcaac 3120
atcatgaact tcttcaagac cgagatcacc ctcgccaacg gcgagatccg caagcgcccg 3180

-continued

```
ctcatcgaga cgaacgggga gaccggcgag atcgtctggg acaaggggcg cgacttcgcc   3240

actgtgcgga aggtgctgtc gatgccccag gtcaacatcg tcaagaagac ggaggtccag   3300

acgggcgggt tcagcaagga gagcatcctg ccgaagcgca acagcgacaa gctgatcgcc   3360

cgcaaaaagg actgggatcc aaaaaagtac ggcggcttcg acagccccac cgtcgcctac   3420

agcgtcctcg tcgtcgctaa agtcgagaag ggcaagtcca aaaagctcaa gagcgtcaag   3480

gagctgctcg ggatcaccat catggagcgg tccagcttcg agaagaaccc aattgatttc   3540

ctggaggcga agggctacaa ggaggtcaag aaagacctca tcataaagct gccgaagtac   3600

tcactcttcg agctggagaa cgggcgcaag cggatgctgg cgtcggccgg agagctccaa   3660

aagggcaacg agctggcgct gccgagcaag tacgtgaact tcctctacct ggcgtcccac   3720

tacgagaagc tcaagggcag tccagaggat aacgagcaga agcagctatt cgtggagcag   3780

cacaagcact acctggacga gatcatcgag cagatcagcg agttctccaa gcgcgtcatc   3840

ctggcggacg ccaacctgga caaggtgctg tccgcgtaca acaagcaccg cgacaagccg   3900

atccgcgagc aagccgagaa catcatccac ctgttcaccc tcacgaacct cggggcaccc   3960

gccgccttca aatatttcga cacgaccatc gaccgcaagc gctacaccag cacgaaggag   4020

gtgctcgacg ccaccctgat ccaccagagc atcaccgggc tgtacgagac ccgcatcgac   4080

ctctcgcagc tcggcgggga c                                             4101


<210> SEQ ID NO 65
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 65

gacaagaagt acagtattgg attggccatc gggacgaaca gcgtgggctg ggccgtcatc     60

accgacgagt acaaggtgcc atccaagaag tttaaggttc tggggaatac cgaccgccac    120

tcgatcaaga aaaatctcat cggggcgctg cttttcgaca gcggcgagac ggcggaagcg    180

acgcggctca agcggacggc tcgtcgccgt tacacccggc gtaagaaccg catctgttac    240

ctccaggaga tattcagcaa cgagatggcg aaggtggacg actccttttt ccaccgtctt    300

gaggagtcct tcctggtcga ggaggacaag aagcacgagc gccaccccat cttcgggaac    360

atcgtggacg aggtggccta ccacgagaag taccccacga tctaccacct ccgcaaaaaa    420

ctcgtggact caactgacaa ggccgatttg aggcttatct acctcgccct cgcccacatg    480

attaagttcc gtgggcactt cctaatcgag ggtgacctca accccgacaa ctctgacgtg    540

gacaagctgt tcatccagct tgtgcagacc tacaatcagc tctttgagga gaatccgatc    600

aacgcatctg gtgtggacgc aaaggccatc ctcagcgcgc ggctgagcaa gtctaggcgg    660

ttggagaacc tgatcgccca actgcccggc gagaagaaaa atggcctctt cggcaacctg    720

atcgccctgt cgctggggct cacgccgaac ttcaagagta actttgacct ggcggaggac    780

gctaagctcc agctatctaa ggacacatac gacgacgacc tggacaacct gctggcccag    840

atcggcgacc agtacgccga cctcttccta gccgccaaga acctgtccga cgccatcctc    900

ctcagcgaca tcctgcgcgt gaacacggag atcacgaagg ctccgctcag cgcctccatg    960

attaagcggt acgacgagca ccaccaagac ctaactttac tcaaagccct cgtgcggcag   1020

cagcttcccg agaagtacaa agagatattt tttgatcagt ccaagaacgg ttatgcgggc   1080

tacatcgacg gcggcgcgag ccaggaggag ttctacaagt tcatcaagcc catcctggag   1140
```

aagatggacg gcacggagga gctgctcgtg aagctcaacc gtgaagacct cctgcgaaag 1200
cagcgaacct tcgacaacgg ttcgatcccg caccagatcc acctcgggga gctgcacgcc 1260
atcctgaggc gacaggagga cttctaccct ttcctaaagg acaaccgcga gaagattgaa 1320
aaaatcctga cgtttcgcat accctactac gtcggcccgc tggcgcgcgg caactcccgg 1380
ttcgcctgga tgacccgtaa gagcgaggag acgatcaccc cgtggaactt cgaggaggtc 1440
gtggacaagg gcgcgagcgc gcagagcttc atcgagcgca tgaccaactt cgacaagaac 1500
ctcccgaacg agaaggtgct cccaaagcac tccctcctgt acgagtattt caccgtgtac 1560
aacgagttga caaaggtgaa gtacgtgacg gagggaatgc ggaagcctgc gttcctctcg 1620
ggcgagcaga agaaggcaat cgtggacctg ctcttcaaga ccaaccggaa ggtgacggtg 1680
aagcagctca aggaggacta cttcaaaaaa atcgagtgct tcgactccgt ggagataagc 1740
ggcgtggagg accgattcaa cgcctccctc ggcacctacc acgacctcct taagatcatc 1800
aaggacaagg acttcctgga caacgaggag aacgaggaca tcctggagga catcgtgctc 1860
accctgaccc tcttcgagga ccgggagatg atcgaggagc gcctcaagac gtacgcccac 1920
ttgttcgacg acaaggtgat gaagcagctc aagcggcggc gatacaccgg gtggggccgc 1980
ctatcccgca aacttatcaa cggcatccgc gacaagcagt ccggcaagac gatcctggat 2040
ttcctcaagt cggacgggtt cgccaaccgg aacttcatgc agctcatcca cgacgacagc 2100
ctcacgttca aggaggacat ccagaaggcc caagtgagcg gtcaagggga cagcctccac 2160
gagcacattg cgaaccttgc tgggagccct gcgatcaaga aggggatatt gcaaaccgtg 2220
aaggtcgtgg acgagttggt gaaggtcatg ggcgacacaa agcccgagaa catcgtgatc 2280
gagatggcca gggaaaatca gaccacgcag aagggccaaa aaaacagccg cgagcggatg 2340
aagcggatcg aggagggcat caaggagctg ggtcgcagat tcctcaagga gcacccggtg 2400
gagaacacgc agctccagaa cgagaagctg tacctctatt acctacagaa cgggcgggat 2460
atgtacgtgg accaggagct agacatcaac cgcctgtccg actacgacgt ggaccatatc 2520
gtcccgcagt cgttcttgaa ggacgacagc atcgacaaca aggtgctcac aagatcggat 2580
aagaatcgag gcaagtccga caacgtgccc tcggaggagg tggtcaagaa aatgaaaaac 2640
tactggcggc agttgctgaa cgccaagctc attacgcagc ggaagttcga caacctgacg 2700
aaggctgaac gtggtgggct cagcgagcta gacaaggcgg ggttcatcaa gcggcagctc 2760
gtcgagaccc ggcagatcac caagcacgtg gcgcagatcc tggactcgcg catgaacacc 2820
aagtacgacg agaacgacaa gctcatccgt gaggtgaagg tcatcaccct taagtctaag 2880
ctggtcagtg acttccgcaa ggacttccag ttctacaagg tccgggagat caacaactac 2940
caccacgcgc acgacgccta cctcaacgcg gtggtgggga cggcgcttat taagaaatat 3000
cccaagctgg aaagcgagtt cgtttacggc gactacaagg tgtacgacgt ccgcaagatg 3060
atcgcaaagt cggaacagga aatcggaaag gcgacggcca aatatttctt ttactccaac 3120
atcatgaatt tttttaagac ggagatcacc ctggcgaacg gggagatccg caagcggccc 3180
ctcatcgaga ccaacgggga gacgggcgag atcgtctggg acaagggccg ggacttcgcc 3240
accgtgcgga aggtgctttc tatgcctcaa gtcaatatcg tcaaaaagac agaggtgcag 3300
accggcgggt tcagcaagga gtctatcctg ccgaagcgca actcggacaa gctcatcgcg 3360
cgcaagaaag actgggaccc caaaaaatat ggcgggttcg actcgccgac cgtcgcctac 3420
agcgtcctcg tggtggctaa ggtcgagaag ggcaagagca aaaagctaaa gtcggtgaag 3480

```
gagctgctgg gcatcaccat catggagcgc tcgtctttcg agaagaatcc aatcgacttc   3540

ctagaggcga aggggtacaa ggaggtcaaa aaggatctta tcatcaaact gccgaagtac   3600

agtctgttcg agctggagaa cgggcggaag cggatgctgg ctagtgcggg cgagttgcag   3660

aagggcaacg agttggcact gccctccaag tacgtgaact tcctgtacct ggcctcccac   3720

tacgagaagc tcaaggggag ccccgaggac aacgagcaga agcagctatt cgtcgagcag   3780

cacaagcact acctggacga gatcatcgag cagatcagtg agttctccaa gcgggtcatc   3840

ctcgcggacg ccaacctgga caaggtgctg agcgcgtaca acaagcacag ggacaagcca   3900

atcagggaac aggccgagaa catcatccac ctgttcaccc tgaccaacct gggtgcaccg   3960

gctgccttca agtactttga cacgaccatc gaccggaagc gctacacctc cacgaaggag   4020

gtgctggacg ccacgctgat ccaccagagc atcaccgggc tctacgagac acggatcgac   4080

ctgagccagc ttggcgggga c                                             4101
```

<210> SEQ ID NO 66
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 66

```
gacaaaaagt attccattgg actcgctatc ggcacgaaca gcgtcgggtg ggcggtcatc     60

actgacgagt acaaggtgcc gagcaagaag tttaaggtgc tgggaaacac cgacaggcac    120

tcgatcaaga aaaatcttat cggggcccta ctcttcgact ccggagaaac cgccgaggcc    180

acccggttga agcgcacggc ccgccgtcgc tacaccaggc gcaagaaccg gatctgctac    240

ctccaggaga tattcagcaa tgagatggcg aaggtggacg actcgttttt tcacaggcta    300

gaggagtctt tcctcgtgga ggaggacaag aaacacgagc gccaccccat cttcggcaac    360

atcgtggatg aggtggcata tcacgagaag tacccaacca tctaccacct ccgcaaaaag    420

ctcgtggact ctaccgacaa ggccgacctc cgtctgatct acctcgcgct ggcccacatg    480

attaagttcc gaggacactt tctgatcgag ggcgacctga acccagacaa cagcgacgtg    540

gacaagctgt tcatccaact tgtccagacc tacaatcagc tcttcgagga gaaccctatc    600

aacgcctcgg gcgtggacgc gaaggccatc ctgtccgccc gcctgagcaa gtcgcggcgg    660

ctggagaacc tgatcgccca gctccccggc gaaaaaaaga acggcctctt cggcaacctc    720

atcgcgttgt cgctggggct caccccgaac ttcaagtcca acttcgacct ggccgaggac    780

gctaaactcc agctctcgaa ggatacctac gacgacgacc tcgacaacct gctggcccag    840

atcggcgacc agtacgcgga ccttttcctg gcggccaaga acctgagcga cgcgatcctc    900

cttagcgaca tactccgtgt gaacaccgag atcacgaagg ccccgctctc cgcgtccatg    960

attaagcgct acgacgagca ccaccaagac cttaccctgc ttaaggcgct ggtcaggcag   1020

cagttaccgg agaagtacaa ggagatcttt tttgatcaat ctaagaacgg ttacgccggg   1080

tacatcgacg gcggcgcgtc ccaggaggag ttctacaagt tcatcaagcc gatcttggag   1140

aaaatggacg ggaccgagga gctgctcgtg aagctcaacc gcgaagacct cctccgcaag   1200

cagcgcacct tcgacaacgg gagcatcccg caccagatcc acctgggaga gctgcacgcg   1260

atcctgcgga gacaagagga cttctacccc ttcctcaagg acaaccggga gaagattgaa   1320

aaaatactta cttttcgtat cccgtactac gtcgggcccc ttgcgagggg caactccaga   1380

ttcgcgtgga tgacccgcaa gtccgaggag accatcaccc cgtggaactt cgaggaggtg   1440
```

gtggacaagg gcgcgtcggc ccagtcgttc atcgagcgca tgaccaactt cgacaagaac 1500
cttccgaacg agaaggtgct cccgaagcac agcctgctct acgaatattt tactgtgtac 1560
aacgagctga cgaaggtcaa gtacgttacg gaggggatga ggaagcccgc cttcctctcc 1620
ggcgagcaga agaaagccat tgtggatctc ctgttcaaga ccaaccgcaa ggtgacggtg 1680
aaacagctca aagaggacta cttcaagaag atcgagtgct tcgactccgt agagatcagc 1740
ggggtcgagg accgcttcaa cgcctcgctg ggcacgtacc acgacctgct aaagattatc 1800
aaggacaaag acttcctaga caatgaggag aacgaggaca ttctggagga catcgtgctg 1860
actctgacgc tgttcgaaga ccgcgagatg atcgaggagc ggcttaagac gtacgcccac 1920
ctgttcgacg acaaggtgat gaagcagttg aaacggcggc gctacaccgg gtggggccgc 1980
ctctcccgca agctcatcaa cggcatccgc gacaagcagt cggggaagac gatcctggac 2040
ttcctcaaga gcgacggctt cgccaaccga aacttcatgc agctaatcca cgacgacagc 2100
ctgacgttca aggaggacat ccagaaggcc caagtgagcg gccagggaga ctcgctacac 2160
gagcatatcg ccaacctggc tggcagcccg gcgattaaga aaggaatcct ccaaaccgtc 2220
aaagtggtgg acgagctggt gaaggtgatg ggccgccaca agcccgagaa cattgtgatc 2280
gagatggcgc gggagaacca gacgacgcag aagggccaaa aaaatagcag ggaaaggatg 2340
aagcgaatag aggaggggat caaggagctg gggagccaga ttctcaaaga gcacccggtc 2400
gagaacacac agctccagaa cgagaagctg tacctctact acctccaaaa cggccgcgat 2460
atgtacgtgg accaggaact agacatcaac cggctgagcg actatgacgt ggaccacatc 2520
gtgccgcagt ccttcctcaa ggacgactcg attgacaaca aagtgctcac tagatccgac 2580
aagaacagag gcaagagcga taacgtcccg tcggaggagg tcgtcaagaa aatgaaaaac 2640
tactggcggc agctcctaaa cgccaagctc atcacgcagc gtaagttcga caacctgacg 2700
aaggcggagc ggggcgggct gagcgagctg gacaaagcgg ggttcatcaa gcggcagctc 2760
gttgagacgc ggcagatcac aaagcacgtc gcgcaaatcc tcgactcccg catgaacacc 2820
aagtacgacg agaacgacaa gctcatccgg gaggtgaagg tcattaccct taaatcgaag 2880
ctcgtcagcg actttcgtaa ggacttccag ttctacaagg tcagagagat caacaactac 2940
caccacgccc acgacgccta tctgaacgcc gtggtgggca ccgcgcttat taagaagtac 3000
cccaagctgg agtccgagtt cgtgtacggc gactacaagg tttatgacgt caggaagatg 3060
atcgccaagt cggaacagga gatcggaaaa gctaccgcca aatatttctt ctatagcaac 3120
atcatgaact tcttcaaaac cgagatcacc ctcgccaacg gcgagatccg gaagcgcccg 3180
ctcatcgaga ccaacgggga gaccggggag atcgtctggg acaaggggcg ggacttcgct 3240
actgtccgaa aggtgctctc catgccacaa gtgaatatcg tcaagaaaac agaggtgcag 3300
accggagggt tcagtaagga gtccatcctg cccaagcgga actccgacaa gctaattgct 3360
cgcaaaaagg attgggatcc taaaaaatat ggcggcttcg actcgcccac ggtcgcctac 3420
tctgtgctgg tcgtggcgaa ggtggagaag ggcaagtcca agaagctcaa gagcgtcaag 3480
gagctgctgg ggatcacgat catggagcgt agttcgtttg agaagaatcc catcgacttc 3540
ctggaggcta agggctacaa ggaggtcaaa aaggacctca tcattaagct gccgaagtac 3600
agcctcttcg agctggagaa cgggcggaag cgtatgctcg cctccgctgg ggagttacaa 3660
aaggggaacg agctggcgct gccgtctaag tacgtcaact tcctgtacct ggcctcccac 3720
tacgagaagc tcaaggggtc gccggaggac aacgagcaga agcagctctt cgtagagcag 3780
cacaagcact acctggacga gatcatcgag cagatttcag agttctcaaa gcgggtcatc 3840
ctcgccgacg ccaacctgga caaggtgctc tcggcctaca acaagcaccg ggacaagccg 3900
atccgcgaac aggccgaaaa catcatccac ctgttcacgc tcaccaacct cggtgccccg 3960
gcggccttca agtactttga cacgaccatc gaccggaagc gctatacctc gacgaaggag 4020
gtgctggacg ccaccctgat ccaccagtcc atcaccgggc tttacgagac ccggatcgac 4080
ctctcgcagc ta 4092

<210> SEQ ID NO 67
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 67
gacaagaagt atagtattgg actcgccatc ggaaccaact ctgtggggtg ggctgttatt 60
acagatgaat ataaggtgcc atccaaaaag tttaaagttc tgggcaatac tgatagacac 120
tcaatcaaga agaatctgat aggtgcactt ctgtttgata gtggagagac tgccgaggca 180
accagactta aaaggactgc aagaagaaga tataccagaa gaaagaatag gatttgctat 240
ttgcaggaaa tcttcagcaa cgaaatggcc aaggttgatg actcattttt ccataggttg 300
gaggagagtt ttcttgtgga ggaagataag aagcacgaaa gacacccaat tttcgggaat 360
atagtggacg aggtggctta tcatgagaag tatcccacta tctaccacct gagaaagaaa 420
cttgtggact caaccgataa ggctgatctt aggcttatat acttggccct tgcacatatg 480
atcaaattca ggggccattt tcttatcgaa ggcgatctta atcccgataa ctcagatgtg 540
gacaagctgt ttatacaact tgtgcaaacc tacaatcaac tcttcgagga gaatcccatt 600
aacgcctccg gcgtggatgc aaaagccata ctgtcagcca gactgagcaa aagtaggaga 660
ctggagaatc ttatagccca actgcccggt gaaaagaaga atgggctctt cggaaatctg 720
atcgctcttt cattggggtt gacacccaac tttaagagta actttgactt ggcagaagat 780
gcaaagttgc agctcagtaa agacacatat gacgatgacc ttgacaatct cttggcacaa 840
ataggggatc aatacgctga ccttttcctc gctgccaaga acctcagcga cgctatactg 900
ttgtccgaca ttcttagggt taataccgaa attacaaagg cccctcttag tgcaagtatg 960
atcaaaaggt atgatgagca tcaccaagac cttacactgc tgaaggctct ggttagacag 1020
caactccctg aaaagtataa ggaaatattc ttcgaccaaa gtaagaacgg gtacgccggt 1080
tatattgatg gggcgcaag tcaagaagaa ttttacaaat tcatcaagcc aattcttgaa 1140
aagatggacg ggactgagga attgctggtg aaactgaata gagaggacct tcttagaaaa 1200
cagaggacat ttgacaatgg gtccatccca caccagattc atctgggga actccacgca 1260 atattgagga gacaagaaga cttttaccca ttccttaagg ataatagaga gaaaatcgaa 1320
aaaatcctga ctttcaggat tccttactat gttgggccac tggccagggg gaactcaaga 1380
ttcgcttgga tgacaaggaa gtcagaagaa accataaccc cttggaattt tgaagaggtg 1440
gttgataagg gggcatcagc ccagtctttc atagagagga tgaccaactt tgataaaaat 1500
cttccaaatg agaaggtttt gccaaaacat agtcttttgt acgagtactt tactgtttat 1560
aacgaattga ccaaggtgaa gtatgtgacc gagggaatga ggaagccagc atttttgtcc 1620
ggggagcaaa agaaagcaat cgttgatctt ctcttcaaga ccaacagaaa agtgaccgtg 1680
aaacaactga aggaagacta cttcaaaaag atagaatgtt tcgattcagt ggaaattagc 1740

```
ggtgttgaag acaggttcaa tgcttcattg ggtacttacc acgacctgtt gaagataatc   1800
aaagacaagg actttctcga taatgaggag aacgaagaca tcttggaaga cattgtgctt   1860
acactcactt tgtttgagga cagggaaatg attgaggaaa gactcaaaac ttacgctcat   1920
ttgtttgatg ataaggttat gaaacaacta aaaagaagaa ggtacaccgg ctggggaaga   1980
ttgagtagga aactgatcaa cggtattaga gataaacaat ccggaaagac tatcctcgat   2040
ttccttaaga gtgatggctt tgcaaatagg aattttatgc agctgattca tgacgactca   2100
cttaccttca aagaagacat ccaaaaagct caggtgtctg ggcaaggcga cagtctgcat   2160
gaacatatag ctaacttggc tgggagtccc gccatcaaga aggggatact tcaaacagtt   2220
aaagttgtgg acgaattggt gaaggtaatg ggaaggcaca agcctgaaaa tatagtgata   2280
gaaatggcaa gggaaaatca aacaacccag aagggacaga agaacagtag ggaaaggatg   2340
aaaaggatag aagaggggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aaggagtgac   2580
aagaatagag ggaaatccga caacgttcca tccgaggaag ttgtgaagaa gatgaagaac   2640
tactggaggc agttgctgaa cgctaagctc attacccaga ggaaattcga taacctgacc   2700
aaagcagaga gaggcgggct gagcgaactc gataaagcag gtttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggttagcg atttcagaaa ggatttccaa ttctataagg ttagagagat caacaattat   2940
catcatgcac atgatgccta tctgaatgct gtggttggta cagcccttat caagaagtac   3000
cctaagctag agagcgagtt tgtgtacgga gattataagg tgtatgatgt gaggaaaatg   3060
atcgctaaaa gtgagcaaga gattggaaag gctaccgcca aatacttctt ttattccaat   3120
attatgaatt tcttcaagac agaaatcacc ctggctaacg gcgagataag gaagaggccg   3180
cttatcgaaa ctaatgggga gacaggcgaa atagtgtggg acaaagggag ggatttcgca   3240
actgtgagga aggttttgag catgcctcag gtgaatatcg ttaagaaaac cgaagttcaa   3300
actggagggt tctctaagga aagcattctc cccaagagga actccgacaa gctgattgct   3360
agaaagaaag actgggaccc caagaagtat ggcggattcg actcacccac tgtggcatat   3420
agcgttctcg tggtggcaaa ggttgaaaag ggtaaatcca aaaaactcaa atccgtgaag   3480
gaactccttg gcataactat tatggaaagg agtagctttg aaaagaatcc catcgacttt   3540
ctcgaagcta agggctataa ggaagttaag aaggacctta taatcaaact tccaaaatac   3600
tccctttttg agttggaaaa cggcagaaag agaatgttgg ccagtgccgg ggagcttcaa   3660
aagggcaacg aactggctct gcctagcaaa tatgtgaact tttgtatct ggcatcacac   3720
tacgagaaac ttaaaggctc tcctgaggac aacgagcaaa aacagctctt tgttgaacag   3780
cataagcact acctcgacga gattattgag cagatcagcg agttctcaaa gagagttatt   3840
ctggctgacg ctaatcttga caaggttttg tccgcttaca acaaacacag ggataagcca   3900
atcagggagc aggcagaaaa cataatccat ctctttaccc tgacaaacct cggtgccccc   3960
gctgctttca agtattttga tactaccatt gacaggaaga gatatacttc cactaaggaa   4020
gtgctcgacg caaccctcat acaccaaagt atcacaggcc tctatgaaac taggatagat   4080
```

-continued

```
ttgtctcaac ttgggggcga t                                       4101


<210> SEQ ID NO 68
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 68

gacaaaaagt attccatcgg gcttgctatc ggaaccaact ctgtggggtg ggcagttatt     60

accgacgaat acaaggtgcc cagcaagaag tttaaggttc tggggaacac agatagacat    120

agcataaaga aaaacctgat aggcgcactg ttgttcgact ccggggaaac agccgaagct    180

accaggctga agagaactgc aagaagaagg tacaccagaa gaaaaaacag aatatgttat    240

ctccaagaga ttttctctaa cgagatggcc aaggtggacg actcattctt tcacagactg    300

gaagaatctt tccttgtgga agaagataag aaacacgaga ggcaccctat ttttggcaat    360

atcgtggatg aggtggctta ccacgaaaaa taccctacaa tataccacct caggaaaaaa    420

ttggttgata gtacagacaa ggccgacctc aggctcatct atttggccct ggcccatatg    480

attaaattca gggggcactt tctcatcgag ggagatttga accccgacaa cagtgatgtt    540

gataagctct ttattcagct cgtgcagact tacaatcagt tgtttgagga aaaccccatt    600

aatgcttccg gggtggacgc caaggcaatc ctttctgcaa gactctcaaa gtcaaggaga    660

ctcgaaaatc tgatagcaca gcttccagga gagaagaaga acgggctctt tggaaacctg    720

atcgctctgt cactcggact cacacccaat ttcaaaagca attttgattt ggcagaggac    780

gctaagctgc aactcagtaa ggatacctac gacgatgact tggataatct gctcgcacaa    840

attggggacc agtatgcaga cctgtttctc gcagctaaga acttgagtga cgccatattg    900

ctcagtgaca tcctcagggt taataccgag attacaaaag ctccactctc tgcaagcatg    960

atcaagaggt atgacgagca ccatcaagac ctgacactcc ttaaggcgtt ggttaggcag   1020

caacttcctg aaaagtataa ggaaatcttc ttcgatcaaa gcaaaaacgg ctacgccggc   1080

tatatagacg gggagcatc ccaagaagaa ttttataagt tcataaaacc tatattggag   1140

aagatggacg ggacagagga attgctcgtg aaactgaaca gggaggatct cctcaggaag   1200

caaaggacct tcgacaatgg ctccatccca catcagattc acctcggcga actgcacgca   1260

atactgagaa gacaagagga cttttatcct ttcctgaagg acaacaggga gaaaatcgag   1320

aaaatcttga cattcagaat cccatactac gttgggcctc tggccagagg taacagtagg   1380

ttcgcctgga tgactaggaa atcagaggag actattacac cctggaactt tgaagaagtt   1440

gttgataagg gagcttcagc acaatcattc atcgaaagaa tgacaaactt tgacaaaaat   1500

ctgcctaatg agaaagtgct cccaaaacat tccctgctgt atgagtattt taccgtttat   1560

aacgagctta ccaaggtgaa atacgttact gaaggtatga gaaagccagc ttttctttca   1620

ggggagcaaa agaaggctat cgtggatctt ctctttaaga ccaacagaaa ggttaccgtg   1680

aagcagctta aggaagacta ctttaaaaag atcgagtgtt ttgactcagt ggaaataagc   1740

ggtgttgaag atagattcaa cgcatccttg ggaacttatc atgatcttct taagataatc   1800

aaggataaag actttctcga caacgaggaa aacgaagata tactggagga catagttctg   1860

acacttactt tgttcgagga tagggagatg atcgaggaaa gactgaaaac atatgctcac   1920

cttttcgacg acaaagttat gaaacaactc aagagaagga gatatacagg gtgggggaga   1980

ttgagcagga aactgattaa tggtatcaga gacaaacagt caggaaaaac aatactcgac   2040
```

tttttgaaat cagacgggtt cgcaaatagg aatttcatgc agcttataca cgacgattca 2100
cttactttta aagaggacat tcaaaaggct caagttagtg gacaaggtga ctccctccac 2160
gaacacatcg caaatctcgc tggcagccct gcaattaaga agggtatact ccagacagtt 2220
aaggttgttg acgagctggt taaagtgatg ggaagacaca aacccgagaa catagtgata 2280
gagatggcca gggaaaacca aaccactcaa aaagggcaga aaaattccag agagaggatg 2340
aaaaggattg aagaaggtat caaggagctg ggtagccaaa ttctgaaaga acatcctgtg 2400
gaaaacactc aactccagaa tgagaaactc tatctgtact atctgcaaaa tgggagagat 2460
atgtatgtgg accaggaact ggacataaac aggctctcag attacgatgt ggatcatatc 2520
gtgccacagt cctttcttaa ggatgatagc atcgacaata aggtgcttac caggtccgac 2580
aagaacaggg gaaagtcaga taacgtgcct tctgaagaag ttgttaaaaa gatgaagaac 2640
tactggagac agctgcttaa cgctaagctc ataacacaga ggaagtttga caacttgacc 2700
aaggccgaga gaggcggact ctcagaattg gataaggcag ggttcataaa aaggcagctg 2760
gtggaaacaa ggcagataac taaacatgtg gctcagatcc tcgatagtag gatgaataca 2820
aaatacgatg agaacgacaa gctcataagg gaggttaaag tgataactct gaaatccaaa 2880
ctggttagcg attttaggaa ggatttccag ttttacaaag ttagggagat caacaattat 2940
catcacgccc acgatgccta cttgaacgca gttgtgggta ctgcacttat caaaaagtac 3000
cctaagctgg aatccgagtt tgtttatgga gactataagg tgtacgacgt tagaaaaatg 3060
attgcaaagt cagagcagga gatagggaaa gccactgcaa aatatttctt ttatagcaat 3120
atcatgaatt tctttaagac agaaatcaca ctggccaatg ggaaataag gaagaggccc 3180 ctgatcgaaa ctaatggcga gacaggggag attgtgtggg ataaaggtag ggactttgca 3240
acagtgagga aagtgctgag catgccccaa gttaatatcg ttaaaaagac cgaggttcaa 3300
acagggggct ttagtaagga aagcattttg cccaagagga atagtgacaa attgattgct 3360
aggaaaaaag attgggaccc caaaaagtat ggcggatttg atagccccac tgttgcttac 3420
tccgtgctcg tggttgcaaa ggtggagaag ggaaagagca agaaactgaa gtcagttaag 3480
gaactccttg gtatcactat catggaaaga agctcctttg agaagaaccc tattgacttc 3540
ctggaggcta aagggtacaa agaggttaag aaagacctta tcattaaatt gcccaaatat 3600
agtcttttcg agcttgaaaa cggaagaaag aggatgcttg catccgctgg cgaattgcaa 3660
aagggcaatg agcttgctct cccttccaag tatgtgaact tcctttatct tgcctcacac 3720
tatgaaaaac tcaaaggttc acccgaagac aacgaacaaa agcaactatt tgtggaacaa 3780
cacaagcact acctggacga aatcattgag caaatttctg agttttcaaa aagggtaatc 3840
ttggctgacg caaatctcga caaagttttg tcagcttaca acaaacatag agataagcca 3900
attagagagc aagctgagaa tatcatccat ctgtttaccc tgactaacct tggagcgcct 3960
gctgctttta aatatttcga caccacaatc gacaggaaga ggtacactag cactaaggaa 4020
gttctcgacg ccaccctcat ccaccagagt attacaggcc tgtacgagac aagaattgat 4080
ctttctcaac ttggtggtga c 4101

<210> SEQ ID NO 69
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 69

```
gataagaagt actcaatcgg tctggcaatc ggaaccaact ctgtgggttg ggcagtgatt     60
acagatgagt ataaggtgcc aagcaaaaaa ttcaaggtgc tgggtaatac cgacagacac    120
agcattaaga agaatttgat tggagcactc ctctttgact caggggaaac agcagaggca    180
acaaggctga agaggacagc aaggcggagg tacacaaggc ggaaaaacag gatatgctac    240
ctccaggaaa tctttagcaa cgagatggct aaagtggatg atagcttttt ccatagactc    300
gaagaatcct ttcttgttga agaggacaaa aagcatgaaa ggcatcccat cttcggcaat    360
atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atccagataa ttcagatgtg    540
gataaactgt ttatacagct ggtgcaaaca tacaaccaac ttttcgagga aaacccaatc    600
aatgcctccg gtgttgatgc aaaggccatc ctgtcagcaa gactcagcaa aagcaggcgg    660
ctcgaaaacc tcatcgccca gcttcccggt gaaaagaaga acgggctctt tggtaatctc    720
atcgcattga gccttggtct tactccaaac ttcaagagca attttgatct ggcagaggat    780
gctaaactgc aactctcaaa ggacacatat gacgatgacc ttgacaatct gttggcccag    840
atcggggacc aatatgcaga cctcttcctg gccgcaaaga atctgtcaga tgcaatcctc    900
ttgtccgaca tactgagagt taacactgag atcacaaagg cacctctgtc cgcctccatg    960
attaagagat acgatgagca tcaccaggat ctgactttgc tcaaagccct cgttagacag   1020
cagttgccag aaaagtacaa agaaatattc tttgatcaat caaaaaacgg atatgcaggg   1080
tacatcgacg gtggggcaag ccaggaagag ttctacaaat tcatcaaacc tatcctggaa   1140
aagatggatg ggacagaaga gctgctggtt aagctgaata gggaagacct cctcagaaag   1200
cagaggacat ttgataacgg gagcatccct catcaaatcc acctcggtga actccatgct   1260
atcctgagaa ggcaggaaga cttttatcca tttttgaagg acaataggga gaaaatcgaa   1320
aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attcctttcc   1620
ggggaacaga agaaagctat tgtggacctc ctgttcaaga caaatagaaa agtgacagtt   1680
aagcaactca aagaggatta cttcaaaaag atcgaatgtt ttgactctgt ggagatcagc   1740
ggggtggagg atagattcaa cgccagcctg ggtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataaagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgagcg gccaagggga tagcctccac   2160
gagcatattg caaatctggc aggttcacca gccatcaaaa agggcatact tcagacagtt   2220
aaggttgtgg acgaattggt taaagttatg ggcaggcata agccagagaa tatcgttatc   2280
gaaatggcaa gggagaacca aacaactcaa aaagggcaga aaaatagcag agagaggatg   2340
```

```
aaaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg accaggagct ggatattaac agactgtcag attatgatgt tgatcatatc   2520
gtgccccagt cattcctgaa ggacgattcc atcgacaaca aagttctcac aaggtccgat   2580
aaaaacaggg gcaagtccga taacgttcca agcgaagaag tggtgaaaaa gatgaaaaac   2640
tattggagac aacttctgaa tgcaaagttg attactcaga gaaagtttga caacctcaca   2700
aaagcagaaa gaggcgggct tagcgaactc gataaggcag ggtttatcaa aagacagctg   2760
gttgagacaa ggcagatcac aaaacatgtg gcacagatcc ttgactcaag gatgaatacc   2820
aagtatgatg agaatgataa gttgatcagg gaggttaaag ttatcacact caaatccaaa   2880
ctggtgtcag acttcaggaa agactttcaa ttttataagg tgagggagat caataactac   2940
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta agtatttctt ttacagtaat   3120
atcatgaatt tctttaaaac tgagattact ctggcaaacg gggagatcag gaaaagaccc   3180
ctcatcgaga ctaatggtga aacaggtgag atcgtttggg acaaggggag ggattttgct   3240
actgttagaa aagttctgag tatgccacaa gtgaatattg tgaaaaagac agaagttcag   3300
acaggtgggt tctccaaaga atccatcctg cccaagagaa attcagacaa gctcatcgca   3360
agaaagaagg actgggaccc taagaagtac ggaggatttg acagccccac cgtggcctat   3420
tccgtgcttg ttgtggcaaa ggtggagaaa gggaagagca aaaaactgaa atccgtgaaa   3480
gaactgctgg gaattaccat catggaaaga agctcctttg agaagaaccc aatcgacttc   3540
ctggaagcaa aggatataa  ggaagtgaaa aaggacctca ttatcaagct cccaaaatac   3600
tcacttttcg agttggagaa cggtagaaag aggatgctgg caagcgcagg ggaacttcag   3660
aaaggcaatg agctggcatt gccatcaaag tatgtgaact tcctctactt ggccagccat   3720
tacgagaaac ttaaaggtag cccagaagat aacgagcaaa aacagctctt tgtggaacag   3780
cataagcatt atctggatga gatcatagaa caaatctcag agttttccaa gagagttatc   3840
ctcgcagatg caaacctgga taaggttctc tcagcctata ataagcatag agacaagcca   3900
attagagagc aagcagagaa cattatccac ttgttcactc ttacaaacct gggggcacca   3960
gccgccttca aatatttcga tacaacaata gacagaaaga ggtataccag caccaaagaa   4020
gttctcgacg ccacactgat ccatcaatca atcacaggcc tttacgaaac taggatcgac   4080
ttgtcacaac tgggtgggga t                                            4101
```

<210> SEQ ID NO 70
<211> LENGTH: 3307
<212> TYPE: DNA
<213> ORGANISM: Artificial sequence
<220> FEATURE:
<223> OTHER INFORMATION: Synthetic polynucleotide

<400> SEQUENCE: 70

```
gagcaaggac acctacgacg acgacttgga caacctattg gcccagatag gtgaccagta     60
tgcagacctc ttccttgcgg ccaagaactt gagtgacgct atactgctca gtgacatcct    120
gagggtgaac actgagatca ctaaggcccc tctctctgcc tcaatgatta agcgttacga    180
cgagcatcac caggatctca ccctgcttaa ggcccttgtt cggcagcagc tccctgagaa    240
```

-continued

```
gtacaaggag atattttttg accagtctaa gaacggctac gccggttaca ttgacggtgg    300
ggcaagccag gaggagttct acaagttcat caagccgatc cttgagaaga tggacggcac    360
cgaggagcta cttgtcaagt tgaaccggga agacctgctc cggaaacagc gtacattcga    420
caacggcagc atccctcacc agatccacct gggcgaacta cacgccatcc tccgacgtca    480
ggaggacttc tatccattct tgaaagataa cagggaaaaa atcgaaaaaa tacttacgtt    540
tcgaatacct tactacgtgg ggccccttgc tcggggaaac tccagattcg catggatgac    600
caggaagtca gaggagacca tcacaccctg gaactttgag gaggtggttg acaaaggtgc    660
ttctgcccag tccttcattg agcggatgac taacttcgac aagaacctgc ccaacgagaa    720
ggtgctgcca aagcacagcc tgctctacga atactttact gtgtacaatg agctgacgaa    780
ggtgaagtac gtgacagagg ggatgcggaa gcccgctttc ctgagcggcg agcaaaaaaa    840
agcaatcgtg gacctactgt tcaagaccaa ccgaaaggtg acagtgaagc agctcaagga    900
ggactacttc aaaaaaatcg agtgcttcga ctctgttgag ataagcggcg tggaggaccg    960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacggggtgg ggaagactct cccgaaaact   1200
gataaacggc atcagggaca agcagtcagg gaagacgatc ttggacttcc tgaaatccga   1260
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
gaaccagact acccagaagg gtcagaagaa ctctcgggaa cgtatgaagc gtattgagga   1560
ggggattaag gagttgggct ctcaaatcct caaggagcac cctgtggaga acactcagct   1620
ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac gacagcatcg acaacaaggt tctgacgagg agcgacaaga atcgagggaa   1800
aagtgacaat gttccatccg aggaggtggt caagaaaatg aagaactatt ggcgtcagct   1860
tctgaacgcc aagctcatca cccagcggaa attcgacaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgagaa   2040
cgacaagctc atcagggagg tgaaggtcat taccettaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtacccca agttggagtc   2220
ggagttcgtt tacggggact acaaggtgta cgacgttcgg aagatgatcg ccaagtctga   2280
acaggagatc gggaaagcaa ccgccaagta tttcttctat agcaacatca tgaacttctt   2340
taaaaccgag atcacacttg ccaatggcga gatccgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaaagactg   2580
ggatccaaag aaatacggcg ggttcgactc gccgacagtc gcatactccg tgttagtggt   2640
```

ggctaaagtg gaaaagggga agtccaagaa gctcaagtcc gtcaaggagt tgctcgggat 2700
caccattatg gaacggtcct cattcgagaa gaatcccatt gacttcctag aggcgaaggg 2760
ctacaaagag gtcaaaaagg acctaattat taagctcccc aagtattcac tcttcgaact 2820
tgaaaatggt cgtaagcgga tgttggcaag cgctggagag cttcagaagg ggaacgagct 2880
tgcactgcct tccaagtacg tgaacttcct gtacctcgcc tctcattacg agaagttgaa 2940
gggctcaccg gaggacaacg agcagaagca gttgttcgtg gagcagcaca agcactacct 3000
cgacgagatc attgagcaga taagtgagtt cagcaaacgg gtgatccttg ccgacgctaa 3060
cctggacaag gtgctgagcg cctacaacaa gcacagagac aagccgatcc gagagcaagc 3120
ggagaacatc atacacctgt tcaccctcac gaacctcggg gctcccgcag ccttcaaata 3180
ttttgacacg accatcgacc gtaaacgcta cactagcacg aaggaggtgc tggacgctac 3240
ccttatccac cagtccatca ccggcctgta cgagacgaga atcgacttgt cgcagctcgg 3300
tggtgac 3307

<210> SEQ ID NO 71
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 71
gacaaaaaat actcaattgg tctggcaatt gggaccaaca gtgtcggatg ggccgtgatt 60
accgacgagt acaaggtgcc gtccaaaaaa ttcaaggtgc ttgggaacac cgaccgccac 120
tcgatcaaga aaaacctaat cggtgcgttg cttttcgaca gtggggagac cgccgaggca 180
acacgcttaa aacgcacagc taggaggaga tatacacggc gcaagaaccg aatatgctac 240
ttacaggaga tattctccaa tgagatggcg aaggtggacg actctttctt ccatcggctt 300
gaggaatcct tcctggtcga ggaggacaag aagcacgagc gacacccgat attcgggaac 360
atcgttgatg aggtggcgta ccacgagaag tacccaacga tataccactt acgcaagaag 420
ctcgtggact ctacggacaa ggccgacttg cgccttatct acttggcact ggcccacatg 480
attaagttcc gaggccactt ccttatcgag ggtgacctga accccgataa ctccgacgtg 540
gacaagctct tcatccaact cgtccagaca tacaaccagc tattcgagga gaatcctatc 600
aacgcctctg gggtggacgc taaagctatc ctctcagccc gcctgtcaaa gtcgaggagg 660
ttggagaacc taatcgccca gcttccaggc gagaagaaaa atgggctgtt cggaaacctt 720
atcgcactct cactgggcct aaccccgaac ttcaagtcca acttcgacct ggcagaggac 780
gcgaaattgc agttgtcgaa agacacctat gacgatgacc tggacaacct gttggcccag 840
ataggggacc agtacgccga cctgttccta gcggccaaga acctgtccga cgccatcttg 900
ctgtcggata tactgcgggt gaacaccgag atcactaaag cacctctctc cgccagcatg 960
attaagcgtt acgacgagca ccaccaagat ttgaccctgc taaaggcact tgtacggcag 1020
cagcttcccg agaagtacaa ggagatcttt ttcgaccaaa gcaagaacgg ctacgccggg 1080
tacatcgacg gaggtgccag ccaggaggag ttctacaagt tcattaagcc catcctggag 1140
aagatggacg ggactgagga actacttgtg aagctgaacc gggaagactt actacggaag 1200
cagcgtacct tcgacaacgg ttctatccca catcagatcc atcttgggga gttgcacgcg 1260
atcctgcgac gccaggagga cttttacccc ttcctgaaag acaaccgcga gaaaatcgag 1320

-continued aagatactga ccttcagaat accttactac gtcggacccc ttgcgcgagg caactcaaga 1380
ttcgcgtgga tgaccaggaa atcagaggag accatcacac cctggaattt cgaggaggtg 1440
gttgacaagg gtgcctccgc ccagtccttt atcgaacgaa tgaccaactt cgacaagaac 1500
ttgcccaacg agaaggtgct ccccaaacac agcctcctct acgaatattt cacagtgtac 1560
aacgagctta ctaaagttaa gtatgttact gagggcatga ggaaacccgc cttcctgtca 1620
ggcgagcaga agaaagctat tgtggacctc cttttcaaga ccaaccggaa ggtgacagtg 1680
aagcagctca aggaggacta cttcaagaag atagagtgct tcgacagcgt ggagatcagc 1740
ggggtggagg acagattcaa tgcctctctc ggaacatacc acgacttgct taagatcatc 1800
aaggacaagg acttcctcga caacgaggaa aacgaggata ttctggagga tattgttctg 1860
actcttaccc tgttcgagga ccgggagatg atcgaggagc gtctcaagac ctacgcccac 1920
ctgttcgacg acaaagttat gaagcagctc aagcgtcgga gatataccgg atggggccgt 1980
ctgtctcgga agctcatcaa cgggatcagg gacaagcagt cagggaagac gatcttagac 2040
ttccttaagt ctgacggctt cgccaacagg aacttcatgc agttgatcca cgacgacagc 2100
cttaccttca aggaggacat ccagaaggcc caagtgagtg gccagggtga cagcctccac 2160
gagcatattg ctaatcttgc gggttcccca gcgattaaaa agggcatact tcaaaccgtt 2220
aaggtggtgg acgagcttgt caaggtgatg gggcgacaca agcccgagaa catcgtgatc 2280
gagatggcca gggagaacca gaccacccag aaggggcaga agaatagccg agaacgcatg 2340
aagcgcatcg aggaggggat taaggagcta gggagccaga tcctcaagga acatcccgtc 2400
gagaacaccc agctccagaa cgagaagcta tacctctact acttgcaaaa cgggagggat 2460
atgtacgtgg atcaggagtt ggacattaac cgcctaagcg actacgacgt agatcacatc 2520
gtgcctcagt cattcctcaa agacgacagc attgacaaca aagtcttgac ccgatccgac 2580
aagaaccgag gaaaatccga caatgtgccc tcagaggagg tcgtcaagaa aatgaagaac 2640
tattggaggc agctacttaa cgccaaactc ataacccagc ggaagttcga caacctgaca 2700
aaggctgagc ggggtgggct cagcgagctt gacaaggctg gcttcatcaa gcggcagttg 2760
gtggagacaa gacagataac gaagcacgtg gctcagatcc tggactctcg catgaacacg 2820
aagtacgacg agaacgacaa attgatccgc gaggtcaagg ttattacgct caagagcaaa 2880
cttgtcagcg atttccgcaa ggacttccag ttctacaagg tgagggagat taacaactac 2940
caccatgcac atgatgccta cttgaacgca gtggtgggga ccgcgcttat taaaaagtac 3000
cctaagttgg agtcagagtt cgtttatggg gactacaagg tgtacgacgt ccggaagatg 3060
attgcaaagt ctgaacagga aatcgggaag gccaccgcca aatatttctt ctacagtaac 3120
attatgaatt tttttaagac tgaaattact ctcgcaaacg gcgagatcag gaagcgtccc 3180
ctcatcgaga caaacgggga gaccggggag atagtctggg acaaggggcg ggacttcgct 3240
acggtgagga aggtgctctc gatgccacaa gtgaacatcg tcaaaaagac agaggtgcag 3300
accggtggct tctcaaagga gtcaatcctg ccaaaacgta acagcgacaa gctcatcgcc 3360
cgcaagaaag actgggaccc taagaagtat ggtgggttcg actcaccgac ggtcgcatac 3420
tccgttctgg tcgtggcaaa ggtggaaaag ggcaagtcca aaaaactgaa atccgtgaag 3480
gagttgcttg gcattaccat catggaacgc agcagcttcg agaagaaccc cattgacttc 3540
ctggaggcta aagggtacaa ggaggtcaag aaagatttaa ttattaagct acctaagtac 3600
agcttgttcg agctggagaa cggccgaaaa cgaatgctcg catccgccgg ggaacttcaa 3660
aagggcaacg agcttgcgct gccctccaag tacgtgaact tcctgtactt ggcatcccac 3720
tacgagaaac tcaagggtag cccagaggac aacgagcaga agcagctatt cgtggagcag 3780
cacaagcact acctcgacga gataatcgag cagatcagtg agttcagtaa gcgggtgata 3840
ctcgcggacg ccaacttgga caaggtgctt agtgcctaca acaagcaccg tgacaagccc 3900
atccgagaac aggctgagaa catcatccac cttttcactc tgacaaacct cggtgctccc 3960
gccgccttca aatacttcga cactaccatc gacaggaagc gctacacatc tacgaaggaa 4020
gttcttgacg ctacgcttat tcatcagtct atcacagggc tgtacgagac aaggatcgac 4080
cttagccaac tcggcgggga t 4101

<210> SEQ ID NO 72
<211> LENGTH: 2391
<212> TYPE: DNA
<213> ORGANISM: Zea mays

<400> SEQUENCE: 72
gccgcggcga cgcccgaggc ctgcaaaacc ctaaccactc aggttctgcc ggccaccgcc 60
accaccacca ccagtccacc accatgctga cagccactcc cctaccccat cagctcctgg 120
ccaccttcct cctcgtcctg gcgtcggcga cccaacctgc agtccctgcc tccaccgacc 180
gcgcagcgct tctcgccttc cgcgcgtccc tgtcgccgcc ctcccgcgcc gcgctatcct 240
cgtggagcgg cccgctctcg ccatcctggc tcggcgtgtc gctccacccc gccacggcgc 300
cagccccttc ggtcaccact ccctccgttg ccgaactctc gctccggggc ctcaacctca 360
cgggcgtgat ccccgcggcg ccgctcgcgc tcctccgacg tctccggacg ctcgacctct 420
ccgccaacgc gctttcggga gagcttccct gctccctccc gcgctcgctc ctcgcgctcg 480
acctctcccg caacgcgctc tcgggggctg tccccacctg cctgccgtcc tcgctccccg 540
cgctccgcac cctcaacctc tccgccaact tcctccgcct cccgctctcc ccgcgtctct 600
ccttccccgc gcgcctcgct gcccttgatc tctcccgcaa cgccatctcc ggcgccgtcc 660
cgccgcggat cgtcgccgac cccgacaact ccgctctcct cctcctcgac ctctcccaca 720
accgcttctc cggcgagatc cccgccggta tcgcagccgt acggagcctg caggggcttt 780
ttctcgcgga caaccagctt tccggggaca ttcctccggg gatagggaac ctgacctatt 840
tgcaggtgct ggatttgtcg aataaccgat tgtccggttc agtgcctgcc ggacttgcag 900
gctgcttcca gcttctgtac ctgcagcttg gggtaacca gctctctggg gcactccgtc 960
cggagctcga cgcactagct agtctcaagg ttctagattt gtcgaataac aagatatctg 1020
gggagattcc cctgccgctg gctgggtgca ggtctttgga ggtggtggac ttgtcaggaa 1080
atgagatctc cggtgagctc agcagtgctg tagcgaaatg gctgagcttg aagttcttat 1140
cactggctgg taaccagctc tccggccacc tacctgactg gatgttctcg ttccccctgc 1200
tccagtggct tgatttgtct agtaataagt ttgtgggttt catcccagat ggggggttca 1260
atgtcagtga agtgcttaac ggtggaggtg gtcaggggac tccatcagag agtgtgcttc 1320
caccccaatt gtttgtgtca gcttctgtgg acacggtgtc atggcagttg gatttggggt 1380
atgatgttca ggcaactact ggtatagacc tgtctgggaa tgagctctgt ggggagatac 1440
cagaagggtt ggttgacatg aaggggttgg agtatttgaa cctctcctgt aattacttgg 1500
ctgggcagat ccctgcgggg cttgggggca tggggaggtt gcatacgctt gacttctcac 1560
ataatgggct gtcaggggag gtgcctcctg gaattgcagc catgacagtg cttgaggtgc 1620
ttaacctctc ctacaatagc ctgtctgggc ctttgccaac aacgaagttc ccaggagcat 1680
tagctggaaa cccaggaatt tgcagtggga aagggtgctc tgagaatgca aggactccag 1740
aagggaaaat ggaaggtagc aatcaccgcg gttggcttgg tggctggcat ggagagaatg 1800
gatgggtatc tcttggtgca ttttgtatca gcacaatgac tagcttctat gtatcattag 1860
caaccttact atgctcctct aatgcaagaa acttcgtgtt tcggcctgtg agggttgaat 1920
attaacaaga ggggagattg caaaatcagg ttgttttgaa gttcgagcga ctctggtctg 1980
cagctgatta acaagaaata tgagcatatg agatggatat cttcagccaa gaggaagtgc 2040
tgtctctttt aatgatcaat caagctctct tgattgtttc ctaatattct tgatcttggg 2100
atgtgtagat ctagttctaa tattcctact gttatagaat gcaatcacct gctggtgctt 2160
ggttgtagcc ctggcgtgtt tggaggattg gacaccaagg atgcacataa tttgaagcgc 2220
tggtactgtg aaccacttca gatgtaaata ttttctttgg tttttagttc tgatctagtt 2280
taaaactgga catgtattta gtgttgttga gctacctttc gatgttatat tatgtcaatt 2340
tgctggaaga tcatttgata acaattgtct aatccagtgg attagtcgtg t 2391

<210> SEQ ID NO 73
<211> LENGTH: 1842
<212> TYPE: DNA
<213> ORGANISM: Zea mays

<400> SEQUENCE: 73
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatccc tgcggggctt 1440

```
gggggcatgg ggaggttgca tacgcttgac ttctcacata atgggctgtc aggggaggtg   1500

cctcctggaa ttgcagccat gacagtgctt gaggtgctta acctctccta caatagcctg   1560

tctgggcctt tgccaacaac gaagttccca ggagcattag ctggaaaccc aggaatttgc   1620

agtgggaaag ggtgctctga gaatgcaagg actccagaag ggaaaatgga aggtagcaat   1680

caccgcggtt ggcttggtgg ctggcatgga gagaatggat gggtatctct tggtgcattt   1740

tgtatcagca caatgactag cttctatgta tcattagcaa ccttactatg ctcctctaat   1800

gcaagaaact tcgtgtttcg gcctgtgagg gttgaatatt aa                      1842
```

<210> SEQ ID NO 74
<211> LENGTH: 613
<212> TYPE: PRT
<213> ORGANISM: Zea mays

<400> SEQUENCE: 74

```
Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300
```

```
Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Pro Ala Gly Leu
465                 470                 475                 480

Gly Gly Met Gly Arg Leu His Thr Leu Asp Phe Ser His Asn Gly Leu
                485                 490                 495

Ser Gly Glu Val Pro Pro Gly Ile Ala Ala Met Thr Val Leu Glu Val
            500                 505                 510

Leu Asn Leu Ser Tyr Asn Ser Leu Ser Gly Pro Leu Pro Thr Thr Lys
        515                 520                 525

Phe Pro Gly Ala Leu Ala Gly Asn Pro Gly Ile Cys Ser Gly Lys Gly
    530                 535                 540

Cys Ser Glu Asn Ala Arg Thr Pro Glu Gly Lys Met Glu Gly Ser Asn
545                 550                 555                 560

His Arg Gly Trp Leu Gly Gly Trp His Gly Glu Asn Gly Trp Val Ser
                565                 570                 575

Leu Gly Ala Phe Cys Ile Ser Thr Met Thr Ser Phe Tyr Val Ser Leu
            580                 585                 590

Ala Thr Leu Leu Cys Ser Ser Asn Ala Arg Asn Phe Val Phe Arg Pro
        595                 600                 605

Val Arg Val Glu Tyr
    610


<210> SEQ ID NO 75
<211> LENGTH: 13
<212> TYPE: PRT
<213> ORGANISM: Zea mays

<400> SEQUENCE: 75

Ala Gly Gln Ile Pro Ala Gly Leu Gly Gly Met Gly Arg
1               5                   10


<210> SEQ ID NO 76
<211> LENGTH: 21
<212> TYPE: PRT
<213> ORGANISM: Zea mays

<400> SEQUENCE: 76
```

```
Cys Asn Tyr Leu Ala Gly Gln Ile Pro Ala Gly Leu Gly Gly Met Gly
1               5                   10                  15

Arg Leu His Thr Leu
            20


<210> SEQ ID NO 77
<211> LENGTH: 39
<212> TYPE: DNA
<213> ORGANISM: Zea mays

<400> SEQUENCE: 77

gctgggcaga tccctgcggg gcttgggggc atggggagg                              39


<210> SEQ ID NO 78
<211> LENGTH: 63
<212> TYPE: DNA
<213> ORGANISM: Zea mays

<400> SEQUENCE: 78

tgtaattact tggctgggca gatccctgcg gggcttgggg gcatggggag gttgcatacg      60

ctt                                                                     63


<210> SEQ ID NO 79
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 79

cagatccctg cggggcttgg ggg                                               23


<210> SEQ ID NO 80
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 80

caacctcccc atgcccccaa gcc                                               23


<210> SEQ ID NO 81
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 81

tgcggggctt gggggcatgg gga                                               23


<210> SEQ ID NO 82
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 82

catgccccca agccccgcag gga                                               23


<210> SEQ ID NO 83
```

<211> LENGTH: 204
<212> TYPE: DNA
<213> ORGANISM: Artificial sequence
<220> FEATURE:
<223> OTHER INFORMATION: Synthetic polynucleotide

<400> SEQUENCE: 83
accagaaggg ttggttgaca tgaaggggtt ggagtatttg aacctctcct gtaattactt 60
ggctgggcag atccctgcgg ggcttgggca tggggaggtt gcatacgctt gacttctcac 120
ataatgggct gtcaggggag gtgcctcctg gaattgcagc catgacagtg cttgaggtgc 180
ttaacctctc ctacaatagc ctgt 204

<210> SEQ ID NO 84
<211> LENGTH: 198
<212> TYPE: DNA
<213> ORGANISM: Artificial sequence
<220> FEATURE:
<223> OTHER INFORMATION: Synthetic polynucleotide

<400> SEQUENCE: 84
accagaaggg ttggttgaca tgaaggggtt ggagtatttg aacctctcct gtaattactt 60
ggctgggcag attgcttggg ggcatgggga ggttgcatac gcttgacttc tcacataatg 120
ggctgtcagg ggaggtgcct cctggaattg cagccatgac agtgcttgag gtgcttaacc 180
tctcctacaa tagcctgt 198

<210> SEQ ID NO 85
<211> LENGTH: 195
<212> TYPE: DNA
<213> ORGANISM: Artificial sequence
<220> FEATURE:
<223> OTHER INFORMATION: Synthetic polynucleotide

<400> SEQUENCE: 85
accagaaggg ttggttgaca tgaaggggtt ggagtatttg aacctctcct gtaattactt 60
ggctgggcgg gcttgggggc atggggaggt tgcatacgct tgacttctca cataatgggc 120
tgtcagggga ggtgcctcct ggaattgcag ccatgacagt gcttgaggtg cttaacctct 180
cctacaatag cctgt 195

<210> SEQ ID NO 86
<211> LENGTH: 195
<212> TYPE: DNA
<213> ORGANISM: Artificial sequence
<220> FEATURE:
<223> OTHER INFORMATION: Synthetic polynucleotide

<400> SEQUENCE: 86
accagaaggg ttggttgaca tgaaggggtt ggagtatttg aacctctcct gtaattactt 60
ggctgggcgg gcttgggggc atggggaggt tgcatacgct tgacttctca cataatgggc 120
tgtcagggga ggtgcctcct ggaattgcag ccatgacagt gcttgaggtg cttaacctct 180
cctacaatag cctgt 195

<210> SEQ ID NO 87
<211> LENGTH: 198
<212> TYPE: DNA
<213> ORGANISM: Artificial sequence
<220> FEATURE:
<223> OTHER INFORMATION: Synthetic polynucleotide

<400> SEQUENCE: 87

```
accagaaggg ttggttgaca tgaaggggtt ggagtatttg aacctctcct gtaattactt     60

ggctgggcag agggcttggg ggcatgggga ggttgcatac gcttgacttc tcacataatg    120

ggctgtcagg ggaggtgcct cctggaattg cagccatgac agtgcttgag gtgcttaacc    180

tctcctacaa tagcctgt                                                   198


<210> SEQ ID NO 88
<211> LENGTH: 202
<212> TYPE: DNA
<213> ORGANISM: Artificial sequence
<220> FEATURE:
<223> OTHER INFORMATION: Synthetic polynucleotide

<400> SEQUENCE: 88

accagaaggg ttggttgaca tgaaggggtt ggagtatttg aacctctcct gtaattactt     60

ggctgggcag atccctgcgg ggggggcatg gggaggttgc atacgcttga cttctcacat    120

aatgggctgt caggggaggt gcctcctgga attgcagcca tgacagtgct tgaggtgctt    180

aacctctcct acaatagcct gt                                              202


<210> SEQ ID NO 89
<211> LENGTH: 199
<212> TYPE: DNA
<213> ORGANISM: Artificial sequence
<220> FEATURE:
<223> OTHER INFORMATION: Synthetic polynucleotide

<400> SEQUENCE: 89

accagaaggg ttggttgaca tgaaggggtt ggagtatttg aacctctcct gtaattactt     60

ggctgggcag aggggcttgg gggcatgggg aggttgcata cgcttgactt ctcacataat    120

gggctgtcag gggaggtgcc tcctggaatt gcagccatga cagtgcttga ggtgcttaac    180

ctctcctaca atagcctgt                                                  199


<210> SEQ ID NO 90
<211> LENGTH: 199
<212> TYPE: DNA
<213> ORGANISM: Artificial sequence
<220> FEATURE:
<223> OTHER INFORMATION: Synthetic polynucleotide

<400> SEQUENCE: 90

accagaaggg ttggttgaca tgaaggggtt ggagtatttg aacctctcct gtaattactt     60

ggctgggcag aggggcttgg gggcatgggg aggttgcata cgcttgactt ctcacataat    120

gggctgtcag gggaggtgcc tcctggaatt gcagccatga cagtgcttga ggtgcttaac    180

ctctcctaca atagcctgt                                                  199


<210> SEQ ID NO 91
<211> LENGTH: 196
<212> TYPE: DNA
<213> ORGANISM: Artificial sequence
<220> FEATURE:
<223> OTHER INFORMATION: Synthetic polynucleotide

<400> SEQUENCE: 91

accagaaggg ttggttgaca tgaaggggtt ggagtatttg aacctctcct gtaattactt     60

ggctgggcag ggcttggggg catggggagg ttgcatacgc ttgacttctc acataatggg    120

ctgtcagggg aggtgcctcc tggaattgca gccatgacag tgcttgaggt gcttaacctc    180
```

tcctacaata gcctgt 196

<210> SEQ ID NO 92
<211> LENGTH: 200
<212> TYPE: DNA
<213> ORGANISM: Artificial sequence
<220> FEATURE:
<223> OTHER INFORMATION: Synthetic polynucleotide

<400> SEQUENCE: 92
accagaaggg ttggttgaca tgaaggggtt ggagtatttg aacctctcct gtaattactt 60
ggctgggcag atcctgcttg ggggcatggg gaggttgcat acgcttgact tctcacataa 120
tgggctgtca ggggaggtgc ctcctggaat tgcagccatg acagtgcttg aggtgcttaa 180
cctctcctac aatagcctgt 200

<210> SEQ ID NO 93
<211> LENGTH: 200
<212> TYPE: DNA
<213> ORGANISM: Artificial sequence
<220> FEATURE:
<223> OTHER INFORMATION: Synthetic polynucleotide

<400> SEQUENCE: 93
accagaaggg ttggttgaca tgaaggggtt ggagtatttg aacctctcct gtaattactt 60
ggctgggcag atccggcttg ggggcatggg gaggttgcat acgcttgact tctcacataa 120
tgggctgtca ggggaggtgc ctcctggaat tgcagccatg acagtgcttg aggtgcttaa 180
cctctcctac aatagcctgt 200

<210> SEQ ID NO 94
<211> LENGTH: 197
<212> TYPE: DNA
<213> ORGANISM: Artificial sequence
<220> FEATURE:
<223> OTHER INFORMATION: Synthetic polynucleotide

<400> SEQUENCE: 94
accagaaggg ttggttgaca tgaaggggtt ggagtatttg aacctctcct gtaattactt 60
ggctgggcag ggacttgggg gcatggggag gttgcatacg cttgacttct cacataatgg 120
gctgtcaggg gaggtgcctc ctggaattgc agccatgaca gtgcttgagg tgcttaacct 180
ctcctacaat agcctgt 197

<210> SEQ ID NO 95
<211> LENGTH: 197
<212> TYPE: DNA
<213> ORGANISM: Artificial sequence
<220> FEATURE:
<223> OTHER INFORMATION: Synthetic polynucleotide

<400> SEQUENCE: 95
accagaaggg ttggttgaca tgaaggggtt ggagtatttg aacctctcct gtaattactt 60
ggctgggcag gggcttgggg gcatggggag gttgcatacg cttgacttct cacataatgg 120
gctgtcaggg gaggtgcctc ctggaattgc agccatgaca gtgcttgagg tgcttaacct 180
ctcctacaat agcctgt 197

<210> SEQ ID NO 96
<211> LENGTH: 197
<212> TYPE: DNA
<213> ORGANISM: Artificial sequence
<220> FEATURE:
<223> OTHER INFORMATION: Synthetic polynucleotide

<400> SEQUENCE: 96
accagaaggg ttggttgaca tgaaggggtt ggagtatttg aacctctcct gtaattactt 60
ggctgggcag cggcttgggg gcatggggag gttgcatacg cttgacttct cacataatgg 120
gctgtcaggg gaggtgcctc ctggaattgc agccatgaca gtgcttgagg tgcttaacct 180
ctcctacaat agcctgt 197

<210> SEQ ID NO 97
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 97
accagaaggg ttggttgaca tgaaggggtt ggagtatttg aacctctcct gtaattactt 60
ggctgggcgg cttgggggca tggggaggtt gcatacgctt gacttctcac ataatgggct 120
gtcaggggag gtgcctcctg gaattgcagc catgacagtg cttgaggtgc ttaacctctc 180
ctacaatagc ctgt 194

<210> SEQ ID NO 98
<211> LENGTH: 173
<212> TYPE: DNA
<213> ORGANISM: Artificial sequence
<220> FEATURE:
<223> OTHER INFORMATION: Synthetic polynucleotide

<400> SEQUENCE: 98
accagaaggg ttggttgaca tgaaggggtt ggagtatttg aacctctcct gtaattacat 60
ggggaggttg catacgcttg acttctcaca taatgggctg tcaggggagg tgcctcctgg 120
aattgcagcc atgacagtgc ttgaggtgct taacctctcc tacaatagcc tgt 173

<210> SEQ ID NO 99
<211> LENGTH: 1839
<212> TYPE: DNA
<213> ORGANISM: Artificial sequence
<220> FEATURE:
<223> OTHER INFORMATION: Synthetic polynucleotide

<400> SEQUENCE: 99
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660

-continued

```
gccggtatcg cagccgtacg gagcctgcag gggctttttc tcgcggacaa ccagctttcc    720

ggggacattc ctccggggat agggaacctg acctatttgc aggtgctgga tttgtcgaat    780

aaccgattgt ccggttcagt gcctgccgga cttgcaggct gcttccagct tctgtacctg    840

cagcttgggg gtaaccagct ctctggggca ctccgtccgg agctcgacgc actagctagt    900

ctcaaggttc tagatttgtc gaataacaag atatctgggg agattcccct gccgctggct    960

gggtgcaggt ctttggaggt ggtggacttg tcaggaaatg agatctccgg tgagctcagc   1020

agtgctgtag cgaaatggct gagcttgaag ttcttatcac tggctggtaa ccagctctcc   1080

ggccacctac ctgactggat gttctcgttc cccctgctcc agtggcttga tttgtctagt   1140

aataagtttg tgggtttcat cccagatggg gggttcaatg tcagtgaagt gcttaacggt   1200

ggaggtggtc aggggactcc atcagagagt gtgcttccac cccaattgtt tgtgtcagct   1260

tctgtggaca cggtgtcatg gcagttggat ttggggtatg atgttcaggc aactactggt   1320

atagacctgt ctgggaatga gctctgtggg gagataccag aagggttggt tgacatgaag   1380

gggttggagt atttgaacct ctcctgtaat tacttggctg ggcagattgc ggggcttggg   1440

ggcatgggga ggttgcatac gcttgacttc tcacataatg ggctgtcagg ggaggtgcct   1500

cctggaattg cagccatgac agtgcttgag gtgcttaacc tctcctacaa tagcctgtct   1560

gggcctttgc caacaacgaa gttcccagga gcattagctg gaaacccagg aatttgcagt   1620

gggaaagggt gctctgagaa tgcaaggact ccagaaggga aaatggaagg tagcaatcac   1680

cgcggttggc ttggtggctg gcatggagag aatggatggg tatctcttgg tgcattttgt   1740

atcagcacaa tgactagctt ctatgtatca ttagcaacct tactatgctc ctctaatgca   1800

agaaacttcg tgtttcggcc tgtgagggtt gaatattaa                          1839
```

```
<210> SEQ ID NO 100
<211> LENGTH: 1842
<212> TYPE: DNA
<213> ORGANISM: Artificial sequence
<220> FEATURE:
<223> OTHER INFORMATION: Synthetic polynucleotide

<400> SEQUENCE: 100

atgctgacag ccactcccct accccatcag ctcctggcca ccttcctcct cgtcctggcg     60

tcggcgaccc aacctgcagt ccctgcctcc accgaccgcg cagcgcttct cgccttccgc    120

gcgtccctgt cgccgccctc ccgcgccgcg ctatcctcgt ggagcggccc gctctcgcca    180

tcctggctcg gcgtgtcgct ccaccccgcc acggcgccag ccccttcggt caccactccc    240

tccgttgccg aactctcgct ccggggcctc aacctcacgg gcgtgatccc cgcggcgccg    300

ctcgcgctcc tccgacgtct ccggacgctc gacctctccg ccaacgcgct ttcgggagag    360

cttccctgct ccctcccgcg ctcgctcctc gcgctcgacc tctcccgcaa cgcgctctcg    420

ggggctgtcc ccacctgcct gccgtcctcg ctccccgcgc tccgcaccct caacctctcc    480

gccaacttcc tccgcctccc gctctccccg cgtctctcct tccccgcgcg cctcgctgcc    540

cttgatctct cccgcaacgc catctccggc gccgtcccgc cgcggatcgt cgccgacccc    600

gacaactccg ctctcctcct cctcgacctc tcccacaacc gcttctccgg cgagatcccc    660

gccggtatcg cagccgtacg gagcctgcag gggctttttc tcgcggacaa ccagctttcc    720

ggggacattc ctccggggat agggaacctg acctatttgc aggtgctgga tttgtcgaat    780

aaccgattgt ccggttcagt gcctgccgga cttgcaggct gcttccagct tctgtacctg    840

cagcttgggg gtaaccagct ctctggggca ctccgtccgg agctcgacgc actagctagt    900
```

ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatttt tgcggggctt 1440
gggggcatgg ggaggttgca tacgcttgac ttctcacata atgggctgtc aggggaggtg 1500
cctcctggaa ttgcagccat gacagtgctt gaggtgctta acctctccta caatagcctg 1560
tctgggcctt tgccaacaac gaagttccca ggagcattag ctggaaaccc aggaatttgc 1620
agtgggaaag ggtgctctga gaatgcaagg actccagaag ggaaaatgga aggtagcaat 1680
caccgcggtt ggcttggtgg ctggcatgga gagaatggat gggtatctct tggtgcattt 1740
tgtatcagca caatgactag cttctatgta tcattagcaa ccttactatg ctcctctaat 1800
gcaagaaact tcgtgtttcg gcctgtgagg gttgaatatt aa 1842

<210> SEQ ID NO 101
<211> LENGTH: 1842
<212> TYPE: DNA
<213> ORGANISM: Artificial sequence
<220> FEATURE:
<223> OTHER INFORMATION: Synthetic polynucleotide

<400> SEQUENCE: 101
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatttc tgcggggctt 1440
gggggcatgg ggaggttgca tacgcttgac ttctcacata atgggctgtc aggggaggtg 1500
cctcctggaa ttgcagccat gacagtgctt gaggtgctta acctctccta caatagcctg 1560
tctgggcctt tgccaacaac gaagttccca ggagcattag ctggaaaccc aggaatttgc 1620
agtgggaaag ggtgctctga gaatgcaagg actccagaag ggaaaatgga aggtagcaat 1680
caccgcggtt ggcttggtgg ctggcatgga gagaatggat gggtatctct tggtgcattt 1740
tgtatcagca caatgactag cttctatgta tcattagcaa ccttactatg ctcctctaat 1800
gcaagaaact tcgtgtttcg gcctgtgagg gttgaatatt aa 1842

<210> SEQ ID NO 102
<211> LENGTH: 1842
<212> TYPE: DNA
<213> ORGANISM: Artificial sequence
<220> FEATURE:
<223> OTHER INFORMATION: Synthetic polynucleotide

<400> SEQUENCE: 102
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagattac tgcggggctt 1440
gggggcatgg ggaggttgca tacgcttgac ttctcacata atgggctgtc aggggaggtg 1500
cctcctggaa ttgcagccat gacagtgctt gaggtgctta acctctccta caatagcctg 1560
tctgggcctt tgccaacaac gaagttccca ggagcattag ctggaaaccc aggaatttgc 1620
agtgggaaag ggtgctctga gaatgcaagg actccagaag ggaaaatgga aggtagcaat 1680
caccgcggtt ggcttggtgg ctggcatgga gagaatggat gggtatctct tggtgcattt 1740
tgtatcagca caatgactag cttctatgta tcattagcaa ccttactatg ctcctctaat 1800
gcaagaaact tcgtgtttcg gcctgtgagg gttgaatatt aa 1842

<210> SEQ ID NO 103
<211> LENGTH: 1842
<212> TYPE: DNA
<213> ORGANISM: Artificial sequence
<220> FEATURE:
<223> OTHER INFORMATION: Synthetic polynucleotide

<400> SEQUENCE: 103
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag cccctcggt caccactccc 240 tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggcttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagattgt tgcggggctt 1440
gggggcatgg ggaggttgca tacgcttgac ttctcacata atgggctgtc aggggaggtg 1500
cctcctggaa ttgcagccat gacagtgctt gaggtgctta acctctccta caatagcctg 1560
tctgggcctt tgccaacaac gaagttccca ggagcattag ctggaaaccc aggaatttgc 1620
agtgggaaag ggtgctctga gaatgcaagg actccagaag ggaaaatgga aggtagcaat 1680
caccgcggtt ggcttggtgg ctggcatgga gagaatggat gggtatctct tggtgcattt 1740
tgtatcagca caatgactag cttctatgta tcattagcaa ccttactatg ctcctctaat 1800
gcaagaaact tcgtgtttcg gcctgtgagg gttgaatatt aa 1842

<210> SEQ ID NO 104
<211> LENGTH: 1842
<212> TYPE: DNA
<213> ORGANISM: Artificial sequence
<220> FEATURE:
<223> OTHER INFORMATION: Synthetic polynucleotide

<400> SEQUENCE: 104
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag ggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg ggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatttg tgcggggctt 1440
gggggcatgg ggaggttgca tacgcttgac ttctcacata atgggctgtc aggggaggtg 1500
cctcctggaa ttgcagccat gacagtgctt gaggtgctta acctctccta caatagcctg 1560
tctgggcctt tgccaacaac gaagttccca ggagcattag ctggaaaccc aggaatttgc 1620
agtgggaaag ggtgctctga gaatgcaagg actccagaag ggaaaatgga aggtagcaat 1680
caccgcggtt ggcttggtgg ctggcatgga gagaatggat gggtatctct tggtgcattt 1740
tgtatcagca caatgactag cttctatgta tcattagcaa ccttactatg ctcctctaat 1800
gcaagaaact tcgtgtttcg gcctgtgagg gttgaatatt aa 1842

<210> SEQ ID NO 105
<211> LENGTH: 1836
<212> TYPE: DNA
<213> ORGANISM: Artificial sequence
<220> FEATURE:
<223> OTHER INFORMATION: Synthetic polynucleotide

<400> SEQUENCE: 105
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag cccctttcggt caccactccc 240 tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctcccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggcttttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatcct gcttgggggc 1440
atggggaggt tgcatacgct tgacttctca cataatgggc tgtcagggga ggtgcctcct 1500
ggaattgcag ccatgacagt gcttgaggtg cttaacctct cctacaatag cctgtctggg 1560
cctttgccaa caacgaagtt cccaggagca ttagctggaa acccaggaat ttgcagtggg 1620
aaagggtgct ctgagaatgc aaggactcca gaagggaaaa tggaaggtag caatcaccgc 1680
ggttggcttg gtggctggca tggagagaat ggatgggtat ctcttggtgc attttgtatc 1740
agcacaatga ctagcttcta tgtatcatta gcaaccttac tatgctcctc taatgcaaga 1800
aacttcgtgt ttcggcctgt gagggttgaa tattaa 1836

<210> SEQ ID NO 106

<211> LENGTH: 1833
<212> TYPE: DNA
<213> ORGANISM: Artificial sequence
<220> FEATURE:
<223> OTHER INFORMATION: Synthetic polynucleotide

<400> SEQUENCE: 106

```
atgctgacag ccactcccct accccatcag ctcctggcca ccttcctcct cgtcctggcg     60
tcggcgaccc aacctgcagt ccctgcctcc accgaccgcg cagcgcttct cgccttccgc    120
gcgtccctgt cgccgccctc ccgcgccgcg ctatcctcgt ggagcggccc gctctcgcca    180
tcctggctcg gcgtgtcgct ccaccccgcc acggcgccag ccccttcggt caccactccc    240
tccgttgccg aactctcgct ccggggcctc aacctcacgg gcgtgatccc cgcggcgccg    300
ctcgcgctcc tccgacgtct ccggacgctc gacctctccg ccaacgcgct ttcgggagag    360
cttccctgct ccctcccgcg ctcgctcctc gcgctcgacc tctcccgcaa cgcgctctcg    420
gggctgtcc ccacctgcct gccgtcctcg ctccccgcgc tccgcaccct caacctctcc    480
gccaacttcc tccgcctccc gctctccccg cgtctctcct tccccgcgcg cctcgctgcc    540
cttgatctct cccgcaacgc catctccggc gccgtcccgc cgcggatcgt cgccgacccc    600
gacaactccg ctctcctcct cctcgacctc tcccacaacc gcttctccgg cgagatcccc    660
gccggtatcg cagccgtacg gagcctgcag gggcttttc tcgcggacaa ccagctttcc    720
ggggacattc ctccggggat agggaacctg acctatttgc aggtgctgga tttgtcgaat    780
aaccgattgt ccggttcagt gcctgccgga cttgcaggct gcttccagct tctgtacctg    840
cagcttgggg gtaaccagct ctctggggca ctccgtccgg agctcgacgc actagctagt    900
ctcaaggttc tagatttgtc gaataacaag atatctgggg agattcccct gccgctggct    960
gggtgcaggt ctttggaggt ggtggacttg tcaggaaatg agatctccgg tgagctcagc   1020
agtgctgtag cgaaatggct gagcttgaag ttcttatcac tggctggtaa ccagctctcc   1080
ggccacctac ctgactggat gttctcgttc cccctgctcc agtggcttga tttgtctagt   1140
aataagtttg tgggtttcat cccagatggg gggttcaatg tcagtgaagt gcttaacggt   1200
ggaggtggtc aggggactcc atcagagagt gtgcttccac cccaattgtt tgtgtcagct   1260
tctgtggaca cggtgtcatg gcagttggat ttggggtatg atgttcaggc aactactggt   1320
atagacctgt ctgggaatga gctctgtggg gagataccag aagggttggt tgacatgaag   1380
gggttggagt atttgaacct ctcctgtaat tacttggctg ggcagcggct tgggggcatg   1440
gggaggttgc atacgcttga cttctcacat aatgggctgt caggggaggt gcctcctgga   1500
attgcagcca tgacagtgct tgaggtgctt aacctctcct acaatagcct gtctgggcct   1560
ttgccaacaa cgaagttccc aggagcatta gctggaaacc caggaatttg cagtgggaaa   1620
gggtgctctg agaatgcaag gactccagaa gggaaaatgg aaggtagcaa tcaccgcggt   1680
tggcttggtg gctggcatgg agagaatgga tgggtatctc ttggtgcatt ttgtatcagc   1740
acaatgacta gcttctatgt atcattagca accttactat gctcctctaa tgcaagaaac   1800
ttcgtgtttc ggcctgtgag ggttgaatat taa                                1833
```

<210> SEQ ID NO 107
<211> LENGTH: 1830
<212> TYPE: DNA
<213> ORGANISM: Artificial sequence
<220> FEATURE:
<223> OTHER INFORMATION: Synthetic polynucleotide

<400> SEQUENCE: 107

-continued

```
atgctgacag ccactcccct accccatcag ctcctggcca ccttcctcct cgtcctggcg     60

tcggcgaccc aacctgcagt ccctgcctcc accgaccgcg cagcgcttct cgccttccgc    120

gcgtccctgt cgccgccctc ccgcgccgcg ctatcctcgt ggagcggccc gctctcgcca    180

tcctggctcg gcgtgtcgct ccaccccgcc acggcgccag cccccttcggt caccactccc    240

tccgttgccg aactctcgct ccggggcctc aacctcacgg gcgtgatccc cgcggcgccg    300

ctcgcgctcc tccgacgtct ccggacgctc gacctctccg ccaacgcgct ttcgggagag    360

cttccctgct ccctcccgcg ctcgctcctc gcgctcgacc tctcccgcaa cgcgctctcg    420

ggggctgtcc ccacctgcct gccgtcctcg ctccccgcgc tccgcaccct caacctctcc    480

gccaacttcc tccgcctccc gctctccccg cgtctctcct tccccgcgcg cctcgctgcc    540

cttgatctct cccgcaacgc catctccggc gccgtcccgc cgcggatcgt cgccgacccc    600

gacaactccg ctctcctcct cctcgacctc tcccacaacc gcttctccgg cgagatcccc    660

gccggtatcg cagccgtacg gagcctgcag gggctttttc tcgcggacaa ccagctttcc    720

ggggacattc ctccggggat agggaacctg acctatttgc aggtgctgga tttgtcgaat    780

aaccgattgt ccggttcagt gcctgccgga cttgcaggct gcttccagct tctgtacctg    840

cagcttgggg gtaaccagct ctctggggca ctccgtccgg agctcgacgc actagctagt    900

ctcaaggttc tagatttgtc gaataacaag atatctgggg agattcccct gccgctggct    960

gggtgcaggt ctttggaggt ggtggacttg tcaggaaatg agatctccgg tgagctcagc   1020

agtgctgtag cgaaatggct gagcttgaag ttcttatcac tggctggtaa ccagctctcc   1080

ggccacctac ctgactggat gttctcgttc cccctgctcc agtggcttga tttgtctagt   1140

aataagtttg tgggtttcat cccagatggg gggttcaatg tcagtgaagt gcttaacggt   1200

ggaggtggtc aggggactcc atcagagagt gtgcttccac cccaattgtt tgtgtcagct   1260

tctgtggaca cggtgtcatg gcagttggat ttggggtatg atgttcaggc aactactggt   1320

atagacctgt ctgggaatga gctctgtggg gagataccag aagggttggt tgacatgaag   1380

gggttggagt atttgaacct ctcctgtaat tacttggctg ggcggcttgg gggcatgggg   1440

aggttgcata cgcttgactt ctcacataat gggctgtcag gggaggtgcc tcctggaatt   1500

gcagccatga cagtgcttga ggtgcttaac ctctcctaca atagcctgtc tgggcctttg   1560

ccaacaacga agttcccagg agcattagct ggaaacccag gaatttgcag tgggaaaggg   1620

tgctctgaga atgcaaggac tccagaaggg aaaatggaag gtagcaatca ccgcggttgg   1680

cttggtggct ggcatggaga gaatggatgg gtatctcttg gtgcattttg tatcagcaca   1740

atgactagct tctatgtatc attagcaacc ttactatgct cctctaatgc aagaaacttc   1800

gtgtttcggc ctgtgagggt tgaatattaa                                    1830
```

<210> SEQ ID NO 108
<211> LENGTH: 1809
<212> TYPE: DNA
<213> ORGANISM: Artificial sequence
<220> FEATURE:
<223> OTHER INFORMATION: Synthetic polynucleotide

<400> SEQUENCE: 108

```
atgctgacag ccactcccct accccatcag ctcctggcca ccttcctcct cgtcctggcg     60

tcggcgaccc aacctgcagt ccctgcctcc accgaccgcg cagcgcttct cgccttccgc    120

gcgtccctgt cgccgccctc ccgcgccgcg ctatcctcgt ggagcggccc gctctcgcca    180
```

tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg ggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacatgggga ggttgcatac gcttgacttc 1440
tcacataatg ggctgtcagg ggaggtgcct cctggaattg cagccatgac agtgcttgag 1500
gtgcttaacc tctcctacaa tagcctgtct gggcctttgc caacaacgaa gttcccagga 1560
gcattagctg gaaacccagg aatttgcagt gggaaagggt gctctgagaa tgcaaggact 1620
ccagaaggga aaatggaagg tagcaatcac cgcggttggc ttggtggctg gcatggagag 1680
aatggatggg tatctcttgg tgcattttgt atcagcacaa tgactagctt ctatgtatca 1740
ttagcaacct tactatgctc ctctaatgca agaaacttcg tgtttcggcc tgtgagggtt 1800
gaatattaa 1809

<210> SEQ ID NO 109
<211> LENGTH: 1461
<212> TYPE: DNA
<213> ORGANISM: Artificial sequence
<220> FEATURE:
<223> OTHER INFORMATION: Synthetic polynucleotide

<400> SEQUENCE: 109
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420 gggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagattgc ttgggggcat 1440
ggggaggttg catacgcttg a 1461

<210> SEQ ID NO 110
<211> LENGTH: 1461
<212> TYPE: DNA
<213> ORGANISM: Artificial sequence
<220> FEATURE:
<223> OTHER INFORMATION: Synthetic polynucleotide

<400> SEQUENCE: 110
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960

-continued

```
gggtgcaggt ctttggaggt ggtggacttg tcaggaaatg agatctccgg tgagctcagc   1020

agtgctgtag cgaaatggct gagcttgaag ttcttatcac tggctggtaa ccagctctcc   1080

ggccacctac ctgactggat gttctcgttc cccctgctcc agtggcttga tttgtctagt   1140

aataagtttg tgggtttcat cccagatggg gggttcaatg tcagtgaagt gcttaacggt   1200

ggaggtggtc aggggactcc atcagagagt gtgcttccac cccaattgtt tgtgtcagct   1260

tctgtggaca cggtgtcatg gcagttggat ttggggtatg atgttcaggc aactactggt   1320

atagacctgt ctgggaatga gctctgtggg gagataccag aagggttggt tgacatgaag   1380

gggttggagt atttgaacct ctcctgtaat tacttggctg ggcagagggc ttgggggcat   1440

ggggaggttg catacgcttg a                                               1461
```

<210> SEQ ID NO 111
<211> LENGTH: 1515
<212> TYPE: DNA
<213> ORGANISM: Artificial sequence
<220> FEATURE:
<223> OTHER INFORMATION: Synthetic polynucleotide

<400> SEQUENCE: 111

```
atgctgacag ccactcccct accccatcag ctcctggcca ccttcctcct cgtcctggcg     60

tcggcgaccc aacctgcagt ccctgcctcc accgaccgcg cagcgcttct cgccttccgc    120

gcgtccctgt cgccgccctc ccgcgccgcg ctatcctcgt ggagcggccc gctctcgcca    180

tcctggctcg gcgtgtcgct ccaccccgcc acggcgccag ccccttcggt caccactccc    240

tccgttgccg aactctcgct ccggggcctc aacctcacgg gcgtgatccc cgcggcgccg    300

ctcgcgctcc tccgacgtct ccggacgctc gacctctccg ccaacgcgct ttcgggagag    360

cttccctgct ccctcccgcg ctcgctcctc gcgctcgacc tctcccgcaa cgcgctctcg    420

ggggctgtcc ccacctgcct gccgtcctcg ctccccgcgc tccgcaccct caacctctcc    480

gccaacttcc tccgcctccc gctctccccg cgtctctcct tccccgcgcg cctcgctgcc    540

cttgatctct cccgcaacgc catctccggc gccgtcccgc cgcggatcgt cgccgacccc    600

gacaactccg ctctcctcct cctcgacctc tcccacaacc gcttctccgg cgagatcccc    660

gccggtatcg cagccgtacg gagcctgcag gggcttttc tcgcggacaa ccagctttcc    720

ggggacattc ctccggggat agggaacctg acctatttgc aggtgctgga tttgtcgaat    780

aaccgattgt ccggttcagt gcctgccgga cttgcaggct gcttccagct tctgtacctg    840

cagcttgggg gtaaccagct ctctggggca ctccgtccgg agctcgacgc actagctagt    900

ctcaaggttc tagatttgtc gaataacaag atatctgggg agattcccct gccgctggct    960

gggtgcaggt ctttggaggt ggtggacttg tcaggaaatg agatctccgg tgagctcagc   1020

agtgctgtag cgaaatggct gagcttgaag ttcttatcac tggctggtaa ccagctctcc   1080

ggccacctac ctgactggat gttctcgttc cccctgctcc agtggcttga tttgtctagt   1140

aataagtttg tgggtttcat cccagatggg gggttcaatg tcagtgaagt gcttaacggt   1200

ggaggtggtc aggggactcc atcagagagt gtgcttccac cccaattgtt tgtgtcagct   1260

tctgtggaca cggtgtcatg gcagttggat ttggggtatg atgttcaggc aactactggt   1320

atagacctgt ctgggaatga gctctgtggg gagataccag aagggttggt tgacatgaag   1380

gggttggagt atttgaacct ctcctgtaat tacttggctg ggcagagggg cttgggggca   1440

tggggaggtt gcatacgctt gacttctcac ataatgggct gtcaggggag gtgcctcctg   1500

gaattgcagc catga                                                     1515
```

<210> SEQ ID NO 112
<211> LENGTH: 1518
<212> TYPE: DNA
<213> ORGANISM: Artificial sequence
<220> FEATURE:
<223> OTHER INFORMATION: Synthetic polynucleotide

<400> SEQUENCE: 112
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180
tcctggctcg gcgtgtcgct ccaccccgcc acggcgccag ccccttcggt caccactccc 240
tccgttgccg aactctcgct ccggggcctc aacctcacgg gcgtgatccc cgcggcgccg 300
ctcgcgctcc tccgacgtct ccggacgctc gacctctccg ccaacgcgct ttcgggagag 360
cttccctgct ccctcccgcg ctcgctcctc gcgctcgacc tctcccgcaa cgcgctctcg 420
ggggctgtcc ccacctgcct gccgtcctcg ctccccgcgc tccgcaccct caacctctcc 480
gccaacttcc tccgcctccc gctctccccg cgtctctcct tccccgcgcg cctcgctgcc 540
cttgatctct cccgcaacgc catctccggc gccgtcccgc cgcggatcgt cgccgacccc 600
gacaactccg ctctcctcct cctcgacctc tcccacaacc gcttctccgg cgagatcccc 660
gccggtatcg cagccgtacg gagcctgcag gggctttttc tcgcggacaa ccagctttcc 720
ggggacattc ctccggggat agggaacctg acctatttgc aggtgctgga tttgtcgaat 780
aaccgattgt ccggttcagt gcctgccgga cttgcaggct gcttccagct tctgtacctg 840
cagcttgggg gtaaccagct ctctggggca ctccgtccgg agctcgacgc actagctagt 900
ctcaaggttc tagatttgtc gaataacaag atatctgggg agattcccct gccgctggct 960
gggtgcaggt ctttggaggt ggtggacttg tcaggaaatg agatctccgg tgagctcagc 1020
agtgctgtag cgaaatggct gagcttgaag ttcttatcac tggctggtaa ccagctctcc 1080
ggccacctac ctgactggat gttctcgttc cccctgctcc agtggcttga tttgtctagt 1140
aataagtttg tgggtttcat cccagatggg gggttcaatg tcagtgaagt gcttaacggt 1200
ggaggtggtc aggggactcc atcagagagt gtgcttccac cccaattgtt tgtgtcagct 1260
tctgtggaca cggtgtcatg gcagttggat ttggggtatg atgttcaggc aactactggt 1320
atagacctgt ctgggaatga gctctgtggg gagataccag aagggttggt tgacatgaag 1380
gggttggagt atttgaacct ctcctgtaat tacttggctg ggcagatccc tgcggggggg 1440
gcatggggag gttgcatacg cttgacttct cacataatgg gctgtcaggg gaggtgcctc 1500
ctggaattgc agccatga 1518

<210> SEQ ID NO 113
<211> LENGTH: 1512
<212> TYPE: DNA
<213> ORGANISM: Artificial sequence
<220> FEATURE:
<223> OTHER INFORMATION: Synthetic polynucleotide

<400> SEQUENCE: 113
atgctgacag ccactcccct accccatcag ctcctggcca ccttcctcct cgtcctggcg 60
tcggcgaccc aacctgcagt ccctgcctcc accgaccgcg cagcgcttct cgccttccgc 120
gcgtccctgt cgccgccctc ccgcgccgcg ctatcctcgt ggagcggccc gctctcgcca 180

-continued

```
tcctggctcg gcgtgtcgct ccaccccgcc acggcgccag ccccttcggt caccactccc    240

tccgttgccg aactctcgct ccggggcctc aacctcacgg gcgtgatccc cgcggcgccg    300

ctcgcgctcc tccgacgtct ccggacgctc gacctctccg ccaacgcgct ttcgggagag    360

cttccctgct ccctcccgcg ctcgctcctc gcgctcgacc tctcccgcaa cgcgctctcg    420

ggggctgtcc ccacctgcct gccgtcctcg ctccccgcgc tccgcaccct caacctctcc    480

gccaacttcc tccgcctccc gctctccccg cgtctctcct tccccgcgcg cctcgctgcc    540

cttgatctct cccgcaacgc catctccggc gccgtcccgc cgcggatcgt cgccgacccc    600

gacaactccg ctctcctcct cctcgacctc tcccacaacc gcttctccgg cgagatcccc    660

gccggtatcg cagccgtacg gagcctgcag gggctttttc tcgcggacaa ccagctttcc    720

ggggacattc ctccggggat agggaacctg acctatttgc aggtgctgga tttgtcgaat    780

aaccgattgt ccggttcagt gcctgccgga cttgcaggct gcttccagct tctgtacctg    840

cagcttgggg gtaaccagct ctctggggca ctccgtccgg agctcgacgc actagctagt    900

ctcaaggttc tagatttgtc gaataacaag atatctgggg agattcccct gccgctggct    960

gggtgcaggt ctttggaggt ggtggacttg tcaggaaatg agatctccgg tgagctcagc   1020

agtgctgtag cgaaatggct gagcttgaag ttcttatcac tggctggtaa ccagctctcc   1080

ggccacctac ctgactggat gttctcgttc cccctgctcc agtggcttga tttgtctagt   1140

aataagtttg tgggtttcat cccagatggg gggttcaatg tcagtgaagt gcttaacggt   1200

ggaggtggtc aggggactcc atcagagagt gtgcttccac cccaattgtt tgtgtcagct   1260

tctgtggaca cggtgtcatg gcagttggat ttggggtatg atgttcaggc aactactggt   1320

atagacctgt ctgggaatga gctctgtggg gagataccag aagggttggt tgacatgaag   1380

gggttggagt atttgaacct ctcctgtaat tacttggctg ggcagggctt gggggcatgg   1440

ggaggttgca tacgcttgac ttctcacata atgggctgtc aggggaggtg cctcctggaa   1500

ttgcagccat ga                                                       1512
```

```
<210> SEQ ID NO 114
<211> LENGTH: 132
<212> TYPE: DNA
<213> ORGANISM: Artificial sequence
<220> FEATURE:
<223> OTHER INFORMATION: Synthetic oligonucleotide

<400> SEQUENCE: 114

gtatttgaac ctctcctgta attacttggc tgggcagatt gcggggcttg gggcatggg     60

gaggttgcat acgcttgact tctcacataa tgggctgtca ggggaggtgc ctcctggaat    120

tgcagccatg ac                                                        132
```

```
<210> SEQ ID NO 115
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 115

gtatttgaac ctctcctgta attacttggc tgggcagatt tttgcggggc ttgggggcat     60

ggggaggttg catacgcttg acttctcaca taatgggctg tcaggggagg tgcctcctgg    120

aattgcagcc atgac                                                     135
```

<210> SEQ ID NO 116
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 116
gtatttgaac ctctcctgta attacttggc tgggcagatt tctgcggggc ttgggggcat 60
ggggaggttg catacgcttg acttctcaca taatgggctg tcaggggagg tgcctcctgg 120
aattgcagcc atgac 135

<210> SEQ ID NO 117
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 117
gtatttgaac ctctcctgta attacttggc tgggcagatt actgcggggc ttgggggcat 60
ggggaggttg catacgcttg acttctcaca taatgggctg tcaggggagg tgcctcctgg 120
aattgcagcc atgac 135

<210> SEQ ID NO 118
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 118
gtatttgaac ctctcctgta attacttggc tgggcagatt gttgcggggc ttgggggcat 60
ggggaggttg catacgcttg acttctcaca taatgggctg tcaggggagg tgcctcctgg 120
aattgcagcc atgac 135

<210> SEQ ID NO 119
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 119
gtatttgaac ctctcctgta attacttggc tgggcagatt tgtgcggggc ttgggggcat 60
ggggaggttg catacgcttg acttctcaca taatgggctg tcaggggagg tgcctcctgg 120
aattgcagcc atgac 135

<210> SEQ ID NO 120
<211> LENGTH: 129
<212> TYPE: DNA
<213> ORGANISM: Artificial sequence
<220> FEATURE:
<223> OTHER INFORMATION: Synthetic oligonucleotide

<400> SEQUENCE: 120
gtatttgaac ctctcctgta attacttggc tgggcagatc ctgcttgggg gcatggggag 60
gttgcatacg cttgacttct cacataatgg gctgtcaggg gaggtgcctc ctggaattgc 120
agccatgac 129

-continued

<210> SEQ ID NO 121
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 121
gtatttgaac ctctcctgta attacttggc tgggcagcgg cttgggggca tggggaggtt 60
gcatacgctt gacttctcac ataatgggct gtcaggggag gtgcctcctg gaattgcagc 120
catgac 126

<210> SEQ ID NO 122
<211> LENGTH: 123
<212> TYPE: DNA
<213> ORGANISM: Artificial sequence
<220> FEATURE:
<223> OTHER INFORMATION: Synthetic oligonucleotide

<400> SEQUENCE: 122
gtatttgaac ctctcctgta attacttggc tgggcggctt gggggcatgg ggaggttgca 60
tacgcttgac ttctcacata atgggctgtc aggggaggtg cctcctggaa ttgcagccat 120
gac 123

<210> SEQ ID NO 123
<211> LENGTH: 102
<212> TYPE: DNA
<213> ORGANISM: Artificial sequence
<220> FEATURE:
<223> OTHER INFORMATION: Synthetic oligonucleotide

<400> SEQUENCE: 123
gtatttgaac ctctcctgta attacatggg gaggttgcat acgcttgact tctcacataa 60
tgggctgtca ggggaggtgc ctcctggaat tgcagccatg ac 102

<210> SEQ ID NO 124
<211> LENGTH: 73
<212> TYPE: DNA
<213> ORGANISM: Artificial sequence
<220> FEATURE:
<223> OTHER INFORMATION: Synthetic oligonucleotide

<400> SEQUENCE: 124
gtatttgaac ctctcctgta attacttggc tgggcagatt gcttgggggc atggggaggt 60
tgcatacgct tga 73

<210> SEQ ID NO 125
<211> LENGTH: 73
<212> TYPE: DNA
<213> ORGANISM: Artificial sequence
<220> FEATURE:
<223> OTHER INFORMATION: Synthetic oligonucleotide

<400> SEQUENCE: 125
gtatttgaac ctctcctgta attacttggc tgggcagagg gcttgggggc atggggaggt 60
tgcatacgct tga 73

<210> SEQ ID NO 126
<211> LENGTH: 127
<212> TYPE: DNA
<213> ORGANISM: Artificial sequence
<220> FEATURE:
<223> OTHER INFORMATION: Synthetic oligonucleotide

<400> SEQUENCE: 126
gtatttgaac ctctcctgta attacttggc tgggcagagg ggcttggggg catggggagg 60
ttgcatacgc ttgacttctc acataatggg ctgtcagggg aggtgcctcc tggaattgca 120
gccatga 127

<210> SEQ ID NO 127
<211> LENGTH: 130
<212> TYPE: DNA
<213> ORGANISM: Artificial sequence
<220> FEATURE:
<223> OTHER INFORMATION: Synthetic oligonucleotide

<400> SEQUENCE: 127
gtatttgaac ctctcctgta attacttggc tgggcagatc cctgcggggg gggcatgggg 60
aggttgcata cgcttgactt ctcacataat gggctgtcag gggaggtgcc tcctggaatt 120
gcagccatga 130

<210> SEQ ID NO 128
<211> LENGTH: 124
<212> TYPE: DNA
<213> ORGANISM: Artificial sequence
<220> FEATURE:
<223> OTHER INFORMATION: Synthetic oligonucleotide

<400> SEQUENCE: 128
gtatttgaac ctctcctgta attacttggc tgggcagggc ttgggggcat ggggaggttg 60
catacgcttg acttctcaca taatgggctg tcaggggagg tgcctcctgg aattgcagcc 120
atga 124

<210> SEQ ID NO 129
<211> LENGTH: 168
<212> TYPE: DNA
<213> ORGANISM: Artificial sequence
<220> FEATURE:
<223> OTHER INFORMATION: Synthetic oligonucleotide

<400> SEQUENCE: 129
tgtggggaga taccagaagg gttggttgac atgaaggggt tggagtattt gaacctctcc 60
tgtaattact tggctgggca gatccctgcg gggcttgggg gcatggggag gttgcatacg 120
cttgacttct cacataatgg gctgtcaggg gaggtgcctc ctggaatt 168

<210> SEQ ID NO 130
<211> LENGTH: 135
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (38)..(47)
<223> OTHER INFORMATION: n is a, c, g, or t

<400> SEQUENCE: 130
gtatttgaac ctctcctgta attacttggc tgggcagnnn nnnnnnnggc ttgggggcat 60
ggggaggttg catacgcttg acttctcaca taatgggctg tcaggggagg tgcctcctgg 120
aattgcagcc atgac 135

<210> SEQ ID NO 131
<211> LENGTH: 135
<212> TYPE: DNA
<213> ORGANISM: Artificial sequence
<220> FEATURE:
<223> OTHER INFORMATION: Synthetic oligonucleotide

<400> SEQUENCE: 131
gtatttgaac ctctcctgta attacttggc tgggcagatc cctgcggggc ttgggggcat 60
ggggaggttg catacgcttg acttctcaca taatgggctg tcaggggagg tgcctcctgg 120
aattgcagcc atgac 135

<210> SEQ ID NO 132
<211> LENGTH: 45
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (13)..(16)
<223> OTHER INFORMATION: Xaa can be any naturally occurring amino acid

<400> SEQUENCE: 132

Tyr Leu Asn Leu Ser Cys Asn Tyr Leu Ala Gly Gln Xaa Xaa Xaa Xaa
1 5 10 15

Leu Gly Gly Met Gly Arg Leu His Thr Leu Asp Phe Ser His Asn Gly
20 25 30

Leu Ser Gly Glu Val Pro Pro Gly Ile Ala Ala Met Thr
35 40 45

<210> SEQ ID NO 133
<211> LENGTH: 45
<212> TYPE: PRT
<213> ORGANISM: Artificial sequence
<220> FEATURE:
<223> OTHER INFORMATION: Synthetic peptide

<400> SEQUENCE: 133

Tyr Leu Asn Leu Ser Cys Asn Tyr Leu Ala Gly Gln Ile Pro Ala Gly
1 5 10 15

Leu Gly Gly Met Gly Arg Leu His Thr Leu Asp Phe Ser His Asn Gly
20 25 30

Leu Ser Gly Glu Val Pro Pro Gly Ile Ala Ala Met Thr
35 40 45

<210> SEQ ID NO 134
<211> LENGTH: 44
<212> TYPE: PRT
<213> ORGANISM: Artificial sequence
<220> FEATURE:
<223> OTHER INFORMATION: Synthetic peptide

<400> SEQUENCE: 134

Tyr Leu Asn Leu Ser Cys Asn Tyr Leu Ala Gly Gln Ile Ala Gly Leu
1 5 10 15

Gly Gly Met Gly Arg Leu His Thr Leu Asp Phe Ser His Asn Gly Leu
20 25 30

Ser Gly Glu Val Pro Pro Gly Ile Ala Ala Met Thr
35 40

<210> SEQ ID NO 135

<211> LENGTH: 45
<212> TYPE: PRT
<213> ORGANISM: Artificial sequence
<220> FEATURE:
<223> OTHER INFORMATION: Synthetic peptide

<400> SEQUENCE: 135

```
Tyr Leu Asn Leu Ser Cys Asn Tyr Leu Ala Gly Gln Ile Phe Ala Gly
1               5                   10                  15

Leu Gly Gly Met Gly Arg Leu His Thr Leu Asp Phe Ser His Asn Gly
            20                  25                  30

Leu Ser Gly Glu Val Pro Pro Gly Ile Ala Ala Met Thr
        35                  40                  45
```

<210> SEQ ID NO 136
<211> LENGTH: 45
<212> TYPE: PRT
<213> ORGANISM: Artificial sequence
<220> FEATURE:
<223> OTHER INFORMATION: Synthetic peptide

<400> SEQUENCE: 136

```
Tyr Leu Asn Leu Ser Cys Asn Tyr Leu Ala Gly Gln Ile Ser Ala Gly
1               5                   10                  15

Leu Gly Gly Met Gly Arg Leu His Thr Leu Asp Phe Ser His Asn Gly
            20                  25                  30

Leu Ser Gly Glu Val Pro Pro Gly Ile Ala Ala Met Thr
        35                  40                  45
```

<210> SEQ ID NO 137
<211> LENGTH: 45
<212> TYPE: PRT
<213> ORGANISM: Artificial sequence
<220> FEATURE:
<223> OTHER INFORMATION: Synthetic peptide

<400> SEQUENCE: 137

```
Tyr Leu Asn Leu Ser Cys Asn Tyr Leu Ala Gly Gln Ile Thr Ala Gly
1               5                   10                  15

Leu Gly Gly Met Gly Arg Leu His Thr Leu Asp Phe Ser His Asn Gly
            20                  25                  30

Leu Ser Gly Glu Val Pro Pro Gly Ile Ala Ala Met Thr
        35                  40                  45
```

<210> SEQ ID NO 138
<211> LENGTH: 45
<212> TYPE: PRT
<213> ORGANISM: Artificial sequence
<220> FEATURE:
<223> OTHER INFORMATION: Synthetic peptide

<400> SEQUENCE: 138

```
Tyr Leu Asn Leu Ser Cys Asn Tyr Leu Ala Gly Gln Ile Val Ala Gly
1               5                   10                  15

Leu Gly Gly Met Gly Arg Leu His Thr Leu Asp Phe Ser His Asn Gly
            20                  25                  30

Leu Ser Gly Glu Val Pro Pro Gly Ile Ala Ala Met Thr
        35                  40                  45
```

<210> SEQ ID NO 139
<211> LENGTH: 45
<212> TYPE: PRT
<213> ORGANISM: Artificial sequence
<220> FEATURE:
<223> OTHER INFORMATION: Synthetic peptide

<400> SEQUENCE: 139

Tyr Leu Asn Leu Ser Cys Asn Tyr Leu Ala Gly Gln Ile Cys Ala Gly
1 5 10 15

Leu Gly Gly Met Gly Arg Leu His Thr Leu Asp Phe Ser His Asn Gly
20 25 30

Leu Ser Gly Glu Val Pro Pro Gly Ile Ala Ala Met Thr
35 40 45

<210> SEQ ID NO 140
<211> LENGTH: 43
<212> TYPE: PRT
<213> ORGANISM: Artificial sequence
<220> FEATURE:
<223> OTHER INFORMATION: Synthetic peptide

<400> SEQUENCE: 140

Tyr Leu Asn Leu Ser Cys Asn Tyr Leu Ala Gly Gln Ile Leu Leu Gly
1 5 10 15

Gly Met Gly Arg Leu His Thr Leu Asp Phe Ser His Asn Gly Leu Ser
20 25 30

Gly Glu Val Pro Pro Gly Ile Ala Ala Met Thr
35 40

<210> SEQ ID NO 141
<211> LENGTH: 42
<212> TYPE: PRT
<213> ORGANISM: Artificial sequence
<220> FEATURE:
<223> OTHER INFORMATION: Synthetic peptide

<400> SEQUENCE: 141

Tyr Leu Asn Leu Ser Cys Asn Tyr Leu Ala Gly Gln Arg Leu Gly Gly
1 5 10 15

Met Gly Arg Leu His Thr Leu Asp Phe Ser His Asn Gly Leu Ser Gly
20 25 30

Glu Val Pro Pro Gly Ile Ala Ala Met Thr
35 40

<210> SEQ ID NO 142
<211> LENGTH: 41
<212> TYPE: PRT
<213> ORGANISM: Artificial sequence
<220> FEATURE:
<223> OTHER INFORMATION: Synthetic peptide

<400> SEQUENCE: 142

Tyr Leu Asn Leu Ser Cys Asn Tyr Leu Ala Gly Arg Leu Gly Gly Met
1 5 10 15

Gly Arg Leu His Thr Leu Asp Phe Ser His Asn Gly Leu Ser Gly Glu
20 25 30

Val Pro Pro Gly Ile Ala Ala Met Thr
35 40

<210> SEQ ID NO 143
<211> LENGTH: 34
<212> TYPE: PRT
<213> ORGANISM: Artificial sequence
<220> FEATURE:
<223> OTHER INFORMATION: Synthetic peptide

<400> SEQUENCE: 143

Tyr Leu Asn Leu Ser Cys Asn Tyr Met Gly Arg Leu His Thr Leu Asp
1               5                   10                  15

Phe Ser His Asn Gly Leu Ser Gly Glu Val Pro Pro Gly Ile Ala Ala
            20                  25                  30

Met Thr

<210> SEQ ID NO 144
<211> LENGTH: 23
<212> TYPE: PRT
<213> ORGANISM: Artificial sequence
<220> FEATURE:
<223> OTHER INFORMATION: Synthetic peptide

<400> SEQUENCE: 144

Tyr Leu Asn Leu Ser Cys Asn Tyr Leu Ala Gly Gln Ile Ala Trp Gly
1               5                   10                  15

His Gly Glu Val Ala Tyr Ala
            20

<210> SEQ ID NO 145
<211> LENGTH: 23
<212> TYPE: PRT
<213> ORGANISM: Artificial sequence
<220> FEATURE:
<223> OTHER INFORMATION: Synthetic peptide

<400> SEQUENCE: 145

Tyr Leu Asn Leu Ser Cys Asn Tyr Leu Ala Gly Gln Arg Ala Trp Gly
1               5                   10                  15

His Gly Glu Val Ala Tyr Ala
            20

<210> SEQ ID NO 146
<211> LENGTH: 41
<212> TYPE: PRT
<213> ORGANISM: Artificial sequence
<220> FEATURE:
<223> OTHER INFORMATION: Synthetic peptide

<400> SEQUENCE: 146

Tyr Leu Asn Leu Ser Cys Asn Tyr Leu Ala Gly Gln Arg Gly Leu Gly
1               5                   10                  15

Ala Trp Gly Gly Cys Ile Arg Leu Thr Ser His Ile Met Gly Cys Gln
            20                  25                  30

Gly Arg Cys Leu Leu Glu Leu Gln Pro
        35                  40

<210> SEQ ID NO 147
<211> LENGTH: 42
<212> TYPE: PRT
<213> ORGANISM: Artificial sequence
<220> FEATURE:
<223> OTHER INFORMATION: Synthetic peptide

<400> SEQUENCE: 147

Tyr Leu Asn Leu Ser Cys Asn Tyr Leu Ala Gly Gln Ile Pro Ala Gly
1               5                   10                  15

Gly Ala Trp Gly Gly Cys Ile Arg Leu Thr Ser His Ile Met Gly Cys
            20                  25                  30

Gln Gly Arg Cys Leu Leu Glu Leu Gln Pro
        35                  40

<210> SEQ ID NO 148
<211> LENGTH: 40
<212> TYPE: PRT
<213> ORGANISM: Artificial sequence
<220> FEATURE:
<223> OTHER INFORMATION: Synthetic peptide

<400> SEQUENCE: 148

```
Tyr Leu Asn Leu Ser Cys Asn Tyr Leu Ala Gly Gln Gly Leu Gly Ala
1               5                   10                  15

Trp Gly Gly Cys Ile Arg Leu Thr Ser His Ile Met Gly Cys Gln Gly
            20                  25                  30

Arg Cys Leu Leu Glu Leu Gln Pro
        35                  40
```

<210> SEQ ID NO 149
<211> LENGTH: 37
<212> TYPE: DNA
<213> ORGANISM: Zea mays

<400> SEQUENCE: 149
gggcagatcc ctgcggggct tgggggcatg gggaggt 37

<210> SEQ ID NO 150
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 150
gggcagattt ctgcggggct tgggggcatg gggaggt 37

<210> SEQ ID NO 151
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 151
gggcagattt gtgcggggct tgggggcatg gggaggt 37

<210> SEQ ID NO 152
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 152
gggcagattt ttgcggggct tgggggcatg gggaggt 37

<210> SEQ ID NO 153
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 153
gggcagggct tgggggcatg gggaggt 27

```
<210> SEQ ID NO 154
<211> LENGTH: 12
<212> TYPE: PRT
<213> ORGANISM: Zea mays

<400> SEQUENCE: 154

Gly Gln Ile Pro Ala Gly Leu Gly Gly Met Gly Arg
1               5                   10


<210> SEQ ID NO 155
<211> LENGTH: 12
<212> TYPE: PRT
<213> ORGANISM: Artificial sequence
<220> FEATURE:
<223> OTHER INFORMATION: Synthetic peptide

<400> SEQUENCE: 155

Gly Gln Ile Ser Ala Gly Leu Gly Gly Met Gly Arg
1               5                   10


<210> SEQ ID NO 156
<211> LENGTH: 12
<212> TYPE: PRT
<213> ORGANISM: Artificial sequence
<220> FEATURE:
<223> OTHER INFORMATION: Synthetic peptide

<400> SEQUENCE: 156

Gly Gln Ile Cys Ala Gly Leu Gly Gly Met Gly Arg
1               5                   10


<210> SEQ ID NO 157
<211> LENGTH: 12
<212> TYPE: PRT
<213> ORGANISM: Artificial sequence
<220> FEATURE:
<223> OTHER INFORMATION: Synthetic peptide

<400> SEQUENCE: 157

Gly Gln Ile Phe Ala Gly Leu Gly Gly Met Gly Arg
1               5                   10


<210> SEQ ID NO 158
<211> LENGTH: 9
<212> TYPE: PRT
<213> ORGANISM: Artificial sequence
<220> FEATURE:
<223> OTHER INFORMATION: Synthetic peptide

<400> SEQUENCE: 158

Gly Gln Gly Leu Gly Ala Trp Gly Gly
1               5


<210> SEQ ID NO 159
<211> LENGTH: 36
<212> TYPE: PRT
<213> ORGANISM: Artificial sequence
<220> FEATURE:
<223> OTHER INFORMATION: Synthetic peptide

<400> SEQUENCE: 159

Pro Glu Gly Leu Val Asp Met Lys Gly Leu Glu Tyr Leu Asn Leu Ser
1               5                   10                  15

Cys Asn Tyr Leu Ala Gly Gln Ile Pro Ala Gly Leu Gly His Gly Glu
            20                  25                  30

Val Ala Tyr Ala
```

35

<210> SEQ ID NO 160
<211> LENGTH: 34
<212> TYPE: PRT
<213> ORGANISM: Artificial sequence
<220> FEATURE:
<223> OTHER INFORMATION: Synthetic peptide

<400> SEQUENCE: 160

Pro Glu Gly Leu Val Asp Met Lys Gly Leu Glu Tyr Leu Asn Leu Ser
1 5 10 15

Cys Asn Tyr Leu Ala Gly Gln Ile Ala Trp Gly His Gly Glu Val Ala
20 25 30

Tyr Ala

<210> SEQ ID NO 161
<211> LENGTH: 33
<212> TYPE: PRT
<213> ORGANISM: Artificial sequence
<220> FEATURE:
<223> OTHER INFORMATION: Synthetic peptide

<400> SEQUENCE: 161

Pro Glu Gly Leu Val Asp Met Lys Gly Leu Glu Tyr Leu Asn Leu Ser
1 5 10 15

Cys Asn Tyr Leu Ala Gly Arg Ala Trp Gly His Gly Glu Val Ala Tyr
20 25 30

Ala

<210> SEQ ID NO 162
<211> LENGTH: 34
<212> TYPE: PRT
<213> ORGANISM: Artificial sequence
<220> FEATURE:
<223> OTHER INFORMATION: Synthetic peptide

<400> SEQUENCE: 162

Pro Glu Gly Leu Val Asp Met Lys Gly Leu Glu Tyr Leu Asn Leu Ser
1 5 10 15

Cys Asn Tyr Leu Ala Gly Gln Arg Ala Trp Gly His Gly Glu Val Ala
20 25 30

Tyr Ala

<210> SEQ ID NO 163
<211> LENGTH: 53
<212> TYPE: PRT
<213> ORGANISM: Artificial sequence
<220> FEATURE:
<223> OTHER INFORMATION: Synthetic peptide

<400> SEQUENCE: 163

Pro Glu Gly Leu Val Asp Met Lys Gly Leu Glu Tyr Leu Asn Leu Ser
1 5 10 15

Cys Asn Tyr Leu Ala Gly Gln Ile Pro Ala Gly Gly Ala Trp Gly Gly
20 25 30

Cys Ile Arg Leu Thr Ser His Ile Met Gly Cys Gln Gly Arg Cys Leu
35 40 45

Leu Glu Leu Gln Pro
50

```
<210> SEQ ID NO 164
<211> LENGTH: 52
<212> TYPE: PRT
<213> ORGANISM: Artificial sequence
<220> FEATURE:
<223> OTHER INFORMATION: Synthetic peptide

<400> SEQUENCE: 164

Pro Glu Gly Leu Val Asp Met Lys Gly Leu Glu Tyr Leu Asn Leu Ser
1               5                   10                  15

Cys Asn Tyr Leu Ala Gly Gln Arg Gly Leu Gly Ala Trp Gly Gly Cys
            20                  25                  30

Ile Arg Leu Thr Ser His Ile Met Gly Cys Gln Gly Arg Cys Leu Leu
        35                  40                  45

Glu Leu Gln Pro
    50


<210> SEQ ID NO 165
<211> LENGTH: 51
<212> TYPE: PRT
<213> ORGANISM: Artificial sequence
<220> FEATURE:
<223> OTHER INFORMATION: Synthetic peptide

<400> SEQUENCE: 165

Pro Glu Gly Leu Val Asp Met Lys Gly Leu Glu Tyr Leu Asn Leu Ser
1               5                   10                  15

Cys Asn Tyr Leu Ala Gly Gln Gly Leu Gly Ala Trp Gly Gly Cys Ile
            20                  25                  30

Arg Leu Thr Ser His Ile Met Gly Cys Gln Gly Arg Cys Leu Leu Glu
        35                  40                  45

Leu Gln Pro
    50


<210> SEQ ID NO 166
<211> LENGTH: 66
<212> TYPE: PRT
<213> ORGANISM: Artificial sequence
<220> FEATURE:
<223> OTHER INFORMATION: Synthetic peptide

<400> SEQUENCE: 166

Pro Glu Gly Leu Val Asp Met Lys Gly Leu Glu Tyr Leu Asn Leu Ser
1               5                   10                  15

Cys Asn Tyr Leu Ala Gly Gln Ile Leu Leu Gly Gly Met Gly Arg Leu
            20                  25                  30

His Thr Leu Asp Phe Ser His Asn Gly Leu Ser Gly Glu Val Pro Pro
        35                  40                  45

Gly Ile Ala Ala Met Thr Val Leu Glu Val Leu Asn Leu Ser Tyr Asn
    50                  55                  60

Ser Leu
65


<210> SEQ ID NO 167
<211> LENGTH: 66
<212> TYPE: PRT
<213> ORGANISM: Artificial sequence
<220> FEATURE:
<223> OTHER INFORMATION: Synthetic peptide

<400> SEQUENCE: 167

Pro Glu Gly Leu Val Asp Met Lys Gly Leu Glu Tyr Leu Asn Leu Ser
```

```
1               5                   10                  15

Cys Asn Tyr Leu Ala Gly Gln Ile Arg Leu Gly Gly Met Gly Arg Leu
            20                  25                  30

His Thr Leu Asp Phe Ser His Asn Gly Leu Ser Gly Glu Val Pro Pro
        35                  40                  45

Gly Ile Ala Ala Met Thr Val Leu Glu Val Leu Asn Leu Ser Tyr Asn
    50                  55                  60

Ser Leu
65
```

<210> SEQ ID NO 168
<211> LENGTH: 65
<212> TYPE: PRT
<213> ORGANISM: Artificial sequence
<220> FEATURE:
<223> OTHER INFORMATION: Synthetic peptide

<400> SEQUENCE: 168

```
Pro Glu Gly Leu Val Asp Met Lys Gly Leu Glu Tyr Leu Asn Leu Ser
1               5                   10                  15

Cys Asn Tyr Leu Ala Gly Gln Gly Leu Gly Gly Met Gly Arg Leu His
            20                  25                  30

Thr Leu Asp Phe Ser His Asn Gly Leu Ser Gly Glu Val Pro Pro Gly
        35                  40                  45

Ile Ala Ala Met Thr Val Leu Glu Val Leu Asn Leu Ser Tyr Asn Ser
    50                  55                  60

Leu
65
```

<210> SEQ ID NO 169
<211> LENGTH: 65
<212> TYPE: PRT
<213> ORGANISM: Artificial sequence
<220> FEATURE:
<223> OTHER INFORMATION: Synthetic peptide

<400> SEQUENCE: 169

```
Pro Glu Gly Leu Val Asp Met Lys Gly Leu Glu Tyr Leu Asn Leu Ser
1               5                   10                  15

Cys Asn Tyr Leu Ala Gly Gln Arg Leu Gly Gly Met Gly Arg Leu His
            20                  25                  30

Thr Leu Asp Phe Ser His Asn Gly Leu Ser Gly Glu Val Pro Pro Gly
        35                  40                  45

Ile Ala Ala Met Thr Val Leu Glu Val Leu Asn Leu Ser Tyr Asn Ser
    50                  55                  60

Leu
65
```

<210> SEQ ID NO 170
<211> LENGTH: 64
<212> TYPE: PRT
<213> ORGANISM: Artificial sequence
<220> FEATURE:
<223> OTHER INFORMATION: Synthetic peptide

<400> SEQUENCE: 170

```
Pro Glu Gly Leu Val Asp Met Lys Gly Leu Glu Tyr Leu Asn Leu Ser
1               5                   10                  15

Cys Asn Tyr Leu Ala Gly Arg Leu Gly Gly Met Gly Arg Leu His Thr
            20                  25                  30
```

```
Leu Asp Phe Ser His Asn Gly Leu Ser Gly Glu Val Pro Pro Gly Ile
        35                  40                  45

Ala Ala Met Thr Val Leu Glu Val Leu Asn Leu Ser Tyr Asn Ser Leu
    50                  55                  60


<210> SEQ ID NO 171
<211> LENGTH: 57
<212> TYPE: PRT
<213> ORGANISM: Artificial sequence
<220> FEATURE:
<223> OTHER INFORMATION: Synthetic peptide

<400> SEQUENCE: 171

Pro Glu Gly Leu Val Asp Met Lys Gly Leu Glu Tyr Leu Asn Leu Ser
1               5                   10                  15

Cys Asn Tyr Met Gly Arg Leu His Thr Leu Asp Phe Ser His Asn Gly
            20                  25                  30

Leu Ser Gly Glu Val Pro Pro Gly Ile Ala Ala Met Thr Val Leu Glu
        35                  40                  45

Val Leu Asn Leu Ser Tyr Asn Ser Leu
    50                  55


<210> SEQ ID NO 172
<211> LENGTH: 612
<212> TYPE: PRT
<213> ORGANISM: Artificial sequence
<220> FEATURE:
<223> OTHER INFORMATION: Synthetic polypeptide

<400> SEQUENCE: 172

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
```

```
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Ala Gly Leu Gly
465                 470                 475                 480

Gly Met Gly Arg Leu His Thr Leu Asp Phe Ser His Asn Gly Leu Ser
                485                 490                 495

Gly Glu Val Pro Pro Gly Ile Ala Ala Met Thr Val Leu Glu Val Leu
            500                 505                 510

Asn Leu Ser Tyr Asn Ser Leu Ser Gly Pro Leu Pro Thr Thr Lys Phe
        515                 520                 525

Pro Gly Ala Leu Ala Gly Asn Pro Gly Ile Cys Ser Gly Lys Gly Cys
    530                 535                 540

Ser Glu Asn Ala Arg Thr Pro Glu Gly Lys Met Glu Gly Ser Asn His
545                 550                 555                 560

Arg Gly Trp Leu Gly Gly Trp His Gly Glu Asn Gly Trp Val Ser Leu
                565                 570                 575

Gly Ala Phe Cys Ile Ser Thr Met Thr Ser Phe Tyr Val Ser Leu Ala
            580                 585                 590

Thr Leu Leu Cys Ser Ser Asn Ala Arg Asn Phe Val Phe Arg Pro Val
        595                 600                 605

Arg Val Glu Tyr
    610
```

<210> SEQ ID NO 173

<211> LENGTH: 613
<212> TYPE: PRT
<213> ORGANISM: Artificial sequence
<220> FEATURE:
<223> OTHER INFORMATION: Synthetic polypeptide

<400> SEQUENCE: 173

```
Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380
```

```
Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Phe Ala Gly Leu
465                 470                 475                 480

Gly Gly Met Gly Arg Leu His Thr Leu Asp Phe Ser His Asn Gly Leu
                485                 490                 495

Ser Gly Glu Val Pro Pro Gly Ile Ala Ala Met Thr Val Leu Glu Val
            500                 505                 510

Leu Asn Leu Ser Tyr Asn Ser Leu Ser Gly Pro Leu Pro Thr Thr Lys
        515                 520                 525

Phe Pro Gly Ala Leu Ala Gly Asn Pro Gly Ile Cys Ser Gly Lys Gly
    530                 535                 540

Cys Ser Glu Asn Ala Arg Thr Pro Glu Gly Lys Met Glu Gly Ser Asn
545                 550                 555                 560

His Arg Gly Trp Leu Gly Gly Trp His Gly Glu Asn Gly Trp Val Ser
                565                 570                 575

Leu Gly Ala Phe Cys Ile Ser Thr Met Thr Ser Phe Tyr Val Ser Leu
            580                 585                 590

Ala Thr Leu Leu Cys Ser Ser Asn Ala Arg Asn Phe Val Phe Arg Pro
        595                 600                 605

Val Arg Val Glu Tyr
    610


<210> SEQ ID NO 174
<211> LENGTH: 613
<212> TYPE: PRT
<213> ORGANISM: Artificial sequence
<220> FEATURE:
<223> OTHER INFORMATION: Synthetic polypeptide

<400> SEQUENCE: 174

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125
```

```
Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Ser Ala Gly Leu
465                 470                 475                 480

Gly Gly Met Gly Arg Leu His Thr Leu Asp Phe Ser His Asn Gly Leu
                485                 490                 495

Ser Gly Glu Val Pro Pro Gly Ile Ala Ala Met Thr Val Leu Glu Val
            500                 505                 510

Leu Asn Leu Ser Tyr Asn Ser Leu Ser Gly Pro Leu Pro Thr Thr Lys
        515                 520                 525

Phe Pro Gly Ala Leu Ala Gly Asn Pro Gly Ile Cys Ser Gly Lys Gly
    530                 535                 540
```

-continued

```
Cys Ser Glu Asn Ala Arg Thr Pro Glu Gly Lys Met Glu Gly Ser Asn
545                 550                 555                 560

His Arg Gly Trp Leu Gly Gly Trp His Gly Glu Asn Gly Trp Val Ser
                565                 570                 575

Leu Gly Ala Phe Cys Ile Ser Thr Met Thr Ser Phe Tyr Val Ser Leu
            580                 585                 590

Ala Thr Leu Leu Cys Ser Ser Asn Ala Arg Asn Phe Val Phe Arg Pro
        595                 600                 605

Val Arg Val Glu Tyr
    610


<210> SEQ ID NO 175
<211> LENGTH: 613
<212> TYPE: PRT
<213> ORGANISM: Artificial sequence
<220> FEATURE:
<223> OTHER INFORMATION: Synthetic polypeptide

<400> SEQUENCE: 175

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285
```

Gly Ala Leu Arg Pro Glu Leu Asp Ala Leu Ala Ser Leu Lys Val Leu
290 295 300

Asp Leu Ser Asn Asn Lys Ile Ser Gly Glu Ile Pro Leu Pro Leu Ala
305 310 315 320

Gly Cys Arg Ser Leu Glu Val Val Asp Leu Ser Gly Asn Glu Ile Ser
325 330 335

Gly Glu Leu Ser Ser Ala Val Ala Lys Trp Leu Ser Leu Lys Phe Leu
340 345 350

Ser Leu Ala Gly Asn Gln Leu Ser Gly His Leu Pro Asp Trp Met Phe
355 360 365

Ser Phe Pro Leu Leu Gln Trp Leu Asp Leu Ser Ser Asn Lys Phe Val
370 375 380

Gly Phe Ile Pro Asp Gly Gly Phe Asn Val Ser Glu Val Leu Asn Gly
385 390 395 400

Gly Gly Gly Gln Gly Thr Pro Ser Glu Ser Val Leu Pro Pro Gln Leu
405 410 415

Phe Val Ser Ala Ser Val Asp Thr Val Ser Trp Gln Leu Asp Leu Gly
420 425 430

Tyr Asp Val Gln Ala Thr Thr Gly Ile Asp Leu Ser Gly Asn Glu Leu
435 440 445

Cys Gly Glu Ile Pro Glu Gly Leu Val Asp Met Lys Gly Leu Glu Tyr
450 455 460

Leu Asn Leu Ser Cys Asn Tyr Leu Ala Gly Gln Ile Thr Ala Gly Leu
465 470 475 480

Gly Gly Met Gly Arg Leu His Thr Leu Asp Phe Ser His Asn Gly Leu
485 490 495

Ser Gly Glu Val Pro Pro Gly Ile Ala Ala Met Thr Val Leu Glu Val
500 505 510

Leu Asn Leu Ser Tyr Asn Ser Leu Ser Gly Pro Leu Pro Thr Thr Lys
515 520 525

Phe Pro Gly Ala Leu Ala Gly Asn Pro Gly Ile Cys Ser Gly Lys Gly
530 535 540

Cys Ser Glu Asn Ala Arg Thr Pro Glu Gly Lys Met Glu Gly Ser Asn
545 550 555 560

His Arg Gly Trp Leu Gly Gly Trp His Gly Glu Asn Gly Trp Val Ser
565 570 575

Leu Gly Ala Phe Cys Ile Ser Thr Met Thr Ser Phe Tyr Val Ser Leu
580 585 590

Ala Thr Leu Leu Cys Ser Ser Asn Ala Arg Asn Phe Val Phe Arg Pro
595 600 605

Val Arg Val Glu Tyr
610

<210> SEQ ID NO 176
<211> LENGTH: 613
<212> TYPE: PRT
<213> ORGANISM: Artificial sequence
<220> FEATURE:
<223> OTHER INFORMATION: Synthetic polypeptide

<400> SEQUENCE: 176

Met Leu Thr Ala Thr Pro Leu Pro His Gln Leu Leu Ala Thr Phe Leu
1 5 10 15

Leu Val Leu Ala Ser Ala Thr Gln Pro Ala Val Pro Ala Ser Thr Asp
20 25 30

```
Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
```

```
    450                 455                 460

Leu Asn Leu Ser Cys Asn Tyr Leu Ala Gly Gln Ile Val Ala Gly Leu
465                 470                 475                 480

Gly Gly Met Gly Arg Leu His Thr Leu Asp Phe Ser His Asn Gly Leu
                485                 490                 495

Ser Gly Glu Val Pro Pro Gly Ile Ala Ala Met Thr Val Leu Glu Val
            500                 505                 510

Leu Asn Leu Ser Tyr Asn Ser Leu Ser Gly Pro Leu Pro Thr Thr Lys
        515                 520                 525

Phe Pro Gly Ala Leu Ala Gly Asn Pro Gly Ile Cys Ser Gly Lys Gly
    530                 535                 540

Cys Ser Glu Asn Ala Arg Thr Pro Glu Gly Lys Met Glu Gly Ser Asn
545                 550                 555                 560

His Arg Gly Trp Leu Gly Gly Trp His Gly Glu Asn Gly Trp Val Ser
                565                 570                 575

Leu Gly Ala Phe Cys Ile Ser Thr Met Thr Ser Phe Tyr Val Ser Leu
            580                 585                 590

Ala Thr Leu Leu Cys Ser Ser Asn Ala Arg Asn Phe Val Phe Arg Pro
        595                 600                 605

Val Arg Val Glu Tyr
    610


<210> SEQ ID NO 177
<211> LENGTH: 613
<212> TYPE: PRT
<213> ORGANISM: Artificial sequence
<220> FEATURE:
<223> OTHER INFORMATION: Synthetic polypeptide

<400> SEQUENCE: 177

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
```

-continued

```
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Cys Ala Gly Leu
465                 470                 475                 480

Gly Gly Met Gly Arg Leu His Thr Leu Asp Phe Ser His Asn Gly Leu
                485                 490                 495

Ser Gly Glu Val Pro Pro Gly Ile Ala Ala Met Thr Val Leu Glu Val
            500                 505                 510

Leu Asn Leu Ser Tyr Asn Ser Leu Ser Gly Pro Leu Pro Thr Thr Lys
        515                 520                 525

Phe Pro Gly Ala Leu Ala Gly Asn Pro Gly Ile Cys Ser Gly Lys Gly
    530                 535                 540

Cys Ser Glu Asn Ala Arg Thr Pro Glu Gly Lys Met Glu Gly Ser Asn
545                 550                 555                 560

His Arg Gly Trp Leu Gly Gly Trp His Gly Glu Asn Gly Trp Val Ser
                565                 570                 575

Leu Gly Ala Phe Cys Ile Ser Thr Met Thr Ser Phe Tyr Val Ser Leu
            580                 585                 590

Ala Thr Leu Leu Cys Ser Ser Asn Ala Arg Asn Phe Val Phe Arg Pro
        595                 600                 605

Val Arg Val Glu Tyr
    610
```

<210> SEQ ID NO 178
<211> LENGTH: 611
<212> TYPE: PRT
<213> ORGANISM: Artificial sequence
<220> FEATURE:
<223> OTHER INFORMATION: Synthetic polypeptide

<400> SEQUENCE: 178

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

```
Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Leu Leu Gly Gly
465                 470                 475                 480

Met Gly Arg Leu His Thr Leu Asp Phe Ser His Asn Gly Leu Ser Gly
                485                 490                 495

Glu Val Pro Pro Gly Ile Ala Ala Met Thr Val Leu Glu Val Leu Asn
            500                 505                 510

Leu Ser Tyr Asn Ser Leu Ser Gly Pro Leu Pro Thr Thr Lys Phe Pro
        515                 520                 525

Gly Ala Leu Ala Gly Asn Pro Gly Ile Cys Ser Gly Lys Gly Cys Ser
    530                 535                 540

Glu Asn Ala Arg Thr Pro Glu Gly Lys Met Glu Gly Ser Asn His Arg
545                 550                 555                 560

Gly Trp Leu Gly Gly Trp His Gly Glu Asn Gly Trp Val Ser Leu Gly
                565                 570                 575

Ala Phe Cys Ile Ser Thr Met Thr Ser Phe Tyr Val Ser Leu Ala Thr
            580                 585                 590

Leu Leu Cys Ser Ser Asn Ala Arg Asn Phe Val Phe Arg Pro Val Arg
        595                 600                 605

Val Glu Tyr
    610


<210> SEQ ID NO 179
<211> LENGTH: 610
<212> TYPE: PRT
<213> ORGANISM: Artificial sequence
<220> FEATURE:
<223> OTHER INFORMATION: Synthetic polypeptide

<400> SEQUENCE: 179

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110
```

```
Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Arg Leu Gly Gly Met
465                 470                 475                 480

Gly Arg Leu His Thr Leu Asp Phe Ser His Asn Gly Leu Ser Gly Glu
                485                 490                 495

Val Pro Pro Gly Ile Ala Ala Met Thr Val Leu Glu Val Leu Asn Leu
            500                 505                 510

Ser Tyr Asn Ser Leu Ser Gly Pro Leu Pro Thr Thr Lys Phe Pro Gly
        515                 520                 525
```

```
Ala Leu Ala Gly Asn Pro Gly Ile Cys Ser Gly Lys Gly Cys Ser Glu
    530                 535                 540

Asn Ala Arg Thr Pro Glu Gly Lys Met Glu Gly Ser Asn His Arg Gly
545                 550                 555                 560

Trp Leu Gly Gly Trp His Gly Glu Asn Gly Trp Val Ser Leu Gly Ala
                565                 570                 575

Phe Cys Ile Ser Thr Met Thr Ser Phe Tyr Val Ser Leu Ala Thr Leu
            580                 585                 590

Leu Cys Ser Ser Asn Ala Arg Asn Phe Val Phe Arg Pro Val Arg Val
        595                 600                 605

Glu Tyr
    610


<210> SEQ ID NO 180
<211> LENGTH: 609
<212> TYPE: PRT
<213> ORGANISM: Artificial sequence
<220> FEATURE:
<223> OTHER INFORMATION: Synthetic polypeptide

<400> SEQUENCE: 180

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270
```

```
Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Arg Leu Gly Gly Met Gly
465                 470                 475                 480

Arg Leu His Thr Leu Asp Phe Ser His Asn Gly Leu Ser Gly Glu Val
                485                 490                 495

Pro Pro Gly Ile Ala Ala Met Thr Val Leu Glu Val Leu Asn Leu Ser
            500                 505                 510

Tyr Asn Ser Leu Ser Gly Pro Leu Pro Thr Thr Lys Phe Pro Gly Ala
        515                 520                 525

Leu Ala Gly Asn Pro Gly Ile Cys Ser Gly Lys Gly Cys Ser Glu Asn
    530                 535                 540

Ala Arg Thr Pro Glu Gly Lys Met Glu Gly Ser Asn His Arg Gly Trp
545                 550                 555                 560

Leu Gly Gly Trp His Gly Glu Asn Gly Trp Val Ser Leu Gly Ala Phe
                565                 570                 575

Cys Ile Ser Thr Met Thr Ser Phe Tyr Val Ser Leu Ala Thr Leu Leu
            580                 585                 590

Cys Ser Ser Asn Ala Arg Asn Phe Val Phe Arg Pro Val Arg Val Glu
        595                 600                 605

Tyr
```

<210> SEQ ID NO 181
<211> LENGTH: 602
<212> TYPE: PRT
<213> ORGANISM: Artificial sequence
<220> FEATURE:
<223> OTHER INFORMATION: Synthetic polypeptide

<400> SEQUENCE: 181

```
Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
```

```
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445
```

```
Cys Gly Glu Ile Pro Glu Gly Leu Val Asp Met Lys Gly Leu Glu Tyr
    450                 455                 460

Leu Asn Leu Ser Cys Asn Tyr Met Gly Arg Leu His Thr Leu Asp Phe
465                 470                 475                 480

Ser His Asn Gly Leu Ser Gly Glu Val Pro Pro Gly Ile Ala Ala Met
                485                 490                 495

Thr Val Leu Glu Val Leu Asn Leu Ser Tyr Asn Ser Leu Ser Gly Pro
            500                 505                 510

Leu Pro Thr Thr Lys Phe Pro Gly Ala Leu Ala Gly Asn Pro Gly Ile
        515                 520                 525

Cys Ser Gly Lys Gly Cys Ser Glu Asn Ala Arg Thr Pro Glu Gly Lys
    530                 535                 540

Met Glu Gly Ser Asn His Arg Gly Trp Leu Gly Gly Trp His Gly Glu
545                 550                 555                 560

Asn Gly Trp Val Ser Leu Gly Ala Phe Cys Ile Ser Thr Met Thr Ser
                565                 570                 575

Phe Tyr Val Ser Leu Ala Thr Leu Leu Cys Ser Ser Asn Ala Arg Asn
            580                 585                 590

Phe Val Phe Arg Pro Val Arg Val Glu Tyr
        595                 600


<210> SEQ ID NO 182
<211> LENGTH: 486
<212> TYPE: PRT
<213> ORGANISM: Artificial sequence
<220> FEATURE:
<223> OTHER INFORMATION: Synthetic polypeptide

<400> SEQUENCE: 182

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205
```

```
Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Ile Ala Trp Gly His
465                 470                 475                 480

Gly Glu Val Ala Tyr Ala
                485
```

<210> SEQ ID NO 183
<211> LENGTH: 486
<212> TYPE: PRT
<213> ORGANISM: Artificial sequence
<220> FEATURE:
<223> OTHER INFORMATION: Synthetic polypeptide

<400> SEQUENCE: 183

```
Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80
```

-continued

```
Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Arg Ala Trp Gly His
465                 470                 475                 480

Gly Glu Val Ala Tyr Ala
                485
```

<210> SEQ ID NO 184
<211> LENGTH: 486
<212> TYPE: PRT
<213> ORGANISM: Artificial sequence
<220> FEATURE:
<223> OTHER INFORMATION: Synthetic polypeptide

<400> SEQUENCE: 184

```
Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365
```

```
Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Arg Ala Trp Gly His
465                 470                 475                 480

Gly Glu Val Ala Tyr Ala
                485


<210> SEQ ID NO 185
<211> LENGTH: 505
<212> TYPE: PRT
<213> ORGANISM: Artificial sequence
<220> FEATURE:
<223> OTHER INFORMATION: Synthetic oligonucleotide

<400> SEQUENCE: 185

Met Leu Thr Ala Thr Pro Leu Pro His Gln Leu Leu Ala Thr Phe Leu
1               5                   10                  15

Leu Val Leu Ala Ser Ala Thr Gln Pro Ala Val Pro Ala Ser Thr Asp
            20                  25                  30

Arg Ala Ala Leu Leu Ala Phe Arg Ala Ser Leu Ser Pro Pro Ser Arg
        35                  40                  45

Ala Ala Leu Ser Ser Trp Ser Gly Pro Leu Ser Pro Ser Trp Leu Gly
    50                  55                  60

Val Ser Leu His Pro Ala Thr Ala Pro Ala Pro Ser Val Thr Thr Pro
65                  70                  75                  80

Ser Val Ala Glu Leu Ser Leu Arg Gly Leu Asn Leu Thr Gly Val Ile
                85                  90                  95

Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240
```

Gly Asp Ile Pro Pro Gly Ile Gly Asn Leu Thr Tyr Leu Gln Val Leu
245 250 255

Asp Leu Ser Asn Asn Arg Leu Ser Gly Ser Val Pro Ala Gly Leu Ala
260 265 270

Gly Cys Phe Gln Leu Leu Tyr Leu Gln Leu Gly Gly Asn Gln Leu Ser
275 280 285

Gly Ala Leu Arg Pro Glu Leu Asp Ala Leu Ala Ser Leu Lys Val Leu
290 295 300

Asp Leu Ser Asn Asn Lys Ile Ser Gly Glu Ile Pro Leu Pro Leu Ala
305 310 315 320

Gly Cys Arg Ser Leu Glu Val Val Asp Leu Ser Gly Asn Glu Ile Ser
325 330 335

Gly Glu Leu Ser Ser Ala Val Ala Lys Trp Leu Ser Leu Lys Phe Leu
340 345 350

Ser Leu Ala Gly Asn Gln Leu Ser Gly His Leu Pro Asp Trp Met Phe
355 360 365

Ser Phe Pro Leu Leu Gln Trp Leu Asp Leu Ser Ser Asn Lys Phe Val
370 375 380

Gly Phe Ile Pro Asp Gly Gly Phe Asn Val Ser Glu Val Leu Asn Gly
385 390 395 400

Gly Gly Gly Gln Gly Thr Pro Ser Glu Ser Val Leu Pro Pro Gln Leu
405 410 415

Phe Val Ser Ala Ser Val Asp Thr Val Ser Trp Gln Leu Asp Leu Gly
420 425 430

Tyr Asp Val Gln Ala Thr Thr Gly Ile Asp Leu Ser Gly Asn Glu Leu
435 440 445

Cys Gly Glu Ile Pro Glu Gly Leu Val Asp Met Lys Gly Leu Glu Tyr
450 455 460

Leu Asn Leu Ser Cys Asn Tyr Leu Ala Gly Gln Ile Pro Ala Gly Gly
465 470 475 480

Ala Trp Gly Gly Cys Ile Arg Leu Thr Ser His Ile Met Gly Cys Gln
485 490 495

Gly Arg Cys Leu Leu Glu Leu Gln Pro
500 505

<210> SEQ ID NO 186
<211> LENGTH: 503
<212> TYPE: PRT
<213> ORGANISM: Artificial sequence
<220> FEATURE:
<223> OTHER INFORMATION: Synthetic polypeptide

<400> SEQUENCE: 186

Met Leu Thr Ala Thr Pro Leu Pro His Gln Leu Leu Ala Thr Phe Leu
1 5 10 15

Leu Val Leu Ala Ser Ala Thr Gln Pro Ala Val Pro Ala Ser Thr Asp
20 25 30

Arg Ala Ala Leu Leu Ala Phe Arg Ala Ser Leu Ser Pro Pro Ser Arg
35 40 45

Ala Ala Leu Ser Ser Trp Ser Gly Pro Leu Ser Pro Ser Trp Leu Gly
50 55 60

Val Ser Leu His Pro Ala Thr Ala Pro Ala Pro Ser Val Thr Thr Pro
65 70 75 80

Ser Val Ala Glu Leu Ser Leu Arg Gly Leu Asn Leu Thr Gly Val Ile
85 90 95

-continued

```
Pro Ala Ala Pro Leu Ala Leu Leu Arg Arg Leu Arg Thr Leu Asp Leu
            100                 105                 110

Ser Ala Asn Ala Leu Ser Gly Glu Leu Pro Cys Ser Leu Pro Arg Ser
        115                 120                 125

Leu Leu Ala Leu Asp Leu Ser Arg Asn Ala Leu Ser Gly Ala Val Pro
    130                 135                 140

Thr Cys Leu Pro Ser Ser Leu Pro Ala Leu Arg Thr Leu Asn Leu Ser
145                 150                 155                 160

Ala Asn Phe Leu Arg Leu Pro Leu Ser Pro Arg Leu Ser Phe Pro Ala
                165                 170                 175

Arg Leu Ala Ala Leu Asp Leu Ser Arg Asn Ala Ile Ser Gly Ala Val
            180                 185                 190

Pro Pro Arg Ile Val Ala Asp Pro Asp Asn Ser Ala Leu Leu Leu Leu
        195                 200                 205

Asp Leu Ser His Asn Arg Phe Ser Gly Glu Ile Pro Ala Gly Ile Ala
    210                 215                 220

Ala Val Arg Ser Leu Gln Gly Leu Phe Leu Ala Asp Asn Gln Leu Ser
225                 230                 235                 240

Gly Asp Ile Pro Pro Gly Ile Gly Asn Leu Thr Tyr Leu Gln Val Leu
                245                 250                 255

Asp Leu Ser Asn Asn Arg Leu Ser Gly Ser Val Pro Ala Gly Leu Ala
            260                 265                 270

Gly Cys Phe Gln Leu Leu Tyr Leu Gln Leu Gly Gly Asn Gln Leu Ser
        275                 280                 285

Gly Ala Leu Arg Pro Glu Leu Asp Ala Leu Ala Ser Leu Lys Val Leu
    290                 295                 300

Asp Leu Ser Asn Asn Lys Ile Ser Gly Glu Ile Pro Leu Pro Leu Ala
305                 310                 315                 320

Gly Cys Arg Ser Leu Glu Val Val Asp Leu Ser Gly Asn Glu Ile Ser
                325                 330                 335

Gly Glu Leu Ser Ser Ala Val Ala Lys Trp Leu Ser Leu Lys Phe Leu
            340                 345                 350

Ser Leu Ala Gly Asn Gln Leu Ser Gly His Leu Pro Asp Trp Met Phe
        355                 360                 365

Ser Phe Pro Leu Leu Gln Trp Leu Asp Leu Ser Ser Asn Lys Phe Val
    370                 375                 380

Gly Phe Ile Pro Asp Gly Gly Phe Asn Val Ser Glu Val Leu Asn Gly
385                 390                 395                 400

Gly Gly Gly Gln Gly Thr Pro Ser Glu Ser Val Leu Pro Pro Gln Leu
                405                 410                 415

Phe Val Ser Ala Ser Val Asp Thr Val Ser Trp Gln Leu Asp Leu Gly
            420                 425                 430

Tyr Asp Val Gln Ala Thr Thr Gly Ile Asp Leu Ser Gly Asn Glu Leu
        435                 440                 445

Cys Gly Glu Ile Pro Glu Gly Leu Val Asp Met Lys Gly Leu Glu Tyr
    450                 455                 460

Leu Asn Leu Ser Cys Asn Tyr Leu Ala Gly Gln Gly Leu Gly Ala Trp
465                 470                 475                 480

Gly Gly Cys Ile Arg Leu Thr Ser His Ile Met Gly Cys Gln Gly Arg
                485                 490                 495

Cys Leu Leu Glu Leu Gln Pro
            500
```